US012788823B2

(12) United States Patent
Kim et al.

(10) Patent No.: US 12,788,823 B2
(45) Date of Patent: Nov. 10, 2026

(54) MITOCHONDRIA COMPRISING ANTICANCER DRUG AND USE THEREOF

(71) Applicant: Paean Biotechnology Inc., Yuseong-gu (KR)

(72) Inventors: Chun-Hyung Kim, Sejong (KR); Kyuboem Han, Yuseong-gu (KR); Shin-Hye Yu, Seongdong-gu (KR); Yu Jin Kim, Dongjak-gu (KR); Seo-Eun Lee, Suwon-si (KR); Jong Hyeok Park, Jung-gu (KR); Gayoung Cho, Gangbuk-gu (KR); Young-Cheol Kang, Wonju-si (KR)

(73) Assignee: Paean Biotechnology Inc., Yuseong-gu (KR)

( * ) Notice: Subject to any disclaimer, the term of this patent is extended or adjusted under 35 U.S.C. 154(b) by 591 days.

(21) Appl. No.: 18/247,857

(22) PCT Filed: Oct. 22, 2021

(86) PCT No.: PCT/KR2021/014886
§ 371 (c)(1),
(2) Date: Apr. 4, 2023

(87) PCT Pub. No.: WO2022/086257
PCT Pub. Date: Apr. 28, 2022

(65) Prior Publication Data

US 2023/0372529 A1 Nov. 23, 2023

(30) Foreign Application Priority Data

Oct. 22, 2020 (KR) ........................ 10-2020-0137779

(51) Int. Cl.

| | |
|---|---|
| ***A61K 47/69*** | (2017.01) |
| ***A61K 31/704*** | (2006.01) |
| ***A61K 39/00*** | (2006.01) |
| ***A61K 47/68*** | (2017.01) |
| ***A61P 35/00*** | (2006.01) |

(52) U.S. Cl.
CPC ........ *A61K 47/6901* (2017.08); *A61K 31/704* (2013.01); *A61K 39/00* (2013.01); *A61K 47/6855* (2017.08); *A61P 35/00* (2018.01)

(58) Field of Classification Search
None
See application file for complete search history.

(56) References Cited

U.S. PATENT DOCUMENTS

| | | | |
|---|---|---|---|
| 2011/0105437 A1 | 5/2011 | Ralph et al. | |
| 2021/0238249 A1 | 8/2021 | Han et al. | |

FOREIGN PATENT DOCUMENTS

| | | | | | |
|---|---|---|---|---|---|
| CA | 3097108 | A1 * | 10/2019 | ............. A61P 35/04 |
| JP | 2017516755 | A | 6/2017 | |
| JP | 2019507729 | A | 3/2019 | |
| KR | 20100135803 | A | 12/2010 | |
| KR | 20190124656 | A | 11/2019 | |
| KR | 102111321 | B1 | 5/2020 | |
| WO | 2015157409 | A1 | 10/2015 | |
| WO | 2017124037 | A1 | 7/2017 | |

OTHER PUBLICATIONS

Battogtokh et al., "Mitochondrial-Targeting Anticancer Agent Conjugates and Nanocarrier Systems for Cancer Treatment", *Frontiers in Pharmacology 9:1*-20, Article No. 922, Aug. 17, 2018.
Han et al., "Mitochondrial Delivery of Doxorubicin via Triphenylphosphine Modification for Overcoming Drug Resistance in MDA-MB-435/DOX Cells," *Molecular Pharmaceutics* 11(8):2640-2649, 2014, 10 pages.
Rodríguez-Enríquez et al., "Molecular mechanism for the selective impairment of cancer mitochondrial function by a mitochondrially targeted vitamin E analogue," Biochimica et Biophysica Acta 1817:1597-1607, May 22, 2012. (11 pages).
Cheng et al., "Targeting lonidamine to mitochondria mitigates lung tumorigenesis and brain metastasis," Nature Communications 10:2205, May 17, 2019. (14 pages).

* cited by examiner

*Primary Examiner* — Brian Gangle
(74) *Attorney, Agent, or Firm* — Seed IP Law Group LLP

(57) ABSTRACT

The present invention relates to a mitochondrion containing a compound having the anticancer efficacy and uses thereof. It was confirmed that the mitochondrion efficiently deliver the compound to the tumor, and the anticancer effect of the mitochondrion containing the compound was confirmed. In particular, when an antibody or a fragment thereof that specifically binds to a tumor is bound to the surface of mitochondrion, the compound may be delivered specifically to the tumor. Therefore, the mitochondrion containing the compound according to the present invention may be effectively used for the treatment of cancer because the side effects of the compound are few.

11 Claims, 59 Drawing Sheets

Specification includes a Sequence Listing.

DOX

| | Curve Name | Curve Formula | A | B | R2 |
|---|---|---|---|---|---|
| | StdCurve | Y=A*X+B | 4.91E+03 | 396 | 1 |

| | 1 | 2 | 3 | 4 | 5 | 6 | 7 | 8 | 9 | 10 | |
|---|---|---|---|---|---|---|---|---|---|---|---|
| A | 40228 | 25540 | 12521 | 6452 | 3211 | 1991 | 1128 | 867 | 618 | 13178 | 530/25,590/35 |

| | 1 | 2 | 3 | 4 | 5 | 6 | 7 | 8 | 9 | 10 | |
|---|---|---|---|---|---|---|---|---|---|---|---|
| A | 9.95 | 5.124 | 2.471 | 1.234 | 0.574 | 0.325 | 0.149 | 0.096 | 0.045 | 2.604 | [Concentration] |

FIG. 23

| | DOX | | DOX-MT$^{\alpha\text{-HER2scFv}}$ | |
|---|---|---|---|---|
| Cell line | IC50 | 95% Confidence Intervals | IC50 | 95% Confidence Intervals |
| NCI-N87 | 0.4312 | 0.2733 to 0.5890 | 0.3356 | 0.2605 to 0.4108 |
| BT-474 | 0.8395 | 0.5799 to 1.099 | 0.5293 | 0.3506 to 0.7080 |
| SK-BR-3 | 0.3036 | 0.2078 to 0.3993 | 0.2721 | 0.2315 to 0.3127 |
| MKN74 | 0.5752 | 0.3766 to 0.7738 | 0.4582 | 0.2600 to 0.6563 |
| NCI-H1975 | 0.265 | 0.04274 to 0.4874 | 0.4670 | 0.2091 to 0.7248 |
| MDA-MB-231 | 0.6971 | 0.3363 to 1.058 | 0.5985 | 0.3720 to 0.8249 |
| CCD-8Lu | 1.694 | 1.642 to 2.247 | 2.076 | 1.777 to 2.374 |
| WI-38 | 1.932 | 1.402 to 2.461 | 1.862 | 1.178 to 2.546 |

FIG. 37

| | TPP-DOX | | TPP-DOX_MT$^{\alpha\text{-HER2scFv}}$ | |
|---|---|---|---|---|
| Cell line | IC50 | 95% Confidence Intervals | IC50 | 95% Confidence Intervals |
| NCI-N87 | 1.311 | 0.9506 to 1.809 | 0.4117 | 0.3403 to 0.4980 |
| BT-474 | 0.6344 | 0.5498 to 0.7321 | 0.2895 | 0.2233 to 0.3753 |
| SK-BR-3 | 0.744 | 0.5975 to 0.9263 | 0.5425 | 0.4009 to 0.7342 |
| MKN74 | 1.202 | 0.9828 to 1.470 | 0.6616 | 0.5948 to 0.7359 |
| NCI-H1975 | 2.338 | 1.250 to 4.375 | 0.8892 | 0.7158 to 1.105 |
| MDA-MB-231 | 1.177 | 0.9062 to 1.528 | 0.7773 | 0.5902 to 1.024 |
| CCD-8Lu | N.A. | No Activity | N.A. | No Activity |
| WI-38 | 3.822 | 1.660 to 8.802 | 4.5 | 2.823 to 7.175 |

SEQUENCE LISTING

```
<160> NUMBER OF SEQ ID NOS: 102

<210> SEQ ID NO 1
<211> LENGTH: 39
<212> TYPE: DNA
<213> ORGANISM: Artificial sequence
<220> FEATURE:
<223> OTHER INFORMATION: T2p53 primer

<400> SEQUENCE: 1

aaaaaaccgc ggtggtgagg agccgcagtc agatcctag                              39


<210> SEQ ID NO 2
<211> LENGTH: 35
<212> TYPE: DNA
<213> ORGANISM: Artificial sequence
<220> FEATURE:
<223> OTHER INFORMATION: Xp53 primer

<400> SEQUENCE: 2

aaaaaactcg agtgagtctg agtcaggccc ttctg                                  35


<210> SEQ ID NO 3
<211> LENGTH: 1186
<212> TYPE: DNA
<213> ORGANISM: Artificial seqeuence
<220> FEATURE:
```

<223> OTHER INFORMATION: nucleotides sequence coding p53

<400> SEQUENCE: 3
ccgcggtggt gaggagccgc agtcagatcc tagcgtcgag ccccctctga gtcaggaaac 60
attttcagac ctgtggaaac tacttcctga aaacaacgtt ctgtccccct tgccgtccca 120
agcaatggat gatttgatgc tgtccccgga cgatattgaa caatggttca ctgaagaccc 180
aggtccagat gaagctccca gaatgccaga ggctgctccc cgcgtggccc ctgcaccagc 240
agctcctaca ccggcggccc ctgcaccagc cccctcctgg cccctgtcat cttctgtccc 300
ttcccagaaa acctaccagg gcagctacgg tttccgtctg ggcttcttgc attctgggac 360
agccaagtct gtgacttgca cgtactcccc tgccctcaac aagatgtttt gccaactggc 420
caagacctgc cctgtgcagc tgtgggttga ttccacaccc ccgcccggca cccgcgtccg 480
cgccatggcc atctacaagc agtcacagca catgacggag gttgtgaggc gctgccccca 540
ccatgagcgc tgctcagata gcgatggtct ggcccctcct cagcatctta tccgagtgga 600
aggaaatttg cgtgtggagt atttggatga cagaaacact tttcgacata gtgtggtggt 660
gccctatgag ccgcctgagg ttggctctga ctgtaccacc atccactaca actacatgtg 720
taacagttcc tgcatgggcg gcatgaaccg gaggcccatc ctcaccatca tcacactgga 780
agactccagt ggtaatctac tgggacggaa cagctttgag gtgcgtgttt gtgcctgtcc 840
tgggagagac cggcgcacag aggaagagaa tctccgcaag aaaggggagc ctcaccacga 900
gctgccccca gggagcacta agcgagcact gcccaacaac accagctcct ctccccagcc 960
aaagaagaaa ccactggatg gagaatattt caccettcag atccgtgggc gtgagcgctt 1020
cgagatgttc cgagagctga atgaggcctt ggaactcaag gatgcccagg ctgggaagga 1080
gccagggggg agcagggctc actccagcca cctgaagtcc aaaaagggtc agtctacctc 1140
ccgccataaa aaactcatgt tcaagacaga agggcctgac tcagac 1186

<210> SEQ ID NO 4
<211> LENGTH: 35
<212> TYPE: DNA
<213> ORGANISM: Artificial sequence
<220> FEATURE:
<223> OTHER INFORMATION: NdeUB primer

<400> SEQUENCE: 4
ggattccata tgcaactttt cgtcaaaact ctaac 35

<210> SEQ ID NO 5
<211> LENGTH: 27
<212> TYPE: DNA
<213> ORGANISM: Artificial sequence
<220> FEATURE:
<223> OTHER INFORMATION: T2UB primer

<400> SEQUENCE: 5
atgaccaccg cggagtctca acaccaa 27

<210> SEQ ID NO 6
<211> LENGTH: 1460
<212> TYPE: DNA
<213> ORGANISM: Artificial sequence
<220> FEATURE:
<223> OTHER INFORMATION: nucleotides sequence coding UB-p53

<400> SEQUENCE: 6
atgggcagca gccatcatca tcatcatcac agcagcggcc tggtgccgcg cggcagccat 60

```
atgcaaatct tcgtcaaaac tctaacaggg aagactataa ccctagaggt tgaaccatcc    120

gacactattg aaaacgtcaa agctaaaatt caagataaag aaggtatccc tccggatcag    180

cagagattga tttttgctgg taagcaacta gaagatggta gaaccttgtc tgactacaac    240

atccaaaagg aatctactct tcacttggtg ttgagactcc gcggtggtga ggagccgcag    300

tcagatccta gcgtcgagcc ccctctgagt caggaaacat tttcagacct gtggaaacta    360

cttcctgaaa acaacgttct gtcccccttg ccgtcccaag caatggatga tttgatgctg    420

tccccggacg atattgaaca atggttcact gaagacccag gtccagatga agctcccaga    480

atgccagagg ctgctccccg cgtggcccct gcaccagcag ctcctacacc ggcggcccct    540

gcaccagccc cctcctggcc cctgtcatct tctgtccctt cccagaaaac ctaccagggc    600

agctacggtt tccgtctggg cttcttgcat tctgggacag ccaagtctgt gacttgcacg    660

tactcccctg ccctcaacaa gatgttttgc caactggcca agacctgccc tgtgcagctg    720

tgggttgatt ccacaccccc gcccggcacc cgcgtccgcg ccatggccat ctacaagcag    780

tcacagcaca tgacggaggt tgtgaggcgc tgcccccacc atgagcgctg ctcagatagc    840

gatggtctgg cccctcctca gcatcttatc cgagtggaag gaaatttgcg tgtggagtat    900

ttggatgaca gaaacacttt tcgacatagt gtggtggtgc cctatgagcc gcctgaggtt    960

ggctctgact gtaccaccat ccactacaac tacatgtgta acagttcctg catgggcggc   1020

atgaaccgga ggcccatcct caccatcatc acactggaag actccagtgg taatctactg   1080

ggacggaaca gctttgaggt gcgtgtttgt gcctgtcctg ggagagaccg gcgcacagag   1140

gaagagaatc tccgcaagaa aggggagcct caccacgagc tgcccccagg gagcactaag   1200

cgagcactgc ccaacaacac cagctcctct ccccagccaa agaagaaacc actggatgga   1260

gaatatttca cccttcagat ccgtgggcgt gagcgcttcg agatgttccg agagctgaat   1320

gaggccttgg aactcaagga tgcccaggct gggaaggagc caggggggag cagggctcac   1380

tccagccacc tgaagtccaa aaagggtcag tctacctccc gccataaaaa actcatgttc   1440

aagacagaag ggcctgatag                                                1460
```

<210> SEQ ID NO 7
<211> LENGTH: 59
<212> TYPE: DNA
<213> ORGANISM: Artificial sequence
<220> FEATURE:
<223> OTHER INFORMATION: NdeTOM70 primer

<400> SEQUENCE: 7

```
gaattccata tgaaaagttt tataactcgg aataaaactg caattttcgc aactgttgc      59
```

<210> SEQ ID NO 8
<211> LENGTH: 38
<212> TYPE: DNA
<213> ORGANISM: Artificial sequence
<220> FEATURE:
<223> OTHER INFORMATION: TOM70-AS primer

<400> SEQUENCE: 8

```
ggtgcatact actattatca aacttttcgt caaaactc                             38
```

<210> SEQ ID NO 9
<211> LENGTH: 36
<212> TYPE: DNA
<213> ORGANISM: Artificial sequence
<220> FEATURE:

<223> OTHER INFORMATION: TOM70UB-S primer

<400> SEQUENCE: 9
ggctacgtat ttatttccaa cttttcgtca aaactc 36

<210> SEQ ID NO 10
<211> LENGTH: 24
<212> TYPE: DNA
<213> ORGANISM: Artificial sequence
<220> FEATURE:
<223> OTHER INFORMATION: T2UB-AS primer

<400> SEQUENCE: 10
ggcaccaccg cggagtctca acac 24

<210> SEQ ID NO 11
<211> LENGTH: 1515
<212> TYPE: DNA
<213> ORGANISM: Artificial sequence
<220> FEATURE:
<223> OTHER INFORMATION: nucleotides sequence coding TOM70-UB-p53

<400> SEQUENCE: 11
atgaaaagtt ttataactcg gaataaaact gcaattttcg caactgttgc tgctacggga 60
accgctattg gtgcatacta ctattatcaa atcttcgtca aaactctaac agggaagact 120
ataaccctag aggttgaacc atccgacact attgaaaacg tcaaagctaa aattcaagat 180
aaagaaggta tccctccgga tcagcagaga ttgatttttg ctggtaagca actagaagat 240
ggtagaacct tgtctgacta caacatccaa aaggaatcta ctcttcactt ggtgttgaga 300
ctccgcggtg gtgaggagcc gcagtcagat cctagcgtcg agccccctct gagtcaggaa 360
acattttcag acctgtggaa actacttcct gaaaacaacg ttctgtcccc cttgccgtcc 420
caagcaatgg atgatttgat gctgtccccg gacgatattg aacaatggtt cactgaagac 480
ccaggtccag atgaagctcc cagaatgcca gaggctgctc cccgcgtggc ccctgcacca 540
gcagctccta caccggcggc ccctgcacca gccccctcct ggcccctgtc atcttctgtc 600
ccttcccaga aaacctacca gggcagctac ggtttccgtc tgggcttctt gcattctggg 660
acagccaagt ctgtgacttg cacgtactcc cctgccctca acaagatgtt ttgccaactg 720
gccaagacct gccctgtgca gctgtgggtt gattccacac ccccgcccgg cacccgcgtc 780
cgcgccatgg ccatctacaa gcagtcacag cacatgacgg aggttgtgag gcgctgcccc 840
caccatgagc gctgctcaga tagcgatggt ctggcccctc ctcagcatct tatccgagtg 900
gaaggaaatt tgcgtgtgga gtatttggat gacagaaaca cttttcgaca tagtgtggtg 960
gtgccctatg agccgcctga ggttggctct gactgtacca ccatccacta caactacatg 1020
tgtaacagtt cctgcatggg cggcatgaac cggaggccca tcctcaccat catcacactg 1080
gaagactcca gtggtaatct actgggacgg aacagctttg aggtgcgtgt ttgtgcctgt 1140
cctgggagag accggcgcac agaggaagag aatctccgca agaaagggga gcctcaccac 1200
gagctgcccc cagggagcac taagcgagca ctgcccaaca acaccagctc ctctccccag 1260
ccaaagaaga aaccactgga tggagaatat ttcacccttc agatccgtgg gcgtgagcgc 1320
ttcgagatgt tccgagagct gaatgaggcc ttggaactca aggatgccca ggctgggaag 1380
gagccagggg ggagcagggc tcactccagc cacctgaagt ccaaaaaggg tcagtctacc 1440
tcccgccata aaaaactcat gttcaagaca gaagggcctg actcagacct cgagcaccac 1500
caccaccacc actag 1515

<210> SEQ ID NO 12
<211> LENGTH: 59
<212> TYPE: DNA
<213> ORGANISM: Artificial sequence
<220> FEATURE:
<223> OTHER INFORMATION: TOM70(G)3-AS primer

<400> SEQUENCE: 12
gcccccggat cctccacccc cgcttccgcc acctccataa tagtagtatg caccaatag 59

<210> SEQ ID NO 13
<211> LENGTH: 32
<212> TYPE: DNA
<213> ORGANISM: Artificial sequence
<220> FEATURE:
<223> OTHER INFORMATION: (G)3UB-S primer

<400> SEQUENCE: 13
ggtggaggat ccgggggcgc ggaagccaaa tc 32

<210> SEQ ID NO 14
<211> LENGTH: 32
<212> TYPE: DNA
<213> ORGANISM: Artificial sequence
<220> FEATURE:
<223> OTHER INFORMATION: Xp53(noT) primer

<400> SEQUENCE: 14
aaaaaactcg aggtctgagt caggcccttc tg 32

<210> SEQ ID NO 15
<211> LENGTH: 1560
<212> TYPE: DNA
<213> ORGANISM: Artificial sequence
<220> FEATURE:
<223> OTHER INFORMATION: nucleotides sequence coding TOM70-(GGGGS)3-UB-p53

<400> SEQUENCE: 15
atgaaaagtt ttataactcg gaataaaact gcaattttcg caactgttgc tgctacggga 60
accgctattg gtgcatacta ctattatgga ggtggcggaa gcgggggtgg aggatccggg 120
ggcggcggaa gccaaatctt cgtcaaaact ctaacaggga agactataac cctagaggtt 180
gaaccatccg acactattga aaacgtcaaa gctaaaattc aagataaaga aggtatccct 240
ccggatcagc agagattgat ttttgctggt aagcaactag aagatggtag aaccttgtct 300
gactacaaca tccaaaagga atctactctt cacttggtgt tgagactccg cggtggtgag 360
gagccgcagt cagatcctag cgtcgagccc cctctgagtc aggaaacatt ttcagacctg 420
tggaaactac ttcctgaaaa caacgttctg tcccccttgc cgtcccaagc aatggatgat 480
ttgatgctgt ccccggacga tattgaacaa tggttcactg aagacccagg tccagatgaa 540
gctcccagaa tgccagaggc tgctccccgc gtggcccctg caccagcagc tcctacaccg 600
gcggcccctg caccagcccc ctcctggccc ctgtcatctt ctgtcccttc ccagaaaacc 660
taccagggca gctacggttt ccgtctgggc ttcttgcatt ctgggacagc caagtctgtg 720
acttgcacgt actcccctgc cctcaacaag atgttttgcc aactggccaa gacctgccct 780
gtgcagctgt gggttgattc cacacccccg cccggcaccc gcgtccgcgc catggccatc 840
tacaagcagt cacagcacat gacggaggtt gtgaggcgct gcccccacca tgagcgctgc 900
tcagatagcg atggtctggc ccctcctcag catcttatcc gagtggaagg aaatttgcgt 960
gtggagtatt tggatgacag aaacactttt cgacatagtg tggtggtgcc ctatgagccg 1020
cctgaggttg gctctgactg taccaccatc cactacaact acatgtgtaa cagttcctgc 1080
atgggcggca tgaaccggag gcccatcctc accatcatca cactggaaga ctccagtggt 1140
aatctactgg gacggaacag ctttgaggtg cgtgtttgtg cctgtcctgg gagagaccgg 1200
cgcacagagg aagagaatct ccgcaagaaa ggggagcctc accacgagct gcccccaggg 1260
agcactaagc gagcactgcc caacaacacc agctcctctc cccagccaaa gaagaaacca 1320
ctggatggag aatatttcac ccttcagatc cgtgggcgtg agcgcttcga gatgttccga 1380
gagctgaatg aggccttgga actcaaggat gcccaggctg ggaaggagcc aggggggagc 1440
agggctcact ccagccacct gaagtccaaa aagggtcagt ctacctcccg ccataaaaaa 1500
ctcatgttca agacagaagg gcctgactca gacctcgagc accaccacca ccaccactag 1560

<210> SEQ ID NO 16
<211> LENGTH: 51
<212> TYPE: DNA
<213> ORGANISM: Artificial sequence
<220> FEATURE:
<223> OTHER INFORMATION: Synthetic sequence B(G)3p53

<400> SEQUENCE: 16
ggtggaggat ccgggggcgg cggaagcgag gagccgcagt cagatcctag c 51

<210> SEQ ID NO 17
<211> LENGTH: 1335
<212> TYPE: DNA
<213> ORGANISM: Artificial sequence
<220> FEATURE:
<223> OTHER INFORMATION: nucleotides sequence coding TOM70-(GGGGS)3-p53

<400> SEQUENCE: 17
atgaaaagtt ttataactcg gaataaaact gcaattttcg caactgttgc tgctacggga 60
accgctattg gtgcatacta ctattatgga ggtggcggaa gcgggggtgg aggatccggg 120
ggcggcggaa gcgaggagcc gcagtcagat cctagcgtcg agccccctct gagtcaggaa 180
acattttcag acctgtggaa actacttcct gaaaacaacg ttctgtcccc cttgccgtcc 240
caagcaatgg atgatttgat gctgtccccg gacgatattg aacaatggtt cactgaagac 300
ccaggtccag atgaagctcc cagaatgcca gaggctgctc cccgcgtggc ccctgcacca 360
gcagctccta caccggcggc ccctgcacca gcccccctcct ggcccctgtc atcttctgtc 420
ccttcccaga aaacctacca gggcagctac ggtttccgtc tgggcttctt gcattctggg 480
acagccaagt ctgtgacttg cacgtactcc cctgccctca acaagatgtt ttgccaactg 540
gccaagacct gccctgtgca gctgtgggtt gattccacac ccccgcccgg cacccgcgtc 600
cgcgccatgg ccatctacaa gcagtcacag cacatgacgg aggttgtgag gcgctgcccc 660
caccatgagc gctgctcaga tagcgatggt ctggcccctc ctcagcatct tatccgagtg 720
gaaggaaatt tgcgtgtgga gtatttggat gacagaaaca cttttcgaca tagtgtggtg 780
gtgccctatg agccgcctga ggttggctct gactgtacca ccatccacta caactacatg 840
tgtaacagtt cctgcatggg cggcatgaac cggaggccca tcctcaccat catcacactg 900
gaagactcca gtggtaatct actgggacgg aacagctttg aggtgcgtgt ttgtgcctgt 960
cctgggagag accggcgcac agaggaagag aatctccgca agaaagggga gcctcaccac 1020
gagctgcccc cagggagcac taagcgagca ctgcccaaca acaccagctc ctctccccag 1080
ccaaagaaga aaccactgga tggagaatat ttcacccttc agatccgtgg gcgtgagcgc 1140
ttcgagatgt tccgagagct gaatgaggcc ttggaactca aggatgccca ggctgggaag 1200
gagccagggg ggagcagggc tcactccagc cacctgaagt ccaaaaaggg tcagtctacc 1260
tcccgccata aaaaactcat gttcaagaca gaagggcctg actcagacct cgagcaccac 1320
caccaccacc actag 1335

<210> SEQ ID NO 18
<211> LENGTH: 32
<212> TYPE: DNA
<213> ORGANISM: Artificial sequence
<220> FEATURE:
<223> OTHER INFORMATION: Xp53(noT) primer

<400> SEQUENCE: 18
aaaaaactcg aggtctgagt caggcccttc tg 32

<210> SEQ ID NO 19
<211> LENGTH: 36
<212> TYPE: DNA
<213> ORGANISM: Artificial sequence
<220> FEATURE:
<223> OTHER INFORMATION: XTOM7 primer

<400> SEQUENCE: 19
aaaaaactcg agtttgccat tcgctggggc tttatc 36

<210> SEQ ID NO 20
<211> LENGTH: 38
<212> TYPE: DNA
<213> ORGANISM: Artificial sequence
<220> FEATURE:
<223> OTHER INFORMATION: LTOM7 primer

<400> SEQUENCE: 20
aaaaaagtcg acttatcccc aaagtaggct caaaacag 38

<210> SEQ ID NO 21
<211> LENGTH: 1578
<212> TYPE: DNA
<213> ORGANISM: Artificial sequence
<220> FEATURE:
<223> OTHER INFORMATION: nucleotides sequence coding UB-p53-TOM7

<400> SEQUENCE: 21
atgggcagca gccatcatca tcatcatcac agcagcggcc tggtgccgcg cggcagccat 60
atgcaaatct tcgtcaaaac tctaacaggg aagactataa ccctagaggt tgaaccatcc 120
gacactattg aaaacgtcaa agctaaaatt caagataaag aaggtatccc tccggatcag 180
cagagattga tttttgctgg taagcaacta gaagatggta gaaccttgtc tgactacaac 240
atccaaaagg aatctactct tcacttggtg ttgagactcc gcggtggtga ggagccgcag 300
tcagatccta gcgtcgagcc ccctctgagt caggaaacat tttcagacct atggaaacta 360
cttcctgaaa acaacgttct gtcccccttg ccgtcccaag caatggatga tttgatgctg 420
tccccggacg atattgaaca atggttcact gaagacccag gtccagatga agctcccaga 480
atgccagagg ctgctccccg cgtggcccct gcaccagcag ctcctacacc ggcggcccct 540
gcaccagccc cctcctggcc cctgtcatct tctgtccctt cccagaaaac ctaccagggc 600
agctacggtt tccgtctggg cttcttgcat tctgggacag ccaagtctgt gacttgcacg 660
tactcccctg ccctcaacaa gatgttttgc caactggcca agacctgccc tgtgcagctg 720

```
tgggttgatt ccacaccccc gcccggcacc cgcgtccgcg ccatggccat ctacaagcag    780

tcacagcaca tgacggaggt tgtgaggcgc tgccccccacc atgagcgctg ctcagatagc    840

gatggtctgg cccctcctca gcatcttatc cgagtggaag gaaatttgcg tgtggagtat    900

ttggatgaca gaaacacttt tcgacatagt gtggtggtgc cctatgagcc gcctgaggtt    960

ggctctgact gtaccaccat ccactacaac tacatgtgta acagttcctg catgggcggc   1020

atgaaccgga ggcccatcct caccatcatc acactggaag actccagtgg taatctactg   1080

ggacggaaca gctttgaggt gcatgtttgt gcctgtcctg ggagagaccg gcgcacagag   1140

gaagagaatc tccgcaagaa aggggagcct caccacgagc tgcccccagg gagcactaag   1200

cgagcactgt ccaacaacac cagctcctct ccccagccaa agaagaaacc actggatgga   1260

gaatatttca cccttcagat ccgtgggcgt gagcgcttcg agatgttccg agagctgaat   1320

gaggccttgg aactcaagga tgcccaggct gggaaggagc caggggggag cagggctcac   1380

tccagccacc tgaagtccaa aaagggtcag tctacctccc gccataaaaa actcatgttc   1440

aagacagaag ggcctgactc agacctcgag tttgccattc gctggggctt tatccctctt   1500

gtgatttacc tgggatttaa gaggggtgca gatcccggaa tgcctgaacc aactgttttg   1560

agcctacttt ggggatag                                                 1578
```

```
<210> SEQ ID NO 22
<211> LENGTH: 35
<212> TYPE: DNA
<213> ORGANISM: Artificial sequence
<220> FEATURE:
<223> OTHER INFORMATION: Rp53 primer

<400> SEQUENCE: 22

aaaaaagaat tcatggtctg agtcaggccc ttctg                                35
```

```
<210> SEQ ID NO 23
<211> LENGTH: 1266
<212> TYPE: DNA
<213> ORGANISM: Artificial sequence
<220> FEATURE:
<223> OTHER INFORMATION: nucleotides sequence coding p53-myc/His

<400> SEQUENCE: 23

atggaggagc cgcagtcaga tcctagcgtc gagccccctc tgagtcagga aacattttca      60

gacctgtgga aactacttcc tgaaaacaac gttctgtccc ccttgccgtc ccaagcaatg     120

gatgatttga tgctgtcccc ggacgatatt gaacaatggt tcactgaaga cccaggtcca     180

gatgaagctc ccagaatgcc agaggctgct ccccgcgtgg cccctgcacc agcagctcct     240

acaccggcgg cccctgcacc agccccctcc tggcccctgt catcttctgt cccttcccag     300

aaaacctacc agggcagcta cggtttccgt ctgggcttct tgcattctgg gacagccaag     360

tctgtgactt gcacgtactc ccctgccctc aacaagatgt tttgccaact ggccaagacc     420

tgccctgtgc agctgtgggt tgattccaca cccccgcccg gcacccgcgt ccgcgccatg     480

gccatctaca agcagtcaca gcacatgacg gaggttgtga ggcgctgccc ccaccatgag     540

cgctgctcag atagcgatgg tctggcccct cctcagcatc ttatccgagt ggaaggaaat     600

ttgcgtgtgg agtatttgga tgacagaaac acttttcgac atagtgtggt ggtgccctat     660

gagccgcctg aggttggctc tgactgtacc accatccact acaactacat gtgtaacagt     720

tcctgcatgg gcggcatgaa ccggaggccc atcctcacca tcatcacact ggaagactcc     780
```

agtggtaatc tactgggacg gaacagcttt gaggtgcgtg tttgtgcctg tcctgggaga 840
gaccggcgca cagaggaaga gaatctccgc aagaaagggg agcctcacca cgagctgccc 900
ccagggagca ctaagcgagc actgcccaac aacaccagct cctctcccca gccaaagaag 960
aaaccactgg atggagaata tttcaccctt cagatccgtg ggcgtgagcg cttcgagatg 1020
ttccgagagc tgaatgaggc cttggaactc aaggatgccc aggctgggaa ggagccaggg 1080
gggagcaggg ctcactccag ccacctgaag tccaaaaagg gtcagtctac ctcccgccat 1140
aaaaaactca tgttcaagac agaagggcct gactcagacc tcgagtctag agggcccttc 1200
gaacaaaaac tcatctcaga agaggatctg aatatgcata ccggtcatca tcaccatcac 1260
cattga 1266

<210> SEQ ID NO 24
<211> LENGTH: 51
<212> TYPE: DNA
<213> ORGANISM: Artificial sequence
<220> FEATURE:
<223> OTHER INFORMATION: T2GZMB primer

<400> SEQUENCE: 24
aaaaaaccgc ggtggtatca tcgggggaca tgaggcacat gaggccaagc c 51

<210> SEQ ID NO 25
<211> LENGTH: 38
<212> TYPE: DNA
<213> ORGANISM: Artificial sequence
<220> FEATURE:
<223> OTHER INFORMATION: XGZMB(noT) primer

<400> SEQUENCE: 25
aaaaaactcg aggtagcgtt tcatggtttt ctttatcc 38

<210> SEQ ID NO 26
<211> LENGTH: 691
<212> TYPE: DNA
<213> ORGANISM: Artificial sequence
<220> FEATURE:
<223> OTHER INFORMATION: nucleotides sequence coding GranzymeB

<400> SEQUENCE: 26
ccgcggtggt atcatcgggg gacatgaggc caagccccac tcccgcccct acatggctta 60
tcttatgatc tgggatcaga agtctctgaa gaggtgcggt ggcttcctga tacaagacga 120
cttcgtgctg acagctgctc actgttgggg aagctccata aatgtcacct tgggggccca 180
caatatcaaa gaacaggagc cgacccagca gtttatccct gtgaaaagac ccatccccca 240
tccagcctat aatcctaaga acttctccaa cgacatcatg ctactgcagc tggagagaaa 300
ggccaagcgg accagagctg tgcagcccct caggctacct agcaacaagg cccaggtgaa 360
gccagggcag acatgcagtg tggccggctg gggcagacg gcccccctgg gaaaacactc 420
acacacacta caagaggtga agatgacagt gcaggaagat cgaaagtgcg aatctgactt 480
acgccattat tacgacagta ccattgagtt gtgcgtgggg gacccagaga ttaaaaagac 540
ttcctttaag ggggactctg gaggccctct tgtgtgtaac aaggtggccc agggcattgt 600
ctcctatgga cgaaacaatg gcatgcctcc acgagcctgc accaaagtct caagctttgt 660
acactggata aagaaaacca tgaaacgcta c 691

<210> SEQ ID NO 27
<211> LENGTH: 1065

<212> TYPE: DNA
<213> ORGANISM: Artificial sequence
<220> FEATURE:
<223> OTHER INFORMATION: nucleotides sequence coding TOM70-(GGGGS)3-UB-Granzyme B

<400> SEQUENCE: 27

```
atgaaaagtt ttataactcg gaataaaact gcaattttcg caactgttgc tgctacggga      60
accgctattg gtgcatacta ctattatgga ggtggcggaa gcgggggtgg aggatccggg     120
ggcggcggaa gccaaatctt cgtcaaaact ctaacaggga agactataac cctagaggtt     180
gaaccatccg acactattga aaacgtcaaa gctaaaattc aagataaaga aggtatccct     240
ccggatcagc agagattgat ttttgctggt aagcaactag aagatggtag aaccttgtct     300
gactacaaca tccaaaagga atctactctt cacttggtgt tgagactccg cggtggtatc     360
atcgggggac atgaggccaa gccccactcc cgcccctaca tggcttatct tatgatctgg     420
gatcagaagt ctctgaagag gtgcggtggc ttcctgatac gagacgactt cgtgctgaca     480
gctgctcact gttggggaag ctccataaat gtcaccttgg gggcccacaa tatcaaagaa     540
caggagccga cccagcagtt tatccctgtg aaaagaccca tcccccatcc agcctataat     600
cctaagaact tctccaacga catcatgcta ctgcagctgg agagaaaggc caagcggacc     660
agagctgtgc agcccctcag gctacctagc aacaaggccc aggtgaagcc agggcagaca     720
tgcagtgtgg ccggctgggg gcagacggcc cccctgggaa aacactcaca cacactacaa     780
gaggtgaaga tgacagtgca ggaagatcga aagtgcgaat ctgacttacg ccattattac     840
gacagtacca ttgagttgtg cgtgggggac ccagagatta aaaagacttc ctttaagggg     900
gactctggag gccctcttgt gtgtaacaag gtggcccagg gcattgtctc ctatggacga     960
aacaatggca tgcctccacg agcctgcacc aaagtctcaa gctttgtaca ctggataaag    1020
aaaaccatga aacgctacct cgagcaccac caccaccacc actag                   1065
```

<210> SEQ ID NO 28
<211> LENGTH: 1083
<212> TYPE: DNA
<213> ORGANISM: Artificial sequence
<220> FEATURE:
<223> OTHER INFORMATION: nucleotides sequence coding UB-Granzyme B-TOM7

<400> SEQUENCE: 28

```
atgggcagca gccatcatca tcatcatcac agcagcggcc tggtgccgcg cggcagccat      60
atgcaaatct tcgtcaaaac tctaacaggg aagactataa ccctagaggt tgaaccatcc     120
gacactattg aaaacgtcaa agctaaaatt caagataaag aaggtatccc tccggatcag     180
cagagattga tttttgctgg taagcaacta gaagatggta gaaccttgtc tgactacaac     240
atccaaaagg aatctactct tcacttggtg ttgagactcc gcggtggtat catcggggga     300
catgaggcca agccccactc ccgcccctac atggcttatc ttatgatctg ggatcagaag     360
tctctgaaga ggtgcggtgg cttcctgata cgagacgact tcgtgctgac agctgctcac     420
tgttggggaa gctccataaa tgtcaccttg ggggcccaca atatcaaaga acaggagccg     480
acccagcagt ttatccctgt gaaaagaccc atcccccatc cagcctataa tcctaagaac     540
ttctccaacg acatcatgct actgcagctg gagagaaagg ccaagcggac cagagctgtg     600
cagcccctca ggctacctag caacaaggcc caggtgaagc cagggcagac atgcagtgtg     660
gccggctggg ggcagacggc ccccctggga aaacactcac acacactaca agaggtgaag     720
atgacagtgc aggaagatcg aaagtgcgaa tctgacttac gccattatta cgacagtacc     780
```

attgagttgt gcgtggggga cccagagatt aaaaagactt cctttaaggg ggactctgga 840
ggccctcttg tgtgtaacaa ggtggcccag ggcattgtct cctatggacg aaacaatggc 900
atgcctccac gagcctgcac caaagtctca agctttgtac actggataaa gaaaaccatg 960
aaacgctacc tcgagtttgc cattcgctgg ggctttatcc ctcttgtgat ttacctggga 1020
tttaagaggg gtgcagatcc cggaatgcct gaaccaactg ttttgagcct actttgggga 1080
tag 1083

<210> SEQ ID NO 29
<211> LENGTH: 39
<212> TYPE: DNA
<213> ORGANISM: Artificial sequence
<220> FEATURE:
<223> OTHER INFORMATION: T2RKIP primer

<400> SEQUENCE: 29
aaaaaaccgc ggtggtccgg tggacctcag caagtggtc 39

<210> SEQ ID NO 30
<211> LENGTH: 41
<212> TYPE: DNA
<213> ORGANISM: Artificial sequence
<220> FEATURE:
<223> OTHER INFORMATION: XRKIP(noT) primer

<400> SEQUENCE: 30
aaaaaactcg agcttcccag acagctgctc gtacagtttg g 41

<210> SEQ ID NO 31
<211> LENGTH: 568
<212> TYPE: DNA
<213> ORGANISM: Artificial sequence
<220> FEATURE:
<223> OTHER INFORMATION: nucleotides sequence coding RKIP

<400> SEQUENCE: 31
ccgcggtggt ccggtggacc tcagcaagtg gtccgggccc ttgagcctgc aagaagtgga 60
cgagcagccg cagcacccac tgcatgtcac ctacgccggg gcggcggtgg acgagctggg 120
caaagtgctg acgcccaccc aggttaagaa tagacccacc agcatttcgt gggatggtct 180
tgattcaggg aagctctaca ccttggtcct gacagacccg gatgctccca gcaggaagga 240
tcccaaatac agagaatggc atcatttcct ggtggtcaac atgaagggca atgacatcag 300
cagtggcaca gtcctctccg attatgtggg ctcggggcct cccaagggca caggcctcca 360
ccgctatgtc tggctggttt acgagcagga caggccgcta aagtgtgacg agcccatcct 420
cagcaaccga tctggagacc accgtggcaa attcaaggtg gcgtccttcc gtaaaaagta 480
tgagctcagg gccccggtgg ctggcacgtg ttaccaggcc gagtgggatg actatgtgcc 540
caaactgtac gagcagctgt ctgggaag 568

<210> SEQ ID NO 32
<211> LENGTH: 942
<212> TYPE: DNA
<213> ORGANISM: Artificial sequence
<220> FEATURE:
<223> OTHER INFORMATION: nucleotides sequence coding TOM70-(GGGGS)3-UB-
RKIP

<400> SEQUENCE: 32
atgaaaagtt ttataactcg gaataaaact gcaattttcg caactgttgc tgctacggga 60

```
accgctattg gtgcatacta ctattatgga ggtggcggaa gcgggggtgg aggatccggg    120

ggcggcggaa gccaaatctt cgtcaaaact ctaacaggga agactataac cctagaggtt    180

gaaccatccg acactattga aaacgtcaaa gctaaaattc aagataaaga aggtatccct    240

ccggatcagc agagattgat ttttgctggt aagcaactag aagatggtag aaccttgtct    300

gactacaaca tccaaaagga atctactctt cacttggtgt tgagactccg cggtggtccg    360

gtggacctca gcaagtggtc cgggcccttg agcctgcaag aagtggacga gcagccgcag    420

cacccactgc atgtcaccta cgccggggcg gcggtggacg agctgggcaa agtgctgacg    480

cccacccagg ttaagaatag acccaccagc atttcgtggg atggtcttga ttcagggaag    540

ctctacacct tggtcctgac agacccggat gctcccagca ggaaggatcc caaatacaga    600

gaatggcatc atttcctggt ggtcaacatg aagggcaatg acatcagcag tggcacagtc    660

ctctccgatt atgtgggctc ggggcctccc aagggcacag gcctccaccg ctatgtctgg    720

ctggtttacg agcaggacag gccgctaaag tgtgacgagc ccatcctcag caaccgatct    780

ggagaccacc gtggcaaatt caaggtggcg tccttccgta aaaagtatga gctcagggcc    840

ccggtggctg gcacgtgtta ccaggccgag tgggatgact atgtgcccaa actgtacgag    900

cagctgtctg ggaagctcga gcaccaccac caccaccact ag                       942
```

```
<210> SEQ ID NO 33
<211> LENGTH: 42
<212> TYPE: DNA
<213> ORGANISM: Artificial sequence
<220> FEATURE:
<223> OTHER INFORMATION: T2PTEN primer

<400> SEQUENCE: 33

aaaaaaccgc ggtggtacag ccatcatcaa agagatcgtt ag                        42
```

```
<210> SEQ ID NO 34
<211> LENGTH: 36
<212> TYPE: DNA
<213> ORGANISM: Artificial sequence
<220> FEATURE:
<223> OTHER INFORMATION: XPTEN(noT) primer

<400> SEQUENCE: 34

aaaaaactcg aggacttttg taatttgtgt atgctg                               36
```

```
<210> SEQ ID NO 35
<211> LENGTH: 1216
<212> TYPE: DNA
<213> ORGANISM: Artificial sequence
<220> FEATURE:
<223> OTHER INFORMATION: nucleotides sequence coding PTEN

<400> SEQUENCE: 35

ccgcggtggt acagccatca tcaaagagat cgttagcaga aacaaaagga gatatcaaga     60

ggatggattc gacttagact tgacctatat ttatccaaac attattgcta tgggatttcc    120

tgcagaaaga cttgaaggcg tatacaggaa caatattgat gatgtagtaa ggtttttgga    180

ttcaaagcat aaaaaccatt acaagatata caatctttgt gctgaaagac attatgacac    240

cgccaaattt aattgcagag ttgcacaata tccttttgaa gaccataacc caccacagct    300

agaacttatc aaacccttttt gtgaagatct tgaccaatgg ctaagtgaag atgacaatca    360

tgttgcagca attcactgta aagctggaaa gggacgaact ggtgtaatga tatgtgcata    420
```

```
tttattacat cggggcaaat ttttaaaggc acaagaggcc ctagatttct atggggaagt    480

aaggaccaga gacaaaaagg gagtaactat tcccagtcag aggcgctatg tgtattatta    540

tagctacctg ttaaagaatc atctggatta tagaccagtg gcactgttgt ttcacaagat    600

gatgtttgaa actattccaa tgttcagtgg cggaacttgc aatcctcagt ttgtggtctg    660

ccagctaaag gtgaagatat attcctccaa ttcaggaccc acacgacggg aagacaagtt    720

catgtacttt gagttccctc agccgttacc tgtgtgtggt gatatcaaag tagagttctt    780

ccacaaacag aacaagatgc taaaaaagga caaaatgttt cacttttggg taaatacatt    840

cttcatacca ggaccagagg aaacctcaga aaaagtagaa aatggaagtc tatgtgatca    900

agaaatcgat agcatttgca gtatagagcg tgcagataat gacaaggaat atctagtact    960

tactttaaca aaaaatgatc ttgacaaagc aaataaagac aaagccaacc gatacttttc   1020

tccaaatttt aaggtgaagc tgtacttcac aaaaacagta gaggagccgt caaatccaga   1080

ggctagcagt tcaacttctg taacaccaga tgttagtgac aatgaacctg atcattatag   1140

atattctgac accactgact ctgatccaga gaatgaacct tttgatgaag atcagcatac   1200

acaaattaca aaagtc                                                   1216
```

```
<210> SEQ ID NO 36
<211> LENGTH: 1590
<212> TYPE: DNA
<213> ORGANISM: Artificial sequence
<220> FEATURE:
<223> OTHER INFORMATION: nucleotides sequence coding TOM70-(GGGGS)3-UB-
      PTEN

<400> SEQUENCE: 36

atgaaaagtt ttataactcg gaataaaact gcaattttcg caactgttgc tgctacggga     60

accgctattg gtgcatacta ctattatgga ggtggcggaa gcgggggtgg aggatccggg    120

ggcggcggaa gccaaatctt cgtcaaaact ctaacaggga agactataac cctagaggtt    180

gaaccatccg acactattga aaacgtcaaa gctaaaattc aagataaaga aggtatccct    240

ccggatcagc agagattgat ttttgctggt aagcaactag aagatggtag aaccttgtct    300

gactacaaca tccaaaagga atctactctt cacttggtgt tgagactccg cggtggtaca    360

gccatcatca aagagatcgt tagcagaaac aaaaggagat atcaagagga tggattcgac    420

ttagacttga cctatattta tccaaacatt attgctatgg gatttcctgc agaaagactt    480

gaaggcgtat acaggaacaa tattgatgat gtagtaaggt ttttggattc aaagcataaa    540

aaccattaca agatatacaa tctttgtgct gaaagacatt atgacaccgc caaatttaat    600

tgcagagttg cacaatatcc ttttgaagac cataacccac cacagctaga acttatcaaa    660

cccttttgtg aagatcttga ccaatggcta agtgaagatg acaatcatgt tgcagcaatt    720

cactgtaaag ctggaaaggg acgaactggt gtaatgatat gtgcatattt attacatcgg    780

ggcaaatttt taaaggcaca agaggcccta gatttctatg gggaagtaag gaccagagac    840

aaaaagggag taactattcc cagtcagagg cgctatgtgt attattatag ctacctgtta    900

aagaatcatc tggattatag accagtggca ctgttgtttc acaagatgat gtttgaaact    960

attccaatgt tcagtggcgg aacttgcaat cctcagtttg tggtctgcca gctaaaggtg   1020

aagatatatt cctccaattc aggacccaca cgacgggaag acaagttcat gtactttgag   1080

ttccctcagc cgttacctgt gtgtggtgat atcaaagtag agttcttcca caaacagaac   1140

aagatgctaa aaaaggacaa aatgtttcac ttttgggtaa atacattctt cataccagga   1200
```

```
ccagaggaaa cctcagaaaa agtagaaaat ggaagtctat gtgatcaaga aatcgatagc   1260

atttgcagta tagagcgtgc agataatgac aaggaatatc tagtacttac tttaacaaaa   1320

aatgatcttg acaaagcaaa taaagacaaa gccaaccgat acttttctcc aaattttaag   1380

gtgaagctgt acttcacaaa aacagtagag gagccgtcaa atccagaggc tagcagttca   1440

acttctgtaa caccagatgt tagtgacaat gaacctgatc attatagata ttctgacacc   1500

actgactctg atccagagaa tgaacctttt gatgaagatc agcatacaca aattacaaaa   1560

gtcctcgagc accaccacca ccaccactag                                    1590


<210> SEQ ID NO 37
<211> LENGTH: 739
<212> TYPE: DNA
<213> ORGANISM: Artificial sequence
<220> FEATURE:
<223> OTHER INFORMATION: nucleotides sequence coding scFvHER2

<400> SEQUENCE: 37

ccgcggtggt gaagtgcaac ttgttgagag tggcggagga ctggtccaac cgggcggttc     60

acttaggctc tcatgtgcag cttcagggtt cacgttcacg gactatacaa tggactgggt    120

gaggcaagcc cctggtaagg gactggagtg ggttgctgac gttaacccta attccggtgg    180

gtccatctac aaccagcgat tcaagggacg atttactctt tcagtcgaca gaagcaaaaa    240

caccctctac ctccagatga actccttgcg ggcagaggat acagcggtct actattgcgc    300

gagaaacttg ggaccaagct tctacttcga ctactggggg caaggaacgc ttgttacggt    360

ttcaagcgga ggtggaggaa gtggaggtgg cggttccggc ggtggcggtt cagatataca    420

gatgacccaa tcacccagtt ctcttagcgc gtctgtaggc gacagggtaa ccataacctg    480

caaggcgtcc caggacgtgt caattggagt tgcctggtat cagcaaaaac ctgggaaagc    540

tccgaagctc ctgatttaca gcgcatctta ccgatatact ggtgtccctt caaggttcag    600

tggcagtgga tctgggacag actttacgct tactatcagc agtctgcaac ctgaggattt    660

cgcgacctac tactgtcagc agtattacat ctatccgtac acgttcggtc aaggtacaaa    720

ggtagaaata aaacgcact                                                 739


<210> SEQ ID NO 38
<211> LENGTH: 1125
<212> TYPE: DNA
<213> ORGANISM: Artificial sequence
<220> FEATURE:
<223> OTHER INFORMATION: nucleotides sequence coding UB-scFvHER2-TOM7

<400> SEQUENCE: 38

atgggcagca gccatcatca tcatcatcac agcagcggcc tggtgccgcg cggcagccat     60

atgcaaatct tcgtcaaaac tctaacaggg aagactataa ccctagaggt tgaaccatcc    120

gacactattg aaaacgtcaa agctaaaatt caagataaag aaggtatccc tccggatcag    180

cagagattga tttttgctgg taagcaacta gaagatggta gaaccttgtc tgactacaac    240

atccaaaagg aatctactct tcacttggtg ttgagactcc gcggtggtga agtgcaactt    300

gttgagagtg gcggaggact ggtccaaccg ggcggttcac ttaggctctc atgtgcagct    360

tcagggttca cgttcacgga ctatacaatg gactgggtga ggcaagcccc tggtaaggga    420

ctggagtggg ttgctgacgt taaccctaat tccggtgggt ccatctacaa ccagcgattc    480

aagggacgat ttactctttc agtcgacaga agcaaaaaca ccctctacct ccagatgaac    540

tccttgcggg cagaggatac agcggtctac tattgcgcga gaaacttggg accaagcttc    600
```

```
tacttcgact actgggggca aggaacgctt gttacggttt caagcggagg tggaggaagt    660

ggaggtggcg gttccggcgg tggcggttca gatatacaga tgacccaatc acccagttct    720

cttagcgcgt ctgtaggcga cagggtaacc ataacctgca aggcgtccca ggacgtgtca    780

attggagttg cctggtatca gcaaaaacct gggaaagctc cgaagctcct gatttacagc    840

gcatcttacc gatatactgg tgtcccttca aggttcagtg gcagtggatc tgggacagac    900

tttacgctta ctatcagcag tctgcaacct gaggatttcg cgacctacta ctgtcagcag    960

tattacatct atccgtacac gttcggtcaa ggtacaaagg tagaaataaa acgcactttt   1020

gccattcgct ggggctttat ccctcttgtg atttacctgg gatttaagag gggtgcagat   1080

cccggaatgc ctgaaccaac tgttttgagc ctactttggg gatag                   1125
```

<210> SEQ ID NO 39
<211> LENGTH: 38
<212> TYPE: DNA
<213> ORGANISM: Artificial sequence
<220> FEATURE:
<223> OTHER INFORMATION: RscFvHER2 primer

<400> SEQUENCE: 39

```
aaaaaagaat tcatggaagt gcaacttgtt gagagtgg                             38
```

<210> SEQ ID NO 40
<211> LENGTH: 35
<212> TYPE: DNA
<213> ORGANISM: Artificial sequence
<220> FEATURE:
<223> OTHER INFORMATION: XTOM7(noT) primer

<400> SEQUENCE: 40

```
aaaaaactcg agtccccaaa gtaggctcaa aacag                                35
```

<210> SEQ ID NO 41
<211> LENGTH: 924
<212> TYPE: DNA
<213> ORGANISM: Artificial sequence
<220> FEATURE:
<223> OTHER INFORMATION: nucleotides sequence coding scFvHER2-TOM7-
      myc/His

<400> SEQUENCE: 41

```
atggaagtgc aacttgttga gagtggcgga ggactggtcc aaccgggcgg ttcacttagg     60

ctctcatgtg cagcttcagg gttcacgttc acggactata caatggactg ggtgaggcaa    120

gcccctggta agggactgga gtgggttgct gacgttaacc ctaattccgg tgggtccatc    180

tacaaccagc gattcaaggg acgatttact ctttcagtcg acagaagcaa aaacaccctc    240

tacctccaga tgaactcctt gcgggcagag gatacagcgg tctactattg cgcgagaaac    300

ttgggaccaa gcttctactt cgactactgg gggcaaggaa cgcttgttac ggtttcaagc    360

ggaggtggag gaagtggagg tggcggttcc ggcggtggcg gttcagatat acagatgacc    420

caatcaccca gttctcttag cgcgtctgta ggcgacaggg taaccataac ctgcaaggcg    480

tcccaggacg tgtcaattgg agttgcctgg tatcagcaaa aacctgggaa agctccgaag    540

ctcctgattt acagcgcatc ttaccgatat actggtgtcc cttcaaggtt cagtggcagt    600

ggatctggga cagactttac gcttactatc agcagtctgc aacctgagga tttcgcgacc    660

tactactgtc agcagtatta catctatccg tacacgttcg gtcaaggtac aaaggtagaa    720

ataaaacgca cttttgccat tcgctggggc tttatccctc ttgtgattta cctgggattt    780
```

```
aagaggggtg cagatcccgg aatgcctgaa ccaactgttt tgagcctact ttggggactc    840

gagtctagag ggcccttcga acaaaaactc atctcagaag aggatctgaa tatgcatacc    900

ggtcatcatc accatcacca ttga                                           924
```

<210> SEQ ID NO 42
<211> LENGTH: 760
<212> TYPE: DNA
<213> ORGANISM: Artificial sequence
<220> FEATURE:
<223> OTHER INFORMATION: nucleotides sequence coding scFvMEL

<400> SEQUENCE: 42

```
ccgcggtggt acggacattg tgatgaccca gtctcaaaaa ttcatgtcca catcagtagg     60

agacagggtc agcgtcacct gcaaggccag tcagaatgtg gatactaatg tagcctggta    120

tcaacaaaaa ccagggcaat ctcctgaacc actgcttttc tcggcatcct accgttacac    180

tggagtccct gatcgcttca caggcagtgg atctgggaca gatttcactc tcaccatcag    240

caatgtgcag tctgaagact tggcagagta tttctgtcag caatataaca gctatcctct    300

gacgttcggt ggaggcacca agctggagat caaaggctcc accagcggca gcggtaagcc    360

aggctccggc gaaggcagca ccaaaggcga agtgaaggtt gaggagtctg gaggaggctt    420

ggtgcaacct ggaggatcca tgaaactctc ctgtgttgtc tctggattca ctttcggtaa    480

ttactggatg aactgggtcc gccagtctcc agagaagggg cttgagtgga ttgcagaaat    540

tagattgaaa tccaataatt ttgcaagata ttatgcggag tctgtgaaag ggaggttcac    600

catctcaaga gatgattcca aaagtagtgt ctacctgcaa atgatcaacc taagagctga    660

agatactggc atttattact gtaccagtta tggtaactac gttgggcact attttgacca    720

ctggggccaa ggcaccactc tcaccgtctc cctttgggga                          760
```

<210> SEQ ID NO 43
<211> LENGTH: 1137
<212> TYPE: DNA
<213> ORGANISM: Artificial sequence
<220> FEATURE:
<223> OTHER INFORMATION: nucleotides sequence coding UB-scFvMEL-TOM7

<400> SEQUENCE: 43

```
atgggcagca gccatcatca tcatcatcac agcagcggcc tggtgccgcg cggcagccat     60

atgcaaatct tcgtcaaaac tctaacaggg aagactataa ccctagaggt tgaaccatcc    120

gacactattg aaaacgtcaa agctaaaatt caagataaag aaggtatccc tccggatcag    180

cagagattga tttttgctgg taagcaacta gaagatggta gaaccttgtc tgactacaac    240

atccaaaagg aatctactct tcacttggtg ttgagactcc gcggtggtac ggacattgtg    300

atgacccagt ctcaaaaatt catgtccaca tcagtaggag acagggtcag cgtcacctgc    360

aaggccagtc agaatgtgga tactaatgta gcctggtatc aacaaaaacc agggcaatct    420

cctgaaccac tgcttttctc ggcatcctac cgttacactg gagtccctga tcgcttcaca    480

ggcagtggat ctgggacaga tttcactctc accatcagca atgtgcagtc tgaagacttg    540

gcagagtatt tctgtcagca atataacagc tatcctctga cgttcggtgg aggcaccaag    600

ctggagatca aaggctccac cagcggcagc ggtaagccag gctccggcga aggcagcacc    660

aaaggcgaag tgaaggttga ggagtctgga ggaggcttgg tgcaacctgg aggatccatg    720

aaactctcct gtgttgtctc tggattcact ttcggtaatt actggatgaa ctgggtccgc    780
```

```
cagtctccag agaaggggct tgagtggatt gcagaaatta gattgaaatc caataatttt    840

gcaagatatt atgcggagtc tgtgaaaggg aggttcacca tctcaagaga tgattccaaa    900

agtagtgtct acctgcaaat gatcaaccta agagctgaag atactggcat ttattactgt    960

accagttatg gtaactacgt tgggcactat tttgaccact ggggccaagg caccactctc   1020

accgtctcct catttgccat tcgctggggc tttatccctc ttgtgattta cctgggattt   1080

aagaggggtg cagatcccgg aatgcctgaa ccaactgttt tgagcctact ttgggga      1137


<210> SEQ ID NO 44
<211> LENGTH: 36
<212> TYPE: DNA
<213> ORGANISM: Artificial sequence
<220> FEATURE:
<223> OTHER INFORMATION: RscFvMEL primer

<400> SEQUENCE: 44

aaaaaagaat tcatgaaaac aagtaaccca ggagtg                               36


<210> SEQ ID NO 45
<211> LENGTH: 939
<212> TYPE: DNA
<213> ORGANISM: Artificial sequence
<220> FEATURE:
<223> OTHER INFORMATION: nucleotides sequence coding scFvMEL-TOM7-
      myc/His

<400> SEQUENCE: 45

atgacggaca ttgtgatgac ccagtctcaa aaattcatgt ccacatcagt aggagacagg     60

gtcagcgtca cctgcaaggc cagtcagaat gtggatacta atgtagcctg gtatcaacaa    120

aaaccagggc aatctcctga accactgctt ttctcggcat cctaccgtta cactggagtc    180

cctgatcgct tcacaggcag tggatctggg acagatttca ctctcaccat cagcaatgtg    240

cagtctgaag acttggcaga gtatttctgt cagcaatata acagctatcc tctgacgttc    300

ggtggaggca ccaagctgga gatcaaaggc tccaccagcg gcagcggtaa gccaggctcc    360

ggcgaaggca gcaccaaagg cgaagtgaag gttgaggagt ctggaggagg cttggtgcaa    420

cctggaggat ccatgaaact ctcctgtgtt gtctctggat tcactttcgg taattactgg    480

atgaactggg tccgccagtc tccagagaag ggcttgagt ggattgcaga aattagattg     540

aaatccaata attttgcaag atattatgcg gagtctgtga aagggaggtt caccatctca    600

agagatgatt ccaaaagtag tgtctacctg caaatgatca acctaagagc tgaagatact    660

ggcatttatt actgtaccag ttatggtaac tacgttgggc actattttga ccactggggc    720

caaggcacca ctctcaccgt ctcctcattt gccattcgct ggggctttat ccctcttgtg    780

atttacctgg gatttaagag gggtgcagat cccggaatgc ctgaaccaac tgttttgagc    840

ctactttggg gactcgagtc tagagggccc ttcgaacaaa aactcatctc agaagaggat    900

ctgaatatgc ataccggtca tcatcaccat caccattga                           939


<210> SEQ ID NO 46
<211> LENGTH: 750
<212> TYPE: DNA
<213> ORGANISM: Artificial sequence
<220> FEATURE:
<223> OTHER INFORMATION: nucleotides sequence coding scFvPD-L1

<400> SEQUENCE: 46

atggacatcg tgatgagcca gtctcccagc agcctggctg tgtctgctgg ggagaaggtg     60
```

```
accatgtcct gcaagagctc ccagtccctg ctgaacagcc gcaccaggaa gaactacctg    120
gcctggtacc agcagaagcc aggccagagc cccaagctcc tcatctactg ggccagcacc    180
cgggagagcg gggtgcctga ccgcttcact ggaagtggca gcggcacaga cttcaccctg    240
accatcagct ctgtgcaggc cgaggacctg gcagtgtact actgccagca aagctatgat    300
gtggtgacat ttggagctgg caccaagctg gagctgaagg gaggtggcgg aagcgggggt    360
ggaggatccg gggcggcgg aagccaggtc caggtgcagc agagcggggc tgagctggcc     420
gagcccgggg cctctgtgaa gatgagctgc aaggcttctg gctacatctt caccagctac    480
tggatgcact ggctcaagca gaggcctggg caggggctgg agtggatcgg ctatatcaac    540
cccagcagtg actacaatga atattctgag aagttcatgg acaaagccac cctgactgct    600
gacaaggcca gcaccaccgc ctacatgcag ctgatcagcc tgacctcaga ggacagcgct    660
gtgtactact gtgcccggag cggctggctg gtgcacgggg actattattt tgattattgg    720
ggccagggca ccacactgac agtgagcagc                                      750
```

```
<210> SEQ ID NO 47
<211> LENGTH: 948
<212> TYPE: DNA
<213> ORGANISM: Artificial sequence
<220> FEATURE:
<223> OTHER INFORMATION: nucleotides sequence coding scFvPD-L1-TOM7-
      myc/His

<400> SEQUENCE: 47

atggacatcg tgatgagcca gtctcccagc agcctggctg tgtctgctgg ggagaaggtg     60
accatgtcct gcaagagctc ccagtccctg ctgaacagcc gcaccaggaa gaactacctg    120
gcctggtacc agcagaagcc aggccagagc cccaagctcc tcatctactg ggccagcacc    180
cgggagagcg gggtgcctga ccgcttcact ggaagtggca gcggcacaga cttcaccctg    240
accatcagct ctgtgcaggc cgaggacctg gcagtgtact actgccagca aagctatgat    300
gtggtgacat ttggagctgg caccaagctg gagctgaagg gaggtggcgg aagcgggggt    360
ggaggatccg gggcggcgg aagccaggtc caggtgcagc agagcggggc tgagctggcc     420
gagcccgggg cctctgtgaa gatgagctgc aaggcttctg gctacatctt caccagctac    480
tggatgcact ggctcaagca gaggcctggg caggggctgg agtggatcgg ctatatcaac    540
cccagcagtg actacaatga atattctgag aagttcatgg acaaagccac cctgactgct    600
gacaaggcca gcaccaccgc ctacatgcag ctgatcagcc tgacctcaga ggacagcgct    660
gtgtactact gtgcccggag cggctggctg gtgcacgggg actattattt tgattattgg    720
ggccagggca ccacactgac agtgagcagc ctcgagtttg ccattcgctg ggctttatc     780
cctcttgtga tttacctggg atttaagagg ggtgcagatc ccggaatgcc tgaaccaact    840
gttttgagcc tactttgggg actcgagtct agagggccct tcgaacaaaa actcatctca    900
gaagaggatc tgaatatgca taccggtcat catcaccatc accattga                 948


<210> SEQ ID NO 48
<211> LENGTH: 395
<212> TYPE: PRT
<213> ORGANISM: Artificial sequence
<220> FEATURE:
<223> OTHER INFORMATION: amino acid sequence of p53

<400> SEQUENCE: 48

Arg Gly Gly Glu Glu Pro Gln Ser Asp Pro Ser Val Glu Pro Pro Leu
1               5                   10                  15
```

```
Ser Gln Glu Thr Phe Ser Asp Leu Trp Lys Leu Leu Pro Glu Asn Asn
            20                  25                  30

Val Leu Ser Pro Leu Pro Ser Gln Ala Met Asp Asp Leu Met Leu Ser
        35                  40                  45

Pro Asp Asp Ile Glu Gln Trp Phe Thr Glu Asp Pro Gly Pro Asp Glu
    50                  55                  60

Ala Pro Arg Met Pro Glu Ala Ala Pro Arg Val Ala Pro Ala Pro Ala
65                  70                  75                  80

Ala Pro Thr Pro Ala Ala Pro Ala Pro Ala Pro Ser Trp Pro Leu Ser
                85                  90                  95

Ser Ser Val Pro Ser Gln Lys Thr Tyr Gln Gly Ser Tyr Gly Phe Arg
            100                 105                 110

Leu Gly Phe Leu His Ser Gly Thr Ala Lys Ser Val Thr Cys Thr Tyr
        115                 120                 125

Ser Pro Ala Leu Asn Lys Met Phe Cys Gln Leu Ala Lys Thr Cys Pro
    130                 135                 140

Val Gln Leu Trp Val Asp Ser Thr Pro Pro Pro Gly Thr Arg Val Arg
145                 150                 155                 160

Ala Met Ala Ile Tyr Lys Gln Ser Gln His Met Thr Glu Val Val Arg
                165                 170                 175

Arg Cys Pro His His Glu Arg Cys Ser Asp Ser Asp Gly Leu Ala Pro
            180                 185                 190

Pro Gln His Leu Ile Arg Val Glu Gly Asn Leu Arg Val Glu Tyr Leu
        195                 200                 205

Asp Asp Arg Asn Thr Phe Arg His Ser Val Val Val Pro Tyr Glu Pro
    210                 215                 220

Pro Glu Val Gly Ser Asp Cys Thr Thr Ile His Tyr Asn Tyr Met Cys
225                 230                 235                 240

Asn Ser Ser Cys Met Gly Gly Met Asn Arg Arg Pro Ile Leu Thr Ile
                245                 250                 255

Ile Thr Leu Glu Asp Ser Ser Gly Asn Leu Leu Gly Arg Asn Ser Phe
            260                 265                 270

Glu Val Arg Val Cys Ala Cys Pro Gly Arg Asp Arg Arg Thr Glu Glu
        275                 280                 285

Glu Asn Leu Arg Lys Lys Gly Glu Pro His His Glu Leu Pro Pro Gly
    290                 295                 300

Ser Thr Lys Arg Ala Leu Pro Asn Asn Thr Ser Ser Ser Pro Gln Pro
305                 310                 315                 320

Lys Lys Lys Pro Leu Asp Gly Glu Tyr Phe Thr Leu Gln Ile Arg Gly
                325                 330                 335

Arg Glu Arg Phe Glu Met Phe Arg Glu Leu Asn Glu Ala Leu Glu Leu
            340                 345                 350

Lys Asp Ala Gln Ala Gly Lys Glu Pro Gly Gly Ser Arg Ala His Ser
        355                 360                 365

Ser His Leu Lys Ser Lys Lys Gly Gln Ser Thr Ser Arg His Lys Lys
    370                 375                 380

Leu Met Phe Lys Thr Glu Gly Pro Asp Ser Asp
385                 390                 395
```

<210> SEQ ID NO 49
<211> LENGTH: 488
<212> TYPE: PRT
<213> ORGANISM: Artificial sequence
<220> FEATURE:

```
<223> OTHER INFORMATION: amino acid sequence of UB-p53

<400> SEQUENCE: 49

Met Gly Ser Ser His His His His His His Ser Ser Gly Leu Val Pro
1               5                   10                  15

Arg Gly Ser His Met Gln Ile Phe Val Lys Thr Leu Thr Gly Lys Thr
            20                  25                  30

Ile Thr Leu Glu Val Glu Pro Ser Asp Thr Ile Glu Asn Val Lys Ala
        35                  40                  45

Lys Ile Gln Asp Lys Glu Gly Ile Pro Pro Asp Gln Gln Arg Leu Ile
    50                  55                  60

Phe Ala Gly Lys Gln Leu Glu Asp Gly Arg Thr Leu Ser Asp Tyr Asn
65                  70                  75                  80

Ile Gln Lys Glu Ser Thr Leu His Leu Val Leu Arg Leu Arg Gly Gly
                85                  90                  95

Glu Glu Pro Gln Ser Asp Pro Ser Val Glu Pro Pro Leu Ser Gln Glu
            100                 105                 110

Thr Phe Ser Asp Leu Trp Lys Leu Leu Pro Glu Asn Asn Val Leu Ser
        115                 120                 125

Pro Leu Pro Ser Gln Ala Met Asp Asp Leu Met Leu Ser Pro Asp Asp
    130                 135                 140

Ile Glu Gln Trp Phe Thr Glu Asp Pro Gly Pro Asp Glu Ala Pro Arg
145                 150                 155                 160

Met Pro Glu Ala Ala Pro Arg Val Ala Pro Ala Pro Ala Ala Pro Thr
                165                 170                 175

Pro Ala Ala Pro Ala Pro Ala Pro Ser Trp Pro Leu Ser Ser Ser Val
            180                 185                 190

Pro Ser Gln Lys Thr Tyr Gln Gly Ser Tyr Gly Phe Arg Leu Gly Phe
        195                 200                 205

Leu His Ser Gly Thr Ala Lys Ser Val Thr Cys Thr Tyr Ser Pro Ala
    210                 215                 220

Leu Asn Lys Met Phe Cys Gln Leu Ala Lys Thr Cys Pro Val Gln Leu
225                 230                 235                 240

Trp Val Asp Ser Thr Pro Pro Pro Gly Thr Arg Val Arg Ala Met Ala
                245                 250                 255

Ile Tyr Lys Gln Ser Gln His Met Thr Glu Val Val Arg Arg Cys Pro
            260                 265                 270

His His Glu Arg Cys Ser Asp Ser Asp Gly Leu Ala Pro Pro Gln His
        275                 280                 285

Leu Ile Arg Val Glu Gly Asn Leu Arg Val Glu Tyr Leu Asp Asp Arg
    290                 295                 300

Asn Thr Phe Arg His Ser Val Val Val Pro Tyr Glu Pro Pro Glu Val
305                 310                 315                 320

Gly Ser Asp Cys Thr Thr Ile His Tyr Asn Tyr Met Cys Asn Ser Ser
                325                 330                 335

Cys Met Gly Gly Met Asn Arg Arg Pro Ile Leu Thr Ile Ile Thr Leu
            340                 345                 350

Glu Asp Ser Ser Gly Asn Leu Leu Gly Arg Asn Ser Phe Glu Val Arg
        355                 360                 365

Val Cys Ala Cys Pro Gly Arg Asp Arg Arg Thr Glu Glu Glu Asn Leu
    370                 375                 380

Arg Lys Lys Gly Glu Pro His His Glu Leu Pro Pro Gly Ser Thr Lys
385                 390                 395                 400
```

```
Arg Ala Leu Pro Asn Asn Thr Ser Ser Ser Pro Gln Pro Lys Lys Lys
                405                 410                 415

Pro Leu Asp Gly Glu Tyr Phe Thr Leu Gln Ile Arg Gly Arg Glu Arg
            420                 425                 430

Phe Glu Met Phe Arg Glu Leu Asn Glu Ala Leu Glu Leu Lys Asp Ala
        435                 440                 445

Gln Ala Gly Lys Glu Pro Gly Gly Ser Arg Ala His Ser Ser His Leu
    450                 455                 460

Lys Ser Lys Lys Gly Gln Ser Thr Ser Arg His Lys Lys Leu Met Phe
465                 470                 475                 480

Lys Thr Glu Gly Pro Asp Ser Asp
                485


<210> SEQ ID NO 50
<211> LENGTH: 504
<212> TYPE: PRT
<213> ORGANISM: Artificial sequence
<220> FEATURE:
<223> OTHER INFORMATION: amino acid sequence of TOM70-UB-p53

<400> SEQUENCE: 50

Met Lys Ser Phe Ile Thr Arg Asn Lys Thr Ala Ile Phe Ala Thr Val
1               5                   10                  15

Ala Ala Thr Gly Thr Ala Ile Gly Ala Tyr Tyr Tyr Tyr Gln Ile Phe
            20                  25                  30

Val Lys Thr Leu Thr Gly Lys Thr Ile Thr Leu Glu Val Glu Pro Ser
        35                  40                  45

Asp Thr Ile Glu Asn Val Lys Ala Lys Ile Gln Asp Lys Glu Gly Ile
    50                  55                  60

Pro Pro Asp Gln Gln Arg Leu Ile Phe Ala Gly Lys Gln Leu Glu Asp
65                  70                  75                  80

Gly Arg Thr Leu Ser Asp Tyr Asn Ile Gln Lys Glu Ser Thr Leu His
                85                  90                  95

Leu Val Leu Arg Leu Arg Gly Gly Glu Glu Pro Gln Ser Asp Pro Ser
            100                 105                 110

Val Glu Pro Pro Leu Ser Gln Glu Thr Phe Ser Asp Leu Trp Lys Leu
        115                 120                 125

Leu Pro Glu Asn Asn Val Leu Ser Pro Leu Pro Ser Gln Ala Met Asp
    130                 135                 140

Asp Leu Met Leu Ser Pro Asp Asp Ile Glu Gln Trp Phe Thr Glu Asp
145                 150                 155                 160

Pro Gly Pro Asp Glu Ala Pro Arg Met Pro Glu Ala Ala Pro Arg Val
                165                 170                 175

Ala Pro Ala Pro Ala Ala Pro Thr Pro Ala Ala Pro Ala Pro Ala Pro
            180                 185                 190

Ser Trp Pro Leu Ser Ser Ser Val Pro Ser Gln Lys Thr Tyr Gln Gly
        195                 200                 205

Ser Tyr Gly Phe Arg Leu Gly Phe Leu His Ser Gly Thr Ala Lys Ser
    210                 215                 220

Val Thr Cys Thr Tyr Ser Pro Ala Leu Asn Lys Met Phe Cys Gln Leu
225                 230                 235                 240

Ala Lys Thr Cys Pro Val Gln Leu Trp Val Asp Ser Thr Pro Pro Pro
                245                 250                 255

Gly Thr Arg Val Arg Ala Met Ala Ile Tyr Lys Gln Ser Gln His Met
            260                 265                 270
```

```
Thr Glu Val Val Arg Arg Cys Pro His His Glu Arg Cys Ser Asp Ser
        275                 280                 285

Asp Gly Leu Ala Pro Pro Gln His Leu Ile Arg Val Glu Gly Asn Leu
    290                 295                 300

Arg Val Glu Tyr Leu Asp Asp Arg Asn Thr Phe Arg His Ser Val Val
305                 310                 315                 320

Val Pro Tyr Glu Pro Pro Glu Val Gly Ser Asp Cys Thr Thr Ile His
                325                 330                 335

Tyr Asn Tyr Met Cys Asn Ser Ser Cys Met Gly Gly Met Asn Arg Arg
            340                 345                 350

Pro Ile Leu Thr Ile Ile Thr Leu Glu Asp Ser Ser Gly Asn Leu Leu
        355                 360                 365

Gly Arg Asn Ser Phe Glu Val Arg Val Cys Ala Cys Pro Gly Arg Asp
    370                 375                 380

Arg Arg Thr Glu Glu Glu Asn Leu Arg Lys Lys Gly Glu Pro His His
385                 390                 395                 400

Glu Leu Pro Pro Gly Ser Thr Lys Arg Ala Leu Pro Asn Asn Thr Ser
                405                 410                 415

Ser Ser Pro Gln Pro Lys Lys Lys Pro Leu Asp Gly Glu Tyr Phe Thr
            420                 425                 430

Leu Gln Ile Arg Gly Arg Glu Arg Phe Glu Met Phe Arg Glu Leu Asn
        435                 440                 445

Glu Ala Leu Glu Leu Lys Asp Ala Gln Ala Gly Lys Glu Pro Gly Gly
    450                 455                 460

Ser Arg Ala His Ser Ser His Leu Lys Ser Lys Lys Gly Gln Ser Thr
465                 470                 475                 480

Ser Arg His Lys Lys Leu Met Phe Lys Thr Glu Gly Pro Asp Ser Asp
                485                 490                 495

Leu Glu His His His His His His
            500
```

<210> SEQ ID NO 51
<211> LENGTH: 519
<212> TYPE: PRT
<213> ORGANISM: Artificial sequence
<220> FEATURE:
<223> OTHER INFORMATION: amino acid sequence of TOM70-(GGGGS)3-UB-p53

<400> SEQUENCE: 51

```
Met Lys Ser Phe Ile Thr Arg Asn Lys Thr Ala Ile Phe Ala Thr Val
1               5                   10                  15

Ala Ala Thr Gly Thr Ala Ile Gly Ala Tyr Tyr Tyr Tyr Gly Gly Gly
            20                  25                  30

Gly Ser Gly Gly Gly Gly Ser Gly Gly Gly Gly Ser Gln Ile Phe Val
        35                  40                  45

Lys Thr Leu Thr Gly Lys Thr Ile Thr Leu Glu Val Glu Pro Ser Asp
    50                  55                  60

Thr Ile Glu Asn Val Lys Ala Lys Ile Gln Asp Lys Glu Gly Ile Pro
65                  70                  75                  80

Pro Asp Gln Gln Arg Leu Ile Phe Ala Gly Lys Gln Leu Glu Asp Gly
                85                  90                  95

Arg Thr Leu Ser Asp Tyr Asn Ile Gln Lys Glu Ser Thr Leu His Leu
            100                 105                 110

Val Leu Arg Leu Arg Gly Gly Glu Glu Pro Gln Ser Asp Pro Ser Val
        115                 120                 125
```

```
Glu Pro Pro Leu Ser Gln Glu Thr Phe Ser Asp Leu Trp Lys Leu Leu
    130                 135                 140

Pro Glu Asn Asn Val Leu Ser Pro Leu Pro Ser Gln Ala Met Asp Asp
145                 150                 155                 160

Leu Met Leu Ser Pro Asp Asp Ile Glu Gln Trp Phe Thr Glu Asp Pro
                165                 170                 175

Gly Pro Asp Glu Ala Pro Arg Met Pro Glu Ala Ala Pro Arg Val Ala
            180                 185                 190

Pro Ala Pro Ala Ala Pro Thr Pro Ala Ala Pro Ala Pro Ala Pro Ser
        195                 200                 205

Trp Pro Leu Ser Ser Ser Val Pro Ser Gln Lys Thr Tyr Gln Gly Ser
    210                 215                 220

Tyr Gly Phe Arg Leu Gly Phe Leu His Ser Gly Thr Ala Lys Ser Val
225                 230                 235                 240

Thr Cys Thr Tyr Ser Pro Ala Leu Asn Lys Met Phe Cys Gln Leu Ala
                245                 250                 255

Lys Thr Cys Pro Val Gln Leu Trp Val Asp Ser Thr Pro Pro Pro Gly
            260                 265                 270

Thr Arg Val Arg Ala Met Ala Ile Tyr Lys Gln Ser Gln His Met Thr
        275                 280                 285

Glu Val Val Arg Arg Cys Pro His His Glu Arg Cys Ser Asp Ser Asp
    290                 295                 300

Gly Leu Ala Pro Pro Gln His Leu Ile Arg Val Glu Gly Asn Leu Arg
305                 310                 315                 320

Val Glu Tyr Leu Asp Asp Arg Asn Thr Phe Arg His Ser Val Val Val
                325                 330                 335

Pro Tyr Glu Pro Pro Glu Val Gly Ser Asp Cys Thr Thr Ile His Tyr
            340                 345                 350

Asn Tyr Met Cys Asn Ser Ser Cys Met Gly Gly Met Asn Arg Arg Pro
        355                 360                 365

Ile Leu Thr Ile Ile Thr Leu Glu Asp Ser Ser Gly Asn Leu Leu Gly
    370                 375                 380

Arg Asn Ser Phe Glu Val Arg Val Cys Ala Cys Pro Gly Arg Asp Arg
385                 390                 395                 400

Arg Thr Glu Glu Glu Asn Leu Arg Lys Lys Gly Glu Pro His His Glu
                405                 410                 415

Leu Pro Pro Gly Ser Thr Lys Arg Ala Leu Pro Asn Asn Thr Ser Ser
            420                 425                 430

Ser Pro Gln Pro Lys Lys Lys Pro Leu Asp Gly Glu Tyr Phe Thr Leu
        435                 440                 445

Gln Ile Arg Gly Arg Glu Arg Phe Glu Met Phe Arg Glu Leu Asn Glu
    450                 455                 460

Ala Leu Glu Leu Lys Asp Ala Gln Ala Gly Lys Glu Pro Gly Gly Ser
465                 470                 475                 480

Arg Ala His Ser Ser His Leu Lys Ser Lys Lys Gly Gln Ser Thr Ser
                485                 490                 495

Arg His Lys Lys Leu Met Phe Lys Thr Glu Gly Pro Asp Ser Asp Leu
            500                 505                 510

Glu His His His His His His
        515
```

<210> SEQ ID NO 52
<211> LENGTH: 444
<212> TYPE: PRT

```
<213> ORGANISM: Artificial sequence
<220> FEATURE:
<223> OTHER INFORMATION: amino acid sequence of TOM70-(GGGGS)3-p53

<400> SEQUENCE: 52

Met Lys Ser Phe Ile Thr Arg Asn Lys Thr Ala Ile Phe Ala Thr Val
1               5                   10                  15

Ala Ala Thr Gly Thr Ala Ile Gly Ala Tyr Tyr Tyr Tyr Gly Gly Gly
            20                  25                  30

Gly Ser Gly Gly Gly Gly Ser Gly Gly Gly Gly Ser Glu Glu Pro Gln
        35                  40                  45

Ser Asp Pro Ser Val Glu Pro Pro Leu Ser Gln Glu Thr Phe Ser Asp
    50                  55                  60

Leu Trp Lys Leu Leu Pro Glu Asn Asn Val Leu Ser Pro Leu Pro Ser
65                  70                  75                  80

Gln Ala Met Asp Asp Leu Met Leu Ser Pro Asp Asp Ile Glu Gln Trp
                85                  90                  95

Phe Thr Glu Asp Pro Gly Pro Asp Glu Ala Pro Arg Met Pro Glu Ala
            100                 105                 110

Ala Pro Arg Val Ala Pro Ala Pro Ala Ala Pro Thr Pro Ala Ala Pro
        115                 120                 125

Ala Pro Ala Pro Ser Trp Pro Leu Ser Ser Ser Val Pro Ser Gln Lys
    130                 135                 140

Thr Tyr Gln Gly Ser Tyr Gly Phe Arg Leu Gly Phe Leu His Ser Gly
145                 150                 155                 160

Thr Ala Lys Ser Val Thr Cys Thr Tyr Ser Pro Ala Leu Asn Lys Met
                165                 170                 175

Phe Cys Gln Leu Ala Lys Thr Cys Pro Val Gln Leu Trp Val Asp Ser
            180                 185                 190

Thr Pro Pro Pro Gly Thr Arg Val Arg Ala Met Ala Ile Tyr Lys Gln
        195                 200                 205

Ser Gln His Met Thr Glu Val Val Arg Arg Cys Pro His His Glu Arg
    210                 215                 220

Cys Ser Asp Ser Asp Gly Leu Ala Pro Pro Gln His Leu Ile Arg Val
225                 230                 235                 240

Glu Gly Asn Leu Arg Val Glu Tyr Leu Asp Asp Arg Asn Thr Phe Arg
                245                 250                 255

His Ser Val Val Val Pro Tyr Glu Pro Pro Glu Val Gly Ser Asp Cys
            260                 265                 270

Thr Thr Ile His Tyr Asn Tyr Met Cys Asn Ser Ser Cys Met Gly Gly
        275                 280                 285

Met Asn Arg Arg Pro Ile Leu Thr Ile Ile Thr Leu Glu Asp Ser Ser
    290                 295                 300

Gly Asn Leu Leu Gly Arg Asn Ser Phe Glu Val Arg Val Cys Ala Cys
305                 310                 315                 320

Pro Gly Arg Asp Arg Arg Thr Glu Glu Glu Asn Leu Arg Lys Lys Gly
                325                 330                 335

Glu Pro His His Glu Leu Pro Pro Gly Ser Thr Lys Arg Ala Leu Pro
            340                 345                 350

Asn Asn Thr Ser Ser Ser Pro Gln Pro Lys Lys Lys Pro Leu Asp Gly
        355                 360                 365

Glu Tyr Phe Thr Leu Gln Ile Arg Gly Arg Glu Arg Phe Glu Met Phe
    370                 375                 380

Arg Glu Leu Asn Glu Ala Leu Glu Leu Lys Asp Ala Gln Ala Gly Lys
```

385 390 395 400

Glu Pro Gly Gly Ser Arg Ala His Ser Ser His Leu Lys Ser Lys Lys
405 410 415

Gly Gln Ser Thr Ser Arg His Lys Lys Leu Met Phe Lys Thr Glu Gly
420 425 430

Pro Asp Ser Asp Leu Glu His His His His His His
435 440

<210> SEQ ID NO 53
<211> LENGTH: 525
<212> TYPE: PRT
<213> ORGANISM: Artificial sequence
<220> FEATURE:
<223> OTHER INFORMATION: amino acid sequence of UB-p53-TOM7

<400> SEQUENCE: 53

Met Gly Ser Ser His His His His His His Ser Ser Gly Leu Val Pro
1 5 10 15

Arg Gly Ser His Met Gln Ile Phe Val Lys Thr Leu Thr Gly Lys Thr
20 25 30

Ile Thr Leu Glu Val Glu Pro Ser Asp Thr Ile Glu Asn Val Lys Ala
35 40 45

Lys Ile Gln Asp Lys Glu Gly Ile Pro Pro Asp Gln Gln Arg Leu Ile
50 55 60

Phe Ala Gly Lys Gln Leu Glu Asp Gly Arg Thr Leu Ser Asp Tyr Asn
65 70 75 80

Ile Gln Lys Glu Ser Thr Leu His Leu Val Leu Arg Leu Arg Gly Gly
85 90 95

Glu Glu Pro Gln Ser Asp Pro Ser Val Glu Pro Pro Leu Ser Gln Glu
100 105 110

Thr Phe Ser Asp Leu Trp Lys Leu Leu Pro Glu Asn Asn Val Leu Ser
115 120 125

Pro Leu Pro Ser Gln Ala Met Asp Asp Leu Met Leu Ser Pro Asp Asp
130 135 140

Ile Glu Gln Trp Phe Thr Glu Asp Pro Gly Pro Asp Glu Ala Pro Arg
145 150 155 160

Met Pro Glu Ala Ala Pro Arg Val Ala Pro Ala Pro Ala Ala Pro Thr
165 170 175

Pro Ala Ala Pro Ala Pro Ala Pro Ser Trp Pro Leu Ser Ser Ser Val
180 185 190

Pro Ser Gln Lys Thr Tyr Gln Gly Ser Tyr Gly Phe Arg Leu Gly Phe
195 200 205

Leu His Ser Gly Thr Ala Lys Ser Val Thr Cys Thr Tyr Ser Pro Ala
210 215 220

Leu Asn Lys Met Phe Cys Gln Leu Ala Lys Thr Cys Pro Val Gln Leu
225 230 235 240

Trp Val Asp Ser Thr Pro Pro Pro Gly Thr Arg Val Arg Ala Met Ala
245 250 255

Ile Tyr Lys Gln Ser Gln His Met Thr Glu Val Val Arg Arg Cys Pro
260 265 270

His His Glu Arg Cys Ser Asp Ser Asp Gly Leu Ala Pro Pro Gln His
275 280 285

Leu Ile Arg Val Glu Gly Asn Leu Arg Val Glu Tyr Leu Asp Asp Arg
290 295 300

Asn Thr Phe Arg His Ser Val Val Val Pro Tyr Glu Pro Pro Glu Val

```
305                 310                 315                 320

Gly Ser Asp Cys Thr Thr Ile His Tyr Asn Tyr Met Cys Asn Ser Ser
                325                 330                 335

Cys Met Gly Gly Met Asn Arg Arg Pro Ile Leu Thr Ile Ile Thr Leu
            340                 345                 350

Glu Asp Ser Ser Gly Asn Leu Leu Gly Arg Asn Ser Phe Glu Val His
        355                 360                 365

Val Cys Ala Cys Pro Gly Arg Asp Arg Arg Thr Glu Glu Glu Asn Leu
    370                 375                 380

Arg Lys Lys Gly Glu Pro His His Glu Leu Pro Pro Gly Ser Thr Lys
385                 390                 395                 400

Arg Ala Leu Ser Asn Asn Thr Ser Ser Ser Pro Gln Pro Lys Lys Lys
                405                 410                 415

Pro Leu Asp Gly Glu Tyr Phe Thr Leu Gln Ile Arg Gly Arg Glu Arg
            420                 425                 430

Phe Glu Met Phe Arg Glu Leu Asn Glu Ala Leu Glu Leu Lys Asp Ala
        435                 440                 445

Gln Ala Gly Lys Glu Pro Gly Gly Ser Arg Ala His Ser Ser His Leu
    450                 455                 460

Lys Ser Lys Lys Gly Gln Ser Thr Ser Arg His Lys Lys Leu Met Phe
465                 470                 475                 480

Lys Thr Glu Gly Pro Asp Ser Asp Leu Glu Phe Ala Ile Arg Trp Gly
                485                 490                 495

Phe Ile Pro Leu Val Ile Tyr Leu Gly Phe Lys Arg Gly Ala Asp Pro
            500                 505                 510

Gly Met Pro Glu Pro Thr Val Leu Ser Leu Leu Trp Gly
        515                 520                 525


<210> SEQ ID NO 54
<211> LENGTH: 421
<212> TYPE: PRT
<213> ORGANISM: Artificial sequence
<220> FEATURE:
<223> OTHER INFORMATION: amino acid sequence of p53-myc/H

<400> SEQUENCE: 54

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Arg Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
```

```
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp Leu Glu Ser Arg Gly Pro Phe
385                 390                 395                 400

Glu Gln Lys Leu Ile Ser Glu Glu Asp Leu Asn Met His Thr Gly His
                405                 410                 415

His His His His His
            420
```

<210> SEQ ID NO 55
<211> LENGTH: 230
<212> TYPE: PRT
<213> ORGANISM: Artificial sequence
<220> FEATURE:
<223> OTHER INFORMATION: amino acid sequence of GranzymeB

<400> SEQUENCE: 55

```
Arg Gly Gly Ile Ile Gly Gly His Glu Ala Lys Pro His Ser Arg Pro
1               5                   10                  15

Tyr Met Ala Tyr Leu Met Ile Trp Asp Gln Lys Ser Leu Lys Arg Cys
            20                  25                  30

Gly Gly Phe Leu Ile Gln Asp Asp Phe Val Leu Thr Ala Ala His Cys
        35                  40                  45

Trp Gly Ser Ser Ile Asn Val Thr Leu Gly Ala His Asn Ile Lys Glu
    50                  55                  60

Gln Glu Pro Thr Gln Gln Phe Ile Pro Val Lys Arg Pro Ile Pro His
65                  70                  75                  80

Pro Ala Tyr Asn Pro Lys Asn Phe Ser Asn Asp Ile Met Leu Leu Gln
```

-continued

```
                85                  90                  95

Leu Glu Arg Lys Ala Lys Arg Thr Arg Ala Val Gln Pro Leu Arg Leu
            100                 105                 110

Pro Ser Asn Lys Ala Gln Val Lys Pro Gly Gln Thr Cys Ser Val Ala
        115                 120                 125

Gly Trp Gly Gln Thr Ala Pro Leu Gly Lys His Ser His Thr Leu Gln
    130                 135                 140

Glu Val Lys Met Thr Val Gln Glu Asp Arg Lys Cys Glu Ser Asp Leu
145                 150                 155                 160

Arg His Tyr Tyr Asp Ser Thr Ile Glu Leu Cys Val Gly Asp Pro Glu
                165                 170                 175

Ile Lys Lys Thr Ser Phe Lys Gly Asp Ser Gly Gly Pro Leu Val Cys
            180                 185                 190

Asn Lys Val Ala Gln Gly Ile Val Ser Tyr Gly Arg Asn Asn Gly Met
        195                 200                 205

Pro Pro Arg Ala Cys Thr Lys Val Ser Ser Phe Val His Trp Ile Lys
    210                 215                 220

Lys Thr Met Lys Arg Tyr
225                 230


<210> SEQ ID NO 56
<211> LENGTH: 354
<212> TYPE: PRT
<213> ORGANISM: Artificial sequence
<220> FEATURE:
<223> OTHER INFORMATION: amino acid sequence of TOM70-(GGGGS)3-UB-
      Granzyme B

<400> SEQUENCE: 56

Met Lys Ser Phe Ile Thr Arg Asn Lys Thr Ala Ile Phe Ala Thr Val
1               5                   10                  15

Ala Ala Thr Gly Thr Ala Ile Gly Ala Tyr Tyr Tyr Tyr Gly Gly Gly
            20                  25                  30

Gly Ser Gly Gly Gly Gly Ser Gly Gly Gly Gly Ser Gln Ile Phe Val
        35                  40                  45

Lys Thr Leu Thr Gly Lys Thr Ile Thr Leu Glu Val Glu Pro Ser Asp
    50                  55                  60

Thr Ile Glu Asn Val Lys Ala Lys Ile Gln Asp Lys Glu Gly Ile Pro
65                  70                  75                  80

Pro Asp Gln Gln Arg Leu Ile Phe Ala Gly Lys Gln Leu Glu Asp Gly
                85                  90                  95

Arg Thr Leu Ser Asp Tyr Asn Ile Gln Lys Glu Ser Thr Leu His Leu
            100                 105                 110

Val Leu Arg Leu Arg Gly Gly Ile Ile Gly Gly His Glu Ala Lys Pro
        115                 120                 125

His Ser Arg Pro Tyr Met Ala Tyr Leu Met Ile Trp Asp Gln Lys Ser
    130                 135                 140

Leu Lys Arg Cys Gly Gly Phe Leu Ile Arg Asp Asp Phe Val Leu Thr
145                 150                 155                 160

Ala Ala His Cys Trp Gly Ser Ser Ile Asn Val Thr Leu Gly Ala His
                165                 170                 175

Asn Ile Lys Glu Gln Glu Pro Thr Gln Gln Phe Ile Pro Val Lys Arg
            180                 185                 190

Pro Ile Pro His Pro Ala Tyr Asn Pro Lys Asn Phe Ser Asn Asp Ile
        195                 200                 205
```

Met Leu Leu Gln Leu Glu Arg Lys Ala Lys Arg Thr Arg Ala Val Gln
    210                 215                 220

Pro Leu Arg Leu Pro Ser Asn Lys Ala Gln Val Lys Pro Gly Gln Thr
225                 230                 235                 240

Cys Ser Val Ala Gly Trp Gly Gln Thr Ala Pro Leu Gly Lys His Ser
                245                 250                 255

His Thr Leu Gln Glu Val Lys Met Thr Val Gln Glu Asp Arg Lys Cys
            260                 265                 270

Glu Ser Asp Leu Arg His Tyr Tyr Asp Ser Thr Ile Glu Leu Cys Val
        275                 280                 285

Gly Asp Pro Glu Ile Lys Lys Thr Ser Phe Lys Gly Asp Ser Gly Gly
    290                 295                 300

Pro Leu Val Cys Asn Lys Val Ala Gln Gly Ile Val Ser Tyr Gly Arg
305                 310                 315                 320

Asn Asn Gly Met Pro Pro Arg Ala Cys Thr Lys Val Ser Ser Phe Val
                325                 330                 335

His Trp Ile Lys Lys Thr Met Lys Arg Tyr Leu Glu His His His His
            340                 345                 350

His His

<210> SEQ ID NO 57
<211> LENGTH: 360
<212> TYPE: PRT
<213> ORGANISM: Artificial sequence
<220> FEATURE:
<223> OTHER INFORMATION: amino acid sequence of UB-Granzyme B-TOM7

<400> SEQUENCE: 57

Met Gly Ser Ser His His His His His His Ser Ser Gly Leu Val Pro
1               5                   10                  15

Arg Gly Ser His Met Gln Ile Phe Val Lys Thr Leu Thr Gly Lys Thr
            20                  25                  30

Ile Thr Leu Glu Val Glu Pro Ser Asp Thr Ile Glu Asn Val Lys Ala
        35                  40                  45

Lys Ile Gln Asp Lys Glu Gly Ile Pro Pro Asp Gln Gln Arg Leu Ile
    50                  55                  60

Phe Ala Gly Lys Gln Leu Glu Asp Gly Arg Thr Leu Ser Asp Tyr Asn
65                  70                  75                  80

Ile Gln Lys Glu Ser Thr Leu His Leu Val Leu Arg Leu Arg Gly Gly
                85                  90                  95

Ile Ile Gly Gly His Glu Ala Lys Pro His Ser Arg Pro Tyr Met Ala
            100                 105                 110

Tyr Leu Met Ile Trp Asp Gln Lys Ser Leu Lys Arg Cys Gly Gly Phe
        115                 120                 125

Leu Ile Arg Asp Asp Phe Val Leu Thr Ala Ala His Cys Trp Gly Ser
    130                 135                 140

Ser Ile Asn Val Thr Leu Gly Ala His Asn Ile Lys Glu Gln Glu Pro
145                 150                 155                 160

Thr Gln Gln Phe Ile Pro Val Lys Arg Pro Ile Pro His Pro Ala Tyr
                165                 170                 175

Asn Pro Lys Asn Phe Ser Asn Asp Ile Met Leu Leu Gln Leu Glu Arg
            180                 185                 190

Lys Ala Lys Arg Thr Arg Ala Val Gln Pro Leu Arg Leu Pro Ser Asn
        195                 200                 205

Lys Ala Gln Val Lys Pro Gly Gln Thr Cys Ser Val Ala Gly Trp Gly

```
    210                 215                 220

Gln Thr Ala Pro Leu Gly Lys His Ser His Thr Leu Gln Glu Val Lys
225                 230                 235                 240

Met Thr Val Gln Glu Asp Arg Lys Cys Glu Ser Asp Leu Arg His Tyr
                245                 250                 255

Tyr Asp Ser Thr Ile Glu Leu Cys Val Gly Asp Pro Glu Ile Lys Lys
            260                 265                 270

Thr Ser Phe Lys Gly Asp Ser Gly Gly Pro Leu Val Cys Asn Lys Val
        275                 280                 285

Ala Gln Gly Ile Val Ser Tyr Gly Arg Asn Asn Gly Met Pro Pro Arg
    290                 295                 300

Ala Cys Thr Lys Val Ser Ser Phe Val His Trp Ile Lys Lys Thr Met
305                 310                 315                 320

Lys Arg Tyr Leu Glu Phe Ala Ile Arg Trp Gly Phe Ile Pro Leu Val
                325                 330                 335

Ile Tyr Leu Gly Phe Lys Arg Gly Ala Asp Pro Gly Met Pro Glu Pro
            340                 345                 350

Thr Val Leu Ser Leu Leu Trp Gly
        355                 360


<210> SEQ ID NO 58
<211> LENGTH: 189
<212> TYPE: PRT
<213> ORGANISM: Artificial sequence
<220> FEATURE:
<223> OTHER INFORMATION: amino acid sequence of RKIP

<400> SEQUENCE: 58

Arg Gly Gly Pro Val Asp Leu Ser Lys Trp Ser Gly Pro Leu Ser Leu
1               5                   10                  15

Gln Glu Val Asp Glu Gln Pro Gln His Pro Leu His Val Thr Tyr Ala
            20                  25                  30

Gly Ala Ala Val Asp Glu Leu Gly Lys Val Leu Thr Pro Thr Gln Val
        35                  40                  45

Lys Asn Arg Pro Thr Ser Ile Ser Trp Asp Gly Leu Asp Ser Gly Lys
    50                  55                  60

Leu Tyr Thr Leu Val Leu Thr Asp Pro Asp Ala Pro Ser Arg Lys Asp
65                  70                  75                  80

Pro Lys Tyr Arg Glu Trp His His Phe Leu Val Val Asn Met Lys Gly
                85                  90                  95

Asn Asp Ile Ser Ser Gly Thr Val Leu Ser Asp Tyr Val Gly Ser Gly
            100                 105                 110

Pro Pro Lys Gly Thr Gly Leu His Arg Tyr Val Trp Leu Val Tyr Glu
        115                 120                 125

Gln Asp Arg Pro Leu Lys Cys Asp Glu Pro Ile Leu Ser Asn Arg Ser
    130                 135                 140

Gly Asp His Arg Gly Lys Phe Lys Val Ala Ser Phe Arg Lys Lys Tyr
145                 150                 155                 160

Glu Leu Arg Ala Pro Val Ala Gly Thr Cys Tyr Gln Ala Glu Trp Asp
                165                 170                 175

Asp Tyr Val Pro Lys Leu Tyr Glu Gln Leu Ser Gly Lys
            180                 185


<210> SEQ ID NO 59
<211> LENGTH: 313
<212> TYPE: PRT
```

<213> ORGANISM: Artificial sequence
<220> FEATURE:
<223> OTHER INFORMATION: amino acid sequence of TOM70-(GGGGS)3-UB-RKIP

<400> SEQUENCE: 59

Met Lys Ser Phe Ile Thr Arg Asn Lys Thr Ala Ile Phe Ala Thr Val
1 5 10 15

Ala Ala Thr Gly Thr Ala Ile Gly Ala Tyr Tyr Tyr Tyr Gly Gly Gly
20 25 30

Gly Ser Gly Gly Gly Gly Ser Gly Gly Gly Gly Ser Gln Ile Phe Val
35 40 45

Lys Thr Leu Thr Gly Lys Thr Ile Thr Leu Glu Val Glu Pro Ser Asp
50 55 60

Thr Ile Glu Asn Val Lys Ala Lys Ile Gln Asp Lys Glu Gly Ile Pro
65 70 75 80

Pro Asp Gln Gln Arg Leu Ile Phe Ala Gly Lys Gln Leu Glu Asp Gly
85 90 95

Arg Thr Leu Ser Asp Tyr Asn Ile Gln Lys Glu Ser Thr Leu His Leu
100 105 110

Val Leu Arg Leu Arg Gly Gly Pro Val Asp Leu Ser Lys Trp Ser Gly
115 120 125

Pro Leu Ser Leu Gln Glu Val Asp Glu Gln Pro Gln His Pro Leu His
130 135 140

Val Thr Tyr Ala Gly Ala Ala Val Asp Glu Leu Gly Lys Val Leu Thr
145 150 155 160

Pro Thr Gln Val Lys Asn Arg Pro Thr Ser Ile Ser Trp Asp Gly Leu
165 170 175

Asp Ser Gly Lys Leu Tyr Thr Leu Val Leu Thr Asp Pro Asp Ala Pro
180 185 190

Ser Arg Lys Asp Pro Lys Tyr Arg Glu Trp His His Phe Leu Val Val
195 200 205

Asn Met Lys Gly Asn Asp Ile Ser Ser Gly Thr Val Leu Ser Asp Tyr
210 215 220

Val Gly Ser Gly Pro Pro Lys Gly Thr Gly Leu His Arg Tyr Val Trp
225 230 235 240

Leu Val Tyr Glu Gln Asp Arg Pro Leu Lys Cys Asp Glu Pro Ile Leu
245 250 255

Ser Asn Arg Ser Gly Asp His Arg Gly Lys Phe Lys Val Ala Ser Phe
260 265 270

Arg Lys Lys Tyr Glu Leu Arg Ala Pro Val Ala Gly Thr Cys Tyr Gln
275 280 285

Ala Glu Trp Asp Asp Tyr Val Pro Lys Leu Tyr Glu Gln Leu Ser Gly
290 295 300

Lys Leu Glu His His His His His His
305 310

<210> SEQ ID NO 60
<211> LENGTH: 405
<212> TYPE: PRT
<213> ORGANISM: Artificial sequence
<220> FEATURE:
<223> OTHER INFORMATION: amino acid sequence of PTEN

<400> SEQUENCE: 60

Arg Gly Gly Thr Ala Ile Ile Lys Glu Ile Val Ser Arg Asn Lys Arg
1 5 10 15

```
Arg Tyr Gln Glu Asp Gly Phe Asp Leu Asp Leu Thr Tyr Ile Tyr Pro
            20                  25                  30

Asn Ile Ile Ala Met Gly Phe Pro Ala Glu Arg Leu Glu Gly Val Tyr
        35                  40                  45

Arg Asn Asn Ile Asp Asp Val Val Arg Phe Leu Asp Ser Lys His Lys
    50                  55                  60

Asn His Tyr Lys Ile Tyr Asn Leu Cys Ala Glu Arg His Tyr Asp Thr
65                  70                  75                  80

Ala Lys Phe Asn Cys Arg Val Ala Gln Tyr Pro Phe Glu Asp His Asn
                85                  90                  95

Pro Pro Gln Leu Glu Leu Ile Lys Pro Phe Cys Glu Asp Leu Asp Gln
            100                 105                 110

Trp Leu Ser Glu Asp Asp Asn His Val Ala Ala Ile His Cys Lys Ala
        115                 120                 125

Gly Lys Gly Arg Thr Gly Val Met Ile Cys Ala Tyr Leu Leu His Arg
    130                 135                 140

Gly Lys Phe Leu Lys Ala Gln Glu Ala Leu Asp Phe Tyr Gly Glu Val
145                 150                 155                 160

Arg Thr Arg Asp Lys Lys Gly Val Thr Ile Pro Ser Gln Arg Arg Tyr
                165                 170                 175

Val Tyr Tyr Tyr Ser Tyr Leu Leu Lys Asn His Leu Asp Tyr Arg Pro
            180                 185                 190

Val Ala Leu Leu Phe His Lys Met Met Phe Glu Thr Ile Pro Met Phe
        195                 200                 205

Ser Gly Gly Thr Cys Asn Pro Gln Phe Val Val Cys Gln Leu Lys Val
    210                 215                 220

Lys Ile Tyr Ser Ser Asn Ser Gly Pro Thr Arg Arg Glu Asp Lys Phe
225                 230                 235                 240

Met Tyr Phe Glu Phe Pro Gln Pro Leu Pro Val Cys Gly Asp Ile Lys
                245                 250                 255

Val Glu Phe Phe His Lys Gln Asn Lys Met Leu Lys Lys Asp Lys Met
            260                 265                 270

Phe His Phe Trp Val Asn Thr Phe Phe Ile Pro Gly Pro Glu Glu Thr
        275                 280                 285

Ser Glu Lys Val Glu Asn Gly Ser Leu Cys Asp Gln Glu Ile Asp Ser
    290                 295                 300

Ile Cys Ser Ile Glu Arg Ala Asp Asn Asp Lys Glu Tyr Leu Val Leu
305                 310                 315                 320

Thr Leu Thr Lys Asn Asp Leu Asp Lys Ala Asn Lys Asp Lys Ala Asn
                325                 330                 335

Arg Tyr Phe Ser Pro Asn Phe Lys Val Lys Leu Tyr Phe Thr Lys Thr
            340                 345                 350

Val Glu Glu Pro Ser Asn Pro Glu Ala Ser Ser Ser Thr Ser Val Thr
        355                 360                 365

Pro Asp Val Ser Asp Asn Glu Pro Asp His Tyr Arg Tyr Ser Asp Thr
    370                 375                 380

Thr Asp Ser Asp Pro Glu Asn Glu Pro Phe Asp Glu Asp Gln His Thr
385                 390                 395                 400

Gln Ile Thr Lys Val
                405
```

<210> SEQ ID NO 61
<211> LENGTH: 529
<212> TYPE: PRT

<213> ORGANISM: Artificial sequence
<220> FEATURE:
<223> OTHER INFORMATION: amino acid sequence of TOM70-(GGGGS)3-UB-PTEN

<400> SEQUENCE: 61

```
Met Lys Ser Phe Ile Thr Arg Asn Lys Thr Ala Ile Phe Ala Thr Val
1               5                   10                  15

Ala Ala Thr Gly Thr Ala Ile Gly Ala Tyr Tyr Tyr Tyr Gly Gly Gly
            20                  25                  30

Gly Ser Gly Gly Gly Gly Ser Gly Gly Gly Gly Ser Gln Ile Phe Val
        35                  40                  45

Lys Thr Leu Thr Gly Lys Thr Ile Thr Leu Glu Val Glu Pro Ser Asp
    50                  55                  60

Thr Ile Glu Asn Val Lys Ala Lys Ile Gln Asp Lys Glu Gly Ile Pro
65                  70                  75                  80

Pro Asp Gln Gln Arg Leu Ile Phe Ala Gly Lys Gln Leu Glu Asp Gly
                85                  90                  95

Arg Thr Leu Ser Asp Tyr Asn Ile Gln Lys Glu Ser Thr Leu His Leu
            100                 105                 110

Val Leu Arg Leu Arg Gly Gly Thr Ala Ile Ile Lys Glu Ile Val Ser
        115                 120                 125

Arg Asn Lys Arg Arg Tyr Gln Glu Asp Gly Phe Asp Leu Asp Leu Thr
    130                 135                 140

Tyr Ile Tyr Pro Asn Ile Ile Ala Met Gly Phe Pro Ala Glu Arg Leu
145                 150                 155                 160

Glu Gly Val Tyr Arg Asn Asn Ile Asp Asp Val Val Arg Phe Leu Asp
                165                 170                 175

Ser Lys His Lys Asn His Tyr Lys Ile Tyr Asn Leu Cys Ala Glu Arg
            180                 185                 190

His Tyr Asp Thr Ala Lys Phe Asn Cys Arg Val Ala Gln Tyr Pro Phe
        195                 200                 205

Glu Asp His Asn Pro Pro Gln Leu Glu Leu Ile Lys Pro Phe Cys Glu
    210                 215                 220

Asp Leu Asp Gln Trp Leu Ser Glu Asp Asp Asn His Val Ala Ala Ile
225                 230                 235                 240

His Cys Lys Ala Gly Lys Gly Arg Thr Gly Val Met Ile Cys Ala Tyr
                245                 250                 255

Leu Leu His Arg Gly Lys Phe Leu Lys Ala Gln Glu Ala Leu Asp Phe
            260                 265                 270

Tyr Gly Glu Val Arg Thr Arg Asp Lys Lys Gly Val Thr Ile Pro Ser
        275                 280                 285

Gln Arg Arg Tyr Val Tyr Tyr Tyr Ser Tyr Leu Leu Lys Asn His Leu
    290                 295                 300

Asp Tyr Arg Pro Val Ala Leu Leu Phe His Lys Met Met Phe Glu Thr
305                 310                 315                 320

Ile Pro Met Phe Ser Gly Gly Thr Cys Asn Pro Gln Phe Val Val Cys
                325                 330                 335

Gln Leu Lys Val Lys Ile Tyr Ser Ser Asn Ser Gly Pro Thr Arg Arg
            340                 345                 350

Glu Asp Lys Phe Met Tyr Phe Glu Phe Pro Gln Pro Leu Pro Val Cys
        355                 360                 365

Gly Asp Ile Lys Val Glu Phe Phe His Lys Gln Asn Lys Met Leu Lys
    370                 375                 380

Lys Asp Lys Met Phe His Phe Trp Val Asn Thr Phe Phe Ile Pro Gly
```

```
385                 390                 395                 400

Pro Glu Glu Thr Ser Glu Lys Val Glu Asn Gly Ser Leu Cys Asp Gln
                405                 410                 415

Glu Ile Asp Ser Ile Cys Ser Ile Glu Arg Ala Asp Asn Asp Lys Glu
            420                 425                 430

Tyr Leu Val Leu Thr Leu Thr Lys Asn Asp Leu Asp Lys Ala Asn Lys
        435                 440                 445

Asp Lys Ala Asn Arg Tyr Phe Ser Pro Asn Phe Lys Val Lys Leu Tyr
    450                 455                 460

Phe Thr Lys Thr Val Glu Glu Pro Ser Asn Pro Glu Ala Ser Ser Ser
465                 470                 475                 480

Thr Ser Val Thr Pro Asp Val Ser Asp Asn Glu Pro Asp His Tyr Arg
                485                 490                 495

Tyr Ser Asp Thr Thr Asp Ser Asp Pro Glu Asn Glu Pro Phe Asp Glu
            500                 505                 510

Asp Gln His Thr Gln Ile Thr Lys Val Leu Glu His His His His His
        515                 520                 525

His


<210> SEQ ID NO 62
<211> LENGTH: 246
<212> TYPE: PRT
<213> ORGANISM: Artificial sequence
<220> FEATURE:
<223> OTHER INFORMATION: amino acid sequence of scFvHER2

<400> SEQUENCE: 62

Arg Gly Gly Glu Val Gln Leu Val Glu Ser Gly Gly Gly Leu Val Gln
1               5                   10                  15

Pro Gly Gly Ser Leu Arg Leu Ser Cys Ala Ala Ser Gly Phe Thr Phe
            20                  25                  30

Thr Asp Tyr Thr Met Asp Trp Val Arg Gln Ala Pro Gly Lys Gly Leu
        35                  40                  45

Glu Trp Val Ala Asp Val Asn Pro Asn Ser Gly Gly Ser Ile Tyr Asn
    50                  55                  60

Gln Arg Phe Lys Gly Arg Phe Thr Leu Ser Val Asp Arg Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Arg Asn Leu Gly Pro Ser Phe Tyr Phe Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

Lys Ala Ser Gln Asp Val Ser Ile Gly Val Ala Trp Tyr Gln Gln Lys
                165                 170                 175

Pro Gly Lys Ala Pro Lys Leu Leu Ile Tyr Ser Ala Ser Tyr Arg Tyr
            180                 185                 190

Thr Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220
```

```
Cys Gln Gln Tyr Tyr Ile Tyr Pro Tyr Thr Phe Gly Gln Gly Thr Lys
225                 230                 235                 240

Val Glu Ile Lys Arg Thr
                245


<210> SEQ ID NO 63
<211> LENGTH: 374
<212> TYPE: PRT
<213> ORGANISM: Artificial sequence
<220> FEATURE:
<223> OTHER INFORMATION: amino acid sequence of UB-scFvHER2-TOM7

<400> SEQUENCE: 63

Met Gly Ser Ser His His His His His His Ser Ser Gly Leu Val Pro
1               5                   10                  15

Arg Gly Ser His Met Gln Ile Phe Val Lys Thr Leu Thr Gly Lys Thr
            20                  25                  30

Ile Thr Leu Glu Val Glu Pro Ser Asp Thr Ile Glu Asn Val Lys Ala
        35                  40                  45

Lys Ile Gln Asp Lys Glu Gly Ile Pro Pro Asp Gln Gln Arg Leu Ile
    50                  55                  60

Phe Ala Gly Lys Gln Leu Glu Asp Gly Arg Thr Leu Ser Asp Tyr Asn
65                  70                  75                  80

Ile Gln Lys Glu Ser Thr Leu His Leu Val Leu Arg Leu Arg Gly Gly
                85                  90                  95

Glu Val Gln Leu Val Glu Ser Gly Gly Gly Leu Val Gln Pro Gly Gly
            100                 105                 110

Ser Leu Arg Leu Ser Cys Ala Ala Ser Gly Phe Thr Phe Thr Asp Tyr
        115                 120                 125

Thr Met Asp Trp Val Arg Gln Ala Pro Gly Lys Gly Leu Glu Trp Val
    130                 135                 140

Ala Asp Val Asn Pro Asn Ser Gly Gly Ser Ile Tyr Asn Gln Arg Phe
145                 150                 155                 160

Lys Gly Arg Phe Thr Leu Ser Val Asp Arg Ser Lys Asn Thr Leu Tyr
                165                 170                 175

Leu Gln Met Asn Ser Leu Arg Ala Glu Asp Thr Ala Val Tyr Tyr Cys
            180                 185                 190

Ala Arg Asn Leu Gly Pro Ser Phe Tyr Phe Asp Tyr Trp Gly Gln Gly
        195                 200                 205

Thr Leu Val Thr Val Ser Ser Gly Gly Gly Gly Ser Gly Gly Gly Gly
    210                 215                 220

Ser Gly Gly Gly Gly Ser Asp Ile Gln Met Thr Gln Ser Pro Ser Ser
225                 230                 235                 240

Leu Ser Ala Ser Val Gly Asp Arg Val Thr Ile Thr Cys Lys Ala Ser
                245                 250                 255

Gln Asp Val Ser Ile Gly Val Ala Trp Tyr Gln Gln Lys Pro Gly Lys
            260                 265                 270

Ala Pro Lys Leu Leu Ile Tyr Ser Ala Ser Tyr Arg Tyr Thr Gly Val
        275                 280                 285

Pro Ser Arg Phe Ser Gly Ser Gly Ser Gly Thr Asp Phe Thr Leu Thr
    290                 295                 300

Ile Ser Ser Leu Gln Pro Glu Asp Phe Ala Thr Tyr Tyr Cys Gln Gln
305                 310                 315                 320

Tyr Tyr Ile Tyr Pro Tyr Thr Phe Gly Gln Gly Thr Lys Val Glu Ile
                325                 330                 335
```

```
Lys Arg Thr Phe Ala Ile Arg Trp Gly Phe Ile Pro Leu Val Ile Tyr
            340                 345                 350

Leu Gly Phe Lys Arg Gly Ala Asp Pro Gly Met Pro Glu Pro Thr Val
        355                 360                 365

Leu Ser Leu Leu Trp Gly
    370


<210> SEQ ID NO 64
<211> LENGTH: 307
<212> TYPE: PRT
<213> ORGANISM: Artificial sequence
<220> FEATURE:
<223> OTHER INFORMATION: amino acid sequence of scFvHER2-TOM7-myc/H

<400> SEQUENCE: 64

Met Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Thr Asp
            20                  25                  30

Tyr Thr Met Asp Trp Val Arg Gln Ala Pro Gly Lys Gly Leu Glu Trp
        35                  40                  45

Val Ala Asp Val Asn Pro Asn Ser Gly Gly Ser Ile Tyr Asn Gln Arg
    50                  55                  60

Phe Lys Gly Arg Phe Thr Leu Ser Val Asp Arg Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asn Leu Gly Pro Ser Phe Tyr Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Lys Ala
145                 150                 155                 160

Ser Gln Asp Val Ser Ile Gly Val Ala Trp Tyr Gln Gln Lys Pro Gly
                165                 170                 175

Lys Ala Pro Lys Leu Leu Ile Tyr Ser Ala Ser Tyr Arg Tyr Thr Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Tyr Tyr Ile Tyr Pro Tyr Thr Phe Gly Gln Gly Thr Lys Val Glu
225                 230                 235                 240

Ile Lys Arg Thr Phe Ala Ile Arg Trp Gly Phe Ile Pro Leu Val Ile
                245                 250                 255

Tyr Leu Gly Phe Lys Arg Gly Ala Asp Pro Gly Met Pro Glu Pro Thr
            260                 265                 270

Val Leu Ser Leu Leu Trp Gly Leu Glu Ser Arg Gly Pro Phe Glu Gln
        275                 280                 285

Lys Leu Ile Ser Glu Glu Asp Leu Asn Met His Thr Gly His His His
    290                 295                 300

His His His
305
```

<210> SEQ ID NO 65
<211> LENGTH: 251
<212> TYPE: PRT
<213> ORGANISM: Artificial sequence
<220> FEATURE:
<223> OTHER INFORMATION: amino acid sequence of scFvMEL

<400> SEQUENCE: 65

```
Arg Gly Gly Thr Asp Ile Val Met Thr Gln Ser Gln Lys Phe Met Ser
1               5                   10                  15

Thr Ser Val Gly Asp Arg Val Ser Val Thr Cys Lys Ala Ser Gln Asn
            20                  25                  30

Val Asp Thr Asn Val Ala Trp Tyr Gln Gln Lys Pro Gly Gln Ser Pro
        35                  40                  45

Glu Pro Leu Leu Phe Ser Ala Ser Tyr Arg Tyr Thr Gly Val Pro Asp
    50                  55                  60

Arg Phe Thr Gly Ser Gly Ser Gly Thr Asp Phe Thr Leu Thr Ile Ser
65                  70                  75                  80

Asn Val Gln Ser Glu Asp Leu Ala Glu Tyr Phe Cys Gln Gln Tyr Asn
                85                  90                  95

Ser Tyr Pro Leu Thr Phe Gly Gly Gly Thr Lys Leu Glu Ile Lys Gly
            100                 105                 110

Ser Thr Ser Gly Ser Gly Lys Pro Gly Ser Gly Glu Gly Ser Thr Lys
        115                 120                 125

Gly Glu Val Lys Val Glu Glu Ser Gly Gly Gly Leu Val Gln Pro Gly
    130                 135                 140

Gly Ser Met Lys Leu Ser Cys Val Val Ser Gly Phe Thr Phe Gly Asn
145                 150                 155                 160

Tyr Trp Met Asn Trp Val Arg Gln Ser Pro Glu Lys Gly Leu Glu Trp
                165                 170                 175

Ile Ala Glu Ile Arg Leu Lys Ser Asn Asn Phe Ala Arg Tyr Tyr Ala
            180                 185                 190

Glu Ser Val Lys Gly Arg Phe Thr Ile Ser Arg Asp Asp Ser Lys Ser
        195                 200                 205

Ser Val Tyr Leu Gln Met Ile Asn Leu Arg Ala Glu Asp Thr Gly Ile
    210                 215                 220

Tyr Tyr Cys Thr Ser Tyr Gly Asn Tyr Val Gly His Tyr Phe Asp His
225                 230                 235                 240

Trp Gly Gln Gly Thr Thr Leu Thr Val Ser Ser
                245                 250
```

<210> SEQ ID NO 66
<211> LENGTH: 378
<212> TYPE: PRT
<213> ORGANISM: Artificial sequence
<220> FEATURE:
<223> OTHER INFORMATION: amino acid sequence of UB-scFvMEL-TOM7

<400> SEQUENCE: 66

```
Met Gly Ser Ser His His His His His His Ser Ser Gly Leu Val Pro
1               5                   10                  15

Arg Gly Ser His Met Gln Ile Phe Val Lys Thr Leu Thr Gly Lys Thr
            20                  25                  30

Ile Thr Leu Glu Val Glu Pro Ser Asp Thr Ile Glu Asn Val Lys Ala
        35                  40                  45

Lys Ile Gln Asp Lys Glu Gly Ile Pro Pro Asp Gln Gln Arg Leu Ile
```

```
    50                  55                  60

Phe Ala Gly Lys Gln Leu Glu Asp Gly Arg Thr Leu Ser Asp Tyr Asn
65                  70                  75                  80

Ile Gln Lys Glu Ser Thr Leu His Leu Val Leu Arg Leu Arg Gly Gly
                85                  90                  95

Thr Asp Ile Met Thr Gln Ser Gln Lys Phe Met Ser Thr Ser Val Gly
            100                 105                 110

Asp Arg Val Ser Val Thr Cys Lys Ala Ser Gln Asn Val Asp Thr Asn
        115                 120                 125

Val Ala Trp Tyr Gln Gln Lys Pro Gly Gln Ser Pro Glu Pro Leu Leu
    130                 135                 140

Phe Ser Ala Ser Tyr Arg Tyr Thr Gly Val Pro Asp Arg Phe Thr Gly
145                 150                 155                 160

Ser Gly Ser Gly Thr Asp Phe Thr Leu Thr Ile Ser Asn Val Gln Ser
                165                 170                 175

Glu Asp Leu Ala Glu Tyr Phe Cys Gln Gln Tyr Asn Ser Tyr Pro Leu
            180                 185                 190

Thr Phe Gly Gly Gly Thr Lys Leu Glu Ile Lys Gly Ser Thr Ser Gly
        195                 200                 205

Ser Gly Lys Pro Gly Ser Gly Glu Gly Ser Thr Lys Gly Glu Val Lys
    210                 215                 220

Val Glu Glu Ser Gly Gly Gly Leu Val Gln Pro Gly Gly Ser Met Lys
225                 230                 235                 240

Leu Ser Cys Val Val Ser Gly Phe Thr Phe Gly Asn Tyr Trp Met Asn
                245                 250                 255

Trp Val Arg Gln Ser Pro Glu Lys Gly Leu Glu Trp Ile Ala Glu Ile
            260                 265                 270

Arg Leu Lys Ser Asn Asn Phe Ala Arg Tyr Tyr Ala Glu Ser Val Lys
        275                 280                 285

Gly Arg Phe Thr Ile Ser Arg Asp Asp Ser Lys Ser Ser Val Tyr Leu
    290                 295                 300

Gln Met Ile Asn Leu Arg Ala Glu Asp Thr Gly Ile Tyr Tyr Cys Thr
305                 310                 315                 320

Ser Tyr Gly Asn Tyr Val Gly His Tyr Phe Asp His Trp Gly Gln Gly
                325                 330                 335

Thr Thr Leu Thr Val Ser Ser Phe Ala Ile Arg Trp Gly Phe Ile Pro
            340                 345                 350

Leu Val Ile Tyr Leu Gly Phe Lys Arg Gly Ala Asp Pro Gly Met Pro
        355                 360                 365

Glu Pro Thr Val Leu Ser Leu Leu Trp Gly
    370                 375
```

<210> SEQ ID NO 67
<211> LENGTH: 312
<212> TYPE: PRT
<213> ORGANISM: Artificial sequence
<220> FEATURE:
<223> OTHER INFORMATION: amino acid sequence of scFvMEL-TOM7-myc/H

<400> SEQUENCE: 67

```
Met Thr Asp Ile Val Met Thr Gln Ser Gln Lys Phe Met Ser Thr Ser
1               5                   10                  15

Val Gly Asp Arg Val Ser Val Thr Cys Lys Ala Ser Gln Asn Val Asp
            20                  25                  30

Thr Asn Val Ala Trp Tyr Gln Gln Lys Pro Gly Gln Ser Pro Glu Pro
```

```
        35                  40                  45

Leu Leu Phe Ser Ala Ser Tyr Arg Tyr Thr Gly Val Pro Asp Arg Phe
    50                  55                  60

Thr Gly Ser Gly Ser Gly Thr Asp Phe Thr Leu Thr Ile Ser Asn Val
65                  70                  75                  80

Gln Ser Glu Asp Leu Ala Glu Tyr Phe Cys Gln Gln Tyr Asn Ser Tyr
                85                  90                  95

Pro Leu Thr Phe Gly Gly Gly Thr Lys Leu Glu Ile Lys Gly Ser Thr
            100                 105                 110

Ser Gly Ser Gly Lys Pro Gly Ser Gly Glu Gly Ser Thr Lys Gly Glu
        115                 120                 125

Val Lys Val Glu Glu Ser Gly Gly Gly Leu Val Gln Pro Gly Gly Ser
    130                 135                 140

Met Lys Leu Ser Cys Val Val Ser Gly Phe Thr Phe Gly Asn Tyr Trp
145                 150                 155                 160

Met Asn Trp Val Arg Gln Ser Pro Glu Lys Gly Leu Glu Trp Ile Ala
                165                 170                 175

Glu Ile Arg Leu Lys Ser Asn Asn Phe Ala Arg Tyr Tyr Ala Glu Ser
            180                 185                 190

Val Lys Gly Arg Phe Thr Ile Ser Arg Asp Asp Ser Lys Ser Ser Val
        195                 200                 205

Tyr Leu Gln Met Ile Asn Leu Arg Ala Glu Asp Thr Gly Ile Tyr Tyr
    210                 215                 220

Cys Thr Ser Tyr Gly Asn Tyr Val Gly His Tyr Phe Asp His Trp Gly
225                 230                 235                 240

Gln Gly Thr Thr Leu Thr Val Ser Ser Phe Ala Ile Arg Trp Gly Phe
                245                 250                 255

Ile Pro Leu Val Ile Tyr Leu Gly Phe Lys Arg Gly Ala Asp Pro Gly
            260                 265                 270

Met Pro Glu Pro Thr Val Leu Ser Leu Leu Trp Gly Leu Glu Ser Arg
        275                 280                 285

Gly Pro Phe Glu Gln Lys Leu Ile Ser Glu Glu Asp Leu Asn Met His
    290                 295                 300

Thr Gly His His His His His His
305                 310


<210> SEQ ID NO 68
<211> LENGTH: 250
<212> TYPE: PRT
<213> ORGANISM: Artificial sequence
<220> FEATURE:
<223> OTHER INFORMATION: amino acid sequence of scFvPD-L1

<400> SEQUENCE: 68

Met Asp Ile Val Met Ser Gln Ser Pro Ser Ser Leu Ala Val Ser Ala
1               5                   10                  15

Gly Glu Lys Val Thr Met Ser Cys Lys Ser Ser Gln Ser Leu Leu Asn
            20                  25                  30

Ser Arg Thr Arg Lys Asn Tyr Leu Ala Trp Tyr Gln Gln Lys Pro Gly
        35                  40                  45

Gln Ser Pro Lys Leu Leu Ile Tyr Trp Ala Ser Thr Arg Glu Ser Gly
    50                  55                  60

Val Pro Asp Arg Phe Thr Gly Ser Gly Ser Gly Thr Asp Phe Thr Leu
65                  70                  75                  80

Thr Ile Ser Ser Val Gln Ala Glu Asp Leu Ala Val Tyr Tyr Cys Gln
```

```
                85                  90                  95

Gln Ser Tyr Asp Val Val Thr Phe Gly Ala Gly Thr Lys Leu Glu Leu
            100                 105                 110

Lys Gly Gly Gly Gly Ser Gly Gly Gly Gly Ser Gly Gly Gly Gly Ser
        115                 120                 125

Gln Val Gln Val Gln Gln Ser Gly Ala Glu Leu Ala Glu Pro Gly Ala
    130                 135                 140

Ser Val Lys Met Ser Cys Lys Ala Ser Gly Tyr Ile Phe Thr Ser Tyr
145                 150                 155                 160

Trp Met His Trp Leu Lys Gln Arg Pro Gly Gln Gly Leu Glu Trp Ile
                165                 170                 175

Gly Tyr Ile Asn Pro Ser Ser Asp Tyr Asn Glu Tyr Ser Glu Lys Phe
            180                 185                 190

Met Asp Lys Ala Thr Leu Thr Ala Asp Lys Ala Ser Thr Thr Ala Tyr
        195                 200                 205

Met Gln Leu Ile Ser Leu Thr Ser Glu Asp Ser Ala Val Tyr Tyr Cys
    210                 215                 220

Ala Arg Ser Gly Trp Leu Val His Gly Asp Tyr Tyr Phe Asp Tyr Trp
225                 230                 235                 240

Gly Gln Gly Thr Thr Leu Thr Val Ser Ser
                245                 250


<210> SEQ ID NO 69
<211> LENGTH: 315
<212> TYPE: PRT
<213> ORGANISM: Artificial sequence
<220> FEATURE:
<223> OTHER INFORMATION: amino acid sequence of scFvPD-L1-TOM7-myc/H

<400> SEQUENCE: 69

Met Asp Ile Val Met Ser Gln Ser Pro Ser Ser Leu Ala Val Ser Ala
1               5                   10                  15

Gly Glu Lys Val Thr Met Ser Cys Lys Ser Ser Gln Ser Leu Leu Asn
            20                  25                  30

Ser Arg Thr Arg Lys Asn Tyr Leu Ala Trp Tyr Gln Gln Lys Pro Gly
        35                  40                  45

Gln Ser Pro Lys Leu Leu Ile Tyr Trp Ala Ser Thr Arg Glu Ser Gly
    50                  55                  60

Val Pro Asp Arg Phe Thr Gly Ser Gly Ser Gly Thr Asp Phe Thr Leu
65                  70                  75                  80

Thr Ile Ser Ser Val Gln Ala Glu Asp Leu Ala Val Tyr Tyr Cys Gln
                85                  90                  95

Gln Ser Tyr Asp Val Val Thr Phe Gly Ala Gly Thr Lys Leu Glu Leu
            100                 105                 110

Lys Gly Gly Gly Gly Ser Gly Gly Gly Gly Ser Gly Gly Gly Gly Ser
        115                 120                 125

Gln Val Gln Val Gln Gln Ser Gly Ala Glu Leu Ala Glu Pro Gly Ala
    130                 135                 140

Ser Val Lys Met Ser Cys Lys Ala Ser Gly Tyr Ile Phe Thr Ser Tyr
145                 150                 155                 160

Trp Met His Trp Leu Lys Gln Arg Pro Gly Gln Gly Leu Glu Trp Ile
                165                 170                 175

Gly Tyr Ile Asn Pro Ser Ser Asp Tyr Asn Glu Tyr Ser Glu Lys Phe
            180                 185                 190

Met Asp Lys Ala Thr Leu Thr Ala Asp Lys Ala Ser Thr Thr Ala Tyr
```

```
        195                 200                 205

Met Gln Leu Ile Ser Leu Thr Ser Glu Asp Ser Ala Val Tyr Tyr Cys
    210                 215                 220

Ala Arg Ser Gly Trp Leu Val His Gly Asp Tyr Tyr Phe Asp Tyr Trp
225                 230                 235                 240

Gly Gln Gly Thr Thr Leu Thr Val Ser Ser Leu Glu Phe Ala Ile Arg
                245                 250                 255

Trp Gly Phe Ile Pro Leu Val Ile Tyr Leu Gly Phe Lys Arg Gly Ala
            260                 265                 270

Asp Pro Gly Met Pro Glu Pro Thr Val Leu Ser Leu Leu Trp Gly Leu
        275                 280                 285

Glu Ser Arg Gly Pro Phe Glu Gln Lys Leu Ile Ser Glu Glu Asp Leu
    290                 295                 300

Asn Met His Thr Gly His His His His His His
305                 310                 315


<210> SEQ ID NO 70
<211> LENGTH: 15
<212> TYPE: DNA
<213> ORGANISM: Artificial sequence
<220> FEATURE:
<223> OTHER INFORMATION: linker

<400> SEQUENCE: 70

ggggsggggs ggggs                                                       15


<210> SEQ ID NO 71
<211> LENGTH: 75
<212> TYPE: PRT
<213> ORGANISM: Artificial sequence
<220> FEATURE:
<223> OTHER INFORMATION: amino acid sequence of ubiquitin

<400> SEQUENCE: 71

Gln Leu Phe Val Lys Thr Leu Thr Gly Lys Thr Val Thr Leu Glu Val
1               5                   10                  15

Glu Ser Ser Asp Thr Ile Asp Asn Val Lys Ser Lys Ile Gln Asp Lys
            20                  25                  30

Glu Gly Ile Pro Pro Asp Gln Gln Arg Leu Ile Phe Ala Gly Lys Gln
        35                  40                  45

Leu Glu Asp Gly Arg Thr Leu Ser Asp Tyr Asn Ile Gln Lys Glu Ser
    50                  55                  60

Thr Leu His Leu Val Leu Arg Leu Arg Gly Gly
65                  70                  75


<210> SEQ ID NO 72
<211> LENGTH: 225
<212> TYPE: DNA
<213> ORGANISM: Artificial sequence
<220> FEATURE:
<223> OTHER INFORMATION: nucleotides sequence coding ubiquitin

<400> SEQUENCE: 72

caacttttcg tcaaaactct aacagggaag actgtaaccc tagaggttga atcttccgac      60

actattgaca acgtcaaaag taaaattcaa gataaagaag gtatccctcc ggatcagcag     120

agattgattt ttgctggtaa gcaactagaa gatggtagaa ccttgtctga ctacaacatc     180

caaaaggaat ctactcttca cttggtgttg agactccgcg gtggt                     225
```

<210> SEQ ID NO 73
<211> LENGTH: 400
<212> TYPE: PRT
<213> ORGANISM: Artificial sequence
<220> FEATURE:
<223> OTHER INFORMATION: amino acid sequence of p53

<400> SEQUENCE: 73

```
Glu Glu Pro Gln Ser Asp Pro Ser Val Glu Pro Pro Leu Ser Gln Glu
1               5                   10                  15

Thr Phe Ser Asp Leu Trp Lys Leu Leu Pro Glu Asn Asn Val Leu Ser
            20                  25                  30

Pro Leu Pro Ser Gln Ala Met Asp Asp Leu Met Leu Ser Pro Asp Asp
        35                  40                  45

Ile Glu Gln Trp Phe Thr Glu Asp Pro Gly Pro Asp Glu Ala Pro Arg
    50                  55                  60

Met Pro Glu Ala Ala Pro Arg Val Ala Pro Ala Pro Ala Ala Pro Thr
65                  70                  75                  80

Pro Ala Ala Pro Ala Pro Ala Pro Ser Trp Pro Leu Ser Ser Ser Val
                85                  90                  95

Pro Ser Gln Lys Thr Tyr Gln Gly Ser Tyr Gly Phe Arg Leu Gly Phe
            100                 105                 110

Leu His Ser Gly Thr Ala Lys Ser Val Thr Cys Thr Tyr Ser Pro Ala
        115                 120                 125

Leu Asn Lys Met Phe Cys Gln Leu Ala Lys Thr Cys Pro Val Gln Leu
    130                 135                 140

Trp Val Asp Ser Thr Pro Pro Pro Gly Thr Arg Val Arg Ala Met Ala
145                 150                 155                 160

Ile Tyr Lys Gln Ser Gln His Met Thr Glu Val Val Arg Arg Cys Pro
                165                 170                 175

His His Glu Arg Cys Ser Asp Ser Asp Gly Leu Ala Pro Pro Gln His
            180                 185                 190

Leu Ile Arg Val Glu Gly Asn Leu Arg Val Glu Tyr Leu Asp Asp Arg
        195                 200                 205

Asn Thr Phe Arg His Ser Val Val Val Pro Tyr Glu Pro Pro Glu Val
    210                 215                 220

Gly Ser Asp Cys Thr Thr Ile His Tyr Asn Tyr Met Cys Asn Ser Ser
225                 230                 235                 240

Cys Met Gly Gly Met Asn Arg Arg Pro Ile Leu Thr Ile Ile Thr Leu
                245                 250                 255

Glu Asp Ser Ser Gly Asn Leu Leu Gly Arg Asn Ser Phe Glu Val Arg
            260                 265                 270

Val Cys Ala Cys Pro Gly Arg Asp Arg Arg Thr Glu Glu Glu Asn Leu
        275                 280                 285

Arg Lys Lys Gly Glu Pro His His Glu Leu Pro Pro Gly Ser Thr Lys
    290                 295                 300

Arg Ala Leu Pro Asn Asn Thr Ser Ser Ser Pro Gln Pro Lys Lys Lys
305                 310                 315                 320

Pro Leu Asp Gly Glu Tyr Phe Thr Leu Gln Ile Arg Gly Arg Glu Arg
                325                 330                 335

Phe Glu Met Phe Arg Glu Leu Asn Glu Ala Leu Glu Leu Lys Asp Ala
            340                 345                 350

Gln Ala Gly Lys Glu Pro Gly Gly Ser Arg Ala His Ser Ser His Leu
        355                 360                 365

Lys Ser Lys Lys Gly Gln Ser Thr Ser Arg His Lys Lys Leu Met Phe
```

370 375 380

Lys Thr Glu Gly Pro Asp Ser Asp Leu Glu His His His His His His
385 390 395 400

<210> SEQ ID NO 74
<211> LENGTH: 1203
<212> TYPE: DNA
<213> ORGANISM: Artificial sequence
<220> FEATURE:
<223> OTHER INFORMATION: nucleotides sequence coding p53

<400> SEQUENCE: 74
gaggagccgc agtcagatcc tagcgtcgag ccccctctga gtcaggaaac attttcagac 60
ctgtggaaac tacttcctga aaacaacgtt ctgtcccccct tgccgtccca agcaatggat 120
gatttgatgc tgtccccgga cgatattgaa caatggttca ctgaagaccc aggtccagat 180
gaagctccca gaatgccaga ggctgctccc cgcgtggccc ctgcaccagc agctcctaca 240
ccggcggccc ctgcaccagc cccctcctgg cccctgtcat cttctgtccc ttcccagaaa 300
acctaccagg gcagctacgg tttccgtctg ggcttcttgc attctgggac agccaagtct 360
gtgacttgca cgtactcccc tgccctcaac aagatgtttt gccaactggc caagacctgc 420
cctgtgcagc tgtgggttga ttccacaccc ccgcccggca cccgcgtccg cgccatggcc 480
atctacaagc agtcacagca catgacggag gttgtgaggc gctgccccca ccatgagcgc 540
tgctcagata gcgatggtct ggcccctcct cagcatctta tccgagtgga aggaaatttg 600
cgtgtggagt atttggatga cagaaacact tttcgacata gtgtggtggt gccctatgag 660
ccgcctgagg ttggctctga ctgtaccacc atccactaca actacatgtg taacagttcc 720
tgcatgggcg gcatgaaccg gaggcccatc ctcaccatca tcacactgga agactccagt 780
ggtaatctac tgggacggaa cagctttgag gtgcgtgttt gtgcctgtcc tgggagagac 840
cggcgcacag aggaagagaa tctccgcaag aaaggggagc ctcaccacga gctgccccca 900
gggagcacta agcgagcact gcccaacaac accagctcct ctccccagcc aaagaagaaa 960
ccactggatg gagaatattt cacccttcag atccgtgggc gtgagcgctt cgagatgttc 1020
cgagagctga atgaggcctt ggaactcaag gatgcccagg ctgggaagga gccagggggg 1080
agcagggctc actccagcca cctgaagtcc aaaaagggtc agtctacctc ccgccataaa 1140
aaactcatgt tcaagacaga agggcctgac tcagacctcg agcaccacca ccaccaccac 1200
tag 1203

<210> SEQ ID NO 75
<211> LENGTH: 29
<212> TYPE: PRT
<213> ORGANISM: Artificial sequence
<220> FEATURE:
<223> OTHER INFORMATION: TOM70 of S. cerevisiae

<400> SEQUENCE: 75

Met Lys Ser Phe Ile Thr Arg Asn Lys Thr Ala Ile Phe Ala Thr Val
1 5 10 15

Ala Ala Thr Gly Thr Ala Ile Gly Ala Tyr Tyr Tyr Tyr
20 25

<210> SEQ ID NO 76
<211> LENGTH: 60
<212> TYPE: PRT
<213> ORGANISM: Artificial sequence
<220> FEATURE:

<223> OTHER INFORMATION: TOM70 of Homo sapiens

<400> SEQUENCE: 76

Met Ala Ala Ser Lys Pro Val Glu Ala Ala Val Val Ala Ala Ala Val
1               5                   10                  15

Pro Ser Ser Gly Ser Gly Val Gly Gly Gly Gly Thr Ala Gly Pro Gly
            20                  25                  30

Thr Gly Gly Leu Pro Arg Trp Gln Leu Ala Leu Ala Val Gly Ala Pro
        35                  40                  45

Leu Leu Leu Gly Ala Gly Ala Ile Tyr Leu Trp Ser
    50                  55                  60

<210> SEQ ID NO 77
<211> LENGTH: 29
<212> TYPE: PRT
<213> ORGANISM: Artificial sequence
<220> FEATURE:
<223> OTHER INFORMATION: TOM20 of S. cerevisiae

<400> SEQUENCE: 77

Met Ser Gln Ser Asn Pro Ile Leu Arg Gly Leu Ala Ile Thr Thr Ala
1               5                   10                  15

Ile Ala Ala Leu Ser Ala Thr Gly Tyr Ala Ile Tyr Phe
            20                  25

<210> SEQ ID NO 78
<211> LENGTH: 24
<212> TYPE: PRT
<213> ORGANISM: Artificial sequence
<220> FEATURE:
<223> OTHER INFORMATION: TOM20 of Homo sapiens

<400> SEQUENCE: 78

Met Val Gly Arg Asn Ser Ala Ile Ala Ala Gly Val Cys Gly Ala Leu
1               5                   10                  15

Phe Ile Gly Tyr Cys Ile Tyr Phe
            20

<210> SEQ ID NO 79
<211> LENGTH: 22
<212> TYPE: PRT
<213> ORGANISM: Artificial sequence
<220> FEATURE:
<223> OTHER INFORMATION: OM45 of S. cerevisiae

<400> SEQUENCE: 79

Met Ser Ser Arg Ile Ile Val Gly Ser Ala Ala Leu Ala Ala Ala Ile
1               5                   10                  15

Thr Ala Ser Ile Met Val
            20

<210> SEQ ID NO 80
<211> LENGTH: 23
<212> TYPE: PRT
<213> ORGANISM: Artificial sequence
<220> FEATURE:
<223> OTHER INFORMATION: TOM5 of S. cerevisiae

<400> SEQUENCE: 80

Ala Ala Tyr Val Ala Ala Phe Leu Trp Val Ser Pro Met Ile Trp His
1               5                   10                  15

Leu Val Lys Lys Gln Trp Lys
            20

<210> SEQ ID NO 81
<211> LENGTH: 24
<212> TYPE: PRT
<213> ORGANISM: Artificial sequence
<220> FEATURE:
<223> OTHER INFORMATION: TOM5 of Homo sapiens

<400> SEQUENCE: 81

```
Ile Arg Asn Phe Leu Ile Tyr Val Ala Leu Leu Arg Val Thr Pro Phe
1               5                   10                  15

Ile Leu Lys Lys Leu Asp Ser Ile
            20
```

<210> SEQ ID NO 82
<211> LENGTH: 41
<212> TYPE: PRT
<213> ORGANISM: Artificial sequence
<220> FEATURE:
<223> OTHER INFORMATION: TOM7 of S. cerevisiae

<400> SEQUENCE: 82

```
Ile Leu Thr Leu Thr His Asn Val Ala His Tyr Gly Trp Ile Pro Phe
1               5                   10                  15

Val Leu Tyr Leu Gly Trp Ala His Thr Ser Asn Arg Pro Asn Phe Leu
            20                  25                  30

Asn Leu Leu Ser Pro Leu Pro Ser Val
        35                  40
```

<210> SEQ ID NO 83
<211> LENGTH: 35
<212> TYPE: PRT
<213> ORGANISM: Artificial sequence
<220> FEATURE:
<223> OTHER INFORMATION: TOM7 of Homo sapiens

<400> SEQUENCE: 83

```
Phe Ala Ile Arg Trp Gly Phe Ile Pro Leu Val Ile Tyr Leu Gly Phe
1               5                   10                  15

Lys Arg Gly Ala Asp Pro Gly Met Pro Glu Pro Thr Val Leu Ser Leu
            20                  25                  30

Leu Trp Gly
        35
```

<210> SEQ ID NO 84
<211> LENGTH: 55
<212> TYPE: PRT
<213> ORGANISM: Artificial sequence
<220> FEATURE:
<223> OTHER INFORMATION: TOM22 of S. cerevisiae

<400> SEQUENCE: 84

```
Leu Ala Trp Thr Leu Thr Thr Thr Ala Leu Leu Leu Gly Val Pro Leu
1               5                   10                  15

Ser Leu Ser Ile Leu Ala Glu Gln Gln Leu Ile Glu Met Glu Lys Thr
            20                  25                  30

Phe Asp Leu Gln Ser Asp Ala Asn Asn Ile Leu Ala Gln Gly Glu Lys
        35                  40                  45

Asp Ala Ala Ala Thr Ala Asn
    50                  55
```

<210> SEQ ID NO 85

<211> LENGTH: 60
<212> TYPE: PRT
<213> ORGANISM: Artificial sequence
<220> FEATURE:
<223> OTHER INFORMATION: TOM22 of Homo sapiens

<400> SEQUENCE: 85

Ala Ala Leu Trp Ile Gly Thr Thr Ser Phe Met Ile Leu Val Leu Pro
1 5 10 15

Val Val Phe Glu Thr Glu Lys Leu Gln Met Glu Gln Gln Gln Gln Leu
20 25 30

Gln Gln Arg Gln Ile Leu Leu Gly Pro Asn Thr Gly Leu Ser Gly Gly
35 40 45

Met Pro Gly Ala Leu Pro Ser Leu Pro Gly Lys Ile
50 55 60

<210> SEQ ID NO 86
<211> LENGTH: 25
<212> TYPE: PRT
<213> ORGANISM: Artificial sequence
<220> FEATURE:
<223> OTHER INFORMATION: Fis1 of S. cerevisiae

<400> SEQUENCE: 86

Gly Val Val Val Ala Gly Gly Val Leu Ala Gly Ala Val Ala Val Ala
1 5 10 15

Ser Phe Phe Leu Arg Asn Lys Arg Arg
20 25

<210> SEQ ID NO 87
<211> LENGTH: 31
<212> TYPE: PRT
<213> ORGANISM: Artificial sequence
<220> FEATURE:
<223> OTHER INFORMATION: Fis1 of Homo sapiens

<400> SEQUENCE: 87

Gly Leu Val Gly Met Ala Ile Val Gly Gly Met Ala Leu Gly Val Ala
1 5 10 15

Gly Leu Ala Gly Leu Ile Gly Leu Ala Val Ser Lys Ser Lys Ser
20 25 30

<210> SEQ ID NO 88
<211> LENGTH: 25
<212> TYPE: PRT
<213> ORGANISM: Artificial sequence
<220> FEATURE:
<223> OTHER INFORMATION: Bcl-2 alpha of Homo sapiens

<400> SEQUENCE: 88

Leu Ser Leu Lys Thr Leu Leu Ser Leu Ala Leu Val Gly Ala Cys Ile
1 5 10 15

Thr Leu Gly Ala Tyr Leu Gly His Lys
20 25

<210> SEQ ID NO 89
<211> LENGTH: 19
<212> TYPE: PRT
<213> ORGANISM: Artificial sequence
<220> FEATURE:
<223> OTHER INFORMATION: VAMP1 of S. cerevisiae

<400> SEQUENCE: 89

Met Ile Met Leu Gly Ala Ile Cys Ala Ile Ile Val Val Val Ile Val

```
1               5                   10                  15

Arg Arg Asp


<210> SEQ ID NO 90
<211> LENGTH: 22
<212> TYPE: PRT
<213> ORGANISM: Artificial sequence
<220> FEATURE:
<223> OTHER INFORMATION: VAMP1 of Homo sapiens

<400> SEQUENCE: 90

Met Met Ile Met Leu Gly Ala Ile Cys Ala Ile Ile Val Val Val Ile
1               5                   10                  15

Val Ile Tyr Phe Phe Thr
            20


<210> SEQ ID NO 91
<211> LENGTH: 60
<212> TYPE: DNA
<213> ORGANISM: Artificial sequence
<220> FEATURE:
<223> OTHER INFORMATION: P53-promter-S

<400> SEQUENCE: 91

gggcatgctc gggcatgccc gggcatgctc gggcatgccc gggcatgctc gggcatgccc     60


<210> SEQ ID NO 92
<211> LENGTH: 60
<212> TYPE: DNA
<213> ORGANISM: Artificial sequence
<220> FEATURE:
<223> OTHER INFORMATION: P53-promter-AS

<400> SEQUENCE: 92

gggcatgccc gagcatgccc gggcatgccc gagcatgccc gggcatgccc gagcatgccc     60


<210> SEQ ID NO 93
<211> LENGTH: 945
<212> TYPE: DNA
<213> ORGANISM: Artificial sequence
<220> FEATURE:
<223> OTHER INFORMATION: nucleotides sequence coding scFvPDL1-myc-TOM7

<400> SEQUENCE: 93

atggacatcg tgatgagcca gtctcccagc agcctggctg tgtctgctgg ggagaaggtg     60

accatgtcct gcaagagctc ccagtccctg ctgaacagcc gcaccaggaa gaactacctg    120

gcctggtacc agcagaagcc aggccagagc cccaagctcc tcatctactg ggccagcacc    180

cgggagagcg gggtgcctga ccgcttcact ggaagtggca gcggcacaga cttcaccctg    240

accatcagct ctgtgcaggc cgaggacctg gcagtgtact actgccagca aagctatgat    300

gtggtgacat ttggagctgg caccaagctg gagctgaagg gaggtggcgg aagcgggggt    360

ggaggatccg ggggcggcgg aagccaggtc caggtgcagc agagcggggc tgagctggcc    420

gagcccgggg cctctgtgaa gatgagctgc aaggcttctg gctacatctt caccagctac    480

tggatgcact ggctcaagca gaggcctggg caggggctgg agtggatcgg ctatatcaac    540

cccagcagtg actacaatga atattctgag aagttcatgg acaaagccac cctgactgct    600

gacaaggcca gcaccaccgc ctacatgcag ctgatcagcc tgacctcaga ggacagcgct    660

gtgtactact gtgcccggag cggctggctg gtgcacgggg actattattt tgattattgg    720

ggccagggca ccacactgac agtgagcagc gaacaaaaac tcatctcaga agaggatctg    780
```

```
gtgaagctga gcaaagaggc caagcagaga ctacagcagc tcttcaaggg gagccagttt    840

gccattcgct ggggctttat ccctcttgtg atttacctgg gatttaagag gggtgcagat    900

cccggaatgc ctgaaccaac tgttttgagc ctactttggg gataa                    945


<210> SEQ ID NO 94
<211> LENGTH: 314
<212> TYPE: PRT
<213> ORGANISM: Artificial sequence
<220> FEATURE:
<223> OTHER INFORMATION: Synthetic amino acid sequence of scFvPDL1-myc-
      TOM7

<400> SEQUENCE: 94

Met Asp Ile Val Met Ser Gln Ser Pro Ser Ser Leu Ala Val Ser Ala
1               5                   10                  15

Gly Glu Lys Val Thr Met Ser Cys Lys Ser Ser Gln Ser Leu Leu Asn
            20                  25                  30

Ser Arg Thr Arg Lys Asn Tyr Leu Ala Trp Tyr Gln Gln Lys Pro Gly
        35                  40                  45

Gln Ser Pro Lys Leu Leu Ile Tyr Trp Ala Ser Thr Arg Glu Ser Gly
    50                  55                  60

Val Pro Asp Arg Phe Thr Gly Ser Gly Ser Gly Thr Asp Phe Thr Leu
65                  70                  75                  80

Thr Ile Ser Ser Val Gln Ala Glu Asp Leu Ala Val Tyr Tyr Cys Gln
                85                  90                  95

Gln Ser Tyr Asp Val Val Thr Phe Gly Ala Gly Thr Lys Leu Glu Leu
            100                 105                 110

Lys Gly Gly Gly Gly Ser Gly Gly Gly Gly Ser Gly Gly Gly Gly Ser
        115                 120                 125

Gln Val Gln Val Gln Gln Ser Gly Ala Glu Leu Ala Glu Pro Gly Ala
    130                 135                 140

Ser Val Lys Met Ser Cys Lys Ala Ser Gly Tyr Ile Phe Thr Ser Tyr
145                 150                 155                 160

Trp Met His Trp Leu Lys Gln Arg Pro Gly Gln Gly Leu Glu Trp Ile
                165                 170                 175

Gly Tyr Ile Asn Pro Ser Ser Asp Tyr Asn Glu Tyr Ser Glu Lys Phe
            180                 185                 190

Met Asp Lys Ala Thr Leu Thr Ala Asp Lys Ala Ser Thr Thr Ala Tyr
        195                 200                 205

Met Gln Leu Ile Ser Leu Thr Ser Glu Asp Ser Ala Val Tyr Tyr Cys
    210                 215                 220

Ala Arg Ser Gly Trp Leu Val His Gly Asp Tyr Tyr Phe Asp Tyr Trp
225                 230                 235                 240

Gly Gln Gly Thr Thr Leu Thr Val Ser Ser Glu Gln Lys Leu Ile Ser
                245                 250                 255

Glu Glu Asp Leu Val Lys Leu Ser Lys Glu Ala Lys Gln Arg Leu Gln
            260                 265                 270

Gln Leu Phe Lys Gly Ser Gln Phe Ala Ile Arg Trp Gly Phe Ile Pro
        275                 280                 285

Leu Val Ile Tyr Leu Gly Phe Lys Arg Gly Ala Asp Pro Gly Met Pro
    290                 295                 300

Glu Pro Thr Val Leu Ser Leu Leu Trp Gly
305                 310
```

<210> SEQ ID NO 95
<211> LENGTH: 732
<212> TYPE: DNA
<213> ORGANISM: Artificial sequence
<220> FEATURE:
<223> OTHER INFORMATION: nucleotides sequence coding scFvHER2

<400> SEQUENCE: 95
atggaagtgc aacttgttga gagtggcgga ggactggtcc aaccgggcgg ttcacttagg 60
ctctcatgtg cagcttcagg gttcacgttc acggactata caatggactg ggtgaggcaa 120
gcccctggta agggactgga gtgggttgct gacgttaacc ctaattccgg tgggtccatc 180
tacaaccagc gattcaaggg acgatttact ctttcagtcg acagaagcaa aaacaccctc 240
tacctccaga tgaactcctt gcgggcagag gatacagcgg tctactattg cgcgagaaac 300
ttgggaccaa gcttctactt cgactactgg gggcaaggaa cgcttgttac ggtttcaagc 360
ggaggtggag gaagtggagg tggcggttcc ggcggtggcg gttcagatat acagatgacc 420
caatcaccca gttctcttag cgcgtctgta ggcgacaggg taaccataac ctgcaaggcg 480
tcccaggacg tgtcaattgg agttgcctgg tatcagcaaa aacctgggaa agctccgaag 540
ctcctgattt acagcgcatc ttaccgatat actggtgtcc cttcaaggtt cagtggcagt 600
ggatctggga cagactttac gcttactatc agcagtctgc aacctgagga tttcgcgacc 660
tactactgtc agcagtatta catctatccg tacacgttcg gtcaaggtac aaaggtagaa 720
ataaaacgca ct 732

<210> SEQ ID NO 96
<211> LENGTH: 244
<212> TYPE: PRT
<213> ORGANISM: Artificial sequence
<220> FEATURE:
<223> OTHER INFORMATION: amino acid sequence of scFvHER2

<400> SEQUENCE: 96

Met Glu Val Gln Leu Val Glu Ser Gly Gly Gly Leu Val Gln Pro Gly
1 5 10 15

Gly Ser Leu Arg Leu Ser Cys Ala Ala Ser Gly Phe Thr Phe Thr Asp
20 25 30

Tyr Thr Met Asp Trp Val Arg Gln Ala Pro Gly Lys Gly Leu Glu Trp
35 40 45

Val Ala Asp Val Asn Pro Asn Ser Gly Gly Ser Ile Tyr Asn Gln Arg
50 55 60

Phe Lys Gly Arg Phe Thr Leu Ser Val Asp Arg Ser Lys Asn Thr Leu
65 70 75 80

Tyr Leu Gln Met Asn Ser Leu Arg Ala Glu Asp Thr Ala Val Tyr Tyr
85 90 95

Cys Ala Arg Asn Leu Gly Pro Ser Phe Tyr Phe Asp Tyr Trp Gly Gln
100 105 110

Gly Thr Leu Val Thr Val Ser Ser Gly Gly Gly Gly Ser Gly Gly Gly
115 120 125

Gly Ser Gly Gly Gly Gly Ser Asp Ile Gln Met Thr Gln Ser Pro Ser
130 135 140

Ser Leu Ser Ala Ser Val Gly Asp Arg Val Thr Ile Thr Cys Lys Ala
145 150 155 160

Ser Gln Asp Val Ser Ile Gly Val Ala Trp Tyr Gln Gln Lys Pro Gly
165 170 175

Lys Ala Pro Lys Leu Leu Ile Tyr Ser Ala Ser Tyr Arg Tyr Thr Gly

```
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Tyr Tyr Ile Tyr Pro Tyr Thr Phe Gly Gln Gly Thr Lys Val Glu
225                 230                 235                 240

Ile Lys Arg Thr
```

<210> SEQ ID NO 97
<211> LENGTH: 927
<212> TYPE: DNA
<213> ORGANISM: Artificial sequence
<220> FEATURE:
<223> OTHER INFORMATION: nucleotides sequence coding scFvHER2-myc-TOM7

<400> SEQUENCE: 97

```
atggaagtgc aacttgttga gagtggcgga ggactggtcc aaccgggcgg ttcacttagg     60

ctctcatgtg cagcttcagg gttcacgttc acggactata caatggactg ggtgaggcaa    120

gcccctggta agggactgga gtgggttgct gacgttaacc ctaattccgg tgggtccatc    180

tacaaccagc gattcaaggg acgatttact ctttcagtcg acagaagcaa aaacaccctc    240

tacctccaga tgaactcctt gcgggcagag gatacagcgg tctactattg cgcgagaaac    300

ttgggaccaa gcttctactt cgactactgg gggcaaggaa cgcttgttac ggtttcaagc    360

ggaggtggag gaagtggagg tggcggttcc ggcggtggcg gttcagatat acagatgacc    420

caatcaccca gttctcttag cgcgtctgta ggcgacaggg taaccataac ctgcaaggcg    480

tcccaggacg tgtcaattgg agttgcctgg tatcagcaaa aacctgggaa agctccgaag    540

ctcctgattt acagcgcatc ttaccgatat actggtgtcc cttcaaggtt cagtggcagt    600

ggatctggga cagactttac gcttactatc agcagtctgc aacctgagga tttcgcgacc    660

tactactgtc agcagtatta catctatccg tacacgttcg gtcaaggtac aaaggtagaa    720

ataaaacgca ctgaacaaaa actcatctca gaagaggatc tggtgaagct gagcaaagag    780

gccaagcaga gactacagca gctcttcaag ggggagccagt ttgccattcg ctggggcttt    840

atccctcttg tgatttacct gggatttaag aggggtgcag atcccggaat gcctgaacca    900

actgttttga gcctactttg gggataa                                        927
```

<210> SEQ ID NO 98
<211> LENGTH: 308
<212> TYPE: PRT
<213> ORGANISM: Artificial sequence
<220> FEATURE:
<223> OTHER INFORMATION: amino acid sequence of scFvHER2-myc-TOM7

<400> SEQUENCE: 98

```
Met Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Thr Asp
            20                  25                  30

Tyr Thr Met Asp Trp Val Arg Gln Ala Pro Gly Lys Gly Leu Glu Trp
        35                  40                  45

Val Ala Asp Val Asn Pro Asn Ser Gly Gly Ser Ile Tyr Asn Gln Arg
    50                  55                  60

Phe Lys Gly Arg Phe Thr Leu Ser Val Asp Arg Ser Lys Asn Thr Leu
65                  70                  75                  80
```

```
Tyr Leu Gln Met Asn Ser Leu Arg Ala Glu Asp Thr Ala Val Tyr Tyr
                85                  90                  95

Cys Ala Arg Asn Leu Gly Pro Ser Phe Tyr Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Lys Ala
145                 150                 155                 160

Ser Gln Asp Val Ser Ile Gly Val Ala Trp Tyr Gln Gln Lys Pro Gly
                165                 170                 175

Lys Ala Pro Lys Leu Leu Ile Tyr Ser Ala Ser Tyr Arg Tyr Thr Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Tyr Tyr Ile Tyr Pro Tyr Thr Phe Gly Gln Gly Thr Lys Val Glu
225                 230                 235                 240

Ile Lys Arg Thr Glu Gln Lys Leu Ile Ser Glu Glu Asp Leu Val Lys
                245                 250                 255

Leu Ser Lys Glu Ala Lys Gln Arg Leu Gln Gln Leu Phe Lys Gly Ser
            260                 265                 270

Gln Phe Ala Ile Arg Trp Gly Phe Ile Pro Leu Val Ile Tyr Leu Gly
        275                 280                 285

Phe Lys Arg Gly Ala Asp Pro Gly Met Pro Glu Pro Thr Val Leu Ser
    290                 295                 300

Leu Leu Trp Gly
305
```

<210> SEQ ID NO 99
<211> LENGTH: 726
<212> TYPE: DNA
<213> ORGANISM: Artificial sequence
<220> FEATURE:
<223> OTHER INFORMATION: nucleotides sequence coding scFvMSLN

<400> SEQUENCE: 99

```
atgcaagtgc agctcgtcca gtctggggct gaggtgaaga ggcctggagc cagtgttcag     60

gtgtcctgcc gggcctctgg ctacagcatc aacacctact atatgcagtg ggtgcggcag    120

gcccctgggg ccggcctgga gtggatgggc gtcatcaatc ccagcggggt gacctcctat    180

gcccagaagt tccagggccg cgtgactctc accaatgaca ccagcaccaa cacagtctac    240

atgcagctga acagcctcac ttcagctgac acagctgtgt actactgtgc ccgctgggcc    300

ctgtggggag actttggcat ggatgtgtgg ggcaagggca ctctggtgac agtgagcagt    360

ggagggggcg gcagcggtgg cggtggaagt ggcggaggag gcagtgacat ccagatgacc    420

cagagcccct ccacactgtc tgcttccatc ggggacagag tcaccatcac ctgccgcgcc    480

agcgagggca tctaccactg gctggcctgg taccagcaga aaccaggaaa agcccccaag    540

ctgctgattt acaaggcctc ctccctggct tcaggcgccc caagccgctt cagcggctcc    600

ggctctggaa cagacttcac cctgacaatc agcagcctgc agccagatga ttttgccacc    660

tattactgcc agcagtactc caactacccc ctgaccttcg gcgggggcac caagttggag    720
```

atcaag 726

<210> SEQ ID NO 100
<211> LENGTH: 242
<212> TYPE: PRT
<213> ORGANISM: Artificial sequence
<220> FEATURE:
<223> OTHER INFORMATION: amino acid sequence of scFvMSLN

<400> SEQUENCE: 100

Met Gln Val Gln Leu Val Gln Ser Gly Ala Glu Val Lys Arg Pro Gly
1 5 10 15

Ala Ser Val Gln Val Ser Cys Arg Ala Ser Gly Tyr Ser Ile Asn Thr
20 25 30

Tyr Tyr Met Gln Trp Val Arg Gln Ala Pro Gly Ala Gly Leu Glu Trp
35 40 45

Met Gly Val Ile Asn Pro Ser Gly Val Thr Ser Tyr Ala Gln Lys Phe
50 55 60

Gln Gly Arg Val Thr Leu Thr Asn Asp Thr Ser Thr Asn Thr Val Tyr
65 70 75 80

Met Gln Leu Asn Ser Leu Thr Ser Ala Asp Thr Ala Val Tyr Tyr Cys
85 90 95

Ala Arg Trp Ala Leu Trp Gly Asp Phe Gly Met Asp Val Trp Gly Lys
100 105 110

Gly Thr Leu Val Thr Val Ser Ser Gly Gly Gly Gly Ser Gly Gly Gly
115 120 125

Gly Ser Gly Gly Gly Gly Ser Asp Ile Gln Met Thr Gln Ser Pro Ser
130 135 140

Thr Leu Ser Ala Ser Ile Gly Asp Arg Val Thr Ile Thr Cys Arg Ala
145 150 155 160

Ser Glu Gly Ile Tyr His Trp Leu Ala Trp Tyr Gln Gln Lys Pro Gly
165 170 175

Lys Ala Pro Lys Leu Leu Ile Tyr Lys Ala Ser Ser Leu Ala Ser Gly
180 185 190

Ala Pro Ser Arg Phe Ser Gly Ser Gly Ser Gly Thr Asp Phe Thr Leu
195 200 205

Thr Ile Ser Ser Leu Gln Pro Asp Asp Phe Ala Thr Tyr Tyr Cys Gln
210 215 220

Gln Tyr Ser Asn Tyr Pro Leu Thr Phe Gly Gly Gly Thr Lys Leu Glu
225 230 235 240

Ile Lys

<210> SEQ ID NO 101
<211> LENGTH: 921
<212> TYPE: DNA
<213> ORGANISM: Artificial sequence
<220> FEATURE:
<223> OTHER INFORMATION: nucleotides sequence coding scFvMSLN-myc-TOM7

<400> SEQUENCE: 101
atgcaagtgc agctcgtcca gtctggggct gaggtgaaga ggcctggagc cagtgttcag 60
gtgtcctgcc gggcctctgg ctacagcatc aacacctact atatgcagtg ggtgcggcag 120
gcccctgggg ccggcctgga gtggatgggc gtcatcaatc ccagcggggt gacctcctat 180
gcccagaagt tccagggccg cgtgactctc accaatgaca ccagcaccaa cacagtctac 240
atgcagctga acagcctcac ttcagctgac acagctgtgt actactgtgc ccgctgggcc 300

```
ctgtggggag actttggcat ggatgtgtgg ggcaagggca ctctggtgac agtgagcagt    360

ggagggggcg gcagcggtgg cggtggaagt ggcggaggag gcagtgacat ccagatgacc    420

cagagcccct ccacactgtc tgcttccatc ggggacagag tcaccatcac ctgccgcgcc    480

agcgagggca tctaccactg gctggcctgg taccagcaga aaccaggaaa agcccccaag    540

ctgctgattt acaaggcctc ctccctggct tcaggcgccc caagccgctt cagcggctcc    600

ggctctggaa cagacttcac cctgacaatc agcagcctgc agccagatga ttttgccacc    660

tattactgcc agcagtactc caactacccc ctgaccttcg gcgggggcac caagttggag    720

atcaaggaac aaaaactcat ctcagaagag gatctggtga agctgagcaa agaggccaag    780

cagagactac agcagctctt caaggggagc cagtttgcca ttcgctgggg ctttatccct    840

cttgtgattt acctgggatt taagaggggt gcagatcccg gaatgcctga accaactgtt    900

ttgagcctac tttggggata a                                              921
```

<210> SEQ ID NO 102
<211> LENGTH: 306
<212> TYPE: PRT
<213> ORGANISM: Artificial sequence
<220> FEATURE:
<223> OTHER INFORMATION: amino acid sequence of scFvMSLN-myc-TOM7

<400> SEQUENCE: 102

```
Met Gln Val Gln Leu Val Gln Ser Gly Ala Glu Val Lys Arg Pro Gly
1               5                   10                  15

Ala Ser Val Gln Val Ser Cys Arg Ala Ser Gly Tyr Ser Ile Asn Thr
            20                  25                  30

Tyr Tyr Met Gln Trp Val Arg Gln Ala Pro Gly Ala Gly Leu Glu Trp
        35                  40                  45

Met Gly Val Ile Asn Pro Ser Gly Val Thr Ser Tyr Ala Gln Lys Phe
    50                  55                  60

Gln Gly Arg Val Thr Leu Thr Asn Asp Thr Ser Thr Asn Thr Val Tyr
65                  70                  75                  80

Met Gln Leu Asn Ser Leu Thr Ser Ala Asp Thr Ala Val Tyr Tyr Cys
                85                  90                  95

Ala Arg Trp Ala Leu Trp Gly Asp Phe Gly Met Asp Val Trp Gly Lys
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Thr Leu Ser Ala Ser Ile Gly Asp Arg Val Thr Ile Thr Cys Arg Ala
145                 150                 155                 160

Ser Glu Gly Ile Tyr His Trp Leu Ala Trp Tyr Gln Gln Lys Pro Gly
                165                 170                 175

Lys Ala Pro Lys Leu Leu Ile Tyr Lys Ala Ser Ser Leu Ala Ser Gly
            180                 185                 190

Ala Pro Ser Arg Phe Ser Gly Ser Gly Ser Gly Thr Asp Phe Thr Leu
        195                 200                 205

Thr Ile Ser Ser Leu Gln Pro Asp Asp Phe Ala Thr Tyr Tyr Cys Gln
    210                 215                 220

Gln Tyr Ser Asn Tyr Pro Leu Thr Phe Gly Gly Gly Thr Lys Leu Glu
225                 230                 235                 240

Ile Lys Glu Gln Lys Leu Ile Ser Glu Glu Asp Leu Val Lys Leu Ser
```

-continued

```
            245                 250                 255

Lys Glu Ala Lys Gln Arg Leu Gln Gln Leu Phe Lys Gly Ser Gln Phe
        260                 265                 270

Ala Ile Arg Trp Gly Phe Ile Pro Leu Val Ile Tyr Leu Gly Phe Lys
        275                 280                 285

Arg Gly Ala Asp Pro Gly Met Pro Glu Pro Thr Val Leu Ser Leu Leu
    290                 295                 300

Trp Gly
305
```

MITOCHONDRIA COMPRISING ANTICANCER DRUG AND USE THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 730210_408USPC_SEQUENCE_LISTING.txt. The text file is 145,517 bytes, was created on Mar. 27, 2022, and is being submitted electronically via EFS-Web.

TECHNICAL FIELD

The present invention provides a compound capable of modifying mitochondrion, mitochondrion containing the compound, and a pharmaceutical composition comprising the same as an active ingredient.

BACKGROUND ART

Mitochondria are cellular organelles of eukaryotic cells involved in the synthesis and regulation of adenosine triphosphate (ATP), an intracellular energy source. Mitochondria are associated with various metabolic pathways in vivo, for example, cell signaling, cell differentiation, cell death, as well as control of cell cycle and cell growth. Mitochondria have their own genomes and are organelles that play a central role in the energy metabolism of cells. Mitochondria produce energy through the electron transport and oxidative phosphorylation process, and play an important role in being involved in apoptosis signaling pathways.

It has been reported that a reduction in energy production due to a decrease in mitochondrial function causes various diseases. When the function of the electron transport chain reaction decreases according to the variation of the mitochondria genome and proteome, a reduction in ATP production, an excessive production of the reactive oxygen species, a decrease in calcium regulation function and the like occur. In this case, a change in the membrane permeability of the mitochondria occurs, and the function of apoptosis may occur abnormally and lead to cancer and incurable diseases.

As such, human diseases that have been reported to result from mitochondrial dysfunction include mitochondria related genetic disease, diabetes mellitus, heart disease, senile dementia such as Parkinson's disease or Alzheimer's disease, and the occurrence of various cancers and cancer metastasis and the like. In addition, features commonly found in more than 200 types of various cancers consisted of impaired apoptosis function, increased inflammatory response, and increased abnormal metabolism. All of these processes are closely related to mitochondrial function, and the correlation between cancer and mitochondria is drawing attention.

On the other hand, it is known that normal cells produce 36 ATP per molecule of glucose through an electron transport system process, but cancer cells, unlike normal cells, produce 2 ATP per molecule of glucose through glycolysis under a sufficient oxygen condition (aerobic glycolysis). As such, it is known that cancer cells, unlike normal cells, use the inefficient glycolysis process in terms of energy in order to produce amino acids, lipids, nucleic acids and the like necessary for rapid cell proliferation. For this reason, it is known that cancer cells require less oxygen and produce a larger amount of lactic acid than normal cells.

Therefore, a change in the composition of the cancer microenvironment due to abnormal metabolism occurring in cancer cells, an inhibition of apoptosis caused by dysfunctional mitochondria, and an increase in inflammatory response, and abnormal metabolic reaction in cancer cells play a very important role in cancer proliferation. Thus, developing metabolism-related anticancer agents using these features may be a good way capable of solving the side effects and economic problems of conventional anticancer agents. On the other hand, recent attempts to directly administer or develop mitochondria as drugs have been made (Korean Patent Registration No. 10-2111321).

DETAILED DESCRIPTION OF INVENTION

Technical Problem

Accordingly, the present inventors completed the present invention by confirming that mitochondria have an excellent anticancer effect when used in combination with a conventionally used anticancer agent in the process of studying the anticancer activity of mitochondria.

Solution to Problem

In one aspect of the present invention, there is provided mitochondrion containing an anticancer agent and a pharmaceutical composition for the prevention or treatment of cancer comprising the same.

In another aspect of the present invention, there is provided a method for preparing mitochondrion containing an anticancer agent, comprising mixing the anticancer agent and the isolated mitochondrion.

In another aspect of the present invention, there is provided a modified anticancer agent to which TPP is chemically bound.

In another aspect of the present invention, there is provided a method for preventing or treating cancer, comprising administering a pharmaceutical composition comprising mitochondrion containing an anticancer agent to a subject.

Effects of the Invention

It was confirmed that the mitochondrion containing the compound having the anticancer efficacy according to the present invention efficiently deliver the compound to the tumor, and the anticancer effect of the mitochondrion containing the compound was confirmed. In particular, when an antibody or a fragment thereof that specifically binds to a tumor is bound to the surface of mitochondria, the compound may be delivered specifically to the tumor. Therefore, the mitochondrion containing the compound according to the present invention may be effectively used for the treatment of cancer because the side effects of the compound are few.

BRIEF DESCRIPTION OF DRAWINGS

FIG. 23 is a view showing the results of confirming the $IC_{50}$ value of DOX or DOX_$MT^{\alpha\text{-}HER2scFv}$ in the human breast cancer cell line (SK-BR-3, BT-474 and MDA-MB-231), the human lung cancer cell line (NCI-H1975), the human gastric cancer cell line (NCI-N87 and MKN-74) and the human lung fibroblast cell line (WI-38 and CCD-8Lu).

FIG. 37 is a view showing the results of confirming the $IC_{50}$ value of TPP-DOX and TPP-DOX_$MT^{\alpha\text{-}HER2scFv}$ in the human breast cancer cell line (SK-BR-3, BT-474 and MDA-MB-231), the human lung cancer cell line (NCI-H1975), the human gastric cancer cell line (NCI-N87 and MKN-74) and the human lung fibroblast cell line (WI-38 and CCD-8Lu).

BEST MODE FOR CARRYING OUT THE INVENTION

Mitochondrion Containing Anticancer Agent

Figure 1:
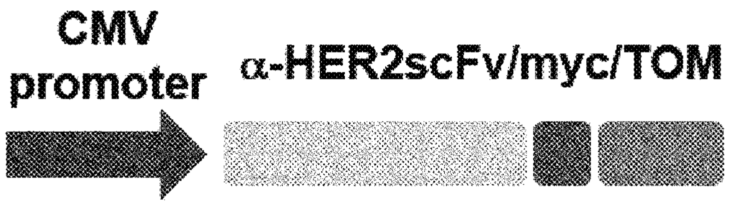
FIG. 1 is a view schematically showing an expression vector for expressing a single chain variable region fragment of an anti-HER2 antibody in a form fused to the mitochondria.

In one aspect of the present invention, there is provided mitochondrion containing an anticancer agent. In addition, in another aspect of the present invention, there is provided a pharmaceutical composition for the prevention or treatment of cancer comprising the mitochondrion containing an anticancer agent as an active ingredient.

As used herein, the term "mitochondrion" is a cellular organelle of eukaryotic cells involved in the synthesis and regulation of adenosine triphosphate (ATP), an intracellular energy source. Mitochondria are associated with various metabolic pathways in vivo, for example, cell signaling, cell differentiation, cell death, as well as control of cell cycle and cell growth. Therefore, it has been reported that mitochondrial hypofunction or dysfunction due to genetic, environmental, or unknown causes is related to the occurrence of mitochondria related genetic disease, inflammatory diseases such as rheumatoid arthritis, ischemic diseases, infectious diseases, heart diseases, muscle disease, degenerative diseases such as Parkinson's disease or Alzheimer's disease, etc. and the development of various diseases such as carcinogenesis and cancer metastasis.

The mitochondrion may be obtained from eukaryotes, and may be obtained from mammals or humans. Specifically, the mitochondrion may be isolated from cells or tissues. For example, the mitochondrion may be obtained from somatic cells, germ cells, or stem cells, and may be isolated from blood cells or platelets. In addition, the mitochondrion may be isolated after disruption by concentrating the tissues or cells, or may be isolated after disruption from a tissue or cell sample thawed after freezing and storage.

Specifically, the somatic cells may be muscle cells, hepatocytes, nerve cells, fibroblasts, epithelial cells, adipocytes, osteocytes, leukocytes, lymphocytes, platelets, or mucosal cells.

In addition, the stem cells are undifferentiated cells having the ability to differentiate into various types of tissue cells, and may be any one selected from the group consisting of mesenchymal stem cells, adult stem cells, induced pluripotent stem cells, embryonic stem cells, bone marrow stem cells, neural stem cells, limbal stem cells, and tissue-derived stem cell, but are not limited thereto. In this case, the mesenchymal stem cells may be obtained from any one selected from the group consisting of umbilical cord, umbilical cord blood, bone marrow, fat, muscle, nerve, skin, synovial fluid, testis, amniotic membrane and placenta.

In addition, the mitochondrion may be isolated by culturing cells or tissues in vitro, or may be isolated from a sample thawed after freezing and storage.

In addition, the mitochondrion may be obtained from an autologous, allogenic, or xenogenic subject. Specifically, the autologous mitochondrion refers to mitochondrion obtained from tissues or cells of the same subject. In addition, the allogenic mitochondrion refers to mitochondrion obtained from a subject that belongs to the same species as the subject and has different genotypes for alleles. In addition, the xenogenic mitochondrion refer to mitochondrion obtained from a subject that belongs to the different species from the subject.

In addition, the mitochondrion may be mitochondrion isolated from cells. In addition, the mitochondrion may be intact and have mitochondrial activity.

On the other hand, when the mitochondria are isolated from specific cells, the mitochondria may be isolated through a variety of modified methods, including various known methods, for example, using a specific buffer solution or using a potential difference and a magnetic field and the like.

The mitochondrial isolation may be obtained by disrupting cells and centrifuging in terms of maintaining mitochondrial activity.

In this case, an anticancer agent may be present in the outer membrane of the mitochondrion. Specifically, the anticancer agent may be located between the outer membrane and the inner membrane. In addition, the anticancer agent may be located in cristae. It may also be present in a matrix inside the inner membrane.

In addition, the mitochondrion may be modified mitochondrion. In this case, the modified mitochondrion may be one in which an antibody or a fragment thereof specifically binding to a tumor-associated antigen (TAA) is present on the surface of a cell.

In this case, the tumor-associated antigen may be any one selected from the group consisting of CD19, CD20, melanoma antigen E (MAGE), NY-ESO-1, carcinoembryonic antigen (CEA), mucin 1 cell surface associated (MUC-1), prostatic acid phosphatase (PAP), prostate specific antigen (PSA), survivin, tyrosine related protein 1 (tyrp1), tyrosine related protein 2 (tyrp2), Brachyury, Mesothelin, Epidermal growth factor receptor (EGFR), human epidermal growth factor receptor 2 (HER-2), ERBB2, Wilms tumor protein (WT1), FAP, EpCAM, PD-L1, ACPP, CPT1A, IFNG, CD274, FOLR1, EPCAM, ICAM2, NCAM1, LRRC4, UNC5H2 LILRB2, CEACAM, MSLN, Nectin-3 and a combination thereof, but is not limited to the above types.

As used herein, the term "cancer" is classified as a disease in which normal tissue cells proliferate unrestrictedly for some reason and continue to grow rapidly regardless of the living phenomenon of the living body or the surrounding tissue condition. In the present invention, cancer may be any one cancer selected from the group consisting of various cancers of the human body, such as breast cancer, lung cancer, pancreatic cancer, glioblastoma, gastric cancer, liver cancer, colorectal cancer, prostate cancer, ovarian cancer, cervical cancer, thyroid cancer, laryngeal cancer, acute myeloid leukemia, brain tumor, neuroblastoma, retinoblastoma, head and neck cancer, salivary gland cancer and lymphoma, but is not limited to the above types.

As used herein, the term "anticancer agent" is a drug used to inhibit the proliferation of cancer cells. In the present invention, the anticancer agent may be selected from the group consisting of a chemical anticancer agent, a target anticancer agent and an anthelmintic agent, but is not limited thereto.

Specifically, the "chemical anticancer agent" may be any one selected from the group consisting of an alkylating agent, a microtuble inhibitor, an antimetabolite and a topoisomerase inhibitor, but is not limited thereto.

The alkylating agent may be any one selected from the group consisting of mechlorethamine, cyclophosphamide, ifosfamide, melphalan, chlorambucil, thiotepa, altretamine, procarbazine, busulfan, streptozocin, carmustine, iomustine, dacarbazine, cisplatin, carboplatin and oxaliplatin, but is not limited thereto. The microtuble inhibitor may be any one selected from the group consisting of docetaxel, vinblastine, oncovin and vinorelbine, but is not limited thereto. The antimetabolite may be any one selected from the group consisting of fluorouracil, capecitabine, cytarabine, gemcitabine, fludarabine, methotrexate, pemetrexed and mercaptopurine, but is not limited thereto. The topoisomerase inhibitor may be any one selected from the group consisting of doxorubicin, hycamtin, camptosar, vepesid, taxol, bleomycin, adriamycin and cerubidine, but is not limited thereto.

In addition, the "target anticancer agent" may be a compound that regulates a specific target biomarker. For example, the target anticancer agent may be any one selected from the group consisting of compounds targeting BTK, Bcr-abl, EGFR, PDGFR/VEGFR/FGFR family, MEK/RAF, HER2/Neu, CDK, ubiquitin, JAK, MAP2K, ALK, PARP, TGFβRI, Proteasome, Bcl-2, Braf, C-Met, VR1, VR2, VR3, c-kit, AXL and RET, but is not limited thereto.

One embodiment of the compound among the target anticancer agents may be ibrutinib, which targets BTK. In addition, it may be dasatinib, nilotinib, imatinib or bosutinib, which targets Bcr-abl. In addition, it may be osimertinib, erlotinib or gefitinib, which targets EGFR, but is not limited thereto. In addition, it may be nintedanib, sunitinib, sorafenib, cabozantinib, lenvatinib, regorafenib, masitinib, semaxanib, tivozanib, vandetanib, axitinib, or pazopanib, which targets PDGFR/VEGFR/FGFR family, but is not limited thereto. In addition, it may be trametinib/dabrafenib, which targets MEK/RAF, but is not limited thereto.

In addition, it may be afatinib, lapatinib or neratinib, which targets HER2/Neu, but is not limited thereto. In addition, it may be abemaciclib or palbociclib, which targets CDK, but is not limited thereto. In addition, it may be lenalidomide, which targets ubiquitin, but is not limited thereto. In addition, it may be ruxolitinib, lestaurtinib or pacritinib, which targets JAK, but is not limited thereto. In addition, it may be cobimethinib, selumetinib, trametinib or binimetinib, which targets MAP2K, but is not limited thereto. In addition, it may be alectinib or crizotinib, which targets ALK, but is not limited thereto. In addition, it may be olaparib, which targets PARP, but is not limited thereto. In addition, it may be galunisertib, which targets TGFβRI, but is not limited thereto. In addition, it may be ixazomib, which targets Proteasome, but is not limited thereto. In addition, it may be venetoclax, which targets Bcl-2, but is not limited thereto. In addition, it may be vemurafenib, which targets Braf, but is not limited thereto.

In addition, the "anthelmintic agent" may be any one selected from the group consisting of an OXPHOS (oxidative phosphorylation) inhibitor, a glycolysis inhibitor, a glycolysis related indirect inhibitor, a PPP (pentose phosphate pathway) inhibitor and an autophagy inhibitor, but is not limited thereto. Specifically, the anthelmintic agent may be any one selected from the group consisting of pyrvinium, niclosamide, nitazoxanide, ivermectin, fenbendazole, nitazoxanide and albendazole, but is not limited thereto.

Modified Mitochondrion

The modified mitochondrion refers to mitochondrion in which a foreign protein is bound to the outer membrane of the mitochondrion. In this case, the modified mitochondrion may be disclosed in Korean Patent Application Publication No. 10-2019-0048279.

As used herein, the term "foreign protein" refers to a protein that includes a target protein capable of functioning inside and outside the cell. In this case, the foreign protein is a protein that does not exist in the mitochondrion and may be a recombinant protein. Specifically, the foreign protein may comprise a mitochondrial anchoring peptide and a target protein. In addition, the foreign protein may be a recombinant fusion protein comprising a mitochondrial anchoring peptide and a target protein. In this case, the foreign protein may comprise a mitochondrial anchoring peptide. Preferably, the mitochondrial anchoring peptide may be a peptide that may be located on the mitochondrial outer membrane. Therefore, the foreign protein may be bound to the outer membrane of the mitochondrion by a mitochondrial anchoring peptide. The mitochondrial anchoring peptide may be a peptide comprising an N terminal region or a C terminal region of a protein present in a mitochondrial membrane protein, and the N terminal region or the C terminal region of a protein present in the outer membrane of the mitochondrial protein may be located on the outer membrane of the mitochondria. In this case, the anchoring peptide may further comprise a mitochondrial signal sequence.

One embodiment of the protein present in a mitochondrial membrane protein may be any one selected from the group consisting of TOM20, TOM70, OM45, TOM5, TOM6, TOM7, TOM22, Fis1, Bcl-2, Bcl-x and VAMPIB. In particular, when the mitochondrial anchoring peptide is derived from any one selected from the group consisting of TOM20, TOM70 and OM45, it may comprise the N terminal region of TOM20, TOM70 or OM45. One embodiment of the mitochondrial anchoring peptide may be TOM70 derived from yeast represented by SEQ ID NO: 75, or TOM70 derived from human represented by SEQ ID NO: 76. Another embodiment may be TOM20 derived from yeast represented by SEQ ID NO: 77, or TOM20 derived from human represented by SEQ ID NO: 78. Another embodiment may be OM45 derived from yeast represented by SEQ ID NO: 79.

In addition, when the mitochondrial anchoring peptide is derived from any one selected from the group consisting of TOM5, TOM6, TOM7, TOM22, Fis1, Bcl-2, Bcl-x and VAMPIB, it may comprise the C terminal region of any one selected from the group consisting of TOM5, TOM6, TOM7, TOM22, Fis1, Bcl-2, Bcl-x and VAMPIB. One embodiment of the mitochondrial anchoring peptide may be TOM5 derived from yeast represented by SEQ ID NO: 80 or TOM5 derived from human represented by SEQ ID NO: 81. Another embodiment may be TOM7 derived from yeast represented by SEQ ID NO: 82, or TOM7 derived from human represented by SEQ ID NO: 83. Another embodiment may be TOM22 derived from yeast represented by SEQ ID NO: 84, or TOM22 derived from human represented by SEQ ID NO: 85. Another embodiment may be Fis1 derived from yeast represented by SEQ ID NO: 86, or Fis1 derived from human represented by SEQ ID NO: 87. Another embodiment may be Bcl-2 alpha derived from human represented by SEQ ID NO: 88. Another embodiment may be VAMP1 derived from yeast represented by SEQ ID NO: 89, or VAMP1 derived from human represented by SEQ ID NO: 90.

In this case, a target protein capable of functioning inside and outside the cell included in the foreign protein may be any one selected from the group consisting of an active protein exhibiting an activity in a cell, a protein present in a cell, and a protein having the ability to bind to a ligand or receptor present in a cell membrane.

An embodiment of the active protein or the protein present in a cell may be any one selected from the group consisting of p53, Granzyme B, Bax, Bak, PDCD5, E2F, AP-1 (Jun/Fos), EGR-1, Retinoblastoma (RB), phosphatase and tensin homolog (PTEN), E-cadherin, Neurofibromin-2 (NF-2), poly[ADP-ribose] synthase 1 (PARP-1), BRCA-1, BRCA-2, Adenomatous polyposis coli (APC), Tumor necrosis factor receptor-associated factor (TRAF), RAF kinase inhibitory protein (RKIP), p16, KLF-10, LKB1, LHX6, C-RASSF, DKK-3PD1, Oct3/4, Sox2, Klf4, and c-Myc. When the target protein is selected from the above group, the target protein may be bound to an anchoring peptide comprising the N terminal region of TOM20, TOM70 or OM45.

Such fusion protein may be bound in the following order:

N terminus-anchoring peptide comprising the N terminal region of TOM20, TOM70 or OM45-target protein-C terminus.

In addition, the foreign protein may further comprise an amino acid sequence recognized by a proteolytic enzyme in eukaryotic cells, or ubiquitin or a fragment thereof between a mitochondrial anchoring peptide and a target protein. The proteolytic enzyme in eukaryotic cells refers to an enzyme that degrades a protein present in eukaryotic cells. In this case, because a foreign protein comprises an amino acid sequence recognized by the enzyme that degrades the protein, the foreign protein bound to the mitochondrial outer membrane may be isolated into an anchoring peptide and a target protein in a cell.

In this case, the ubiquitin fragment may comprise the C terminal Gly-Gly of an amino acid sequence of SEQ ID NO: 71, and may comprise 3 to 75 amino acids consecutive from the C terminus. In addition, the foreign protein may further comprise a linker between a target protein and ubiquitin or a fragment thereof. In this case, the linker may be composed of 1 to 150 amino acids, or be composed of 10 to 100 amino acids, or be composed of 20 to 50 amino acids, but is not limited thereto. The linker may be composed of amino acids that are appropriately selected from 20 amino acids, preferably be composed of glycine and/or serine. One embodiment of the linker may be composed of 5 to 50 amino acids consisting of glycine and serine. One embodiment of the linker may be (G4S)n, in which n is an integer of 1 to 10, and n may be 1, 2, 3, 4, 5, 6, 7, 8, 9, or 10.

In addition, the protein having the ability to bind to a ligand or receptor present in a cell membrane may be a ligand or receptor present on the surface of a tumor cell. In this case, the ligand or receptor present on the surface of a tumor cell may be, but is not limited to, any one selected from the group consisting of CD19, CD20, melanoma antigen E (MAGE), NY-ESO-1, carcinoembryonic antigen (CEA), mucin 1 cell surface associated (MUC-1), prostatic acid phosphatase (PAP), prostate specific antigen (PSA), survivin, tyrosine related protein 1 (tyrp1), tyrosine related protein 2 (tyrp2), Brachyury, Mesothelin, Epidermal growth factor receptor (EGFR), human epidermal growth factor receptor 2 (HER-2), ERBB2, Wilms tumor protein (WT1), FAP, EpCAM, PD-L1, ACPP, CPT1A, IFNG, CD274, FOLR1, EPCAM, ICAM2, NCAM1, LRRC4, UNC5H2 LILRB2, CEACAM, Nectin-3 and a combination thereof.

In addition, the protein having the ability to bind to a ligand or receptor present in a cell membrane may be an antibody or a fragment thereof that binds to any one selected from the above group. In particular, a fragment of an antibody refers to a fragment having the same complementarity determining region (CDR) as that of the antibody. Specifically, it may be Fab, scFv, $F(ab')_2$ or a combination thereof.

In this case, the target protein may be bound to an anchoring peptide comprising an C terminal region of any one selected from the group consisting of TOM5, TOM6, TOM7, TOM22, Fis1, Bcl-2, Bcl-x and VAMPIB, and the foreign protein may be bound in the following order: N terminus-target protein-anchoring peptide comprising a C terminal region of any one selected from the group consisting of TOM5, TOM6, TOM7, TOM22, Fis1, Bcl-2, Bcl-x and VAMP1B-C terminus.

In addition, the foreign protein may further comprise a linker between a target protein and a C terminal region of any one selected from the group consisting of TOM5, TOM6, TOM7, TOM22, Fis1, Bcl-2, Bcl-x and VAMPIB. In this case, a linker is as described above. In this case, a target protein, an active protein, a protein present in a cell, and a protein having the ability to bind to a ligand or receptor present in a cell membrane and the like are as described above.

In one embodiment of the target protein, an antibody or a fragment thereof targeting a specific cell may be in a form bound to the anchoring peptide comprising the C terminal region of any one selected from the group consisting of TOM5, TOM6, TOM7, TOM22, Fis1, Bcl-2, Bcl-x and VAMPIB. The modified mitochondrion to which the target protein is bound may be easily introduced into a specific target, so that the mitochondrion may be efficiently entered into a specific cell.

One embodiment of the modified mitochondrion may be in a form to which one or more target proteins are bound. Specifically, it may be in a form to which a target protein comprising p53 and a target protein comprising anti-HER-2 antibody or a fragment thereof are bound. Such modified mitochondrion may effectively deliver the mitochondrion into cancer cells expressing HER-2. In addition, cancer cells may be effectively killed by p53 bound to the modified mitochondrion.

Depending on the purpose of the modified mitochondrion, a target protein comprising one or more active proteins may be constructed and be allowed to be bound to the mitochondrion. In addition, a target protein targeting a cell may be constructed in various ways depending on the targeted cell.

The fusion protein comprising the mitochondrial outer membrane targeting protein and the target protein may be referred to as a fusion protein that modifies the mitochondrial activity.

Such fusion protein may have any one of the following structures:

N terminus-mitochondrial outer membrane anchoring peptide-target protein-C terminus <Structural Formula 1>

N terminus-mitochondrial outer membrane anchoring peptide-ubiquitin or fragment thereof-target protein-C terminus <Structural Formula 2>

N terminus-mitochondrial outer membrane targeting peptide-linker 1-ubiquitin or fragment thereof-target protein-C terminus <Structural Formula 3>

N terminus-mitochondrial outer membrane anchoring peptide-ubiquitin or fragment thereof-linker 2-target protein-C terminus <Structural Formula 4>

N terminus-mitochondrial outer membrane anchoring peptide-linker 1-ubiquitin or fragment thereof-linker 2-target protein-C terminus <Structural Formula 5>

In the above Structural Formulae 1 to 5, the outer membrane anchoring peptide may be a terminal sequence of a protein selected from the group consisting of TOM20, TOM70 and OM45, and the target protein may be any one selected from the group consisting of p53, Granzyme B, Bax, Bak, PDCD5, E2F, AP-1 (Jun/Fos), EGR-1, Retinoblastoma (RB), phosphatase and tensin homolog (PTEN), E-cadherin, Neurofibromin-2 (NF-2), poly[ADP-ribose] synthase 1 (PARP-1), BRCA-1, BRCA-2, Adenomatous polyposis coli (APC), Tumor necrosis factor receptor-associated factor (TRAF), RAF kinase inhibitory protein (RKIP), p16, KLF-10, LKB1, LHX6, C-RASSF and DKK-3PD1.

In this case, the linker 1 or 2 may be a polypeptide composed of 1 to 100, 1 to 80, 1 to 50, or 1 to 30 amino acids, respectively, and may be preferably a polypeptide composed of 1 to 30 amino acids that consist of serine, glycine or threonine alone or in combination. In addition, the linker 1 or 2 may be a polypeptide composed of 5 to 15 amino acids, respectively, and may be preferably a polypeptide composed of 5 to 15 amino acids that consist of serine, glycine or threonine alone or in combination. One embodiment of the linker may be (GGGGS)3 (SEQ ID NO: 70).

N terminus-target protein-mitochondrial outer membrane anchoring peptide-C terminus <Structural Formula 6>

N terminus-target protein-ubiquitin or fragment thereof-mitochondrial outer membrane anchoring peptide-C terminus <Structural Formula 7>

N terminus-target protein-linker 1-ubiquitin or fragment thereof-mitochondrial outer membrane anchoring peptide-C terminus <Structural Formula 8>

N terminus-target protein-ubiquitin or fragment thereof-linker 2-mitochondrial outer membrane anchoring peptide-C terminus <Structural Formula 9>

N terminus-target protein-linker 1-ubiquitin or fragment thereof-linker 2-mitochondrial outer membrane targeting peptide-C terminus <Structural Formula 10>

In the above Structural Formulae 6 to 10, the outer membrane anchoring peptide may be a terminal sequence of a protein selected from the group consisting of TOM5, TOM6, TOM7, TOM22, Fis1, Bcl-2, Bcl-X, and VAMPIB, and the target protein may be any one selected from the group consisting of p53, Granzyme B, Bax, Bak, PDCD5, E2F, AP-1 (Jun/Fos), EGR-1, Retinoblastoma (RB), phosphatase and tensin homolog (PTEN), E-cadherin, Neurofibromin-2 (NF-2), poly[ADP-ribose] synthase 1 (PARP-1), BRCA-1, BRCA-2, Adenomatous polyposis coli (APC), Tumor necrosis factor receptor-associated factor (TRAF), RAF kinase inhibitory protein (RKIP), p16, KLF-10, LKB1, LHX6, C-RASSF, DKK-3PD1, Oct3/4, Sox2, Klf4, and c-Myc. In this case, the linker 1 or 2 is as described above.

For the pharmaceutical composition, the mitochondrion may be included at a concentration of about 0.1 μg/mL to about 500 μg/mL, about 0.2 μg/mL to about 450 μg/mL, or about 0.5 μg/mL to about 400 μg/mL, but is not limited thereto. The inclusion of the mitochondria in the above range may facilitate the dose adjustment of mitochondria upon administration and may enhance the degree of improvement of the symptoms of a disease of a patient. In this case, the dose of mitochondria may be determined through the quantification of mitochondria by quantifying the membrane protein of the isolated mitochondria. Specifically, the isolated mitochondria may be quantified through the Bradford protein assay.

In addition, for the pharmaceutical composition, an anticancer agent binding to mitochondrion may be included at a concentration of 0.1 μg/mL to 500 μg/mL, 0.2 μg/mL to 450 μg/mL, or 0.5 μg/mL to 400 μg/mL, but is not limited thereto. The inclusion of the anticancer agent in the above range may facilitate the dose adjustment of the anticancer agent upon administration and may enhance the degree of improvement of the symptoms of a disease of a patient.

The anticancer agent binding to mitochondrion may be included in an amount of about 0.01 μg to 1 μg, about 0.05 μg to 0.5 μg, or about 0.1 μg to 0.3 μg per 1 μg of mitochondria. Preferably, it may be included in an amount of about 0.2 μg.

The anticancer agent and the mitochondrion may be mixed in an appropriate ratio so the anticancer agent may be contained in the mitochondrion. For example, the mixing ratio of the anticancer agent and the mitochondrion based on a weight ratio may be a weight ratio of about 1:10 to about 10:1, about 1:9 to about 9:1, about 1:8 to about 8:1, about 1:7 to about 7:1, about 1:6 to about 6:1, about 1:5 to about 5:1, about 1:4 to about 4:1, about 1:3 to about 3:1, about 1:2 to about 2:1, or about 1:1. Preferably, it may be about 1:5.

In particular, the anticancer agent may be one to which triphenylphosphonium (TPP) is bound.

As used herein, the term “triphenylphosphonium (TPP)” is a lipophilic cationic compound, which may easily penetrate cell membrane and mitochondrial membrane, and is absorbed directly into the mitochondrion in response to a negative voltage (−150 to −170 mV) present inside the mitochondrial membrane. Due to these properties, TPP is used as a material for targeting cancer cells, cancer stem cells and fibroblasts because it accumulates more in the mitochondria of cancer cells or cardiomyocytes having a large difference in the membrane potential of mitochondria compared to normal cells.

In this case, the anticancer agent in which TPP is bound to mitochondrion may be included in an amount of about 0.01 μg to 1 μg, about 0.05 μg to 0.5 μg, or about 0.1 μg to 0.3 μg per 1 μg of mitochondria. Preferably, it may be included in an amount of about 0.25 μg.

In addition, the anticancer agent and the mitochondrion to which TPP is bound may be mixed in an appropriate ratio so the anticancer agent may be contained in the mitochondrion. For example, the mixing ratio of the anticancer agent and the mitochondrion to which TPP is bound based on a weight ratio may be a weight ratio of about 1:10 to about 10:1, about 1:9 to about 9:1, about 1:8 to about 8:1, about 1:7 to about 7:1, about 1:6 to about 6:1, about 1:5 to about 5:1, about 1:4 to about 4:1, about 1:3 to about 3:1, about 1:2 to about 2:1, or about 1:1. Preferably, it may be about 1:4.

In one embodiment of the present specification, a mitochondrion (TPP-DOX_MT$^{\alpha\text{-}HER2scFv}$) fused with an anti-HER2 antibody fragment comprising TPP-DOX in which TPP is bound to doxorubicin (DOX) was constructed (FIGS. 30 to 32), and the excellent anticancer activity was confirmed in a cancer cell (FIGS. 33 to 43) and a tumor mouse model (FIGS. 65 to 68) using the same.

In addition, the TPP may include a TPP derivative. The TPP derivative may be 2-butene-1,4-bis-TPP, 2-chlorobenzyl-TPP, 3-methylbenzyl-TPP, 2,4-dichlorobenzyl-TPP, 1-naphthylmethyl-TPP and p-xylylenebis-TPP and the like, but is not limited thereto. In addition, the TPP derivative may further include a derivative thereof. For example, it may be a derivative of 2-butene-1,4-bis-TPP, a derivative of 2-chlorobenzyl-TPP, a derivative of 3-methylbenzyl-TPP, a derivative of 2,4-dichlorobenzyl-TPP, a derivative of 1-naphthylmethyl-TPP and a derivative of p-xylylenebis-TPP and the like, but is not limited thereto.

The pharmaceutical composition comprising the mitochondrion containing the anticancer agent of the present invention may be for the prevention or treatment of cancer, and/or may increase therapeutic effect (efficacy). In this case, the mitochondrion and the anticancer agent are as described above.

The cancer may be any one selected from the group consisting of breast cancer, lung cancer, pancreatic cancer, glioblastoma, gastric cancer, liver cancer, colorectal cancer, prostate cancer, ovarian cancer, cervical cancer, thyroid cancer, laryngeal cancer, acute myeloid leukemia, brain tumor, neuroblastoma, retinoblastoma, head and neck cancer, salivary gland cancer and lymphoma, but is not limited thereto.

As used herein, the term “prevention” refers to any action that inhibits or delays the onset of cancer by administration of the pharmaceutical composition. In addition, “treatment” refers to any action that ameliorates or beneficially changes cancer symptoms by administration of the pharmaceutical composition.

As used herein, the term “efficacy” may be determined by one or more parameters, such as survival or disease-free survival over a period of time, such as 1 year, 5 years, or 10 years. In addition, the parameter may include the inhibition of the size of at least one tumor in a subject.

Pharmacokinetic parameters such as bioavailability and underlying parameters such as clearance rate may also have an influence on efficacy. Therefore, “enhanced efficacy” (for example, improvement in efficacy) may be attributed to enhanced pharmacokinetic parameters and enhanced efficacy, and may be measured by comparing clearance rate and tumor growth in a test animal or human subject, or by comparing parameters such as survival, recurrence rate or disease-free survival.

The preferred dosage of the pharmaceutical composition varies depending on the condition and body weight of the patient, the severity of disease, the form of drug, the route and duration of administration, but may be appropriately selected by those of ordinary skill in the art. In the pharmaceutical composition for the prevention or treatment of cancer of the present invention, the active ingredient may be included in any amount (effective amount) depending on the use, formulation, purpose of combining, and the like as long as it may exhibit anticancer activity. Here, “effective amount” refers to an amount of an active ingredient capable of inducing an anticancer effect. Such effective amount may be determined experimentally within the ordinary ability of those of ordinary skill in the art.

The pharmaceutical composition of the present invention may further comprise a pharmaceutically acceptable carrier. The pharmaceutically acceptable carrier may be any carrier as long as it is non-toxic material suitable for delivery to a patient. Distilled water, alcohol, fats, waxes and inert solids may be included as a carrier. In addition, a pharmaceutically acceptable adjuvant (buffering agent, dispersing agent) may be included in the pharmaceutical composition.

Specifically, the pharmaceutical composition may be prepared as a parenteral formulation according to the route of administration by a conventional method known in the art, including a pharmaceutically acceptable carrier in addition to the active ingredient. Here, “pharmaceutically acceptable” means that it does not inhibit the activity of the active ingredient and does not have toxicity beyond what the application (prescription) target may adapt.

When the pharmaceutical composition of the present invention is prepared as a parenteral formulation, it may be formulated in the form of an injection, a transdermal preparation and a nasal inhalant together with suitable carriers according to methods known in the art. When it is formulated as an injection, as a suitable carrier, sterile water, ethanol, polyol such as glycerol or propylene glycol, or a mixture thereof may be used, and Ringer’s solution, PBS (Phosphate Buffered Saline) containing triethanolamine, or sterile water for injection, an isotonic solution such as 5% dextrose, and the like may be preferably used.

The pharmaceutical composition of the present invention may be an injectable preparation. Therefore, the pharmaceutical composition according to the present invention may be manufactured as an injection that is very stable physically or chemically by adjusting the pH using a buffer solution such as an acidic aqueous solution or phosphate, which may be used as an injection, in order to secure product stability according to the distribution of an injection that is prescribed.

Specifically, the pharmaceutical composition of the present invention may comprise water for injection. The water for injection refers to distilled water prepared for dissolving a solid injection or for diluting a water-soluble injection. It may be glucose injection, xylitol injection, D-mannitol injection, fructose injection, physiological saline, dextran 40 injection, dextran 70 injection, amino acid injection, Ringer’s solution, lactic acid-Ringer’s solution, or a phosphate buffer solution or sodium dihydrogen phosphate-citrate buffer solution having a pH of about 3.5 to 7.5.

On the other hand, the pharmaceutical composition of the present invention is administered in a pharmaceutically effective amount. The term “therapeutically effective amount” or “pharmaceutically effective amount” refers to an amount of a compound or composition effective for preventing or treating a target disease, which is an amount that is sufficient to treat the disease with a reasonable benefit/risk ratio applicable to medical treatment and that does not cause side effects. The level of the effective amount may be determined according to factors including the health condition of the patient, the type and severity of the disease, the activity of the drug, sensitivity to the drug, administration method, administration time, the route of administration and excretion rate, treatment period, the drug to be combined or concurrently used, and other factors well known in the medical field. In one embodiment, a therapeutically effective amount refers to an amount of a drug effective to treat cancer.

As used herein, the term “administration” refers to introducing a predetermined substance to a subject by an appropriate method, and the route of administration of the composition may be through any general route as long as it may reach a target tissue. It may be intraperitoneal administration, intravenous administration, intramuscular administration, subcutaneous administration, intradermal administration, topical administration, intranasal administration, intrarectal administration, but is not limited thereto.

A preferred dosage of the pharmaceutical composition of the present invention may be administered once in an amount of 0.01 mg/kg to 5 mg/kg, 0.1 mg/kg to 4 mg/kg or 0.25 mg/kg to 2.5 mg/kg of mitochondria based on the body weight of the subject to be administered, but is not limited thereto. That is, it is most preferable in terms of cell activity that the pharmaceutical composition is administered with the modified mitochondrion containing the anticancer agent in an amount in the above range based on the body weight of the subject having cancer tissue. In addition, the pharmaceutical composition may be administered 1 to 10 times, 3 to 8 times, or 5 to 6 times, preferably 5 times. In this case, the administration interval may be an interval of 1 to 7 days or 2 to 5 days, preferably an interval of 3 days. Such dosage should not be construed as limiting the scope of the present invention in any aspect.

The term "subject" refers to a subject to which the composition of the present invention may be applied (prescribed), and may be a subject suffering from cancer. In addition, the subject may be a mammal, such as a rat, a mouse, or a livestock, including a human, and preferably a human. The composition of the present invention may further include any compound or natural extract known to have anticancer activity and safety, which has already been verified, for the enhancement and reinforcement of anticancer activity, in addition to the mitochondrion containing the anticancer agent. In this case, the pharmaceutical composition and the compound or natural extract having anticancer activity may be administered simultaneously or sequentially.

In another aspect of the present invention, there is provided a method for preparing mitochondrion containing an anticancer agent, comprising mixing the anticancer agent and the isolated mitochondrion. In this case, the anticancer agent and the mitochondrion are as described above.

The anticancer agent and the mitochondrion may be mixed in an appropriate ratio so the anticancer agent may be contained in the mitochondrion. For example, the mixing ratio of the anticancer agent and the mitochondrion based on a weight ratio may be a weight ratio of about 1:10 to about 10:1, about 1:9 to about 9:1, about 1:8 to about 8:1, about 1:7 to about 7:1, about 1:6 to about 6:1, about 1:5 to about 5:1, about 1:4 to about 4:1, about 1:3 to about 3:1, about 1:2 to about 2:1 or about 1:1. Preferably, it may be about 1:5.

In another aspect of the present invention, there is provided a modified anticancer agent to which TPP is chemically bound. In this case, TPP and the anticancer agent are as described above.

In another aspect of the present invention, there is provided use of a pharmaceutical composition comprising mitochondrion containing an anticancer agent for the prevention or the enhancement of therapeutic effect of cancer. In this case, the anticancer agent and the mitochondrion are as described above.

In another aspect of the present invention, there is provided a method for treating cancer and/or a method for enhancing therapeutic effect, comprising administering a pharmaceutical composition comprising mitochondrion containing an anticancer agent to a subject. In this case, the anticancer agent, the mitochondrion and the administration are as described above. The subject may be a subject suffering from cancer. In addition, the subject may be a mammal, preferably a human.

MODE FOR CARRYING OUT THE INVENTION

Hereinafter, the present invention will be described in more detail by way of the following examples. However, the following examples are only for illustrating the present invention, and the scope of the present invention is not limited thereto.

I. Confirmation of Targeting Ability of Mitochondria to which Targeting Protein is Bound

Figure 2:
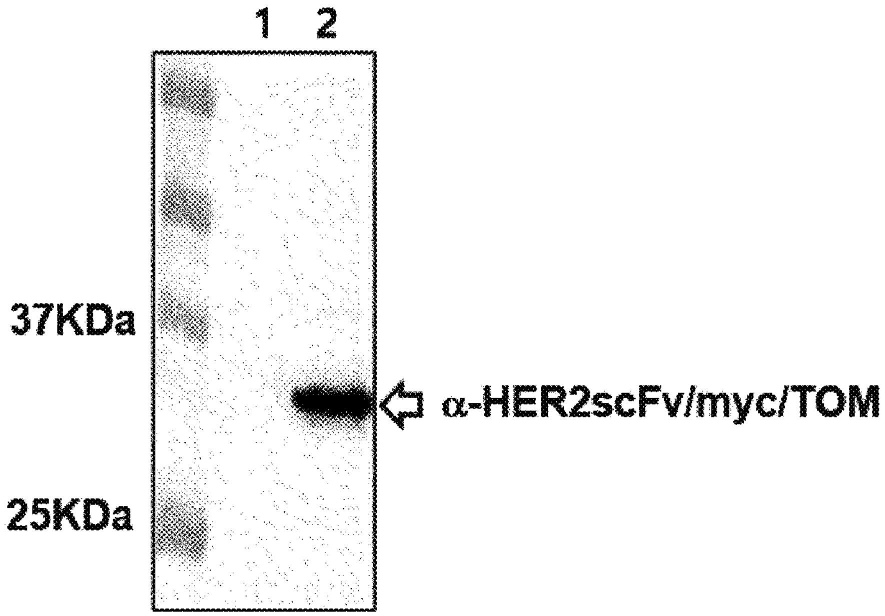
FIG. 2 is a view showing the results of confirming a single chain variable region fragment of an anti-HER2 antibody expressed in the human fetal kidney cell line (HEK293) by Western blot.

Preparation Example 1. Preparation of HEK293 Cell Line Comprising Mitochondrion Fused with Anti-HER2scFv Antibody In order to specifically introduce mitochondria into tumor cells in which HER2 is expressed, mitochondria in which an anti-HER2scFv antibody (SEQ ID NO: 98) that specifically binds to HER2 is fused to the mitochondrial outer membrane were construct (FIGS. 1 and 2). A specific constructing method was performed according to the method described in Korean Patent Application Publication No. 10-2019-0124656.

Example 1. Confirmation of Property of Mitochondria Fused with Anti-HER2scFv Antibody

Example 1.1. Analysis of Anti-HER2scFv Antibody Expression

In order to confirm the expression level of anti-HER2scFv in HEK293 cells comprising the mitochondria ($MT^{\alpha\text{-}HER2scFv}$) fused with an anti-HER2scFv antibody constructed in Preparation Example 1 above, the cells were stained using immunocytochemistry staining, and the images were observed using a confocal microscope.

Specifically, HEK293 cells were inoculated into a 24-well plate at $3\times10^4$ cells/well and cultured for 24 hours. After culturing for 24 hours, the cells were stained with MitoTracker Red for about 30 minutes, and washed with PBS, and then fixed with 3.7% formaldehyde. Formaldehyde was removed, and a primary antibody, anti-myc antibody (Roche, 11667149001), was diluted 1:1,000 in PBS containing 1% goat serum, and the cells were treated with the dilution and reacted for 18 hours. After the reaction was completed, the primary antibody was removed by washing with PBS, and then a secondary antibody labeled with Alexa Fluor® 488 (Invitrogen, 11001), an anti-mouse IgG antibody, was diluted 1:500 in PBS containing 0.1% BSA, and the cells were treated with the dilution and reacted for about 1 hour. After the reaction was completed, the cells were washed with PBS, mounted, and the cells were observed by a confocal microscope. At this time, the nuclei of the cells were observed by staining with DAPI.

Figure 3:
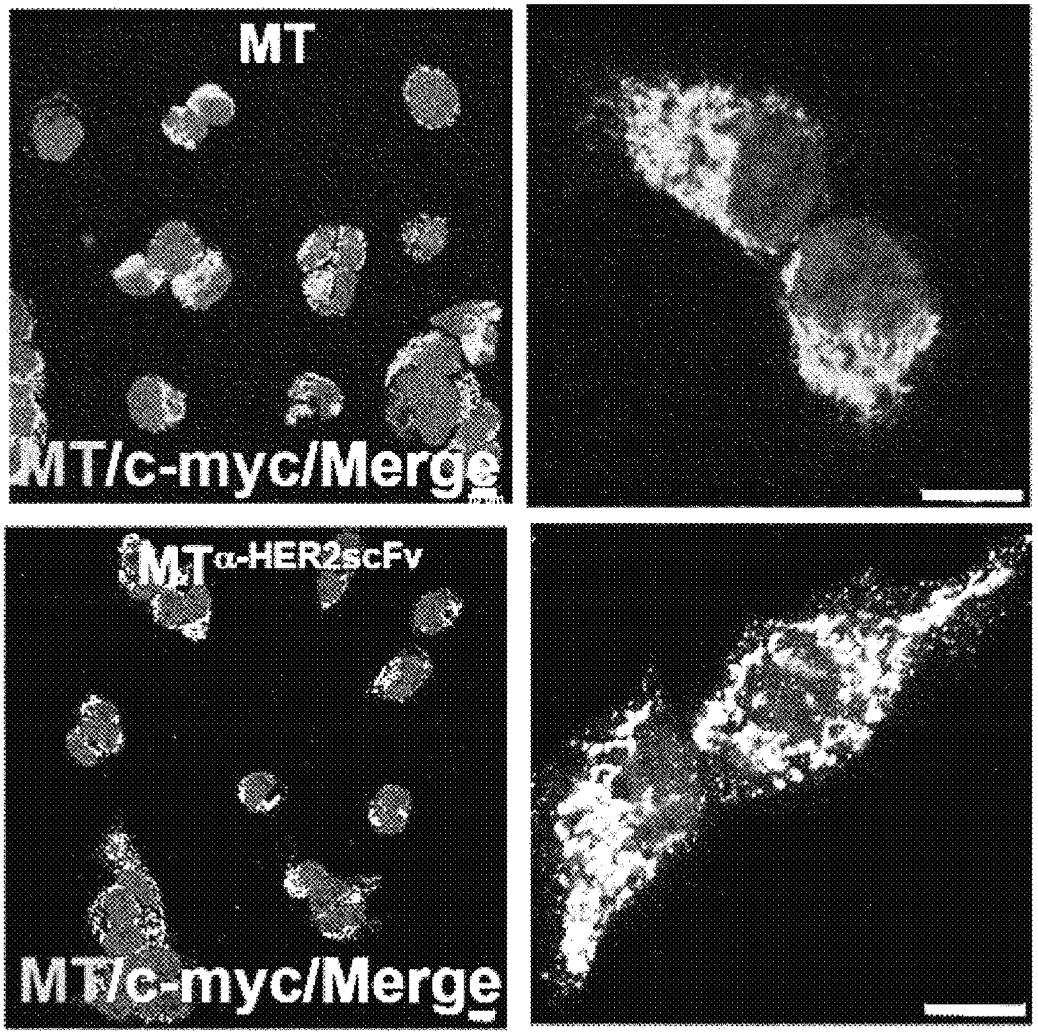
FIG. 3 is a view showing the results of confirming the intracellular location of a single chain variable region fragment of an anti-HER2 antibody expressed in the human fetal kidney cell line (HEK293) by a confocal microscope. The scale bar represents 10 m.

As a result, it was confirmed that the location of the red fluorescence labeling the mitochondria is coincident with the location of the green fluorescence labeling the anti-HER2scFv antibody (FIG. 3).

Example 1.2. Confirmation of Expression Location of Anti-HER2scFv Antibody

Western blot was performed to confirm whether the anti-HER2scFv antibody constructed in the same manner as in Preparation Example 1 above was expressed in the mitochondria of HEK293 cells.

Specifically, after disrupting the cells in which anti-HER2scFv was expressed, the cell extract was separated into a mitochondria fraction and a cytoplasm fraction by centrifugation. Each of the fractions was electrophoresed and Western blot was performed. In order to identify anti-HER2scFv, a mitochondrial marker and a cytoplasmic marker protein, anti-myc antibody (Roche, 11667149001), anti-COX4 antibody (abcam, 33985) and anti-β-tubulin antibody (Thermo, MA5-16308) were used as primary antibodies, respectively. Anti-mouse IgG HRP or anti-rabbit IgG HRP was used as a secondary antibody.

Figure 4:
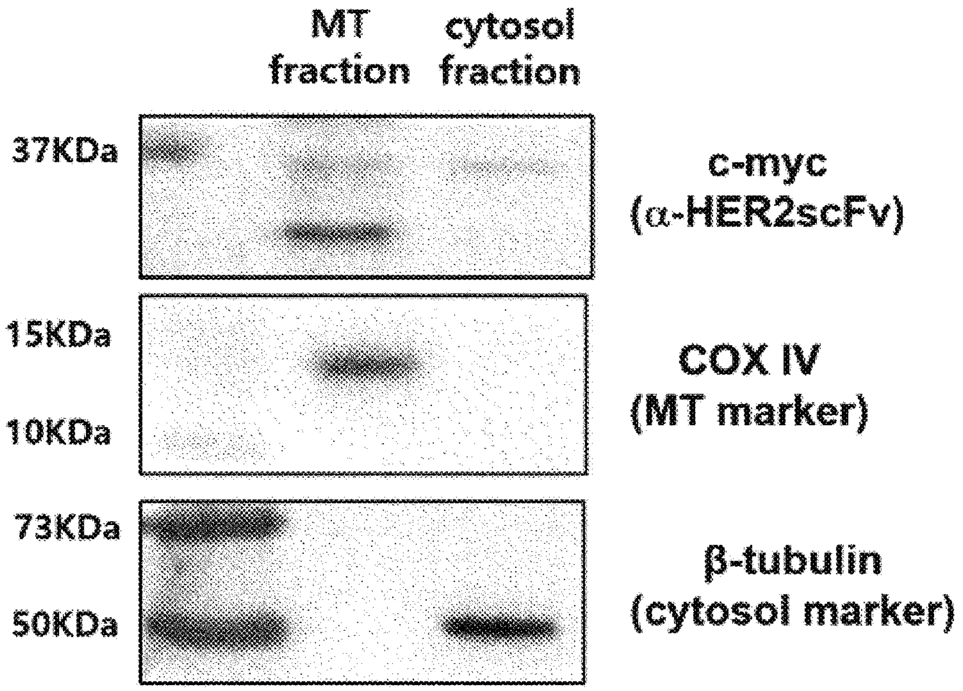
FIG. 4 is a view showing the results of confirming by Western blot that a single chain variable region fragment of an anti-HER2 antibody expressed in the human fetal kidney cell line (HEK293) exists at the same location as the mitochondria in the cell.

As a result, it was confirmed that the anti-HER2scFv antibody was present in the mitochondria fraction together with COX4 used as a mitochondrial positive marker, and was not present in the fraction in which the cytoplasmic positive marker 0-tubulin was present (FIG. 4). It was confirmed that the anti-HER2scFv antibody was expressed in the mitochondria of HEK293 cells through the results of immunocytochemistry staining and Western blot analysis in the above Example.

Example 1.3. Measurement of Ability to Produce ATP of Mitochondria Fused with Anti-HER2scFv Antibody In order to compare the functional difference between the mitochondria fused with the anti-HER2scFv antibody constructed in the same manner as in Preparation Example 1 above and the normal mitochondria, the mitochondria were isolated from HEK293 cells ($MT^{\alpha\text{-}HER2scFv}$) a cell line expressing the mitochondria fused with the anti-HER2scFv antibody, and HEK293 cells to compare their ability to produce ATP, which is one of the main functions of mitochondria.

Figure 5:
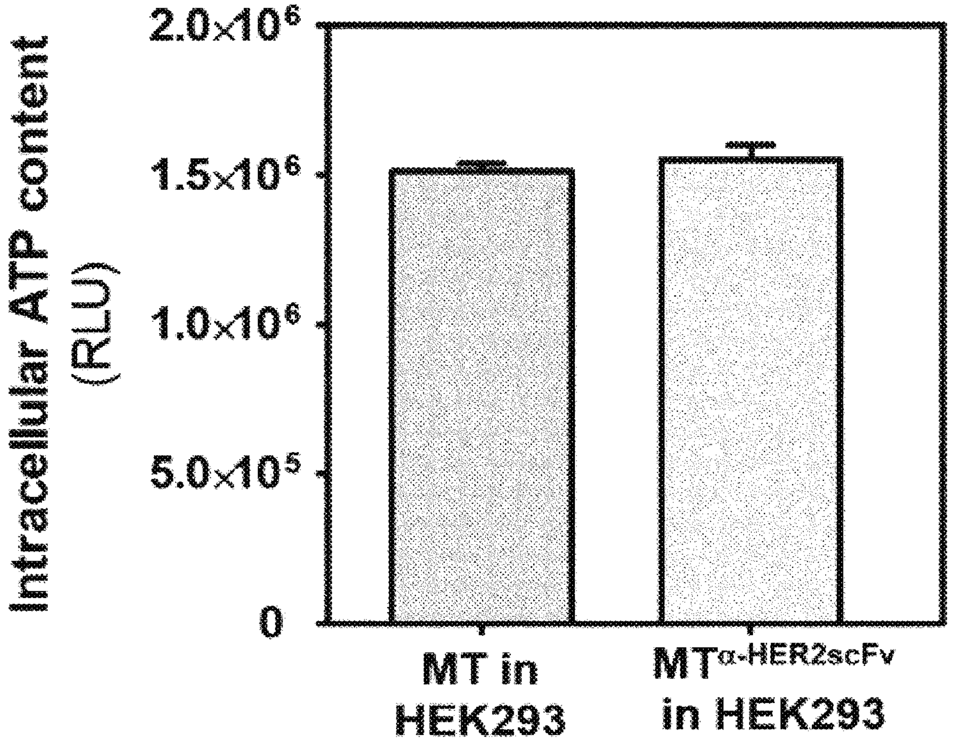
FIG. 5 is a graph showing the results of measuring ATP in the mitochondria ($MT^{\alpha\text{-}HER2scFv}$) isolated from the human fetal kidney cell line (HEK293) that expresses a single chain variable region fragment of an anti-HER2 antibody. In this case, the control group is the mitochondria isolated from the HEK293 cells that do not express a single chain variable region fragment of an anti-HER2 antibody.

Specifically, the ability to produce ATP was confirmed by treating 5 μg/100 μL of the isolated mitochondria with 25 μM ADP and 100 μL of luciferin, and measuring the luminescence value (RLU) generated by the reaction of ATP and luciferin produced in the mitochondria. As a result, there was no difference in the ability to produce ATP of MT and $MT^{\alpha\text{-}HER2scFv}$ (FIG. 5).

Example 1.4. Measurement of Membrane Potential of Mitochondria Fused with Anti-HER2scFv Antibody In order to compare the functional difference between the mitochondria fused with the anti-HER2scFv antibody constructed in the same manner as in Preparation Example 1 above and the normal mitochondria, the membrane potential, which is one of the main characteristics of mitochondria, of HEK293 cells comprising the mitochondria fused with the anti-HER2scFv antibody ($MT^{\alpha\text{-}HER2scFv}$) and untreated HEK293 cells (MT) was compared.

Figure 6:
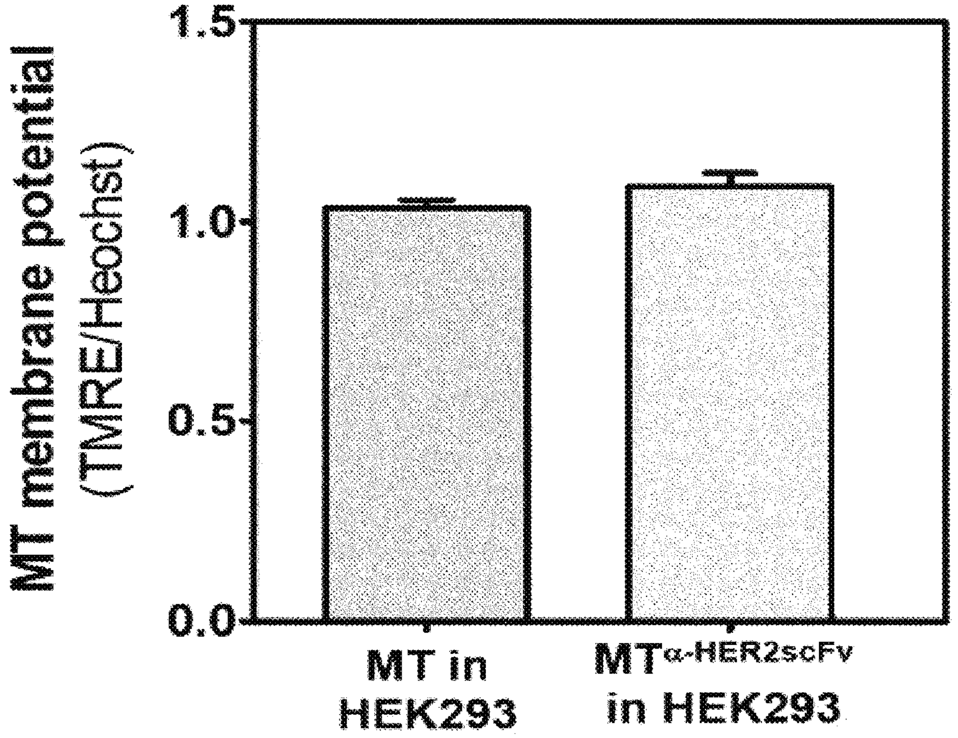
FIG. 6 is a graph showing the results of measuring the membrane potential in the mitochondria ($MT^{\alpha\text{-}HER2scFv}$) isolated from the human fetal kidney cell line (HEK293) that expresses a single chain variable region fragment of an anti-HER2 antibody. In this case, the control group is the mitochondria isolated from the HEK293 cells that do not express a single chain variable region fragment of an anti-HER2 antibody.

Specifically, the cells were inoculated into a 96-well plate at $3\times10^4$ cells/well and cultured for 24 hours. After 24 hours, the cells were treated with DCFDA (Invitrogen, C6827) dye and reacted for 1 hour. Thereafter, the cells were washed with PBS and treated with Hoechst33242 to stain the cells for 10 minutes. The fluorescence values of DCFDA and Hoechst33242 were measured, and then the membrane potential was determined by calculating their ratio (the fluorescence value of DAFDA/the fluorescence value of Hoechst33242). As a result, there was no difference in the membrane potential of MT and $MT^{\alpha\text{-}HER2scFv}$ (FIG. 6).

Example 1.5. Measurement of Reactive Oxygen Species of Mitochondria Fused with Anti-HER2scFv Antibody In order to compare the production level of the reactive oxygen species (ROS) of the mitochondria fused with the anti-HER2scFv antibody constructed in the same manner as in Preparation Example 1 above and the normal mitochondria, the reactive oxygen species of the mitochondria in HEK293 cells comprising the mitochondria fused with the anti-HER2scFv antibody ($MT^{\alpha\text{-}HER2scFv}$) and untreated HEK293 cells (MT) was measured.

Figure 7:
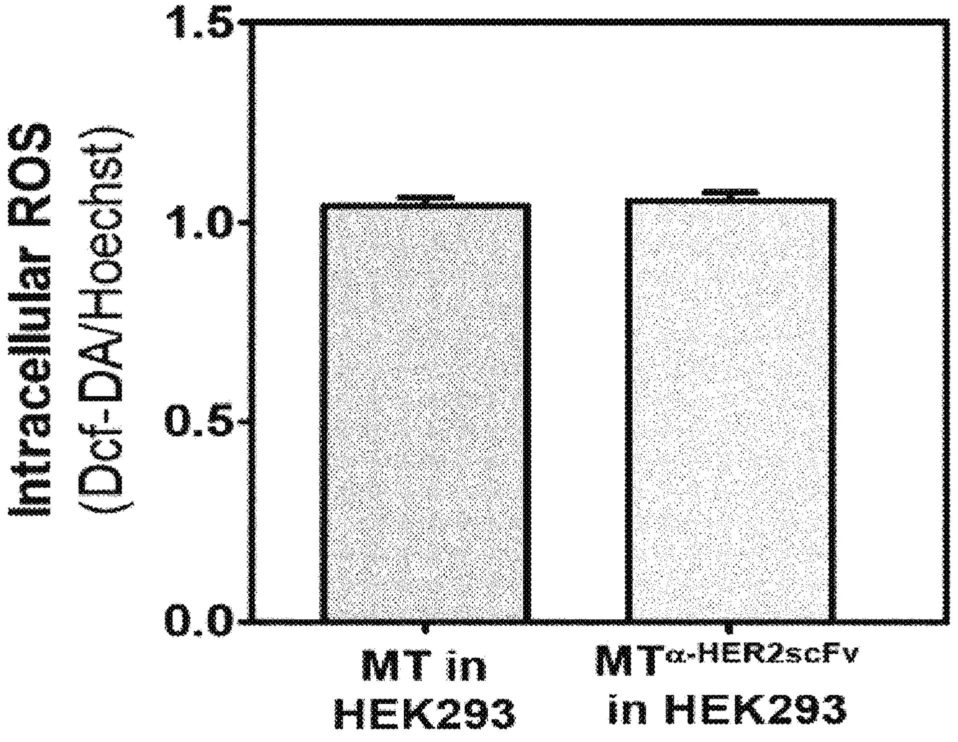
FIG. 7 is a graph showing the results of measuring the reactive oxygen species (ROS) in the mitochondria ($MT^{\alpha\text{-}HER2scFv}$) isolated from the human fetal kidney cell line (HEK293) that expresses a single chain variable region fragment of an anti-HER2 antibody. In this case, the control group is the mitochondria isolated from the HEK293 cells that do not express a single chain variable region fragment of an anti-HER2 antibody.

Specifically, the cells were inoculated into a 96-well plate at $3\times10^4$ cells/well and cultured for 24 hours. After 24 hours, each cell was treated with TMRE (Invitrogen, T669) dye and reacted for 1 hour. The cells were washed with PBS and then stained with Hoechst33242 for 10 minutes. The fluorescence values of TMRE and Hoechst33242 were measured, and then the amount of the reactive oxygen species production was determined by calculating their ratio (the fluorescence value of TMRE/the fluorescence value of Hoechst33242). As a result, there was no difference in the amount of the reactive oxygen species production of MT and $MT^{\alpha\text{-}HER2scFv}$ isolated from cells (FIG. 7).

Example 2. Analysis of HER2 Expression in Human Cancer Cell Line and Normal Cell Line Example 2.1. Confirmation of HER2 Expression in Human Cancer Cell Line and Normal Cell Line Through Western Blot Analysis Western blot was performed to confirm the expression level of HER2 in the human breast cancer, lung cancer, gastric cancer cell line and the lung fibroblast cell line.

Specifically, the human breast cancer cell line (SK-BR-3, BT-474 and MDA-MB-231), the human lung cancer cell line (NCI-H1975), the human gastric cancer cell line (MKN-74 and NCI-N87) and the human lung fibroblast cell line (WI-38) were inoculated into a 6-well plate at about $1\times10^6$ cells/well and then cultured for 24 hours. At this time, SK-BR-3, BT-474 and NCI-N87 cells were prepared by culturing in RPMI-1640 medium containing 10% FBS, and MDA-MB-231, NCI-H1975, MKN-74 and WI-38 cells were prepared by culturing in DMEM medium containing 10% FBS.

After 24 hours, the culture solution was removed, and the cells were washed twice with PBS, and then 100 μL of RIPA buffer containing a protease inhibitor was added directly to the cells. After 10 minutes, the cells were recovered using a scraper, transferred to a microtube, and then centrifuged at about 12,000×g for 10 minutes. The separated supernatant was obtained and transferred to a new microtube, and then protein was quantified using the BCA analysis. The same amount of protein for each sample was electrophoresed, and then Western blot was performed. Anti-HER2 antibody (Cell signaling, 29D8) and anti-β actin antibody (Sigma, A2208) were used as primary antibodies, and anti-mouse IgG HRP and anti-rabbit IgG HRP were used as secondary antibodies.

Figure 8:
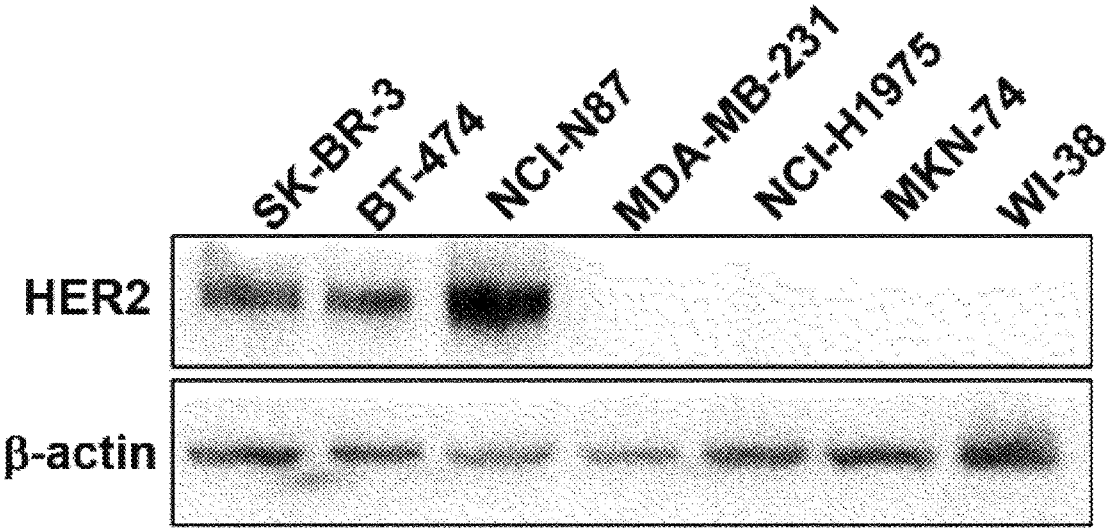
FIG. 8 is a view showing the results of confirming the expression of HER2 in the human breast cancer cell line (SK-BR-3, BT-474 and MDA-MB-231), the human lung cancer cell line (NCI-H1975), the lung fibroblast cell line (WI-38) and the human gastric cancer cell line (NCI-N87 and MKN-74) by Western blot.

As a result, it was confirmed that SK-BR-3, BT-474, and NCI-N87 cells were $HER2^+$ cells expressing HER2. On the other hand, it was found that MDA-MB-231, NCI-H1975, MKN-74 and WI-38 cells showed almost no HER2 expression, indicating that they were $HER2^-$ cells (FIG. 8).

Example 2.2. Confirmation of HER2 Expression in Human Cancer Cell Line and Normal Cell Line Through Immunocytochemistry Staining In order to confirm the expression level of HER2 in the human breast cancer, lung cancer, gastric cancer cell line and the human lung fibroblast cell line, immunocytochemistry staining was performed using an anti-HER2 antibody.

Specifically, the cells were inoculated into a 24-well plate at $3\times10^4$ cells/well, respectively, and cultured for 24 hours. After 24 hours, the cells were fixed with 3.7% formaldehyde. Formaldehyde was removed, and a primary antibody, anti-HER2 antibody (Cell Signaling Technology, 2165), was diluted 1:1,000 in PBS containing 1% goat serum, and the cells were treated with the dilution and reacted for 18 hours. The primary antibody was removed by washing with PBS, and then a secondary antibody labeled with Alexa Fluor® 488 (Invitrogen, 11008), an anti-rabbit IgG antibody, was diluted 1:500 in PBS containing 0.1% BSA, and the cells were treated with the dilution and reacted for 1 hour. After the reaction was completed, the cells were washed with PBS, mounted, and the cells were observed by a confocal microscope. At this time, the nuclei of the cells were observed by staining with DAPI.

Figure 9:
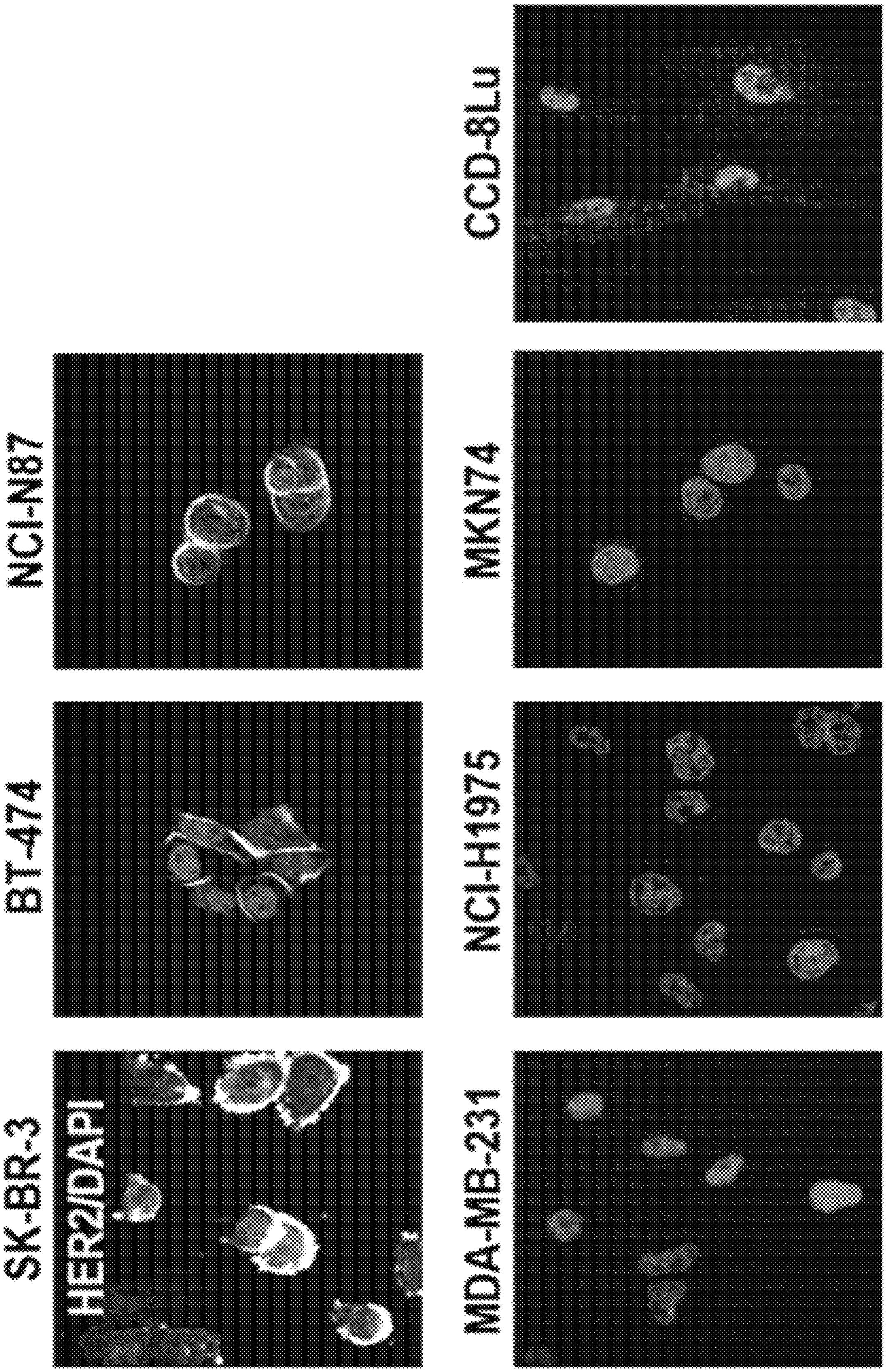
FIG. 9 is a view showing the results of confirming the expression of HER2 in the human breast cancer cell line (SK-BR-3, BT-474 and MDA-MB-231), the human lung cancer cell line (NCI-H1975), the human lung fibroblast cell line (WI-38) and the human gastric cancer cell line (NCI-N87 and MKN-74) by immunocytochemistry staining.

As a result, in the case of SK-BR-3, BT-474, and NCI-N87 cells, which are $HER2^+$ cells, HER2 was expressed on the cell surface and green fluorescence was observed, and in the case of MDA-MB-231, NCI-H1975, MKN74, and CCD-8Lu cells, which are $HER2^-$ cells, green fluorescence was not observed (FIG. 9).

Example 2.3. Confirmation of HER2 Expression in Human Cancer Cell Line Through Flow Cytometry In order to confirm the expression level of HER2 in the human breast cancer, lung cancer and gastric cancer cell line, flow cytometry was performed using an anti-HER2 antibody.

Specifically, the human breast cancer cell line (SK-BR-3, BT-474 and MDA-MB-231), the human gastric cancer cell line (NCI-N87 and MKN-74) and the human lung cancer cell line (NCI-H1975) were inoculated into a 6-well plate at about $1\times10^6$ cells/well, respectively, and cultured for 24 hours. After 24 hours, the culture solution was removed, and the cells were collected by treatment with 0.05% trypsin-EDTA and fixed with 3.7% formaldehyde. A primary antibody, an anti-HER2 antibody (Cell Signaling Technology, 2165), was diluted 1:1,000 in PBS containing 1% goat serum, and the cells were treated with the dilution and reacted for 18 hours. The primary antibody was removed by washing with PBS, and then a secondary antibody labeled with Alexa Fluor® 555 (Invitrogen, 21428), an anti-rabbit IgG antibody, was diluted 1:500 in PBS containing 0.1% BSA, and the cells were treated with the dilution and reacted for 1 hour. After the reaction was completed, the cells were washed with PBS, and the expression of HER2 was confirmed through flow cytometer.

Figure 10:
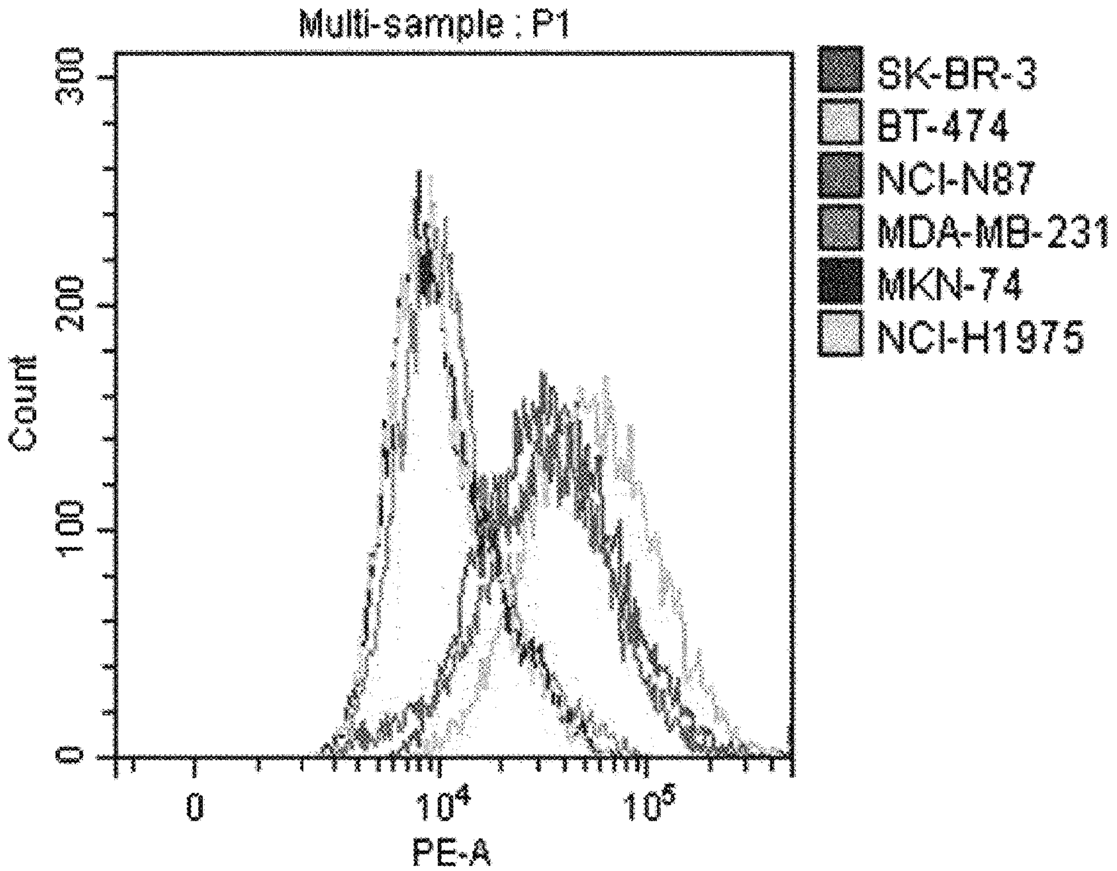
FIG. 10 is a view showing the results of confirming the expression of HER2 in the human breast cancer cell line (SK-BR-3, BT-474 and MDA-MB-231), the human lung cancer cell line (NCI-H1975) and the human gastric cancer cell line (NCI-N87 and MKN-74) by flow cytometry.

As a result, in the case of SK-BR-3, BT-474 and NCI-N87 cells, which are $HER2^+$ cells, HER2 was expressed on the cell surface and the fluorescence value (PE-A) was observed to be high, whereas MDA-MB-231, NCI-H1975 and MKN-74 cells, which are $HER2^-$ cells, showed lower fluorescence value than $HER2^+$ cells (FIG. 10).

From the above results of the Western blot analysis, immunocytochemistry staining and flow cytometry, it was confirmed that SK-BR-3, BT-474 and NCI-N87 cells were $HER2^+$ cells expressing HER2, and MDA-MB-231, NCI-H1975, MKN-74, WI-38 cells, and CCD-8Lu cells were $HER2^-$ cells.

Example 3. Verification of HER2 Targeting of Mitochondria Fused with Anti-HER2scFv Antibody In order to confirm the HER2 targeting ability of the mitochondria fused with the anti-HER2scFv antibody constructed in the same manner as in Preparation Example 1 above, the mitochondria fused with the anti-HER2scFv antibody ($MT^{\alpha\text{-}HER2scFv}$) were treated with the co-cultured $HER2^+$ cells and $HER2^-$ cells, and then immunocytochemistry staining was performed.

Figure 11:
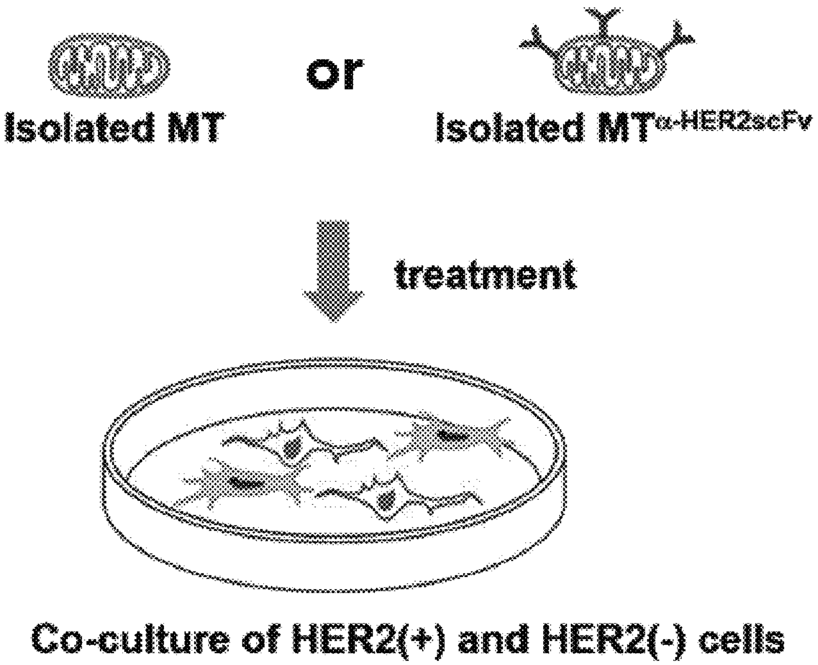
FIG. 11 is a view showing an experimental method for verifying the HER2 targeting ability of the mitochondria ($MT^{\alpha\text{-}HER2scFv}$) isolated from the human fetal kidney cell line (HEK293) that expresses a single chain variable region fragment of an anti-HER2 antibody.

Specifically, $HER2^+$ cells and $HER2^-$ cells were inoculated together into a 24-well plate at $1.5\times10^4$ cells/well and co-cultured in DMEM medium containing 10% FBS for 24 hours. At this time, $HER2^+$ cells SK-BR-3, BT-474 and NCI-N87 were prepared by culturing in RPMI-1640 medium containing 10% FBS, and $HER2^-$ cells MDA-MB-231, NCI-H1975 and MKN-74 were prepared by culturing in DMEM medium containing 10% FBS. The mitochondria were prepared by treating untreated HEK293 cells (MT) and HEK293 cells comprising mitochondria fused with an anti-HER2scFv antibody ($MT^{\alpha\text{-}HER2scFv}$) with MitoTracker Red, respectively, and isolating the stained mitochondria. After co-culture for 24 hours, each isolated mitochondrion was treated with the co-cultured cells and reacted for 12 hours (FIG. 11).

Example 3.1. Confirmation of Location of Mitochondria Fused with Anti-HER2scFv Antibody in HER2 Positive and Negative Cell Lines The cells treated in the same manner as in Example 3 above were washed once with PBS, and fixed by adding 3.7% formaldehyde at room temperature for 30 minutes, and then immunocytochemistry staining was performed. At this time, an anti-HER2 antibody (Cell signaling, 29D8) was used as a primary antibody, and an anti-rabbit IgG antibody labeled with Alexa Fluor® 488 (Invitrogen, 11008) was used as a secondary antibody. The nuclei of the cells were observed by staining with DAPI.

Figure 12:
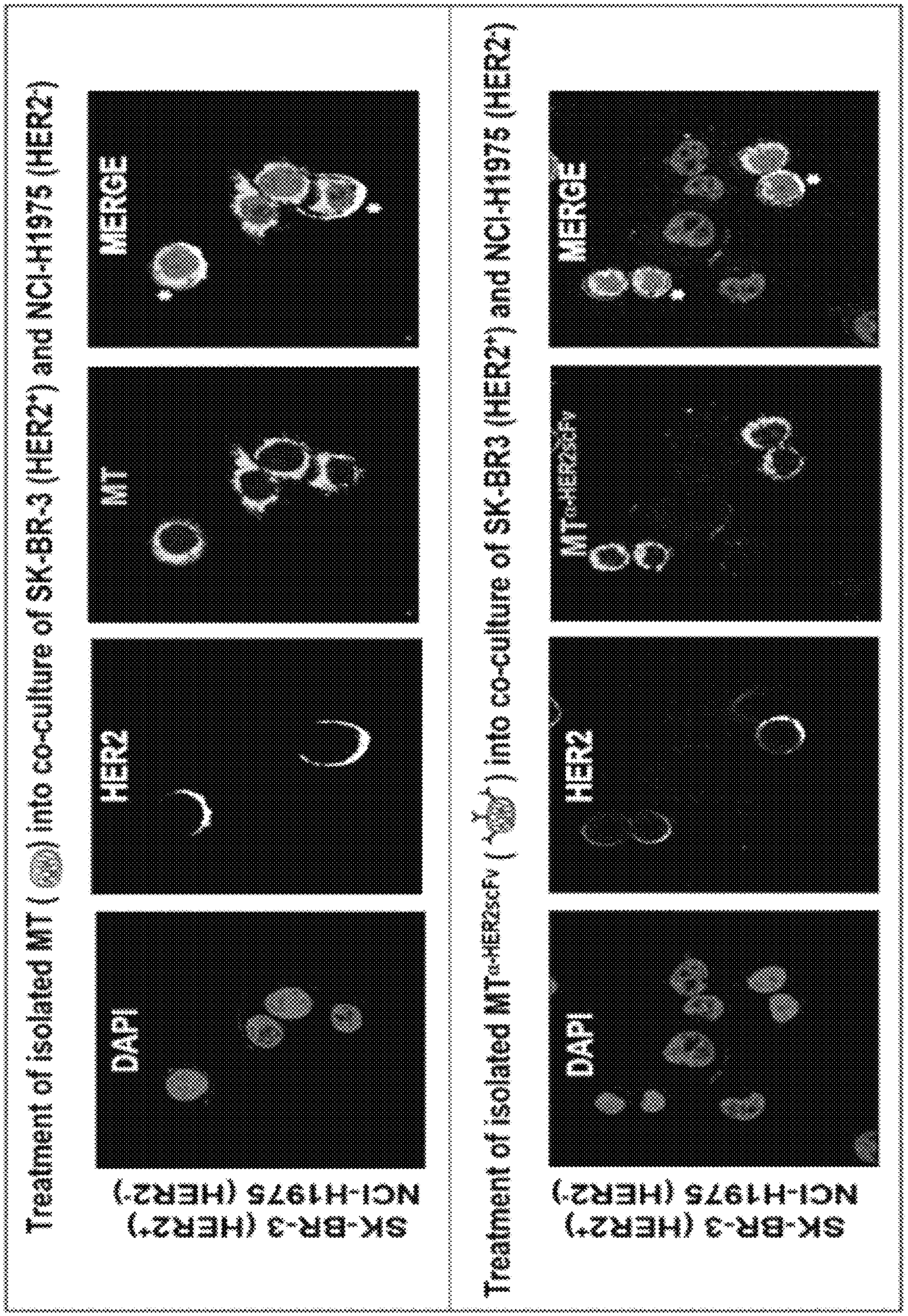
FIG. 12 is a view showing the results of confirming the intracellular expression of HER2 and a single chain variable region fragment of an anti-HER2 antibody by immunocytochemistry staining after co-culture of $HER2^+$ cells, the human breast cancer cell line SK-BR-3, and $HER2^-$ cells, the human lung cancer cell line NCI-H1975 cells, and then treatment of the culture solution with $MT^{\alpha\text{-}HER2scFv}$. In this case, MT is the mitochondria, to which a single chain variable region fragment of an anti-HER2 antibody is not fused, isolated from the HEK293 cells.

As a result, as shown in FIG. 12, when the co-cultured SK-BR-3 ($HER2^+$) and NCI-H1975 ($HER2^-$) cells were treated with untreated HEK293 cell-derived mitochondria (MT), the mitochondria stained with Mitotracker Red (red fluorescence) were observed equally in SK-BR-3 ($HER2^+$) cells and NCI-H1975 ($HER2^-$) cells. On the other hand, when the cells were treated with the mitochondria ($MT^{\alpha\text{-}HER2scFv}$) derived from HEK293 cells comprising the mitochondria fused with the anti-HER2scFv antibody, the mitochondria stained with Mitotracker Red were observed specifically in $HER2^+$ cells, SK-BR-3 cells.

Figure 13:
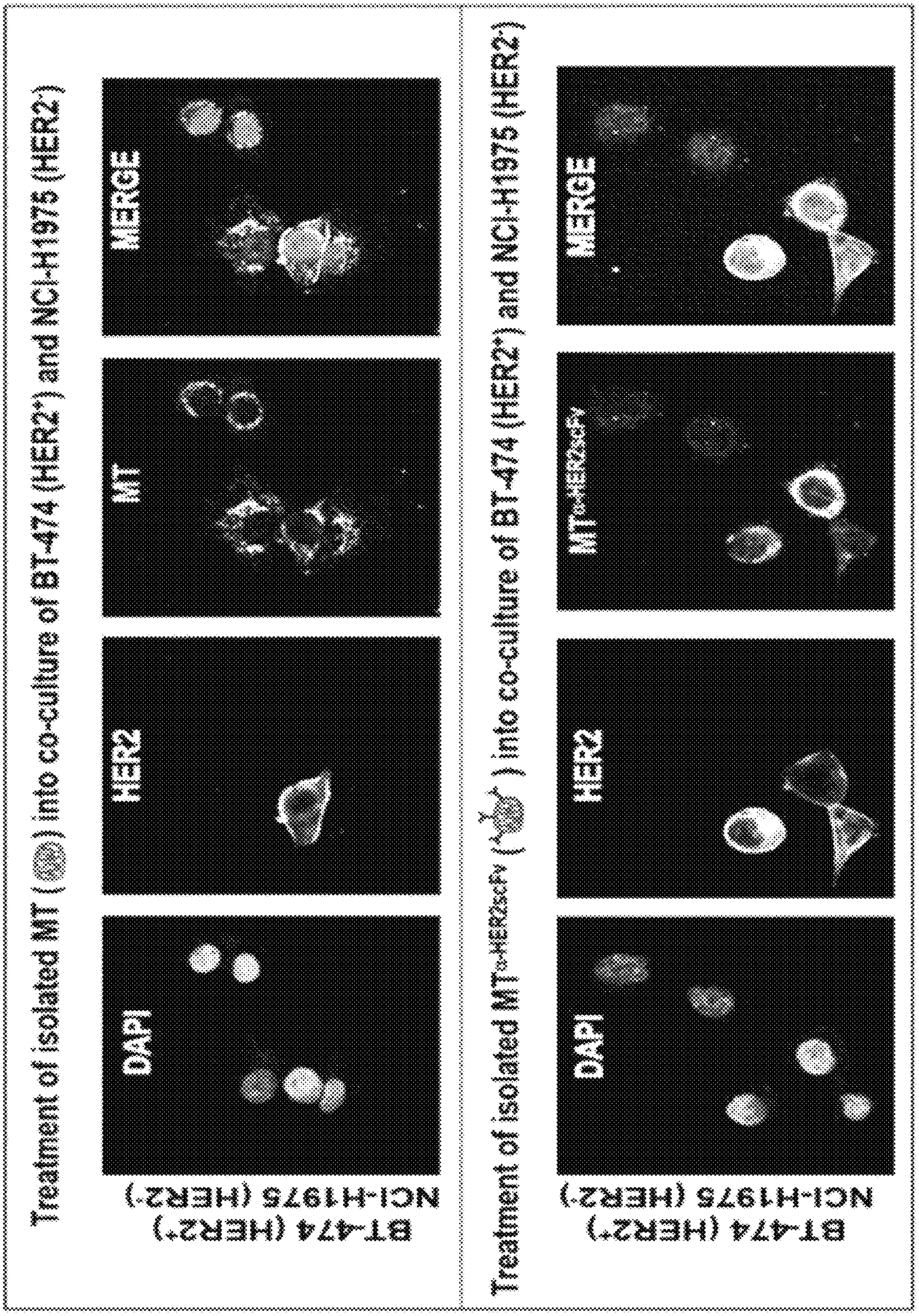
FIG. 13 is a view showing the results of confirming the intracellular expression of HER2 and a single chain variable region fragment of an anti-HER2 antibody by immunocytochemistry staining after co-culture of $HER2^+$ cells, the human breast cancer cell line BT-474, and $HER2^-$ cells, the human lung cancer cell line NCI-H1975 cells, and then treatment of the cells with $MT^{\alpha\text{-}HER2scFv}$ In this case, MT is the mitochondria, to which a single chain variable region fragment of an anti-HER2 antibody is not fused, isolated from the HEK293 cells.

In the case of the co-cultured BT-474 ($HER2^+$) and NCI-H1975 ($HER2^-$) cells, in the case of MT treated group, the mitochondria stained with Mitotracker Red were observed equally in BT-474 ($HER2^+$) cells and NCI-H1975 ($HER2^-$) cells, whereas in the case of $MT^{\alpha\text{-}HER2scFv}$ treated group, they were specifically observed only in $HER2^+$ cells, BT-474 cells (FIG. 13).

Figure 14:
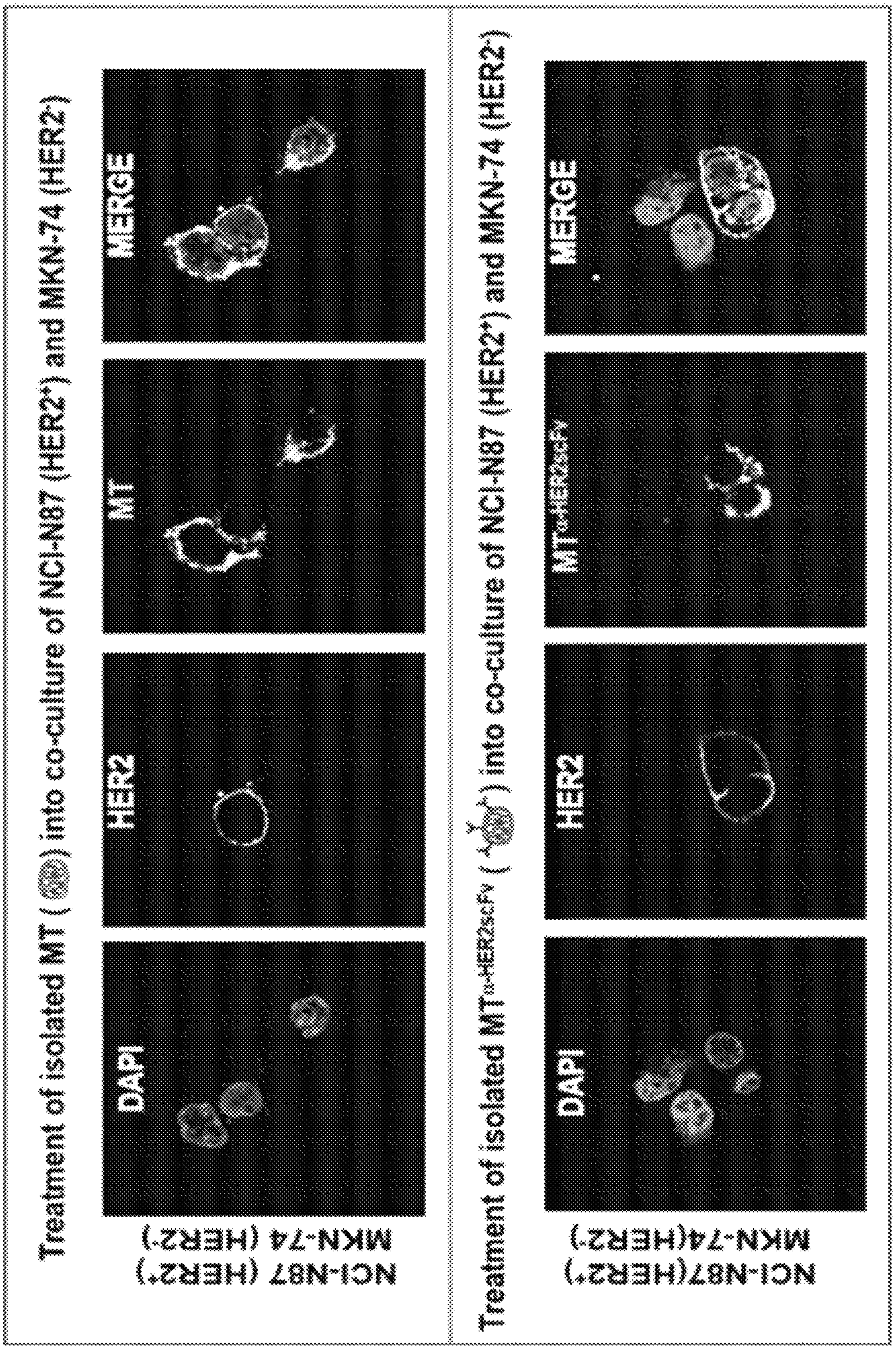
FIG. 14 is a view showing the results of confirming the intracellular expression of HER2 and a single chain variable region fragment of an anti-HER2 antibody by immunocytochemistry staining after co-culture of $HER2^+$ cells, the human gastric cancer cell line NCI-N87, and $HER2^-$ cells, the human gastric cancer cell line MKN-74 cells, and then treatment of the cells with $MT^{\alpha\text{-}HER2scFv}$ In this case, MT is the mitochondria, to which a single chain variable region fragment of an anti-HER2 antibody is not fused, isolated from the HEK293 cells.

In the case of the co-cultured NCI-N87 ($HER2^+$) and MKN-74 ($HER2^-$) cells, in the case of MT treated group, the mitochondria stained with Mitotracker Red were observed equally in NCI-N87 ($HER2^+$) cells and MKN-74 ($HER2^-$) cells, whereas in the case of $MT^{\alpha\text{-}HER2scFv}$ treated group, they were specifically observed only in $HER2^+$ cells, NCI-N87 (FIG. 14).

Figure 15:
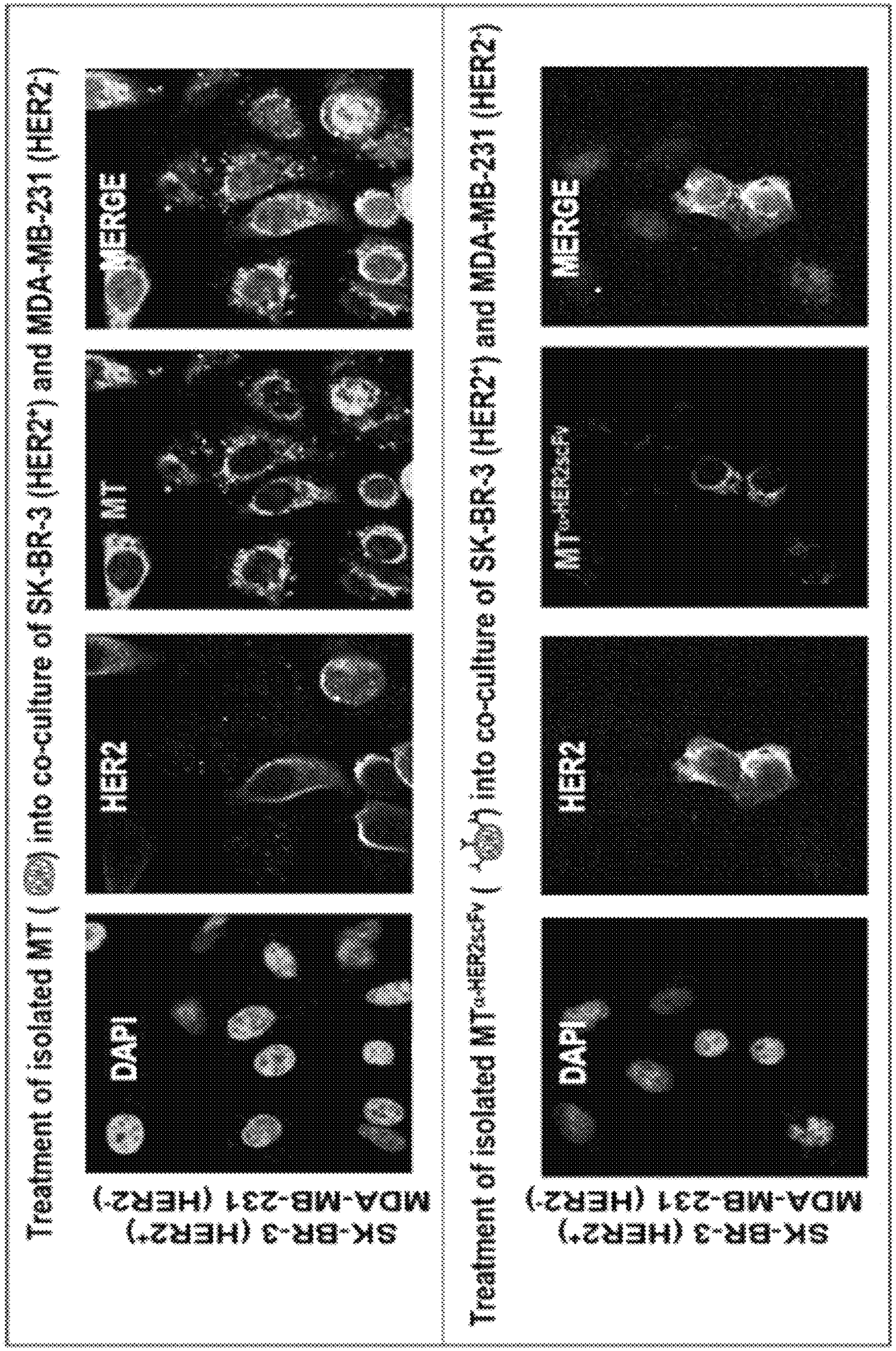
FIG. 15 is a view showing the results of confirming the intracellular expression of HER2 and a single chain variable region fragment of an anti-HER2 antibody by immunocytochemistry staining after co-culture of $HER2^+$ cells, the human breast cancer cell line SK-BR-3, and $HER2^-$ cells, the human breast cancer cell line MDA-MB-231 cells, and then treatment of the cells with $MT^{\alpha\text{-}HER2scFv}$. In this case, MT is the mitochondria, to which a single chain variable region fragment of an anti-HER2 antibody is not fused, isolated from the HEK293 cells.

In the case of the co-cultured SK-BR-3 ($HER2^+$) and MDA-MB-231 ($HER2^-$) cells, in the case of MT treated group, the mitochondria stained with Mitotracker Red were observed equally in SK-BR-3 ($HER2^+$) cells and MDA-MB-231 ($HER2^-$) cells, whereas in the case of $MT^{\alpha\text{-}HER2scFv}$ treated group, they were specifically observed only in $HER2^+$ cells, SK-BR-3 cell (FIG. 15).

Figure 16:
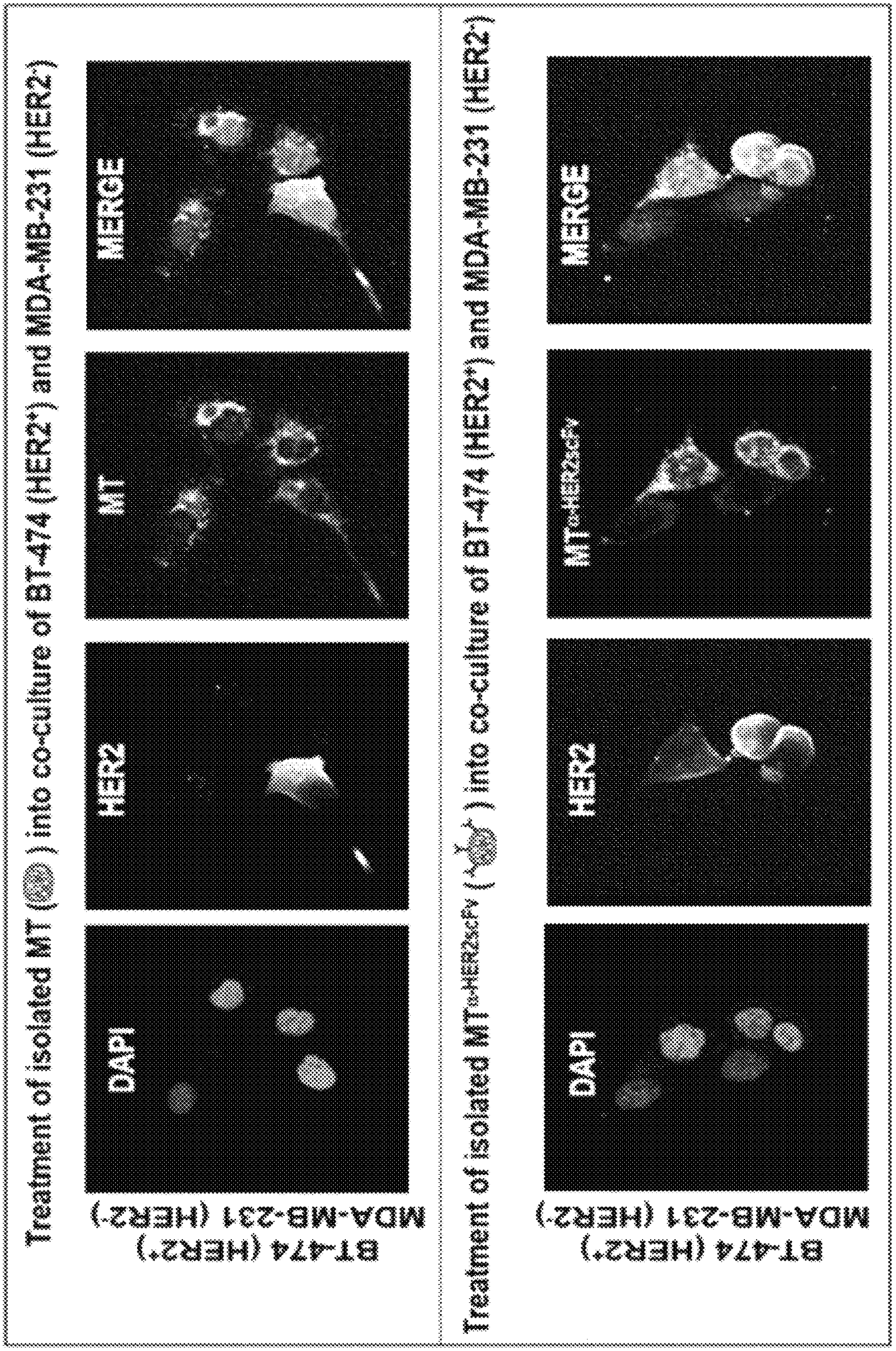
FIG. 16 is a view showing the results of confirming the intracellular expression of HER2 and a single chain variable region fragment of an anti-HER2 antibody by immunocytochemistry staining after co-culture of $HER2^+$ cells, the human breast cancer cell line BT-474, and $HER2^-$ cells, the human breast cancer cell line MDA-MB-231 cells, and then treatment of the cells with $MT^{\alpha\text{-}HER2scFv}$. In this case, MT is the mitochondria, to which a single chain variable region fragment of an anti-HER2 antibody is not fused, isolated from the HEK293 cells.

In the case of the co-cultured BT-474 ($HER2^+$) and MDA-MB-231 ($HER2^-$) cells, in the case of MT treated group, the mitochondria stained with Mitotracker Red were observed equally in BT-474 ($HER2^+$) cells and MDA-MB-231 ($HER2^-$) cells, whereas in the case of $MT^{\alpha\text{-}HER2scFv}$ treated group, they were specifically observed only in $HER2^+$ cells, BT-474 cell (FIG. 16).

From the above results, it was confirmed that the mitochondria fused with the anti-HER2scFv antibody ($MT^{\alpha\text{-}HER2scFv}$) could specifically target $HER2^+$ cells expressing a HER2 antigen.

Figure 17:
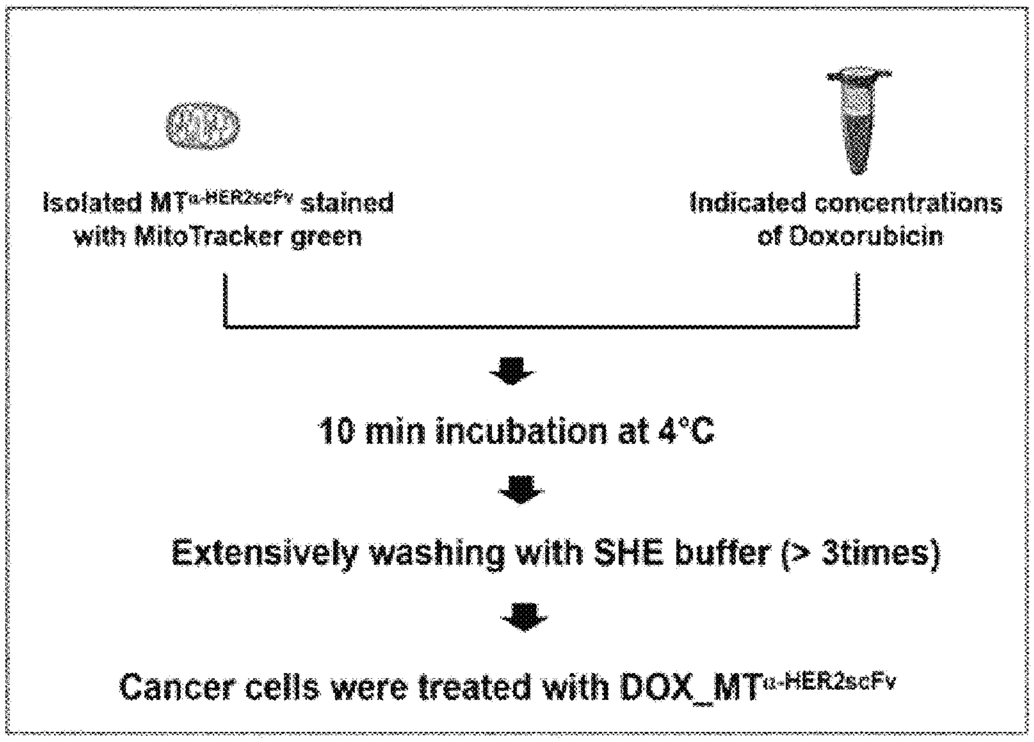
FIG. 17 is a view showing a method for preparing $DOX\_MT^{\alpha\text{-}HER2scFv}$ in which $MT^{\alpha\text{-}HER2scFv}$ stained with MitoTracker green and doxorubicin, a compound payload, are bound.

II. Preparation of Mitochondria in which an Anticancer Agent is Contained and a Targeting Protein is Bound, and Confirmation of their Activity Preparation Example 2. Preparation of Complex of Mitochondria Fused with Anti-HER2scFv Antibody and Doxorubicin HEK293 cells comprising mitochondria fused with an anti-HER2scFv antibody were treated with MitoTracker green to stain the mitochondria (green fluorescence), and then the mitochondria ($MT^{\alpha\text{-}HER2scFv}$) were isolated. 30 μg of the isolated mitochondria were reacted with 100 μM doxorubicin (DOX) at 4° C. for 10 minutes, and then centrifuged at about 12,000×g for 10 minutes to remove unreacted doxorubicin. Thereafter, they were washed twice with 500 μL of SHE (250 mM Sucrose, 20 mM HEPES (pH 7.4), 2 mM EGTA) buffer to finally obtain the mitochondria comprising doxorubicin ($DOX\_MT^{\alpha\text{-}HER2scFv}$) (FIG. 17).

Example 4. Evaluation of Anticancer Activity of $DOX\_MT^{\alpha\text{-}HER2scFv}$ Against Cancer Cells Example 4.1. Confirmation of Delivery Property of $DOX\_MT^{\alpha\text{-}HER2scFv}$ into Cancer Cells The human breast cancer cell line (SK-BR-3, BT-474 and MDA-MB-231) and the human lung cancer cell line (NCI-H1975) were treated with $DOX\_MT^{\alpha\text{-}HER2scFv}$ obtained in the same manner as in Preparation Example 2 above, respectively, and then the cells were observed by a confocal microscope. At this time, the nuclei of the cells were observed by staining with DAPI.

Figure 18:
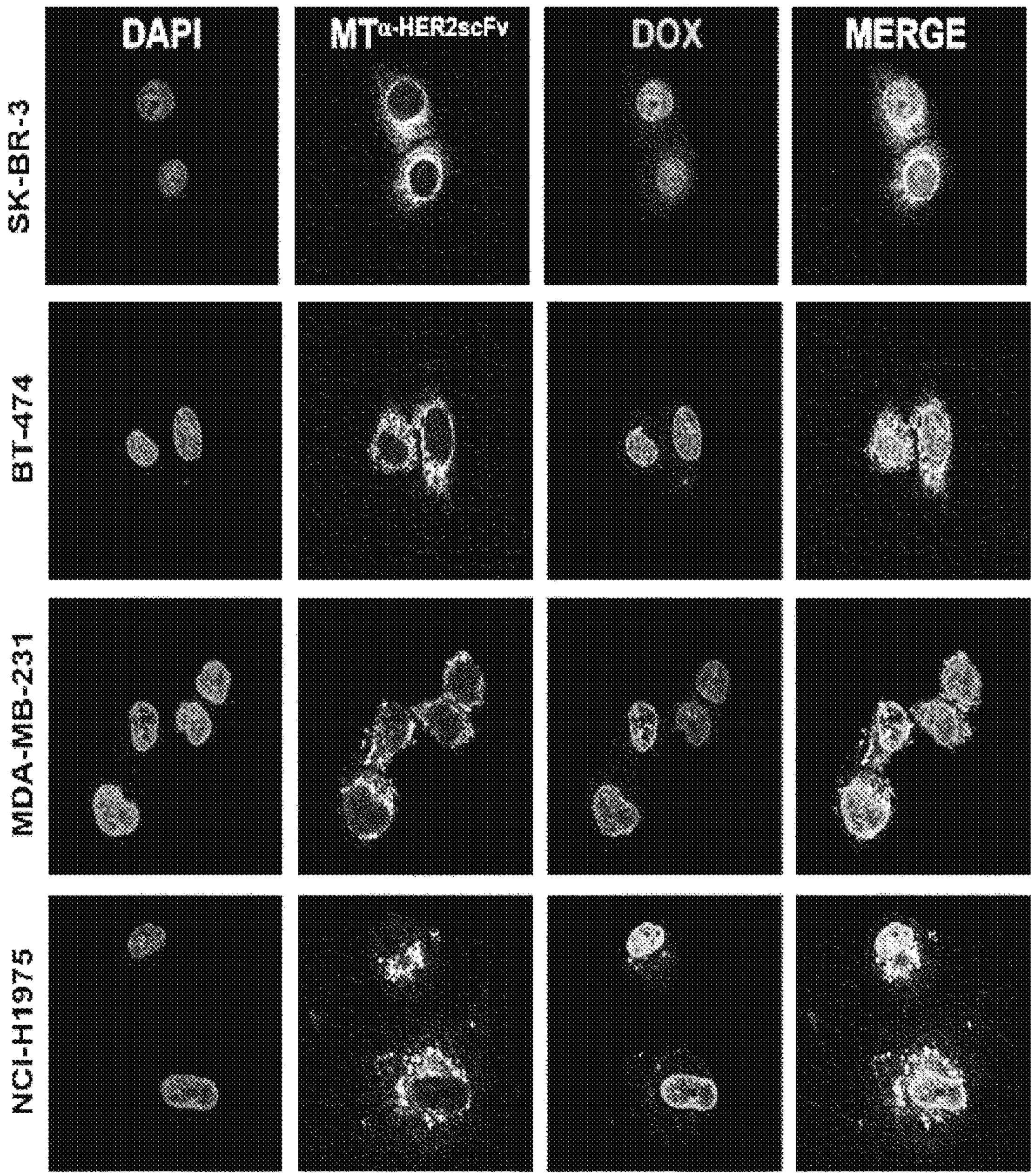
FIG. 18 is a view showing the results of observing the human breast cancer cell line (SK-BR-3, BT-474 and MDA-MB-231) and the human lung cancer cell line (NCI-H1975) after treatment with $DOX\_MT^{\alpha\text{-}HER2scFv}$ by a confocal microscope.

As a result, the mitochondria stained with MitoTracker green ($MT^{\alpha\text{-}HER2scFv}$ green fluorescence) were observed in the cytoplasm, and doxorubicin (DOX) showing red fluorescence was observed in the nucleus (FIG. 18). From the above results, it was found that doxorubicin of $DOX\_MT^{\alpha\text{-}HER2scFv}$ transported into the cell moved to the nucleus and was located in DNA in the nucleus.

Example 4.2. Confirmation of Morphological Change in Cancer Cells by Treatment with $DOX\_MT^{\alpha\text{-}HER2scFv}$ The human breast cancer cell line (SK-BR-3 and BT-474) and the human gastric cancer cell line (NCI-N87) were treated with $DOX\_MT^{\alpha HER2scFv}$ obtained in the same manner as in Preparation Example 2 above, respectively, and then the morphological change in cancer cells over time was observed by a confocal microscope. At this time, the nuclei of the cells were observed by staining with DAPI.

Figure 19:
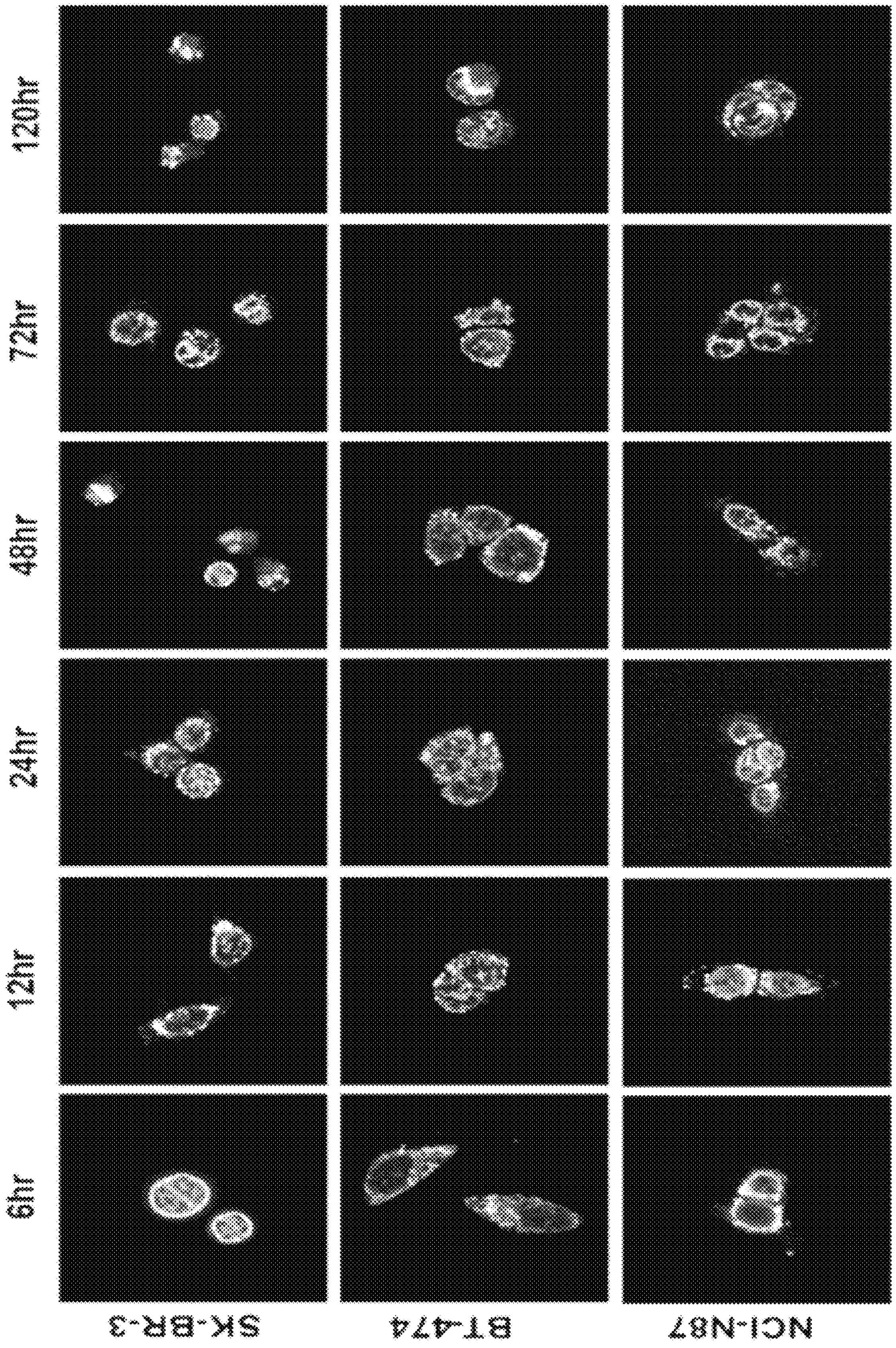
FIG. 19 is a view showing the results of observing the morphological change and death process of cancer cells over time by a confocal microscope after treatment of the human breast cancer cell line (SK-BR-3 and BT-474) and the human gastric cancer cell line (NCI-N87) with $DOX\_MT^{\alpha\text{-}HER2scFv}$.

As a result, it was observed that most of doxorubicin (DOX, red fluorescence) exists together in the mitochondria (green fluorescence) after 6 hours of treatment with $DOX\_MT^{\alpha\text{-}HER2scFv}$ (yellow fluorescence). However, doxorubicin was observed in the nucleus over time, and the morphological change in the cells was remarkably observed after 72 hours of treatment with $DOX\_MT^{\alpha\text{-}HER2scFv}$ (FIG. 19).

Example 4.3. Determination of Concentration of Doxorubicin Bound to $MT^{\alpha\text{-}HER2scFv}$ In order to quantify the concentration of doxorubicin bound to $DOX\_MT^{\alpha\text{-}HER2scFv}$ obtained in the same manner as in Preparation Example 2 above, a standard curve was prepared by measuring the absorbance for each concentration of doxorubicin, and then the concentration of doxorubicin bound to $DOX\_MT^{\alpha HER2scFv}$ was calculated.

Figure 20:
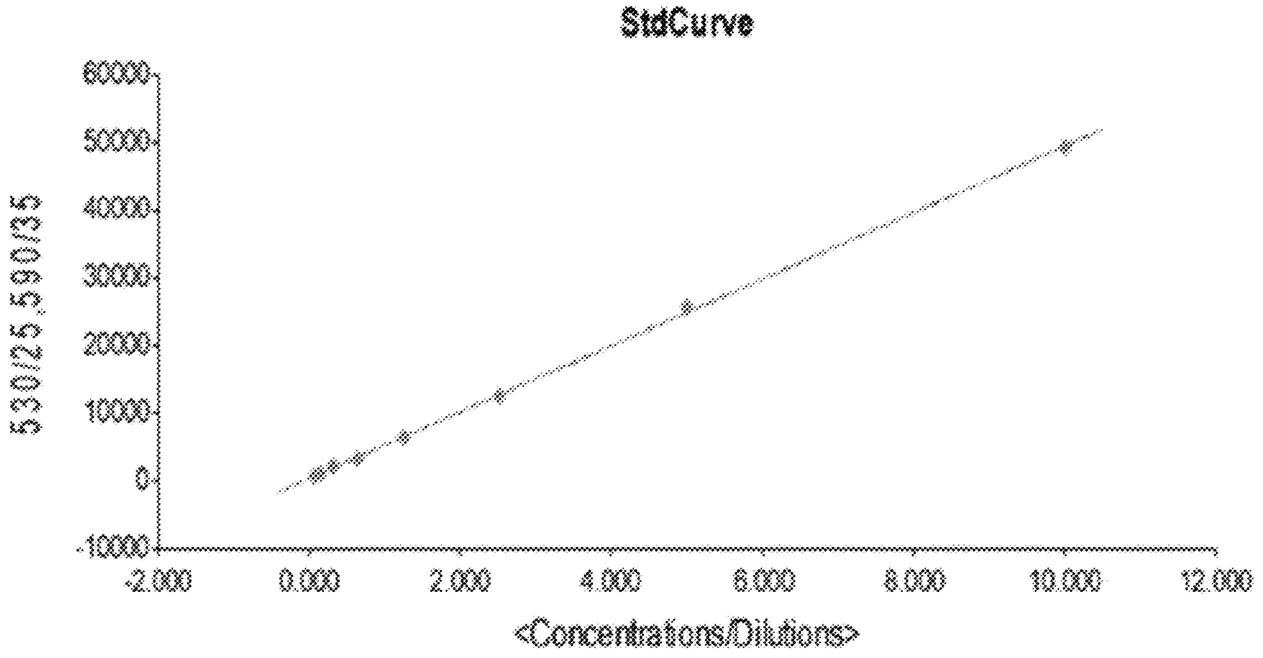
FIG. 20 is a graph showing a standard curve obtained by measuring the absorbance for each concentration of doxorubicin.

Specifically, 100 μL each of doxorubicin solution at a concentration of 20 PM, 10 μM, 5 M, 2.5 μM, 1.25 μM, 0.625 μM, and 0 μM, and $DOX\_MT^{\alpha\text{-}HER2scFv}$ diluted 1/20 in PBS was dispensed into a 96-well plate. Thereafter, the absorbance (emission wavelength of 590 nm) was measured with a multi-reader (BioTek, Synerge HTX). A standard curve was prepared using the absorbance values according to the concentration of doxorubicin, and then the concentration of doxorubicin bound to $DOX\_MT^{\alpha HER2scFv}$ was determined by substituting the absorbance values of the $DOX\_MT^{\alpha\text{-}HER2scFv}$ diluted solution (FIG. 20).

Example 4.4. Confirmation of Cancer Cell Proliferation Inhibitory Ability by Treatment with $DOX\_MT^{\alpha\text{-}HER2scFv}$ for Each Concentration In order to confirm the anticancer activity of $DOX\_MT^{\alpha\text{-}HER2scFv}$ obtained in the same manner as in Preparation Example 2 above using 200 μg of $MT^{\alpha\text{-}HER2scFv}$ and 100 μM doxorubicin (DOX), the cell proliferation inhibitory effect by treating the human breast cancer, lung cancer and gastric cancer cell lines with $DOX\_MT^{\alpha\text{-}HER2scFv}$ was evaluated.

Specifically, the human breast cancer (SK-BR-3, BT-474 and MDA-MB-231), lung cancer (NCI-H1975) and gastric cancer (NCI-N87 and MKN-74) cell lines were inoculated into a 96-well plate at about $3\times10^3$ cells/well, respectively, and cultured for 24 hours. At this time, SK-BR-3, BT-474 and NCI-N87 cells were cultured in RPMI-1640 medium containing 10% FBS, and MDA-MB-231, NCI-H1975 and MKN-74 cells were cultured in DMEM medium containing 10% FBS. After culturing for 24 hours, each cell was treated with doxorubicin (DOX) or $DOX\_MT^{\alpha\text{-}HER2scFv}$ at a concentration of 2 μM, 1 μM, 0.5 μM, 0.25 μM, 0.1 μM, 0.05 μM, 0.025 μM, and 0.01 μM. After 144 hours of sample treatment, cell proliferation was measured by WST-1 assay.

Figure 21:
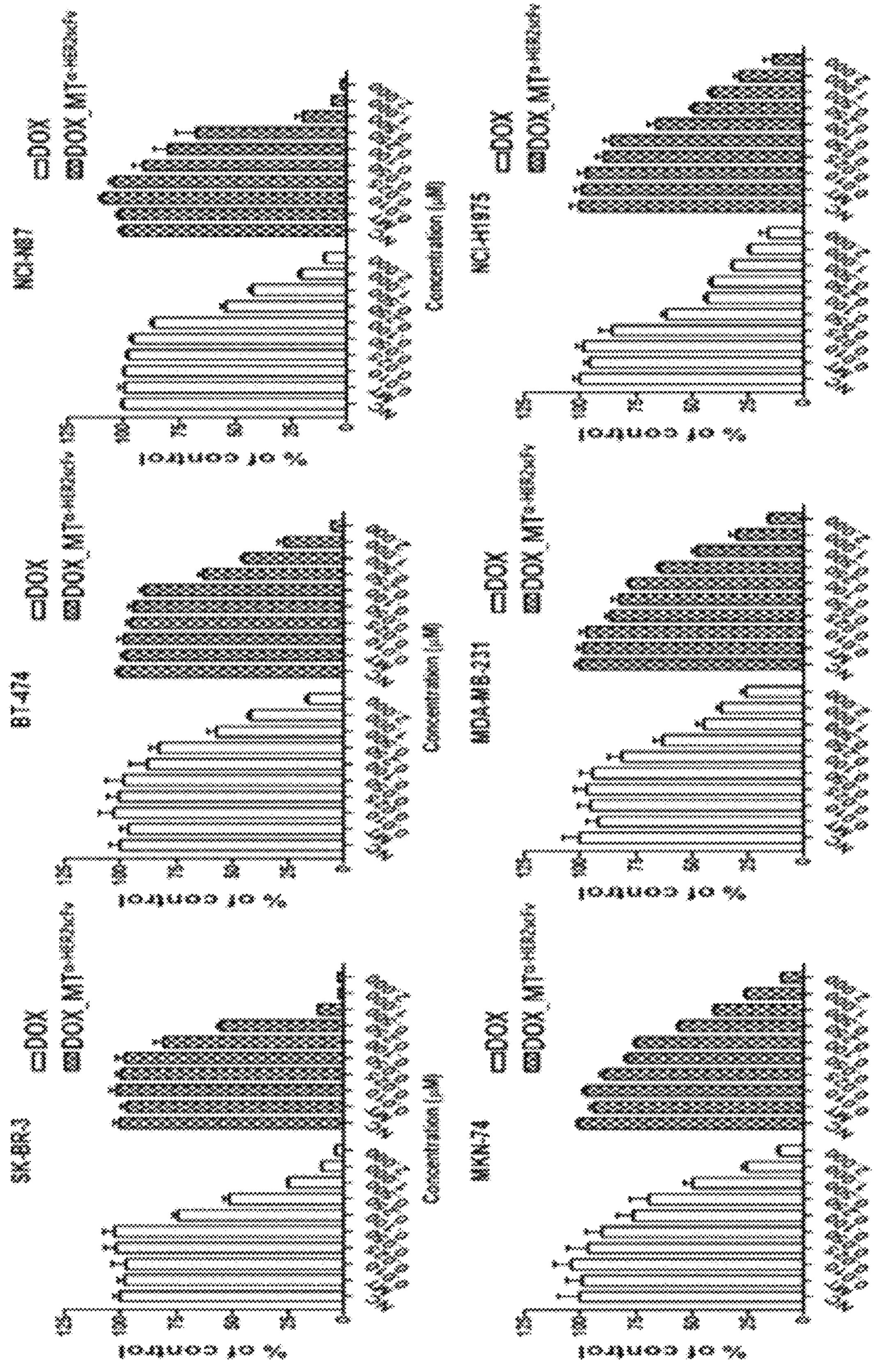
FIG. 21 is a graph showing the results of measuring the cytotoxicity by treatment of the human breast cancer cell line (SK-BR-3, BT-474 and MDA-MB-231), the human lung cancer cell line (NCI-H1975) and the human gastric cancer cell line (NCI-N87 and MKN-74) with DOX or $DOX\_MT^{\alpha\text{-}HER2scFv}$. In this case, MT is $MT^{\alpha\text{-}HER2scFv}$ in which DOX is not loaded.

As a result, as shown in FIG. 21, for the untreated group (NC), cell proliferation inhibitory effect was not observed in the mitochondria-only treated group (MT). On the other hand, in DOX treated group and $DOX\_MT^{\alpha\text{-}HER2scFv}$ treated group, cancer cell proliferation was inhibited in a concentration-dependent manner. In particular, it was confirmed that when treated with 1 μM $DOX\_MT^{\alpha\text{-}HER2scFv}$, cell growth was inhibited by about 60% to 90% compared to the untreated group depending on the cancer cell line (FIG. 21).

Example 4.5. Confirmation of Proliferation Inhibitory Ability by Treatment with $DOX\_MT^{\alpha\text{-}HER2scFv}$ for Each Concentration in Normal Cells 200 μg of $MT^{\alpha\text{-}HER2scFv}$ and 100 μM doxorubicin (DOX) were reacted in the same manner as in Preparation Example 2 above. In order to confirm the influence of the obtained $DOX\_MT^{\alpha\text{-}HER2scFv}$ on cell proliferation in normal cells, the cell proliferation inhibitory effect by treatment with $DOX\_MT^{\alpha\text{-}HER2scFv}$ in human lung fibroblasts was evaluated.

Specifically, the human lung fibroblast cell lines WI-38 and CCD-8Lu were inoculated into a 96-well plate at about $3\times10^3$ cells/well, respectively, and cultured for 24 hours. At this time, WI-38 and CCD-8Lu were cultured in DMEM medium containing 10% FBS. After culturing for 24 hours, each cell was treated with doxorubicin (DOX) or $DOX\_MT^{\alpha\text{-}HER2scFv}$ at a concentration of 2 μM, 1 μM, 0.5

μM, 0.25 μM, 0.1 μM, 0.05 μM, 0.025 μM, and 0.01 μM. After 144 hours of sample treatment, cell proliferation was measured by WST-1 assay.

Figure 22:
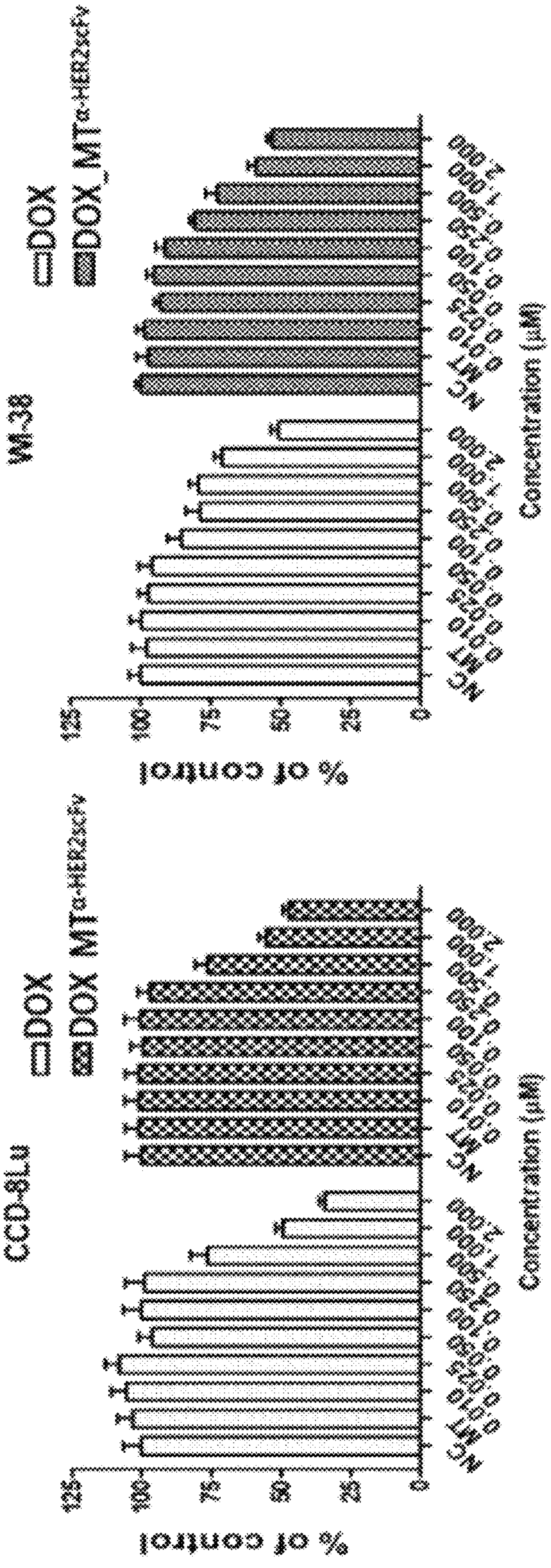
FIG. 22 is a graph showing the results of measuring the cytotoxicity by treatment of the human lung fibroblast cell line (WI-38 and CCD-8Lu) with DOX or DOX_$MT^{\alpha\text{-}HER2scFv}$. In this case, MT is $MT^{\alpha\text{-}HER2scFv}$ in which DOX is not loaded.

As a result, as shown in FIG. 22, for the untreated group (NC), cell proliferation inhibitory effect was not observed in the mitochondria-only treated group (MT). In addition, it was confirmed that in DOX treated group and DOX_MT$^{\alpha HER2scFv}$ treated group, cell proliferation inhibitory ability was weaker than that of cancer cells.

Example 4.6. Analysis of $IC_{50}$ Value by Treatment with DOX_MT$^{\alpha\text{-}HER2scFv}$ in Cancer Cells and Normal Cells Based on the cell proliferation inhibition results of DOX_MT$^{\alpha\text{-}HER2scFv}$ for each concentration in Example 4.4 and Example 4.5, $IC_{50}$ values in each cell were analyzed and shown in FIG. 23.

Example 4.7. Comparison of Proliferation Inhibitory Ability by Treatment with DOX_MT$^{\alpha\text{-}HER2scFv}$ in Cancer Cells and Normal Cells 200 μg of MT$^{\alpha\text{-}HER2scFv}$ and 100 μM doxorubicin (DOX) were reacted in the same manner as in Preparation Example 2 above. In order to compare the influence of the obtained DOX_MT$^{\alpha\text{-}HER2scFv}$ on cell proliferation in cancer cells and normal cells, after treatment with DOX_MT$^{\alpha\text{-}HER2scFv}$ at the same concentration in the human breast cancer, lung cancer, gastric cancer cell lines and the lung fibroblast cell line, the cell proliferation inhibitory ability was measured.

Specifically, the human breast cancer (SK-BR-3, BT-474 and MDA-MB-231), lung cancer (NCI-H1975), gastric cancer (MKN-74 and NCI-N87) cell lines and the lung fibroblast cell line (CCD-8Lu and WI-38) were inoculated into a 96-well plate at about $3\times10^3$ cells/well, respectively, and cultured for 24 hours. At this time, SK-BR-3, BT-474 and NCI-N87 cells were cultured in RPMI-1640 medium containing 10% FBS. MDA-MB-231, NCI-H1975, MKN-74, CCD-8Lu, and WI-38 cells were cultured in DMEM medium containing 10% FBS. After culturing for 24 hours, the cells were treated with 0.5 μM doxorubicin (DOX) or DOX_MT$^{\alpha\text{-}HER2scFv}$ respectively, and after 144 hours, the cell proliferation inhibitory ability was evaluated by WST-1 assay. At this time, the mitochondria-only treated group (MT$^{\alpha\text{-}HER2scFv}$) was used as a negative control for DOX_MT$^{\alpha\text{-}HER2scFv}$. Statistical processing was performed using Graphpad 5.0 software, and p values were measured with one-way ANOVA (Turkey's) test (*$p<0.05$, $p<0.01$, and *$p<0.001$).

Figure 24:
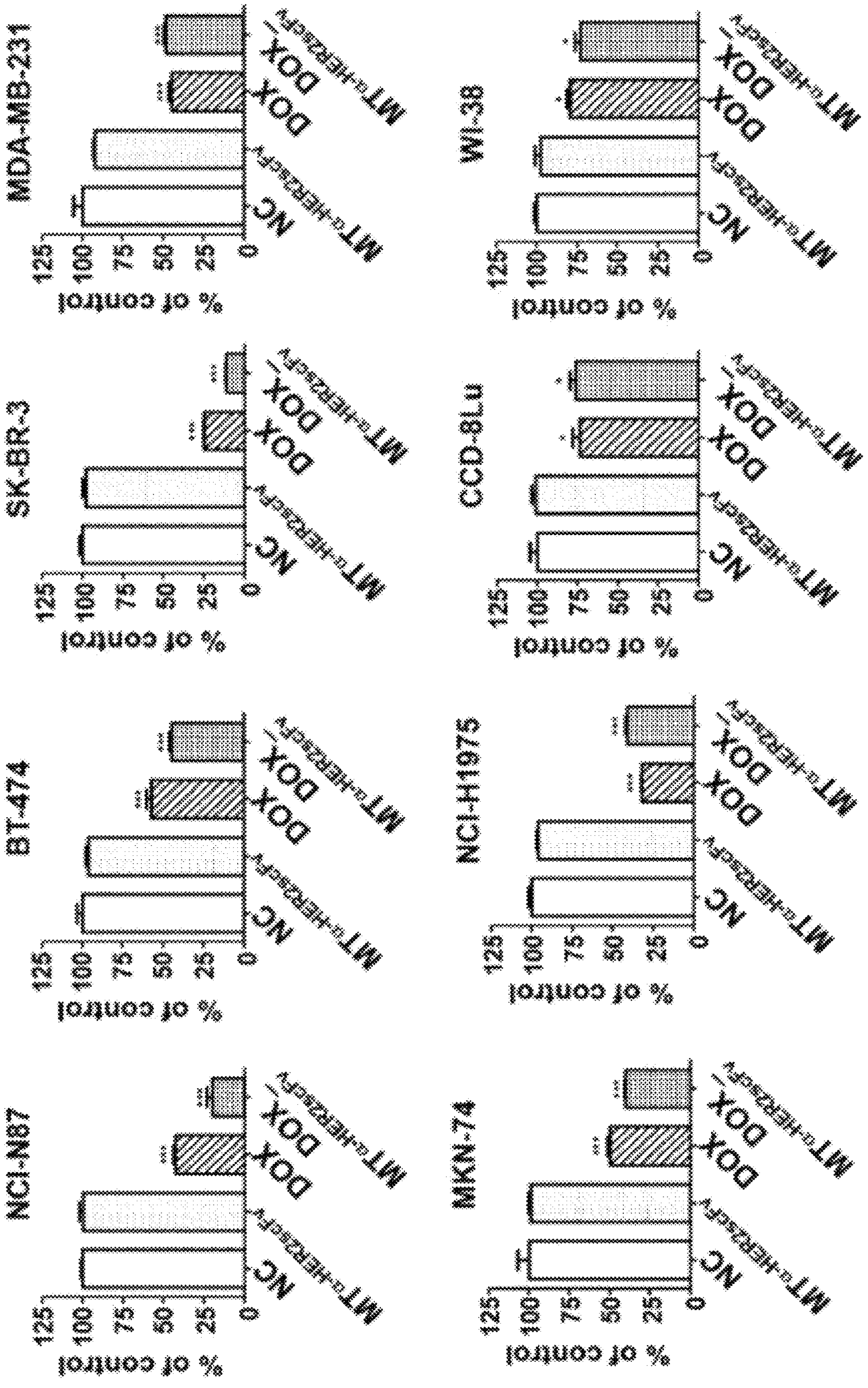
FIG. 24 is a graph showing the results of measuring the cytotoxicity by treatment of the human breast cancer cell line (SK-BR-3, BT-474 and MDA-MB-231), the human lung cancer cell line (NCI-H1975), the human gastric cancer cell line (NCI-N87 and MKN-74), the human lung fibroblast cell line (WI-38 and CCD-8Lu) with 0.5 μM DOX or DOX_$MT^{\alpha\text{-}HER2scFv}$. In this case, MT is $MT^{\alpha\text{-}HER2scFv}$ in which DOX is not loaded.

As a result, as shown in FIG. 24, for the untreated group (NC) in cancer cells and normal cells, cell proliferation inhibitory effect was not observed in the mitochondria-only treated group (MT$^{\alpha\text{-}HER2scFv}$). In the case of DOX treated group and DOX_MT$^{\alpha\text{-}HER2scFv}$ treated group, cell proliferation inhibitory effect was shown by about 50% to 80% or higher compared to the untreated group in cancer cells, whereas cell proliferation inhibitory effect was shown by about 25% or lower in normal cells.

Example 4.8. Confirmation of Cancer Cell Apoptosis by Treatment with DOX_MT$^{\alpha\text{-}HER2scFv}$ by TUNEL Assay In order to confirm the apoptosis inducing activity of DOX_MT$^{\alpha\text{-}HER2scFv}$ obtained in the same manner as in Preparation Example 2 above in cancer cells, after treatment with DOX_MT$^{\alpha\text{-}HER2scFv}$ in the human breast cancer and gastric cancer cell lines, TUNEL assay was performed.

Specifically, the human breast cancer cell line (SK-BR-3 and BT-474) and the human gastric cancer cell line (NCI-N87) were inoculated into a 24-well plate at about $3\times10^4$ cells/well and cultured for 24 hours. After culturing for 24 hours, the cells were treated with MT$^{\alpha\text{-}HER2scFv}$ or 1 μM DOX_MT$^{\alpha\text{-}HER2scFv}$, and after 48 hours, TUNEL assay was performed to confirm the apoptosis. At this time, the mitochondria-only treated group (MT$^{\alpha\text{-}HER2scFv}$) was used as a control group for DOX_MT$^{\alpha\text{-}HER2scFv}$. The nuclei of the cells were observed by staining with DAPI.

Figure 25:
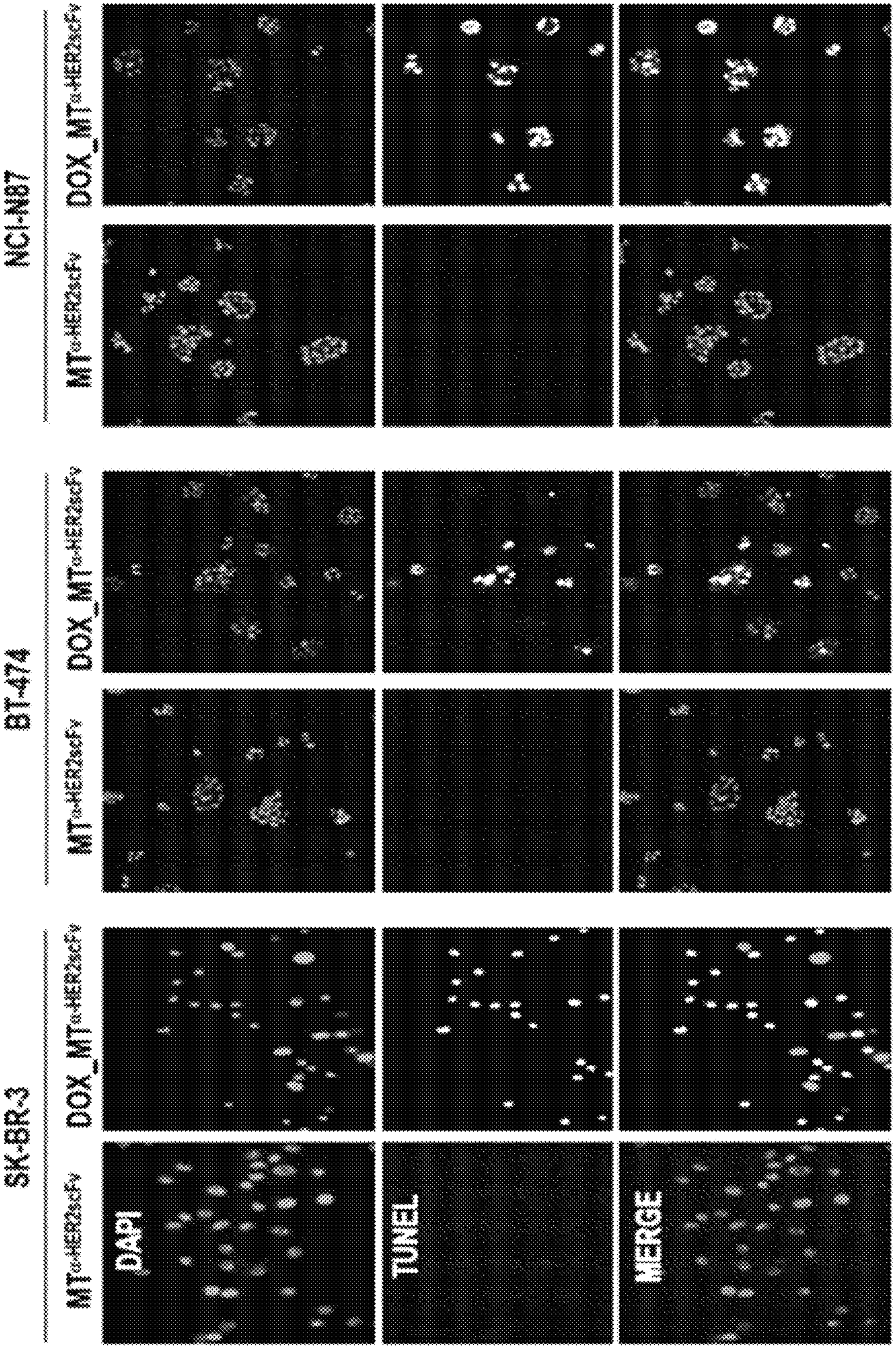
FIG. 25 is a view showing the results of confirming the apoptosis by treatment of the human breast cancer cell line (SK-BR-3 and BT-474) and the human gastric cancer cell line (NCI-N87) with $MT^{\alpha\text{-}HER2scFv}$ or DOX_$MT^{\alpha\text{-}HER2scFv}$ by TUNEL assay.

As a result, almost no apoptosis (green fluorescence) was observed in the mitochondria-only treated group (MT$^{\alpha\text{-}HER2scFv}$). However, an increase in apoptosis was observed in the cell nucleus of DOX_MT$^{\alpha\text{-}HER2scFv}$ treated group. From the above results, it was confirmed that the apoptosis was induced by treatment with DOX_MT$^{\alpha\text{-}HER2scFv}$ (FIG. 25).

Example 4.9. Confirmation of Cancer Cell Apoptosis by Treatment with DOX_MT$^{\alpha\text{-}HER2scFv}$ Through Western Blot Analysis In order to confirm the apoptosis effect of DOX_MT$^{\alpha\text{-}HER2scFv}$ obtained in the same manner as in Preparation Example 2 above in cancer cells, after treatment with DOX_MT$^{\alpha\text{-}HER2scFv}$ in the human breast cancer cell line, Western blot was performed using an antibody against an apoptosis marker.

Specifically, the human breast cancer cell lines (SK-BR-3 and BT-474) were inoculated into a 6-well plate at about $5\times10^6$ cells/well, respectively, and cultured for 24 hours. After culturing for 24 hours, the cells were treated with MT$^{\alpha\text{-}HER2scFv}$ or DOX_MT$^{\alpha\text{-}HER2scFv}$ respectively, and after 96 hours, the cells were lyzed, proteins were extracted, and Western blot was performed. Anti-cleaved PARP antibody (Cell signaling, 9541S), anti-cleaved caspase 3 antibody (Cell signaling, 9664S), anti-phospho-p53 antibody (ABclonal, AP0762) and anti-β actin antibody (Sigma, A2228) were used as primary antibodies. Anti-mouse IgG HRP or anti-rabbit IgG HRP was used as a secondary antibody. The amount of protein was corrected through the expression level of R actin protein. At this time, the mitochondria-only treated group (MT$^{\alpha\text{-}HER2scFv}$) was used as a negative control for DOX_MT$^{\alpha\text{-}HER2scFv}$.

Figure 26:
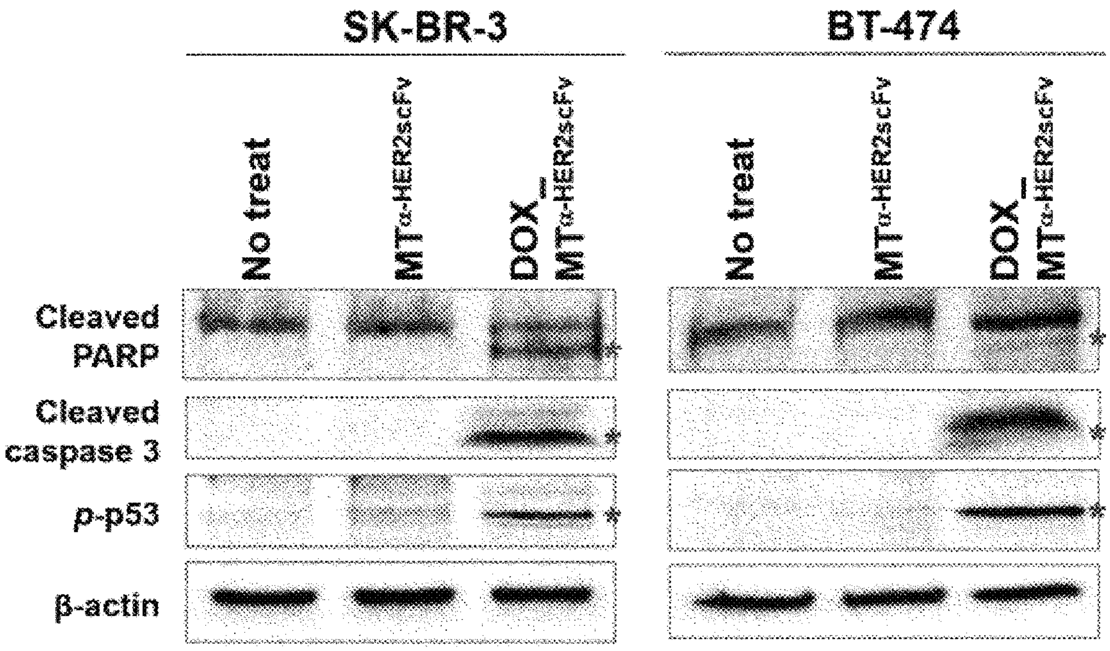
FIG. 26 is a view showing the results of confirming the apoptosis caused by treatment of the human breast cancer cell line (SK-BR-3 and BT-474) with $MT^{\alpha\text{-}HER2scFv}$ or DOX_$MT^{\alpha\text{-}HER2scFv}$ by Western blot.

As a result, in the mitochondria-only treated group (MT$^{\alpha\text{-}HER2scFv}$), similar to the untreated group (No treat), the cleaved forms of PARP and caspase 3 observed during the apoptosis were not observed, and the phosphorylated form of p53 was not also observed. On the other hand, in DOX_MT$^{\alpha\text{-}HER2scFv}$ treated group, the expression of the phosphorylated p53 and the cleaved forms of PARP and caspase 3 was observed (FIG. 26). From the above results, it was confirmed that the apoptosis was induced by treatment with DOX_MT$^{\alpha\text{-}HER2scFv}$.

Example 4.10. Confirmation of Cancer Cell Apoptosis by DOX_MT$^{\alpha\text{-}HER2scFv}$ Through Flow Cytometry In order to confirm the apoptosis effect by DOX_MT$^{\alpha\text{-}HER2scFv}$ obtained in the same manner as in Preparation Example 2 above in cancer cells, after treatment with DOX_MT$^{\alpha\text{-}HER2scFv}$ in the human breast cancer and gastric cancer cell lines, flow cytometry was performed by staining with Annexin V/PI.

Specifically, the human breast cancer cell line (SK-BR-3 and BT-474) and the human gastric cancer cell line (NCI-N87) were inoculated into a 6-well plate at about $5\times10^6$ cells/well, respectively, and cultured for 24 hours. After culturing for 24 hours, the cells were treated with $MT^{\alpha\text{-}HER2scFv}$ or 1 μM DOX_$MT^{\alpha\text{-}HER2scFv}$. After 96 hours of treatment, the cells were washed twice with PBS and obtained by treatment with 0.05% Trypsin-EDTA. The obtained cells were centrifuged and then washed with PBS to remove 0.05% Trypsin-EDTA. Thereafter, the cells were stained for 10 minutes using Annexin V/PI staining kit (Roche, 11988549001), and the stained cells were analyzed using FACS equipment (Beckman Coulter, CytoFLEX). At this time, the mitochondria-only treated group ($MT^{\alpha\text{-}HER2scFv}$) was used as a negative control for DOX_$MT^{\alpha\text{-}HER2scFv}$.

Figure 27:
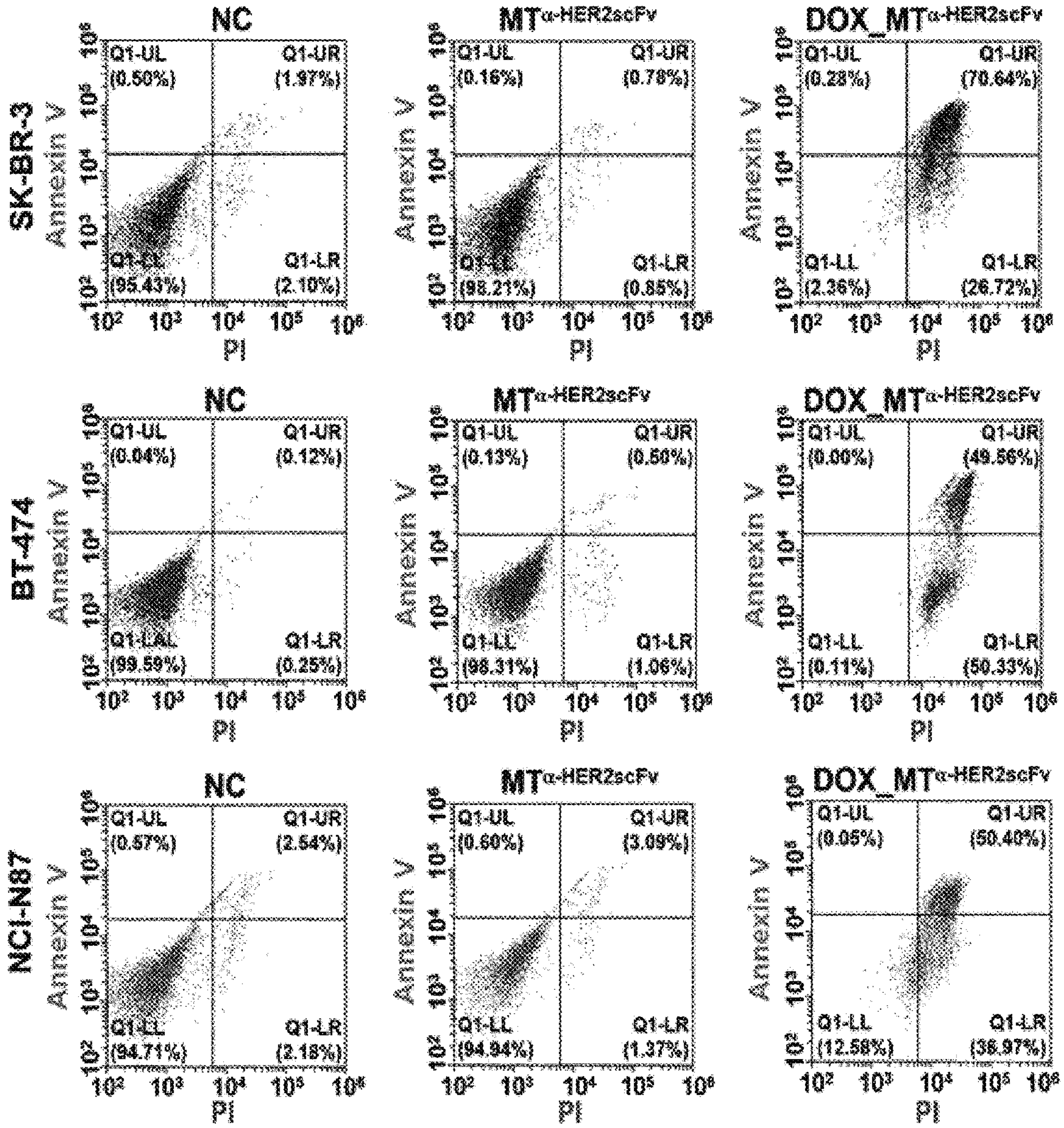
FIG. 27 is a graph showing the results of confirming the apoptosis by treatment of the human breast cancer cell line (SK-BR-3 and BT-474) and the human gastric cancer cell line (NCI-N87) with $MT^{\alpha\text{-}HER2scFv}$ or DOX_$MT^{\alpha\text{-}HER2scFv}$ by flow cytometry. In this case, MT is $MT^{\alpha\text{-}HER2scFv}$ in which DOX is not loaded.

As a result, for the untreated group (NC), no change in Annexin V/PI values was observed in the mitochondria-only treated group ($MT^{\alpha\text{-}HER2scFv}$). On the other hand, the Annexin V/PI value was increased in DOX_$MT^{\alpha\text{-}HER2scFv}$ treated group (FIG. 27). From the above results, it was confirmed that the apoptosis was induced by treatment with DOX_$MT^{\alpha\text{-}HER2scFv}$.

Example 4.11. Evaluation of HER2 Expressing Cell Selective Apoptosis Inducing Activity of DOX_$MT^{\alpha\text{-}HER2scFv}$ In order to confirm the HER2 selective apoptosis inducing effect of DOX_$MT^{\alpha\text{-}HER2scFv}$ obtained in the same manner as in Preparation Example 2 above, the co-cultured $HER2^+$ cancer cells and $HER2^-$ normal cells were treated with DOX_$MT^{\alpha\text{-}HER2scFv}$, and then TUNEL assay and immunocytochemistry staining were performed.

Figure 28:
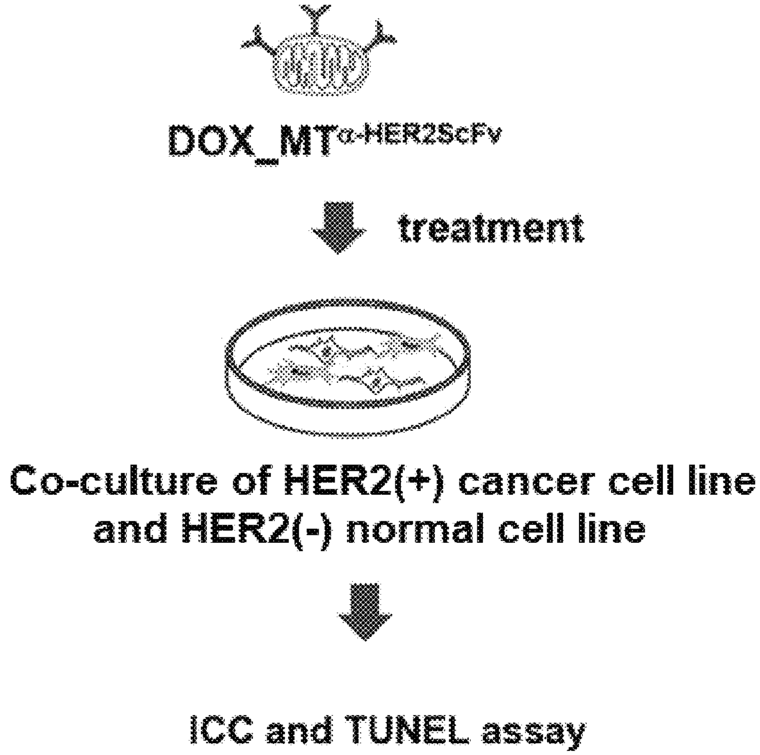
FIG. 28 is a view showing an experimental method for confirming the selective killing effect of HER2 expressing cancer cells by DOX_$MT^{\alpha\text{-}HER2scFv}$.

Specifically, the human breast cancer cell line BT-474 ($HER2^+$) and the human lung fibroblast cell line WI-38 ($HER2^-$) were inoculated together into a 24-well plate at $3\times10^4$ cells/well and co-cultured in DMEM medium containing 10% FBS for 24 hours. At this time, BT-474 cells were prepared by culturing in RPMI-1640 medium containing 10% FBS, and WI-38 cells were prepared by culturing in DMEM medium containing 10% FBS. After culturing for 24 hours, the co-cultured cells were treated with 1 μM DOX_$MT^{\alpha\text{-}HER2scFv}$ and cultured for additional 48 hours. The apoptosis was evaluated by TUNEL assay and immunocytochemistry staining (FIG. 28).

Example 4.12. Confirmation of HER2 Expressing Cell Selective Apoptosis Inducing Activity of DOX_$MT^{\alpha\text{-}HER2scFv}$ by TUNEL Assay The cells treated in the same manner as in Example 4.11 above were washed twice with PBS and then were fixed by adding 3.7% formaldehyde at room temperature for 30 minutes. Thereafter, anti-HER2 antibody (Cell Signaling Technology, 2165) was used as a primary antibody, and anti-rabbit IgG antibody labeled with Alexa Fluor® 555 (Invitrogen, 21428) was used as a secondary antibody, and $HER2^+$ cells were labeled with red fluorescence. Thereafter, the cells were stained with TUNEL solution for 30 minutes, and the cells in which the apoptosis occurs were labeled with green fluorescence and mounted, and the cells were observed by a confocal microscope. At this time, the nuclei of the cells were observed by staining with DAPI.

Figure 29:
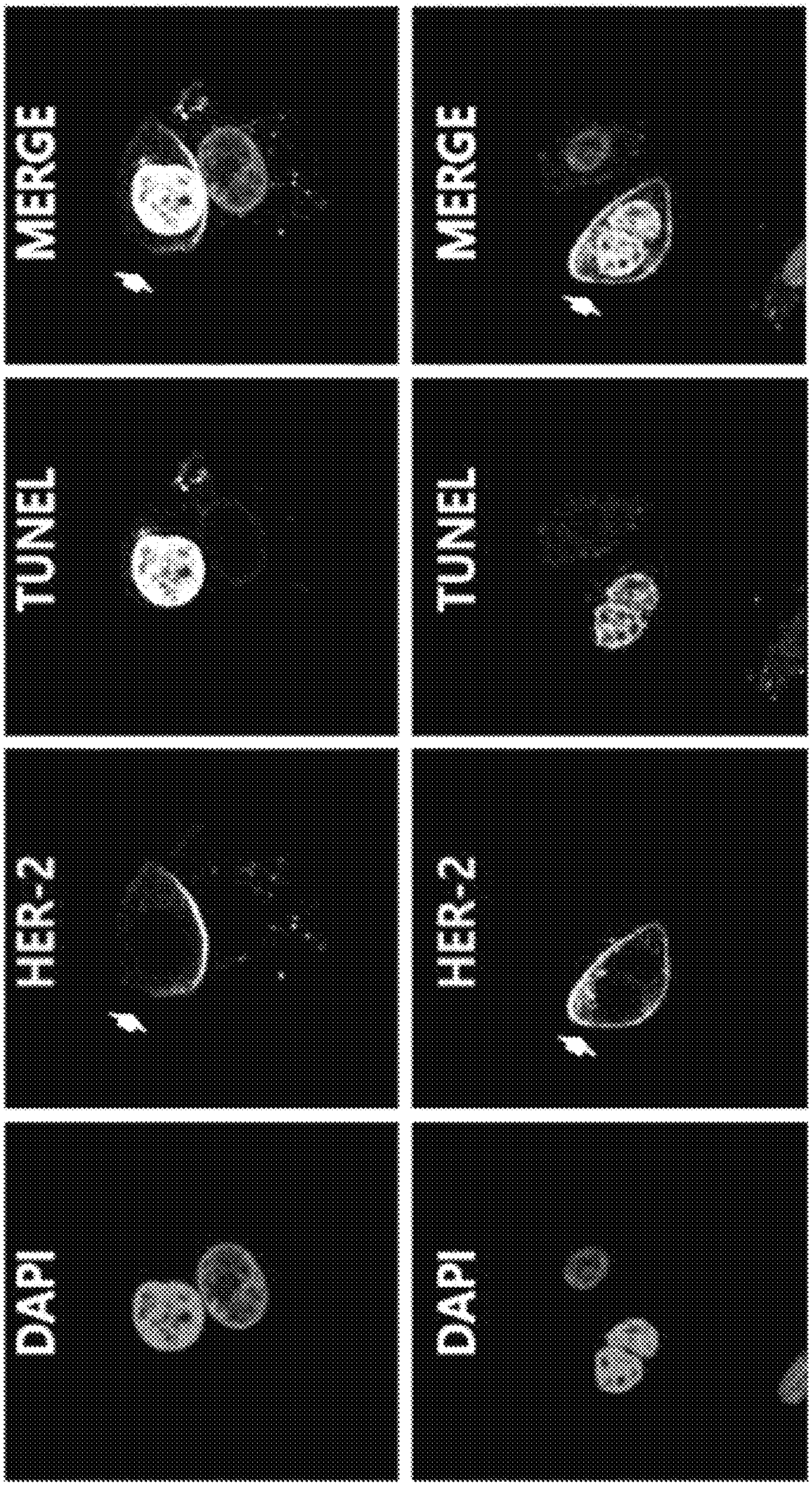
FIG. 29 is a view showing the results of confirming the apoptosis by co-culture of the human breast cancer cell line BT-474 (HER2+, white arrow) and the human lung fibroblast cell line WI-38 ($HER2^{-}$), and then treatment of the cells with DOX_$MT^{\alpha\text{-}HER2scFv}$ by TUNEL assay.

As a result, strong green fluorescence was selectively observed only in BT-474 cells (white arrow), which are $HER2^+$ cancer cells (FIG. 29). From the above results, it was confirmed that the apoptosis by DOX_$MT^{\alpha\text{-}HER2scFv}$ could be selectively induced depending on the presence or absence of HER2 expression.

Figure 30:
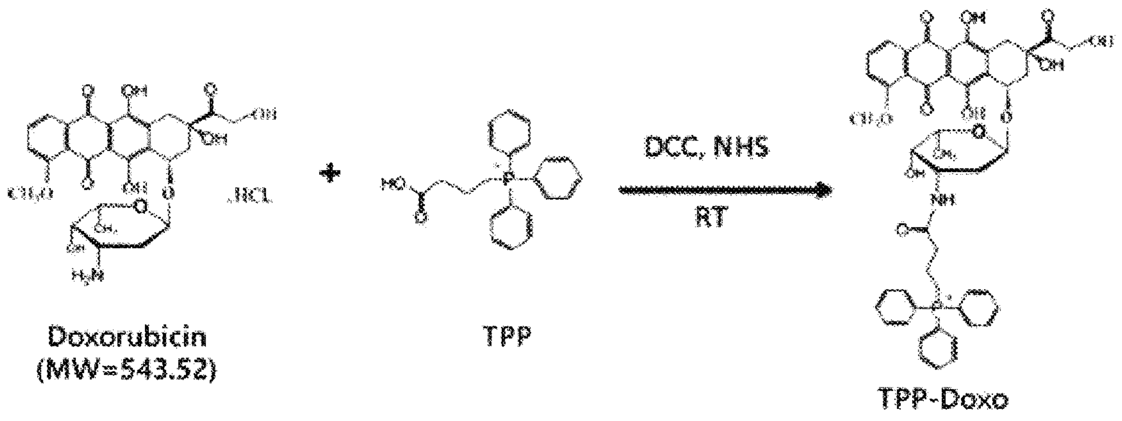
FIG. 30 is a view showing the synthesis process of triphenylphosphonium (TPP)-doxorubicin (TPP-DOX).
Figure 31:
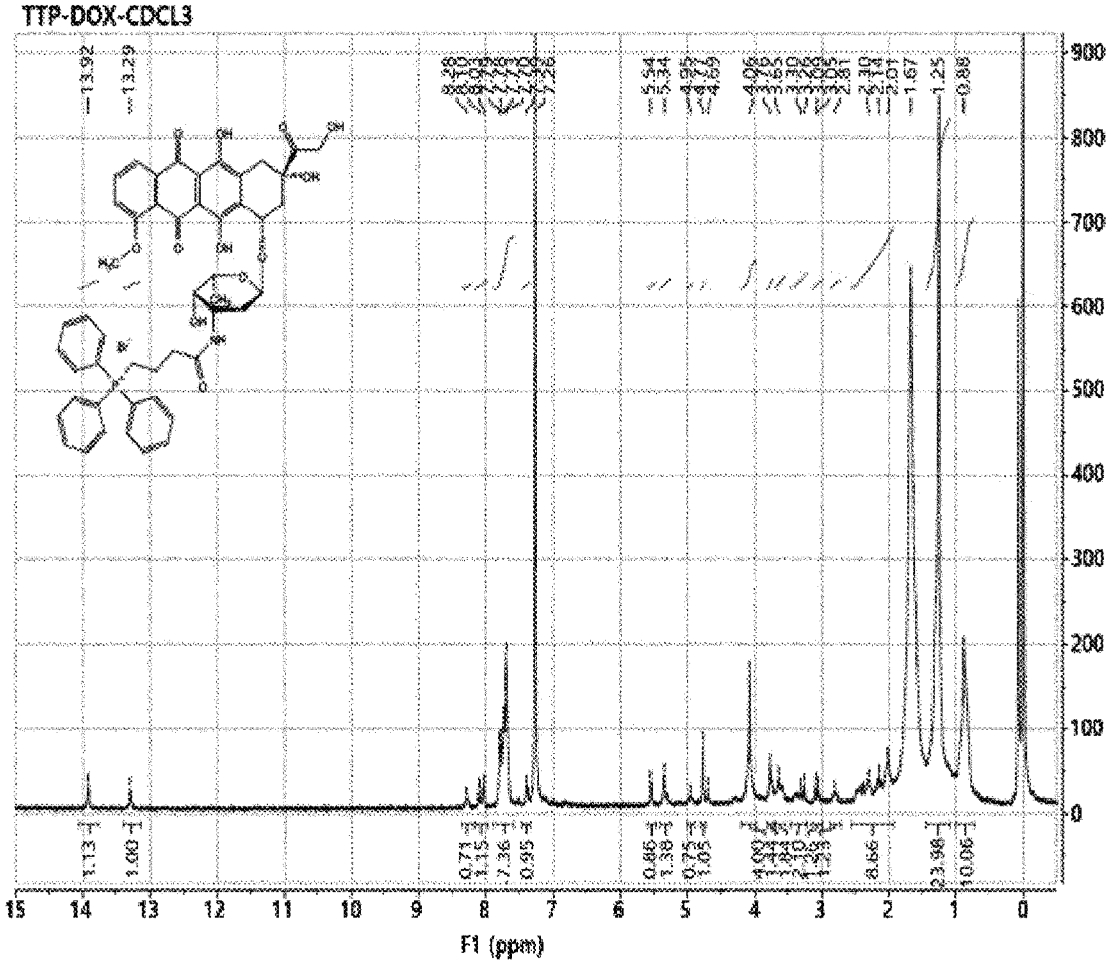
FIG. 31 is a view showing the results of MRI analysis of TPP-DOX.

Preparation Example 3. Preparation of Compound to which Triphenylphosphonium-Doxorubicin is Bound In order to efficiently deliver the anticancer drug doxorubicin (DOX) into the isolated mitochondria, a compound capable of targeting mitochondria was fused with doxorubicin. The most representative mitochondria targeting compound is triphenylphosphonium (TPP), and the anticancer agent to which TPP is bound was reacted as shown in FIG. 30 using a method known in "Mitochondrial Delivery of Doxorubicin via Triphenylphosphine Modification for Overcoming Drug Resistance in MDA-MB-435/DOX Cells" (Molecular Pharmaceutics, 11 (8), 2640-2649) to prepare TPP-doxorubicin (TPP-DOX), and the compound was confirmed to be TPP-doxorubicin by MRI analysis of the compound (FIG. 31).

Figure 32:
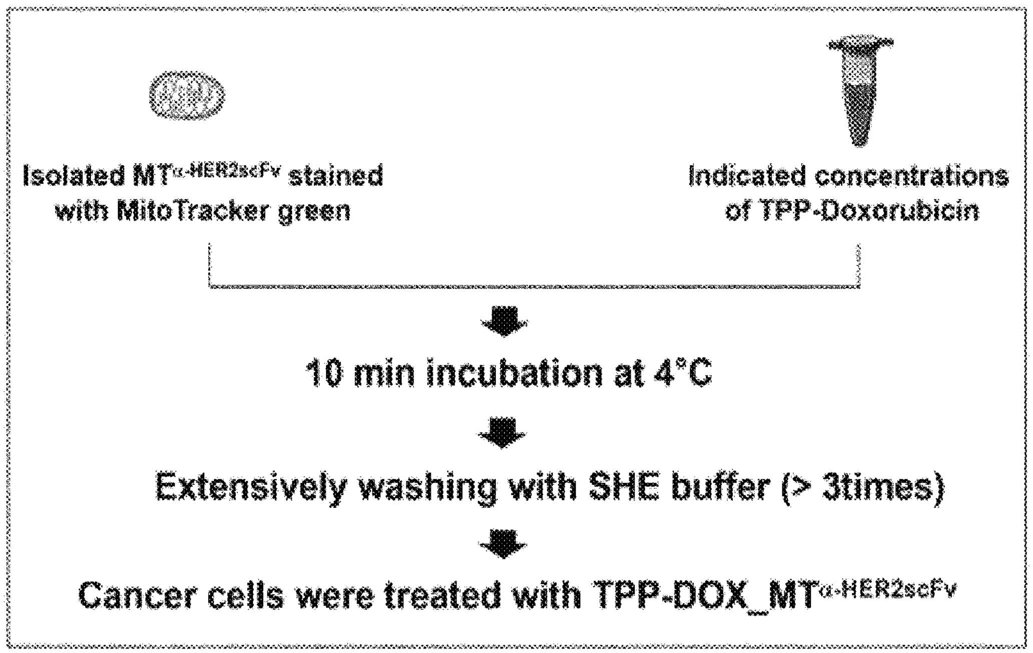
FIG. 32 is a view showing a method for preparing TPP-DOX_$MT^{\alpha\text{-}HER2scFv}$ in which $MT^{\alpha\text{-}HER2scFv}$ stained with MitoTracker green and TPP-DOX, a compound payload, are bound.

Preparation Example 4. Preparation of Complex of Mitochondria-TPP and Doxorubicin HEK293 cells in which an anti-HER2scFv antibody is expressed were treated with MitoTracker green to stain the mitochondria, and then the mitochondria $MT^{\alpha\text{-}HER2scFv}$) were isolated. Thereafter, 30 μg of the mitochondria fused with an anti-HER2scFv antibody ($MT^{\alpha\text{-}HER2scFv}$) were reacted with 100 μM TPP-doxorubicin at 4° C. for 10 minutes, and then centrifuged at about 12,000×g for 10 minutes to remove unreacted TPP-doxorubicin. The reaction products were washed twice with 500 μL of SHE (250 mM Sucrose, 20 mM HEPES (pH 7.4), 2 mM EGTA) buffer to finally obtain the mitochondria comprising TPP-doxorubicin (TPP-DOX_$MT^{\alpha\text{-}HER2scFv}$) (FIG. 32).

Example 5. Evaluation of Anticancer Activity of TPP-DOX_$MT^{\alpha\text{-}HER2scFv}$ Against Cancer Cells

Example 5.1. Confirmation of Delivery Property of TPP-DOX_$MT^{\alpha\text{-}HER2scFv}$ into Cancer Cells The human breast cancer cell line (SK-BR-3, BT-474 and MDA-MB-231) and the human lung cancer cell line (NCI-H1975) were treated with TPP-DOX_$MT^{\alpha\text{-}HER2scFv}$ obtained in the same manner as in Preparation Example 4 above, respectively, and then the cells were observed by a confocal microscope. At this time, the nuclei of the cells were observed by staining with DAPI.

Figure 33:
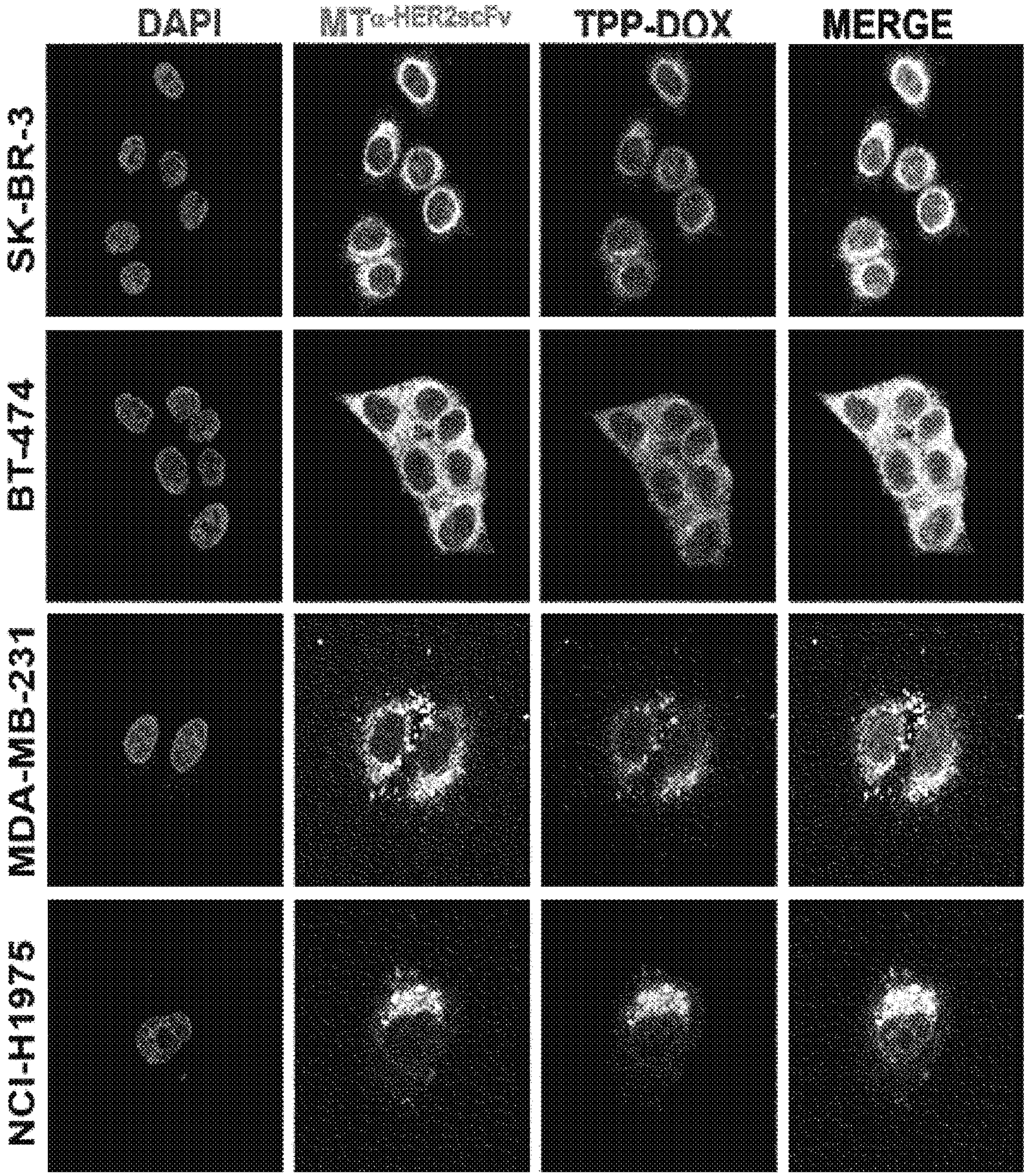
FIG. 33 is a view showing the results of observing the human breast cancer cell line (SK-BR-3, BT-474 and MDA-MB-231) and the lung cancer cell line (NCI-H1975) after treatment with TPP-DOX_$MT^{\alpha\text{-}HER2scFv}$ by a confocal microscope.

As a result, the mitochondria stained with MitoTracker green ($MT^{\alpha\text{-}HER2scFv}$) and doxorubicin showing red fluorescence (TPP-DOX) were observed at the same location in the cytoplasm (FIG. 33). From the above results, it was confirmed that both TPP-DOX and $MT^{\alpha\text{-}HER2scFv}$ transported by TPP-DOX_$MT^{\alpha\text{-}HER2scFv}$ were located in the cytoplasm.

Example 5.2. Confirmation of Morphological Change in Cancer Cells by Treatment with TPP-DOX_$MT^{\alpha\text{-}HER2scFv}$ The human breast cancer cell line (SK-BR-3 and BT-474) and the human gastric cancer cell line (NCI-N87) were treated with TPP-DOX_$MT^{\alpha\text{-}HER2scFv}$ obtained in the same manner as in Preparation Example 4 above, respectively, and then the morphological change in cancer cells over time was observed by a confocal microscope. At this time, the nuclei of the cells were observed by staining with DAPI.

Figure 34:
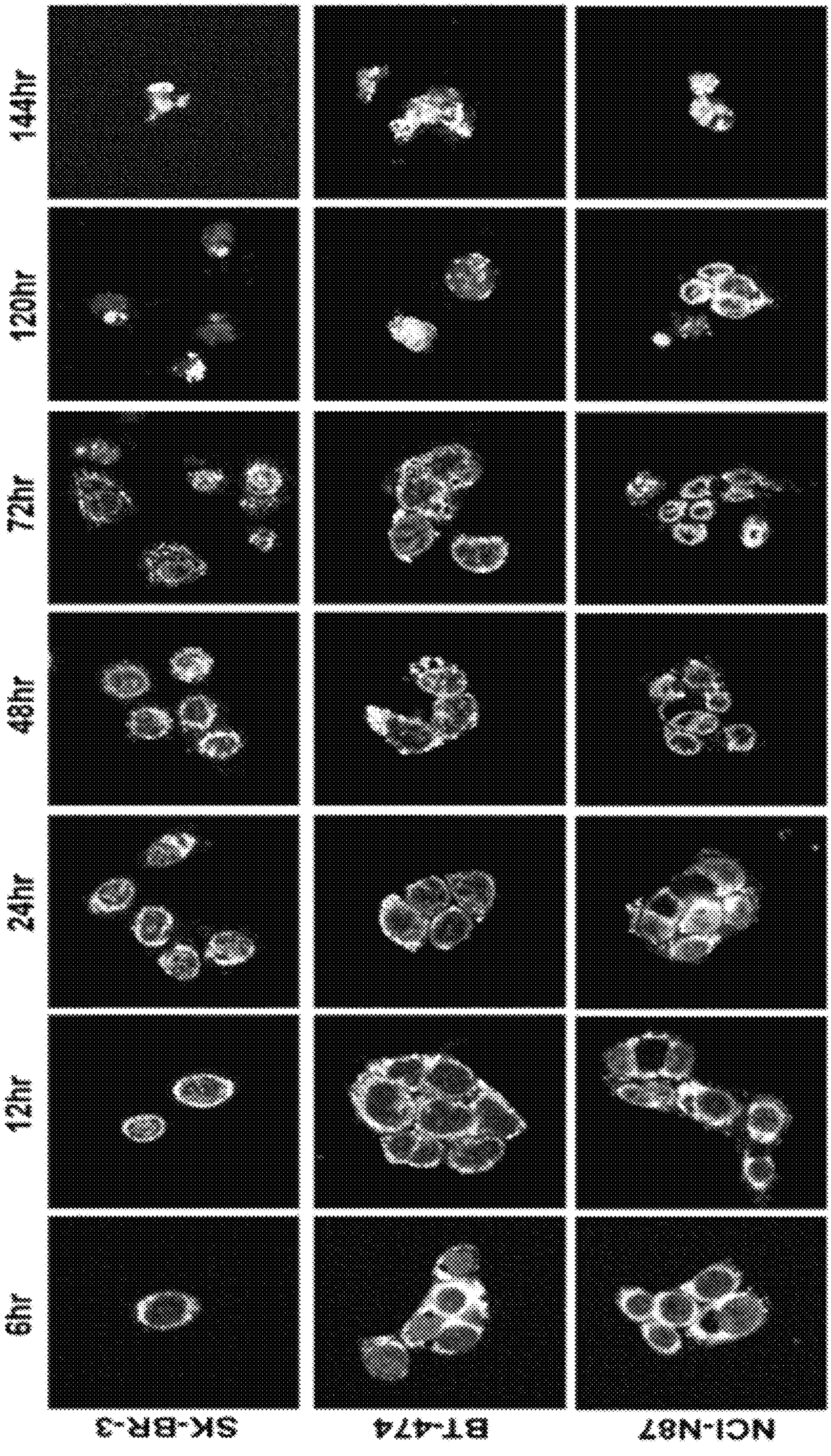
FIG. 34 is a view showing the results of observing the morphological change and death process of cancer cells over time by a confocal microscope after treatment of the human breast cancer cell line (SK-BR-3 and BT-474) and the human gastric cancer cell line (NCI-N87) with TPP-DOX_$MT^{\alpha\text{-}HER2scFv}$.

As a result, it was observed that most of TPP-DOX (red fluorescence) exists together in the mitochondria (green fluorescence) after 12 hours of treatment with TPP-DOX_MT$^{\alpha\text{-}HER2scFv}$(yellow fluorescence). However, TPP-DOX was observed in the nucleus over time, and the morphological change in the cells was remarkably observed after 72 hours of treatment with TPP-DOX_MT$^{\alpha\text{-}HER2scFv}$ (FIG. 34).

Example 5.3. Confirmation of Cancer Cell Proliferation Inhibitory Ability by Treatment with TPP-DOX_MT$^{\alpha\text{-}HER2scFv}$ for Each Concentration In order to confirm the anticancer activity of TPP-DOX_MT$^{\alpha\text{-}HER2scFv}$ obtained in the same manner as in Preparation Example 4 above, the cell proliferation inhibitory effect by treating the human breast cancer, lung cancer and gastric cancer cell lines with TPP-DOX_MT$^{\alpha\text{-}HER2scFv}$ was evaluated.

Specifically, the human breast cancer (SK-BR-3, BT-474 and MDA-MB-231), lung cancer (NCI-H1975) and gastric cancer (NCI-N87 and MKN-74) cell lines were inoculated into a 96-well plate at about $3\times10^3$ cells/well, respectively, and cultured for 24 hours. At this time, the human breast cancer cell line (SK-BR-3 and BT-474) and the human gastric cancer cell line (NCI-N87) were cultured in RPMI-1640 medium containing 10% FBS, and the human breast cancer cell line MDA-MB-231, the human lung cancer cell line NCI-H1975 and the human gastric cancer cell line MKN-74 were cultured in DMEM medium containing 10% FBS. After culturing for 24 hours, each cell was treated with TPP-DOX or TPP-DOX_MT$^{\alpha\text{-}HER2scFv}$ at a concentration of 2 μM, 1 μM, 0.5 μM, 0.25 μM, 0.1 μM, 0.05 μM, 0.025 μM and 0.01 μM. After 144 hours of sample treatment, cell proliferation was measured by WST-1 assay. At this time, the mitochondria-only treated group (MT, MT$^{\alpha\text{-}HER2scFv}$) was used as a negative control for TPP-DOX MT$^{\alpha\text{-}HER2scFv}$.

Figure 35:
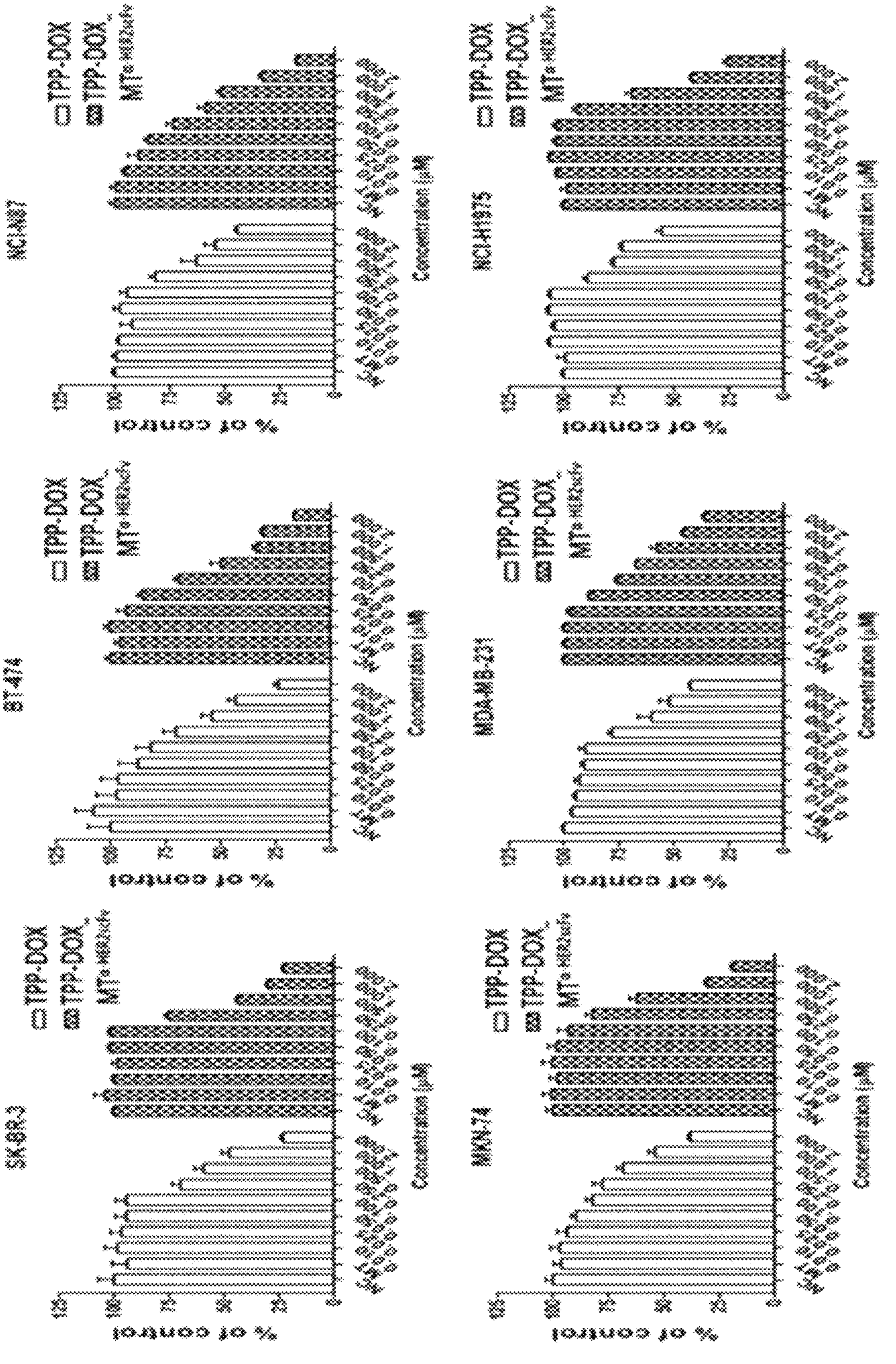
FIG. 35 is a view showing the results of measuring the cytotoxicity by treatment of the human breast cancer cell line (SK-BR-3, BT-474 and MDA-MB-231), the human lung cancer cell line (NCI-H1975) and the human gastric cancer cell line (NCI-N87 and MKN-74) with TPP-DOX and TPP-DOX_$MT^{\alpha\text{-}HER2scFv}$. In this case, MT is $MT^{\alpha\text{-}HER2scFv}$ in which DOX is not loaded.

As a result, as shown in FIG. 35, for the untreated group (NC), cell proliferation inhibitory effect was not observed in the mitochondria-only treated group (MT). On the other hand, in TPP-DOX treated group and TPP-DOX_MT$^{\alpha\text{-}HER2scFv}$ treated group, cancer cell proliferation was inhibited in a concentration-dependent manner. In particular, it was confirmed that when treated with 1 μM TPP-DOX_MT$^{\alpha\text{-}HER2scFv}$, cell growth was inhibited by about 60% to 70% compared to the untreated group depending on the cancer cell line.

Example 5.4. Confirmation of Proliferation Inhibitory Ability by Treatment with TPP-DOX_MT$^{\alpha\text{-}HER2scFv}$ for Each Concentration in Normal Cells In order to confirm the influence of TPP-DOX_MT$^{\alpha\text{-}HER2scFv}$ obtained in the same manner as in Preparation Example 4 above on cell proliferation in normal cells, the cell proliferation inhibitory effect after treating the human lung fibroblasts with TPP-DOX_MT$^{\alpha\text{-}HER2scFv}$ was evaluated.

Specifically, the human lung fibroblast cell lines WI-38 and CCD-8Lu were inoculated into a 96-well plate at about $3\times10^3$ cells/well, respectively, and cultured for 24 hours. At this time, WI-38 and CCD-8Lu were cultured in DMEM medium containing 10% FBS. After culturing for 24 hours, each cell was treated with TPP-DOX or TPP-DOX_MT$^{\alpha\text{-}HER2scFv}$ at a concentration of 2 μM, 1 μM, 0.5 μM, 0.25 μM, 0.1 μM, 0.05 μM, 0.025 μM and 0.01 μM. After 144 hours of sample treatment, cell proliferation was measured by WST-1 assay. At this time, the mitochondria-only treated group (MT, MT$^{\alpha\text{-}HER2scFv}$) was used as a negative control for TPP-DOX MT$^{\alpha\text{-}HER2scFv}$.

Figure 36:
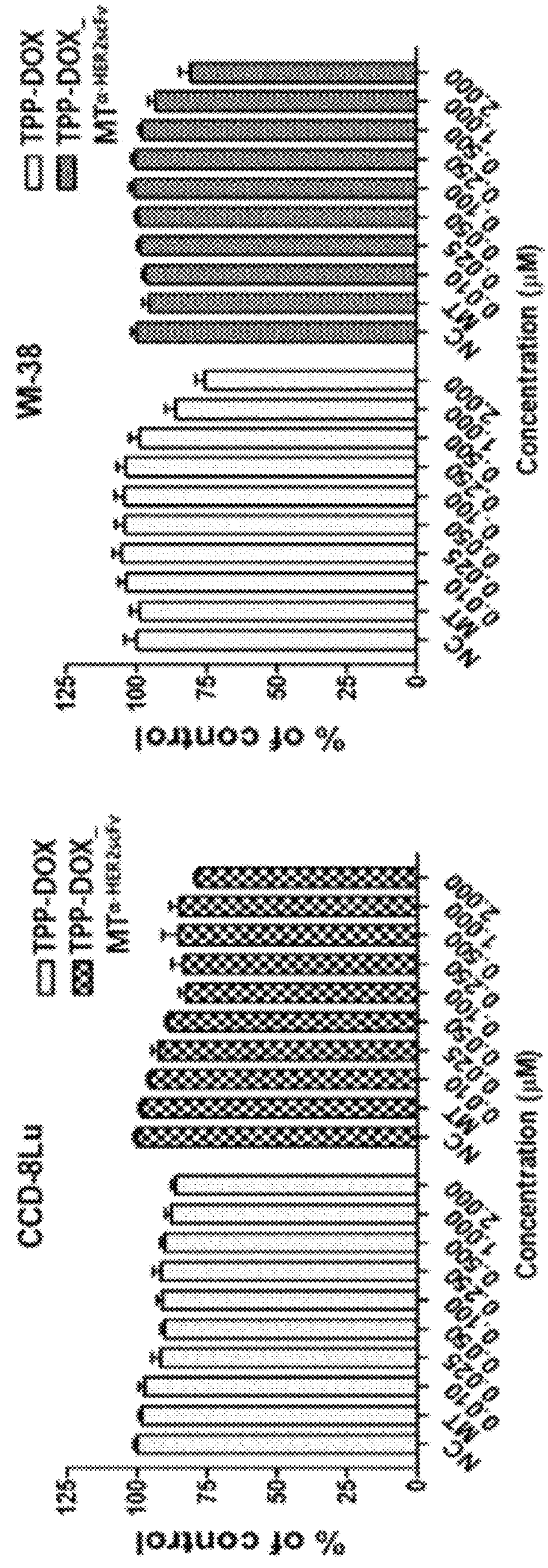
FIG. 36 is a view showing the results of measuring the cytotoxicity by treatment of the human lung fibroblast cell line (WI-38 and CCD-8Lu) with TPP-DOX and TPP-DOX_$MT^{\alpha\text{-}HER2scFv}$ In this case, MT is $MT^{\alpha\text{-}HER2scFv}$ in which DOX is not loaded.

As a result, as shown in FIG. 36, for the untreated group (NC), cell proliferation inhibitory effect was not observed in the mitochondria-only treated group (MT). In addition, it was confirmed that in TPP-DOX treated group and TPP-DOX_MT$^{\alpha\text{-}HER2scFv}$ treated group, cell proliferation inhibitory ability was weaker than that of cancer cells.

Example 5.5. Analysis of $IC_{50}$ Value by Treatment with TPP-DOX_MT$^{\alpha\text{-}HER2scFv}$ in Cancer Cells and Normal Cells Based on the cell proliferation inhibition results of TPP-DOX_MT$^{\alpha\text{-}HER2scFv}$ for each concentration in Example 5.3 and Example 5.4, $IC_{50}$ values in each cell were analyzed and shown in FIG. 37.

Example 5.6. Comparison of Proliferation Inhibitory Ability by Treatment with TPP-DOX_MT$^{\alpha\text{-}HER2scFv}$ in Cancer Cells and Normal Cells In order to compare the influence of TPP-DOX_MT$^{\alpha\text{-}HER2scFv}$ obtained in the same manner as in Preparation Example 4 above on cell proliferation in cancer cells and normal cells, after treatment with TPP-DOX_MT$^{\alpha\text{-}HER2scFv}$ at the same concentration in the human breast cancer, lung cancer, gastric cancer cell lines and the lung fibroblast cell line, the cell proliferation inhibitory ability was measured.

Specifically, the human breast cancer (SK-BR-3, BT-474 and MDA-MB-231), lung cancer (NCI-H1975), gastric cancer (MKN-74 and NCI-N87) cell lines and the lung fibroblast cell line (CCD-8Lu and WI-38) were inoculated into a 96-well plate at about $3\times10^3$ cells/well, respectively, and cultured for 24 hours. At this time, SK-BR-3, BT-474 and NCI-N87 cells were cultured in RPMI-1640 medium containing 10% FBS, and MDA-MB-231, NCI-H1975, MKN-74, CCD-8Lu and WI-38 cells were cultured in DMEM medium containing 10% FBS. After culturing for 24 hours, the cells were treated with 0.5 μM TPP-DOX or TPP-DOX_MT$^{\alpha\text{-}HER2scFv}$ respectively, and after 144 hours, the cell proliferation inhibitory ability was evaluated by WST-1 assay. At this time, the mitochondria-only treated group (MT$^{\alpha\text{-}HER2scFv}$) was used as a negative control for TPP-DOX_MT$^{\alpha\text{-}HER2scFv}$. Statistical processing was performed using Graphpad 5.0 software, and p values were measured with one-way ANOVA (Turkey's) test ($^*p<0.05$, $^{}p<0.01$ and $^{*}p<0.001$).

Figure 38:
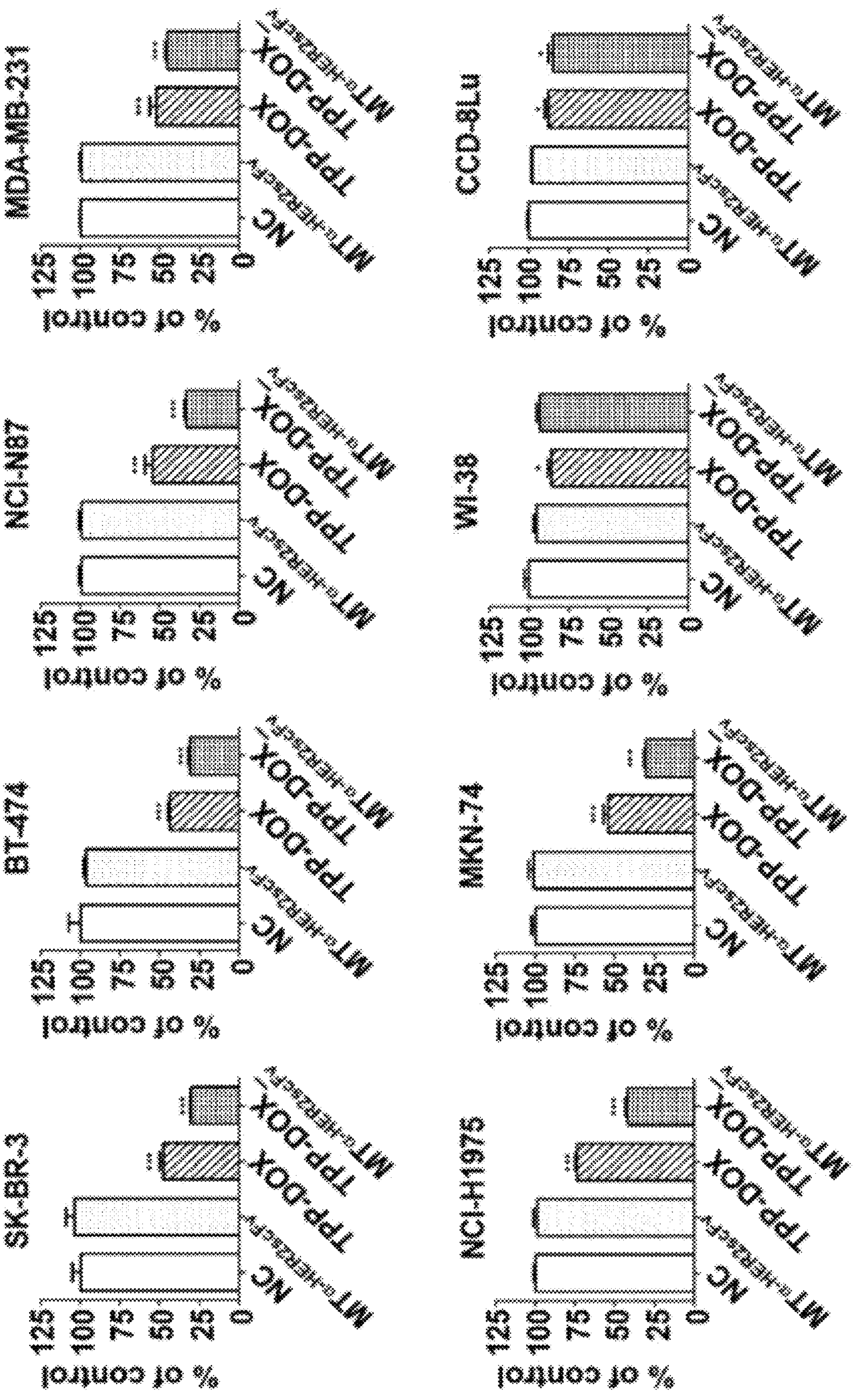
FIG. 38 is a view showing the results of measuring the cytotoxicity by treatment of the human breast cancer cell line (SK-BR-3, BT-474 and MDA-MB-231), the human lung cancer cell line (NCI-H1975), the human gastric cancer cell line (NCI-N87 and MKN-74) and the human lung fibroblast cell line (WI-38 and CCD-8Lu) with 0.5 μM TPP-DOX or TPP-DOX $MT^{\alpha\text{-}HER2scFv}$.

As a result, as shown in FIG. 38, for the untreated group (NC) in cancer cells and normal cells, cell proliferation inhibitory effect was not observed in the mitochondria-only treated group (MT$^{\alpha\text{-}HER2scFv}$). In the case of TPP-DOX-only treated group and TPP-DOX_MT$^{\alpha\text{-}HER2scFv}$ treated group, cell proliferation inhibitory effect was shown by about 60% to 75% or higher compared to the untreated group in cancer cells. However, it was confirmed that proliferation inhibitory ability was weak in normal cells unlike in cancer cells.

Example 5.7. Confirmation of Cancer Cell Apoptosis by TPP-DOX_MT$^{\alpha\text{-}HER2scFv}$ by TUNEL Assay In order to confirm the apoptosis inducing activity of TPP-DOX_MT$^{\alpha\text{-}HER2scFv}$ obtained in the same manner as in Preparation Example 4 above in cancer cells, after treatment with TPP-DOX_MT$^{\alpha\text{-}HER2scFv}$ in the human breast cancer and gastric cancer cell lines, TUNEL assay was performed.

Specifically, the human breast cancer cell line (SK-BR-3 and BT-474) and the human gastric cancer cell line (NCI-N87) were inoculated into a 24-well plate at about $3\times10^4$ cells/well, respectively, and cultured for 24 hours. After culturing for 24 hours, the cells were treated with MT$^{\alpha\text{-}HER2scFv}$ or 1 μM TPP-DOX_MT$^{\alpha\text{-}HER2scFv}$, and after 48 hours, TUNEL assay was performed to confirm the apoptosis. At this time, the mitochondria-only treated group (MT$^{\alpha\text{-}HER2scFv}$) was used as a control group for TPP-DOX_MT$^{\alpha\text{-}HER2scFv}$. The nuclei of the cells were observed by staining with DAPI.

Figure 39:
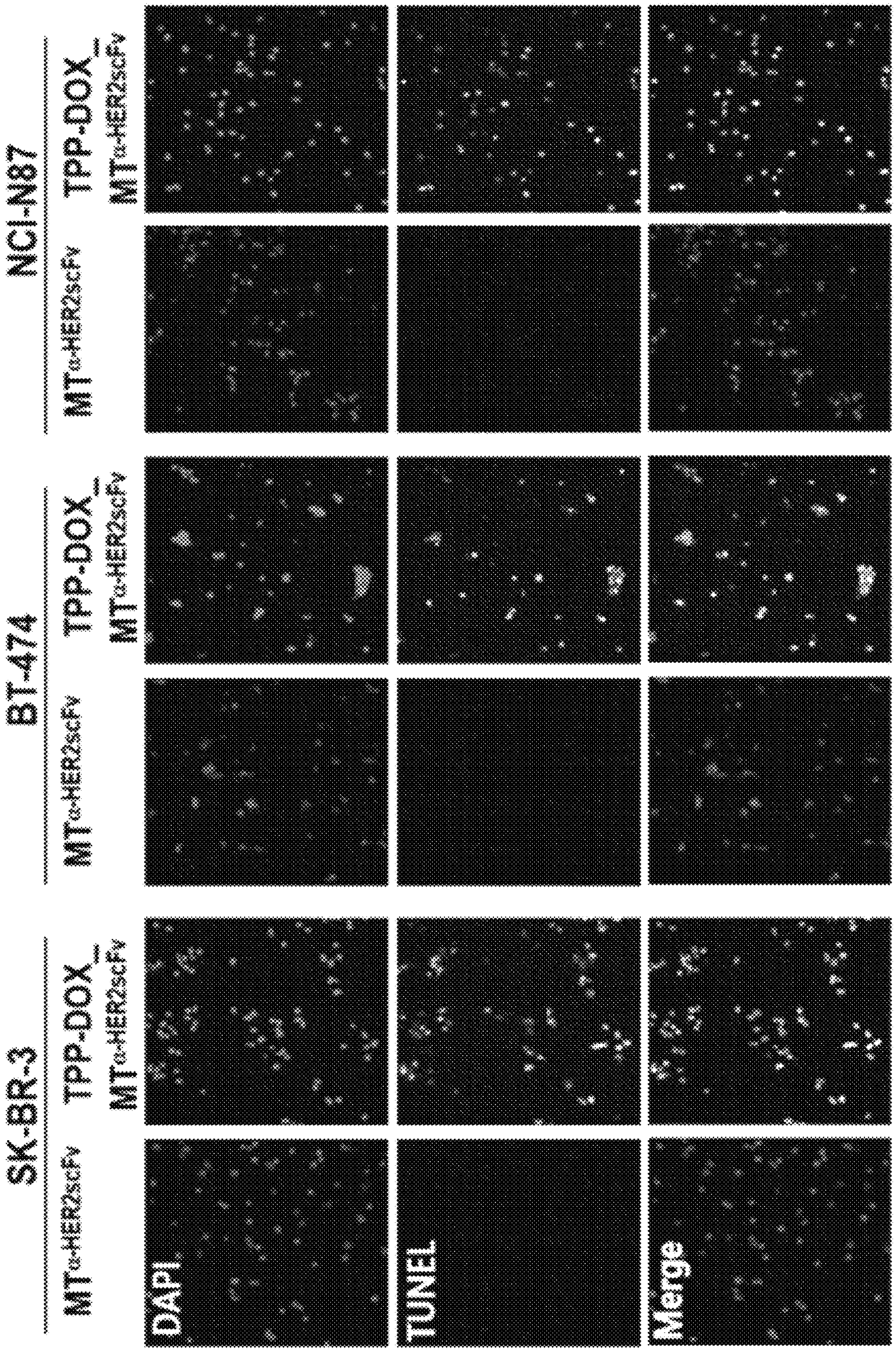
FIG. 39 is a view showing the results of confirming the apoptosis by treatment of the human breast cancer cell line (SK-BR-3 and BT-474 and MDA-MB-231) and the gastric cancer cell line (NCI-N87) with $MT^{\alpha\text{-}HER2scFv}$ or TPP-DOX_$MT^{\alpha\text{-}HER2scFv}$ by TUNEL assay.

As a result, almost no apoptosis (green fluorescence) was observed in the mitochondria-only treated group (MT$^{\alpha\text{-}HER2scFv}$). However, an increase in apoptosis was observed in the cell nucleus of TPP-DOX_MT$^{\alpha\text{-}HER2scFv}$ treated group. From the above results, it was confirmed that the apoptosis was induced by treatment with TPP-DOX_MT$^{\alpha\text{-}HER2scFv}$ (FIG. 39).

Example 5.8. Confirmation of Cancer Cell Apoptosis by Treatment with TPP-DOX_MT$^{\alpha\text{-}HER2scFv}$ Through Western Blot Analysis In order to confirm the apoptosis effect by treatment with TPP-DOX_MT$^{\alpha\text{-}HER2scFv}$ obtained in the same manner as in Preparation Example 4 above in cancer cells, after treatment with TPP-DOX_MT$^{\alpha\text{-}HER2scFv}$ in the human breast cancer and gastric cancer cell lines, Western blot was performed using an antibody against a apoptosis marker.

Specifically, the human breast cancer cell line (SK-BR-3 and BT-474) and the human gastric cancer cell line (NCI-N87) were inoculated into a 6-well plate at about $5\times10^6$ cells/well, respectively, and cultured for 24 hours. After culturing for 24 hours, the cells were treated with MT$^{\alpha\text{-}HER2scFv}$ or 1 μM TPP-DOX_MT$^{\alpha\text{-}HER2scFv}$, respectively, and after 96 hours, the cells were disrupted, proteins were extracted, and Western blot was performed. Anti-cleaved PARP antibody (Cell signaling, 9541S), anti-cleaved caspase 3 antibody (Cell signaling, 9664S), anti-phospho-p53 antibody (ABclonal, AP0762) and anti-β actin antibody (Sigma, A2228) were used as primary antibodies. Anti-mouse IgG HRP or anti-rabbit IgG HRP was used as a secondary antibody. The amount of protein was corrected through the expression level of R actin protein. At this time, the mitochondria-only treated group (MT$^{\alpha\text{-}HER2scFv}$) was used as a control group for TPP-DOX_MT$^{\alpha\text{-}HER2scFv}$.

Figure 40:
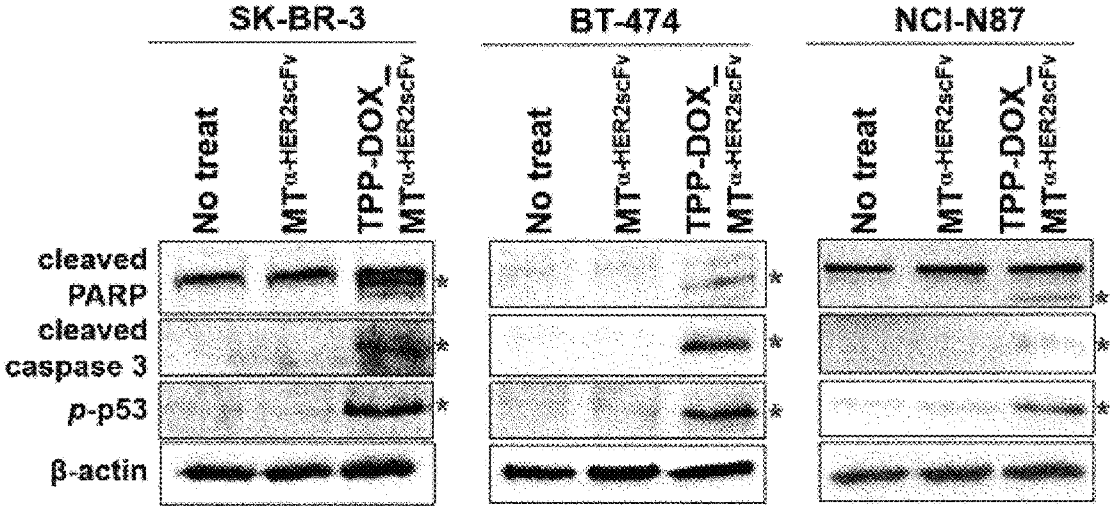
FIG. 40 is a view showing the results of confirming the apoptosis caused by treatment of the human breast cancer cell line (SK-BR-3 and BT-474) and the human gastric cancer cell line (NCI-N87) with $MT^{\alpha\text{-}HER2scFv}$ or TPP-DOX_$MT^{\alpha\text{-}HER2scFv}$ by Western blot.

As a result, in the mitochondria-only treated group (MT$^{\alpha\text{-}HER2scFv}$), similar to the untreated group (No treat), the cleaved forms of PARP and caspase 3 observed during the apoptosis were not observed, and the phosphorylated form of p53 was not also observed. On the other hand, in TPP-DOX_MT$^{\alpha HER2scFv}$ treated group, the expression of the phosphorylated p53 and the cleaved forms of PARP and caspase 3 was observed (FIG. 40). From the above results, it was confirmed that the apoptosis was induced by treatment with TPP-DOX_MT$^{\alpha\text{-}HER2scFv}$.

Example 5.9. Confirmation of Cancer Cell Apoptosis by Treatment with TPP-DOX_MT$^{\alpha\text{-}HER2scFv}$ Through Flow Cytometry In order to confirm the apoptosis effect by treatment with TPP-DOX_MT$^{\alpha\text{-}HER2scFv}$ obtained in the same manner as in Preparation Example 4 above in cancer cells, after treatment with TPP-DOX_MT$^{\alpha HER2scFv}$ in the human breast cancer and gastric cancer cell lines, flow cytometry was performed by staining with Annexin V/PI.

Specifically, the human breast cancer cell line (SK-BR-3 and BT-474) and the human gastric cancer cell line (NCI-N87) were inoculated into a 6-well plate at about $5\times10^6$ cells/well, respectively, and cultured for 24 hours. After culturing for 24 hours, the cells were treated with MT$^{\alpha\text{-}HER2scFv}$ or 1 μM TPP-DOX_MT$^{\alpha\text{-}HER2scFv}$. After 96 hours, the cells were washed twice with PBS and obtained by treatment with 0.05% Trypsin-EDTA. The obtained cells were centrifuged and then washed with PBS to remove 0.05% Trypsin-EDTA. Thereafter, the cells were stained for 10 minutes using Annexin V/PI staining kit (Roche, 11988549001), and the stained cells were analyzed using FACS equipment (Beckman Coulter, CytoFLEX). At this time, the mitochondria-only treated group (MT$^{\alpha\text{-}HER2scFv}$) was used as a negative control for TPP-DOX MT$^{\alpha\text{-}HER2scFv}$.

Figure 41:
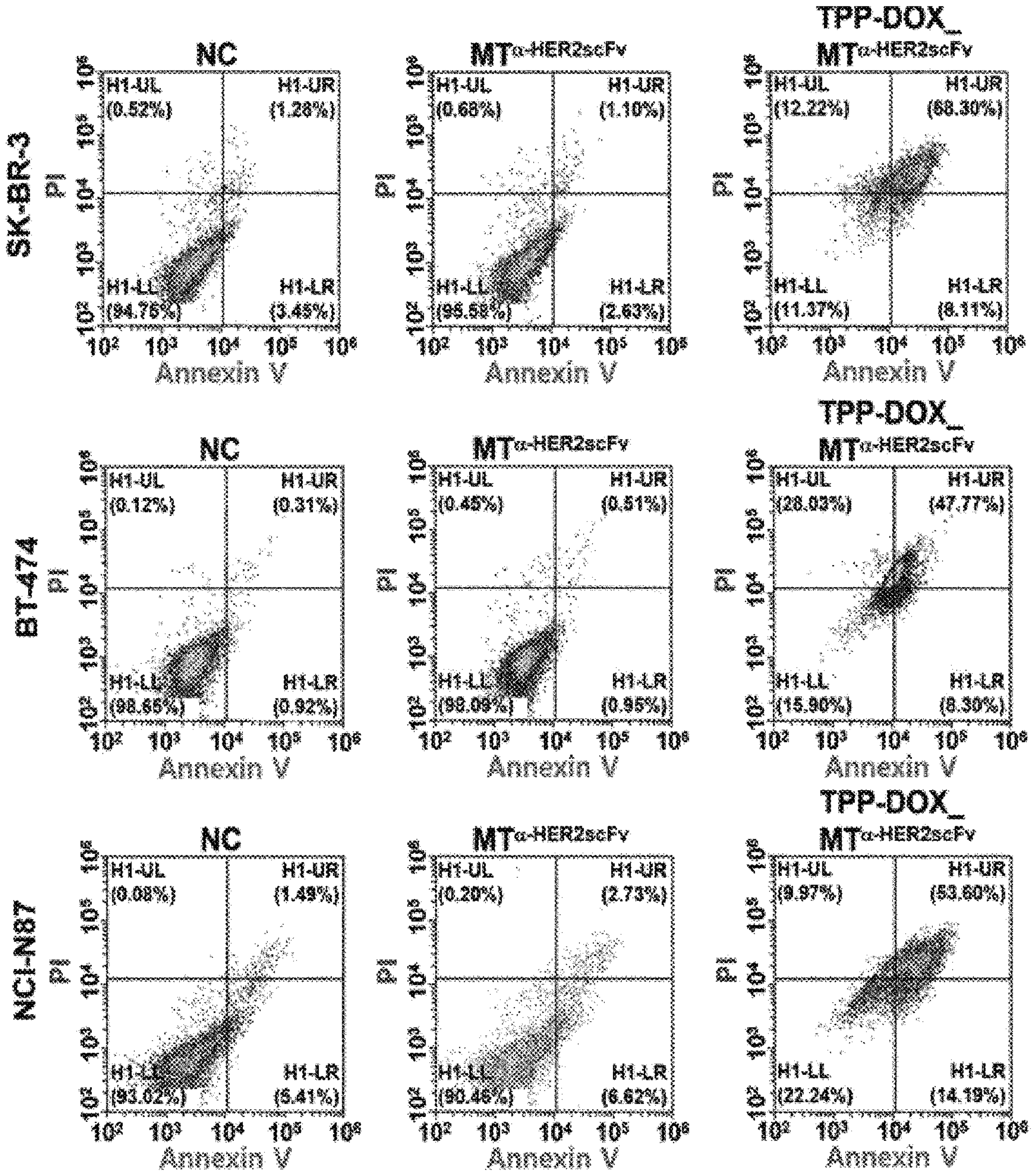
FIG. 41 is a graph showing the results of confirming the apoptosis caused by treatment of the human breast cancer cell line (SK-BR-3 and BT-474) and the gastric cancer cell line (NCI-N87) with $MT^{\alpha\text{-}HER2scFv}$ or TPP-DOX_$MT^{\alpha\text{-}HER2scFv}$ by flow cytometry.

As a result, for the untreated group (NC), no change in Annexin V/PI values was observed in the mitochondria-only treated group (MT$^{\alpha\text{-}HER2scFv}$). On the other hand, the Annexin V/PI value was increased in TPP-DOX_MT$^{\alpha\text{-}HER2scFv}$ treated group (FIG. 41). From the above results, it was confirmed that the apoptosis was induced by treatment with TPP-DOX_MT$^{\alpha\text{-}HER2scFv}$.

Example 5.10. Evaluation of HER2 Expressing Cell Selective Apoptosis Inducing Activity of TPP-DOX_MT$^{\alpha\text{-}HER2scFv}$ In order to confirm the HER2 selective apoptosis inducing effect of TPP-DOX_MT$^{\alpha\text{-}HER2scFv}$ obtained in the same manner as in Preparation Example 4 above, the co-cultured $HER2^+$ cancer cells and $HER2^-$ normal cells were treated with TPP-DOX_MT$^{\alpha\text{-}HER2scFv}$, and then TUNEL assay and immunocytochemistry staining were performed.

Figure 42:
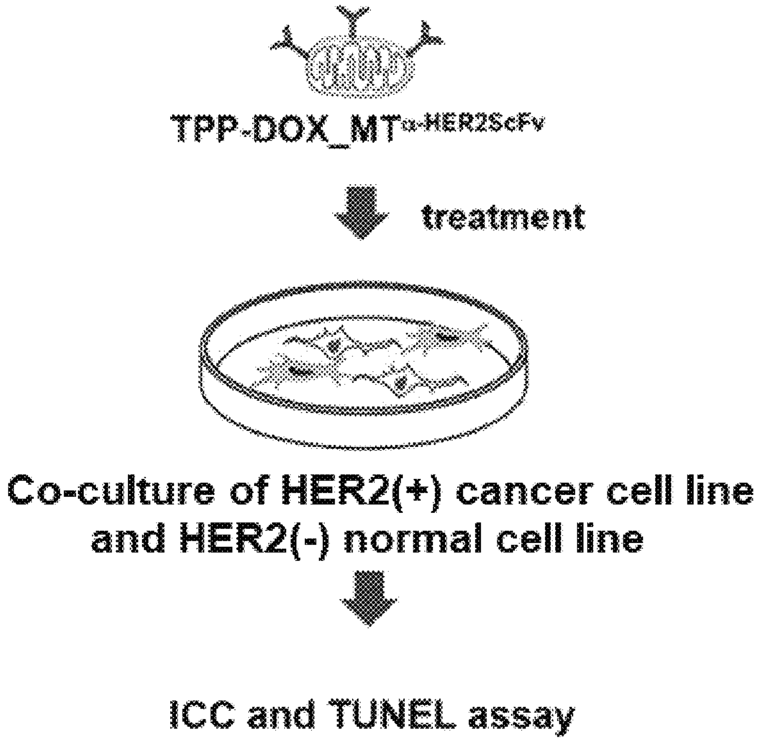
FIG. 42 is a view showing an experimental method for confirming the selective killing effect of HER2 expressing cells by TPP-DOX_$MT^{\alpha\text{-}HER2scFv}$.

Specifically, the human breast cancer cell line SK-BR-3 ($HER2^+$) and the human lung fibroblast cell line CCD-8Lu ($HER2^-$) were inoculated together into a 24-well plate at $3\times10^4$ cells/well and co-cultured in DMEM medium containing 10% FBS for 24 hours. At this time, SK-BR-3 cells were prepared by culturing in RPMI-1640 medium containing 10% FBS, and WI-38 cells were prepared by culturing in DMEM medium containing 10% FBS. After culturing for 24 hours, the co-cultured cells were treated with 1 μM TPP-DOX_MT$^{\alpha\text{-}HER2scFv}$ and cultured for additional 48 hours. The apoptosis was evaluated by TUNEL assay and immunocytochemistry staining (FIG. 42).

Example 5.11. Confirmation of HER2 Expressing Cell Selective Apoptosis Inducing Activity of TPP-DOX_MT$^{\alpha\text{-}HER2scFv}$ by TUNEL Assay The cells treated in the same manner as in Example 5.10 above were washed twice with PBS and then fixed by adding 3.7% formaldehyde at room temperature for 30 minutes. Thereafter, anti-HER2 antibody (Cell signaling, 29D8) was used as a primary antibody, and Alexa Fluor® 555 (Invitrogen, 21428) was used as a secondary antibody, and $HER2^+$ cells were labeled with red fluorescence. Thereafter, the cells were stained with TUNEL solution for 30 minutes, and the cells in which the apoptosis occurs were labeled with green fluorescence and mounted, and the cells were observed by a confocal microscope. At this time, the nuclei of the cells were observed by staining with DAPI.

Figure 43:
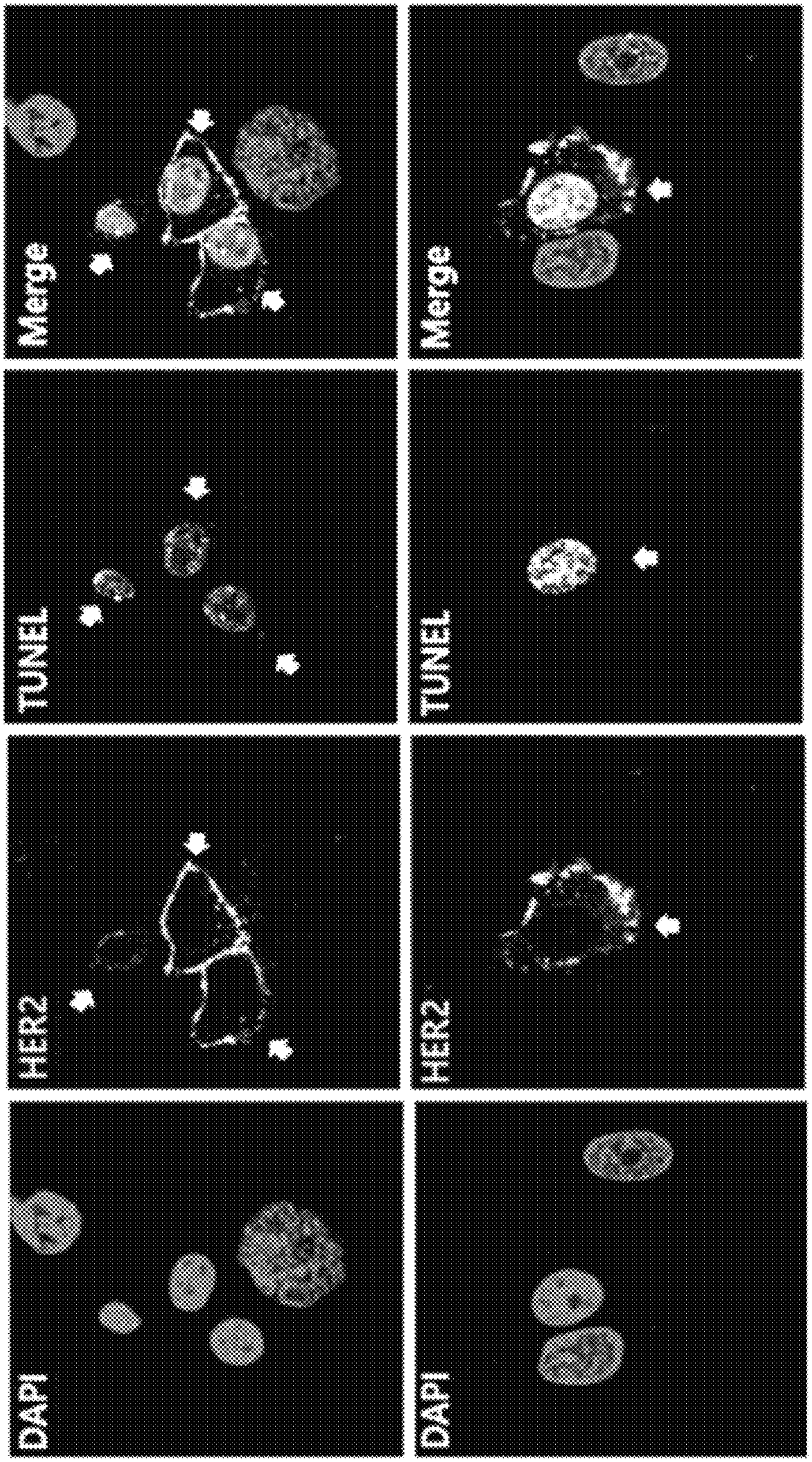
FIG. 43 is a view showing the results of confirming the apoptosis by co-culture of the human breast cancer cell line SK-BR-3 (HER2+, white arrow) and the human lung fibroblast cell line CCD-8Lu ($HER2^{-}$), and then treatment of the cells with TTP-DOX_$MT^{\alpha\text{-}HER2scFv}$ by TUNEL assay.

As a result, strong green fluorescence was selectively observed only in SK-BR-3 cells (white arrow), which are $HER2^+$ cells (FIG. 43). From the above results, it was confirmed that the apoptosis by TPP-DOX_MT$^{\alpha\text{-}HER2scFv}$ could be selectively induced depending on the presence or absence of HER2 expression.

Figure 44:
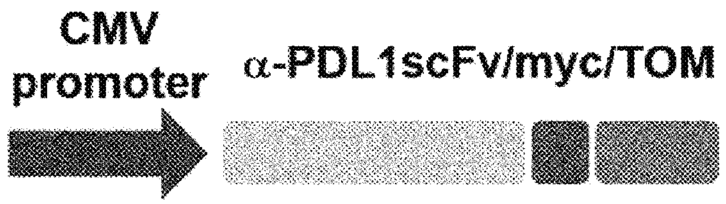
FIG. 44 is a view schematically showing an expression vector for expressing a single chain variable region fragment of an anti-PDL1 antibody in a form fused to the mitochondria.
Figure 45:
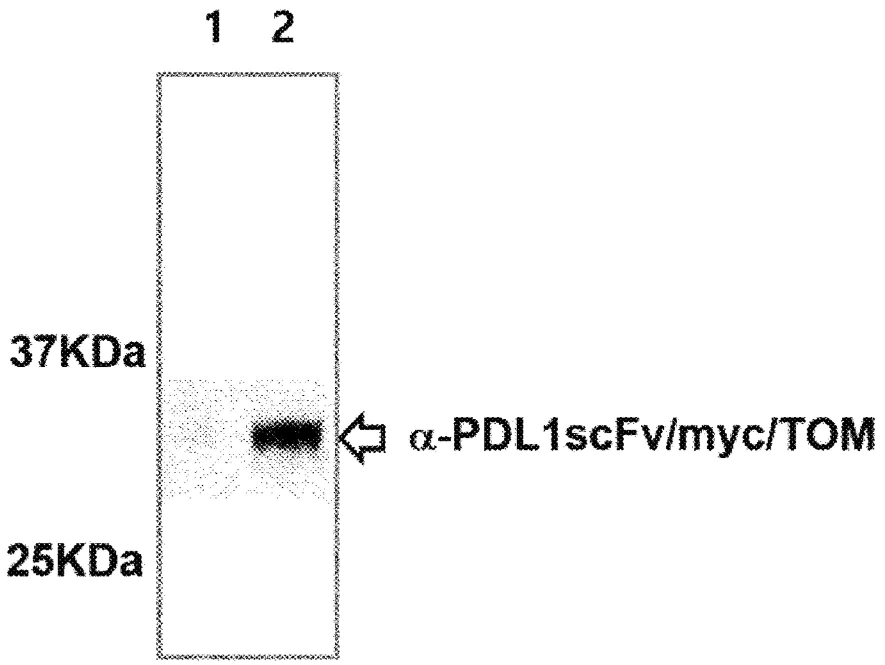
FIG. 45 is a view showing the results of confirming a single chain variable region fragment of an anti-PDL1 antibody expressed in the human fetal kidney cell line (HEK293) by Western blot.

Preparation Example 5. Preparation of HEK293 Cell Line Comprising Mitochondria Fused with Anti-PDL1scFv Antibody In order to specifically introduce mitochondria into tumor cells in which PDL1 is expressed, mitochondria in which an anti-PDL1scFv antibody (SEQ ID NO: 94) that specifically binds to PDL1 is fused to the mitochondrial outer membrane were construct (FIGS. 44 and 45). A specific constructing method was performed according to the method described in Korean Patent Application Publication No. 10-2019-0124656.

Example 6. Analysis of PDL1 Expression in Human Cancer Cell Line Through Western Blot Analysis Western blot was performed to confirm the expression level of PDL1 in the human pancreatic cancer cell line (BXPC-3 and CFPAC-1) and the human gastric cancer cell line (SNU-216 and SNU-484).

Specifically, the human pancreatic cancer cell line (BXPC-3 and CFPAC-1) and the human gastric cancer cell line (SNU-216 and SNU-484) were inoculated into a 6-well plate at about $1\times10^6$ cells/well and then cultured in DMEM medium containing 10% FBS for 24 hours. After 24 hours, the culture solution was removed, and the cells were washed twice with PBS, and then 100 μL of RIPA buffer containing a protease inhibitor was added directly to the cells. After 10 minutes, the cells were recovered using a scraper, transferred to a microtube, and then centrifuged at about 12,000×g for 10 minutes. The separated supernatant was obtained and transferred to a new microtube, and then protein was quantified using the BCA analysis. The same amount of protein for each sample was electrophoresed, and then Western blot was performed. Anti-PDL1 antibody (Cell signaling, 13684) and anti-β tubulin antibody (Thermo Fisher, MA5-16308) were used as primary antibodies, and anti-mouse IgG HRP antibody or anti-rabbit IgG HRP antibody were used as a secondary antibody.

Figure 46:
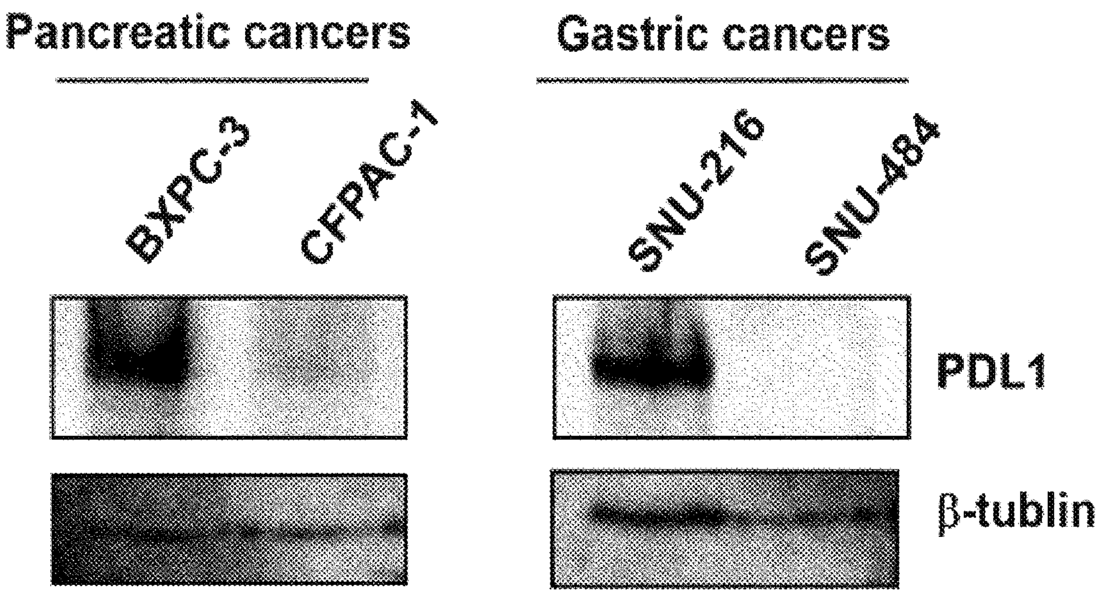
FIG. 46 is a view showing the results of confirming the expression of PD-L1 in the human pancreatic cancer cell line (BXPC-3 and CFPAC-1) and the human gastric cancer cell line (SNU-216 and SNU-484) by Western blot.

As a result, as shown in FIG. 46, it was confirmed that BXPC-3 and SNU-216 cells were PDL1$^+$ cells expressing PDL1. On the other hand, it was confirmed that CFPAC-1 and SNU-484 cells showed almost no PDL1 expression, indicating that they were PDL1$^-$ cells.

Example 7. Verification of PDL1 Targeting of Mitochondria Fused with Anti-PDL1scFv Antibody In order to confirm the PDL1 targeting ability of the mitochondria fused with the anti-PDL1scFv antibody constructed in Preparation Example 5 above, the mitochondria fused with the anti-PDL1scFv antibody (MT$^{\alpha\text{-}PDL1scFv}$) were treated with the co-cultured PDL1$^+$ cells and PDL1$^-$ cells, and then immunocytochemistry staining was performed.

Figure 47:
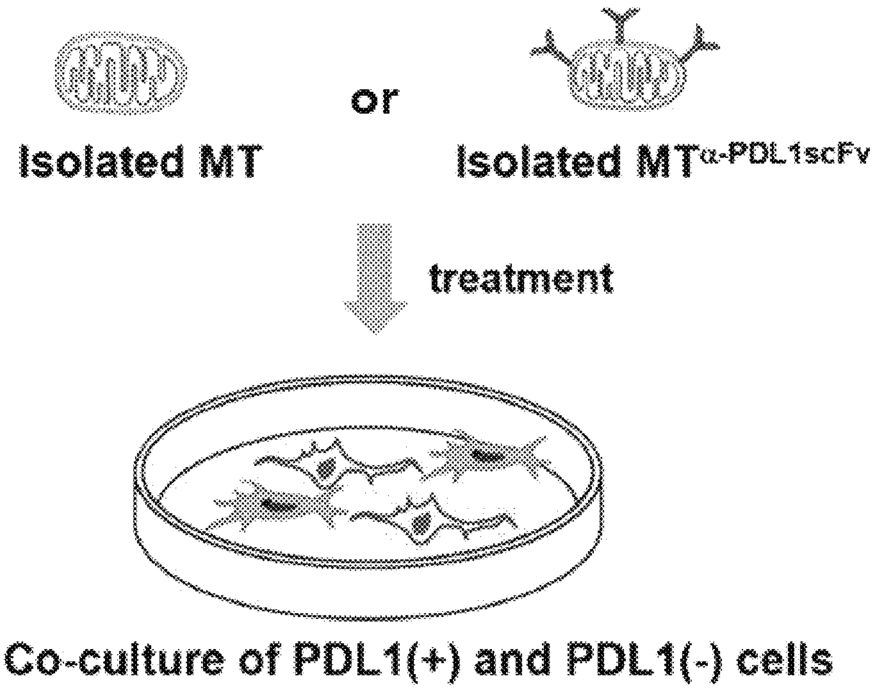
FIG. 47 is a view showing an experimental method for verifying the PDL1 targeting ability of $MT^{\alpha\text{-}PDL1scFv}$ after co-culture of $PDL1^{+}$ cells and $PDL1^{-}$ cells, and then treatment of the cells with the mitochondria ($MT^{\alpha\text{-}PDL1scFv}$) isolated from the human fetal kidney cell line (HEK293) that expresses a single chain variable region fragment of an anti-PDL1 antibody.

Specifically, BXPC-3 (PDL1V) and CFPAC-1 (PDL1$^-$), or SNU-216 (PDL1V) and SNU-484 (PDL1$^-$) were inoculated together into a 24-well plate at $1.5\times10^4$ cells/well and co-cultured in DMEM medium containing 10% FBS for 24 hours. Mitochondria to be used as samples were prepared by treating untreated HEK293 cells (MT) and HEK293 cells comprising mitochondria fused with an anti-PDL1scFv antibody (MT$^{\alpha\text{-}PDL1scFv}$) with MitoTracker Red to stain the mitochondria, and then isolating the mitochondria. After co-culture for 24 hours, each isolated mitochondrion was treated with the co-cultured cells and reacted for 24 hours (FIG. 47).

Example 7.1. Confirmation of Location of Mitochondria Fused with Anti-PDL1scFv Antibody in PDL1 Positive and Negative Cell Lines The cells treated in the same manner as in Example 4 above were washed once with PBS, and fixed by adding 3.7% formaldehyde at room temperature for 30 minutes, and then immunocytochemistry staining was performed. At this time, an anti-PDL1 antibody (Cell signaling, 86744) was used as a primary antibody, and Alexa Fluor 488 goat anti-rabbit IgG (H+L) was used as a secondary antibody. The nuclei of the cells were observed by staining with DAPI.

Figure 48:
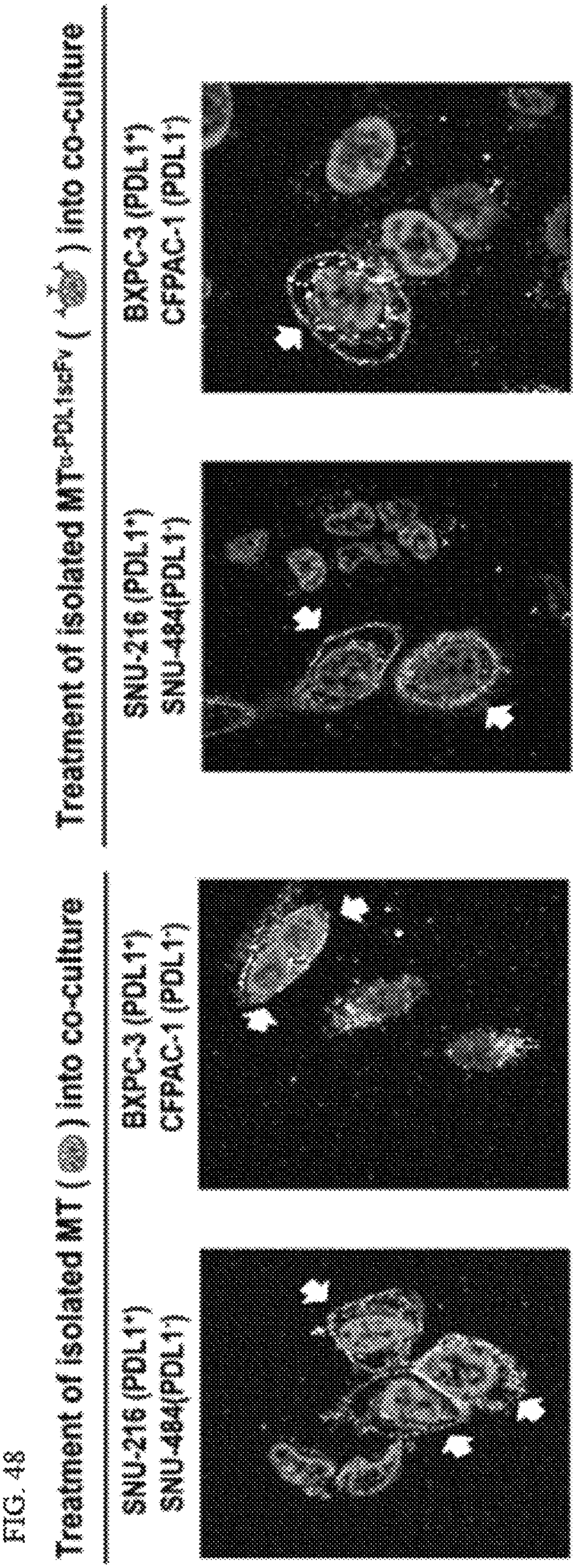
FIG. 48 is a view showing the results of confirming the intracellular expression of a single chain variable region fragment of an anti-PDL1 antibody by immunocytochemistry staining after co-culture of the human gastric cancer cell line SNU-216 ($PDL1^{+}$, white arrow) and SNU-484 ($PDL1^{-}$) or co-culture of the human pancreatic cancer cell line BXPC-3 ($PDL1^+$, white arrow) and the human pancreatic cancer cell line CFPAC-1 ($PDL1^-$), and then treatment of the cells with $MT^{\alpha\text{-}PDL1scFv}$. In this case, MT is the mitochondriua to which a single chain variable region fragment of an anti-PDL1 antibody is not fused, isolated from the HEK293 cells.

As a result, as shown in FIG. 48, when the co-cultured BXPC-3 (PDL1V) and CFPAC-1 (PDL1$^-$) cells were treated with untreated HEK293 cell-derived mitochondria (MT), the mitochondria stained with Mitotracker Red (red fluorescence) were observed equally in BXPC-3 (PDL1$^+$) and CFPAC-1 (PDL1$^-$) cells. On the other hand, when the cells were treated with the mitochondria (MT$^{\alpha\text{-}PDL1scFv}$) derived from HEK293 cells comprising the mitochondria fused with the anti-PDL1scFv antibody, the mitochondria stained with Mitotracker Red were observed specifically in PDL1*cells, BXPC-3 cells.

In addition, equally, in the case of the co-cultured SNU-216 (PDL1$^+$) and SNU-484 (PDL1$^-$) cells, in the case of MT treated group, the mitochondria stained with Mitotracker Red were observed equally in PDL1$^+$ (SNU-216) and SNU-484 (PDL1$^-$) cells, whereas in the case of MT$^{\alpha\text{-}PDL1scFv}$ treated group, they were specifically observed only in PDL1*cells, SNU-216 cells. From the above results, it was found that the mitochondria fused with the anti-PDL1scFv antibody specifically targeted the cells expressing a PDL1 antigen.

Figure 49:
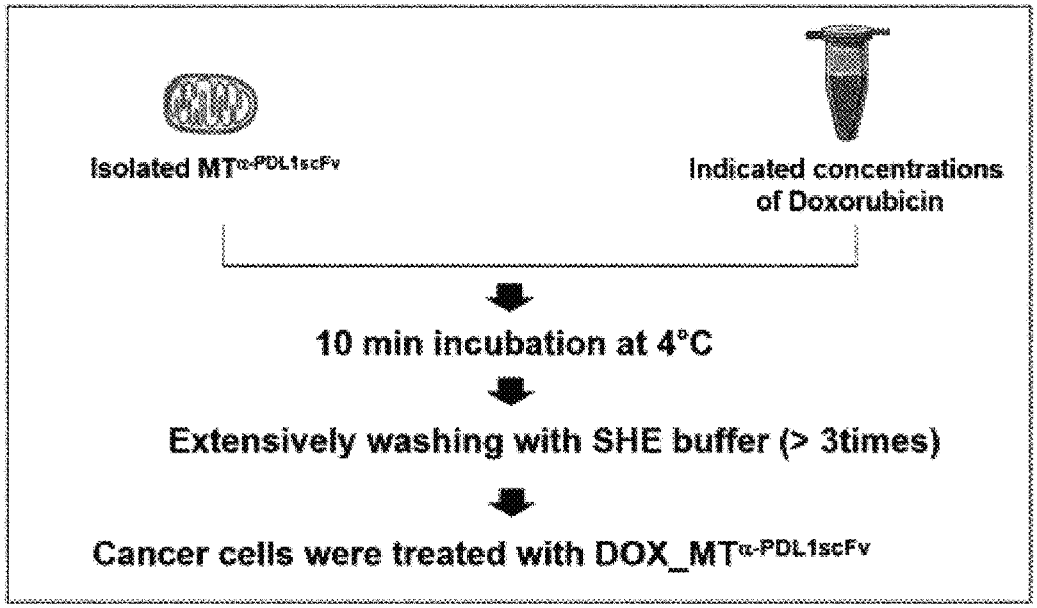
FIG. 49 is a view showing a method for preparing DOX_$MT^{\alpha\text{-}PDL1scFv}$ in which $MT^{\alpha\text{-}PDL1scFv}$ stained with MitoTracker green and doxorubicin (DOX), a compound payload, are bound.

Preparation Example 6. Preparation of Complex of Mitochondria Fused with Anti-PDL1scFv Antibody and Doxorubicin 30 μg of mitochondria (MT$^{\alpha\text{-}PDL1scFv}$) isolated from the HEK293 cells comprising mitochondria fused with an anti-PDL1scFv antibody were reacted with 100 μM doxorubicin (DOX) at 4° C. for 10 minutes, and then centrifuged at about 12,000×g for 10 minutes to remove unreacted doxorubicin. Thereafter, they were washed twice with 500 μL of SHE (250 mM Sucrose, 20 mM HEPES (pH 7.4), 2 mM EGTA) buffer to finally obtain the mitochondria comprising doxorubicin (DOX_MT$^{\alpha\text{-}PDL1scFv}$) (FIG. 49).

Example 8. Evaluation of Anticancer Activity of DOX_MT$^{\alpha\text{-}PDL1scFv}$ Against Cancer Cells

Example 8.1. Confirmation of Cell Proliferation Inhibitory Ability by Treatment with DOX_MT$^{\alpha\text{-}PDL1scFv}$ for Each Concentration In order to confirm the anticancer activity of DOX_MT$^{\alpha\text{-}PDL1scFv}$ obtained in the same manner as in Preparation Example 6 above, after treating the human pancreatic cancer and gastric cancer cell lines with DOX_MT$^{\alpha\text{-}PDL1scFv}$, the cell proliferation inhibitory effect was evaluated.

Figure 50:
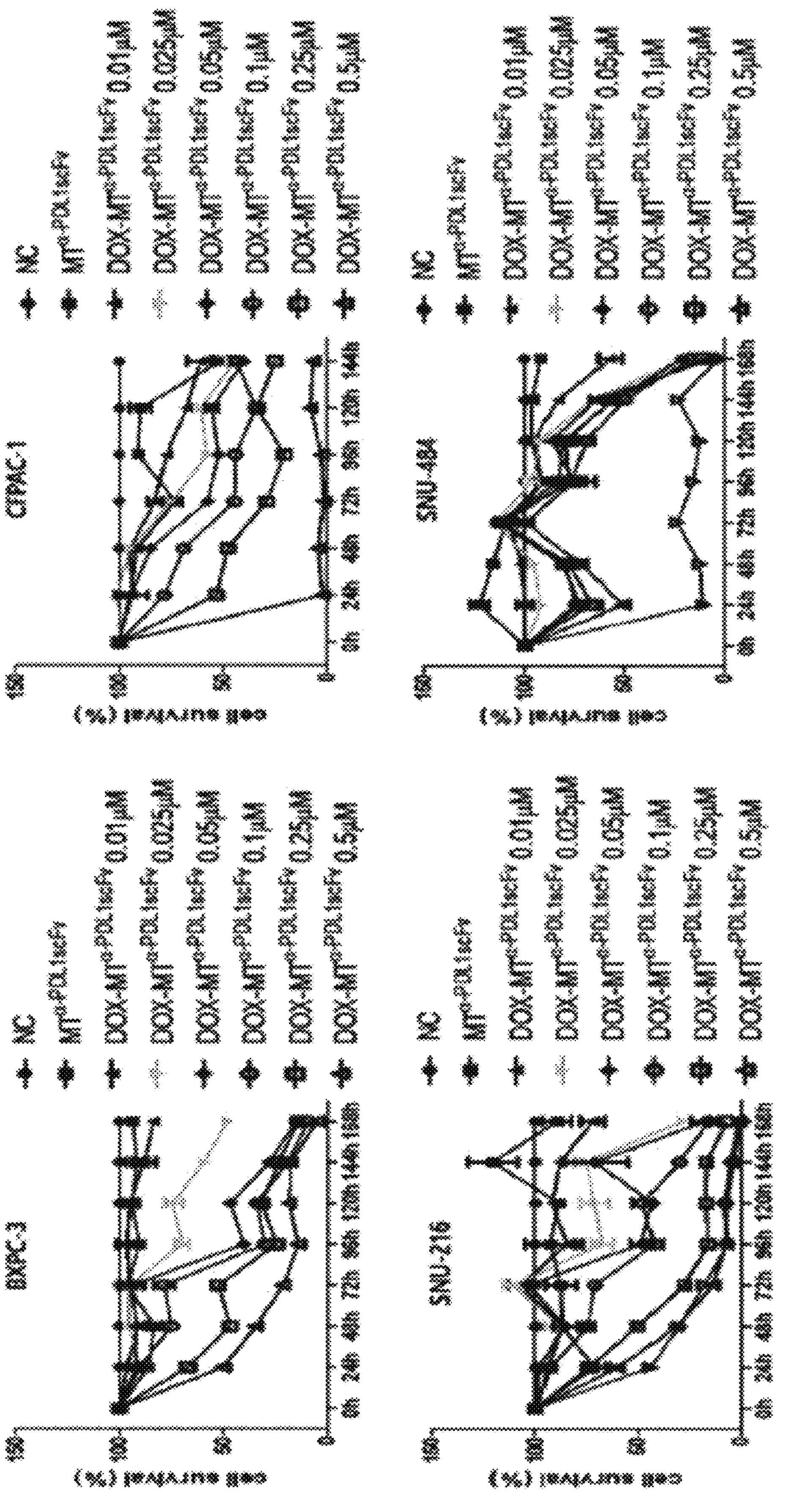
FIG. 50 is a graph showing the results of measuring the cytotoxicity by treatment of the human pancreatic cancer cell line (BXPC-3 and CFPAC-1) and the human gastric cancer cell line (SNU-216 and SNU-484) with $MT^{\alpha\text{-}PDL1scFv}$ or DOX_$MT^{\alpha\text{-}PDL1scFv}$.

Specifically, the human pancreatic cancer cell line (BXPC-3 and CFPAC-1) and the human gastric cancer cell line (SNU-216 and SNU-484) were inoculated into a 96-well plate at about $5\times10^3$ cells/well and cultured for 24 hours. After culturing for 24 hours, each cell was treated with DOX_MT$^{\alpha\text{-}PDL1scFv}$ at a concentration of 0.01 μM, 0.025 μM, 0.05 μM, 0.1 μM, 0.25 M, 0.5 μM and 1 μM. Cell proliferation was measured by WST-1 assay every 24 hours until 168 hours after sample treatment. At this time, the mitochondria-only treated group (MT$^{\alpha\text{-}PDL1scFv}$) was used as a negative control for DOX_MT$^{\alpha\text{-}PDL1scFv}$As a result, for the untreated group (NC), cell proliferation inhibitory effect was not observed in the mitochondria-only treated group (MT$^{\alpha\text{-}PDL1scFv}$). On the other hand, in DOX_MT$^{\alpha\text{-}PDL1scFv}$ treated group, cancer cell proliferation was inhibited over time in a concentration-dependent manner (FIG. 50).

Example 8.2. Confirmation of Cancer Cell Apoptosis by DOX_MT$^{\alpha\text{-}PDL1scFv}$ Through Western Blot Analysis In order to confirm the apoptosis effect by DOX_MT$^{\alpha\text{-}PDL1scFv}$ in cancer cells, after treatment with DOX_MT$^{\alpha\text{-}PDL1scFv}$ in the human pancreatic cancer and gastric cancer cell lines, Western blot was performed using an antibody against an apoptosis marker.

Specifically, the human pancreatic cancer cell line (BXPC-3 and CFPAC-1) and the human gastric cancer cell line (SNU-216 and SNU-484) were inoculated at about $5\times10^6$ cells/well, respectively, and cultured for 24 hours.

After culturing for 24 hours, the cells were treated with MT$^{\alpha\text{-}PDL1scFv}$ or DOX_MT$^{\alpha\text{-}PDL1scFv}$ respectively, and after 96 hours, the cells were disrupted, proteins were extracted, and Western blot was performed. Anti-cleaved PARP antibody (Cell signaling, 9541S), anti-cleaved caspase 3 antibody (Cell signaling, 9664), anti-phospho-p53 antibody (ABelonal, AP0762) and anti-β actin antibody (Sigma, A2228) were used as primary antibodies, and anti-mouse IgG HRP or anti-rabbit IgG HRP was used as a secondary antibody. The amount of protein was corrected through the expression level of R actin protein. At this time, the mitochondria-only treated group (MT$^{\alpha\text{-}PDL1scFv}$) was used as a negative control for DOX_MT$^{\alpha\text{-}PDL1scFv}$.

Figure 51:
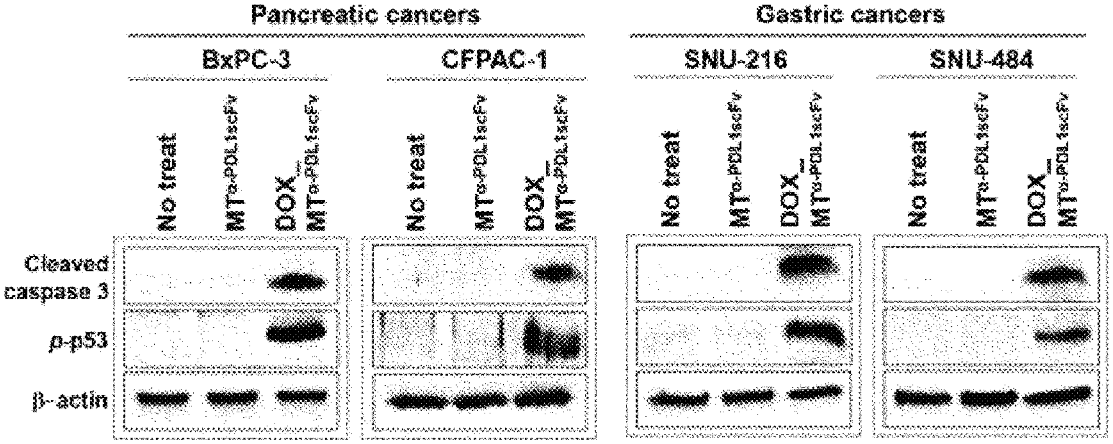
FIG. 51 is a view showing the results of confirming the apoptosis by treatment of the human pancreatic cancer cell line (BXPC-3 and CFPAC-1) and the human gastric cancer cell line (SNU-216 and SNU-484) with $MT^{\alpha\text{-}PDL1scFv}$ or DOX_$MT^{\alpha\text{-}PDL1scFv}$ by Western blot.

As a result, in the mitochondria-only treated group (MT$^{\alpha\text{-}PDL1scFv}$), similar to the untreated group (No treat), the cleaved forms of PARP and caspase 3 observed during the apoptosis were not observed, and the phosphorylated form of p53 was not also observed. On the other hand, in DOX_MT$^{\alpha\text{-}PDL1scFv}$ treated group, the expression of the phosphorylated p53 and the cleaved forms of PARP and caspase 3 was observed (FIG. 51). From the above results, it was confirmed that the apoptosis was induced by treatment with DOX_MT$^{\alpha\text{-}PDL1scFv}$.

Figure 52:
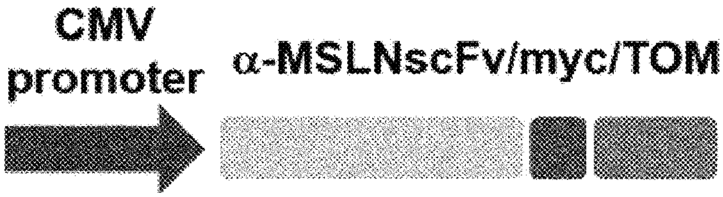
FIG. 52 is a view schematically showing an expression vector for expressing a single chain variable region fragment of an anti-Mesothelin (MSLN) antibody in a form fused to the mitochondria.
Figure 53:
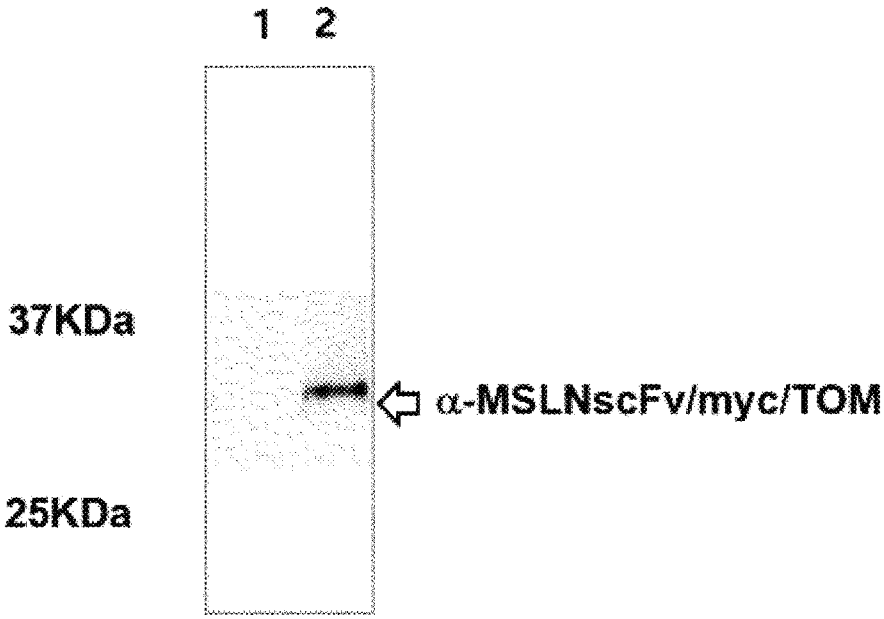
FIG. 53 is a view showing the results of confirming a single chain variable region fragment of an anti-MSLN antibody expressed in the human fetal kidney cell line (HEK293) by Western blot.

Preparation Example 7. Preparation of HEK293 Cell Line Comprising Mitochondria Fused with Anti-MSLN scFv Antibody In order to specifically introduce mitochondria into tumor cells in which mesothelin (MSLN) is expressed, mitochondria in which an anti-MSLNscFv antibody (SEQ ID NO: 102) that specifically binds to MSLN is fused to the mitochondrial outer membrane were construct (FIGS. 52 and 53). A specific method was performed according to the method described in Korean Patent Application Publication No. 10-2019-0124656.

Figure 54:
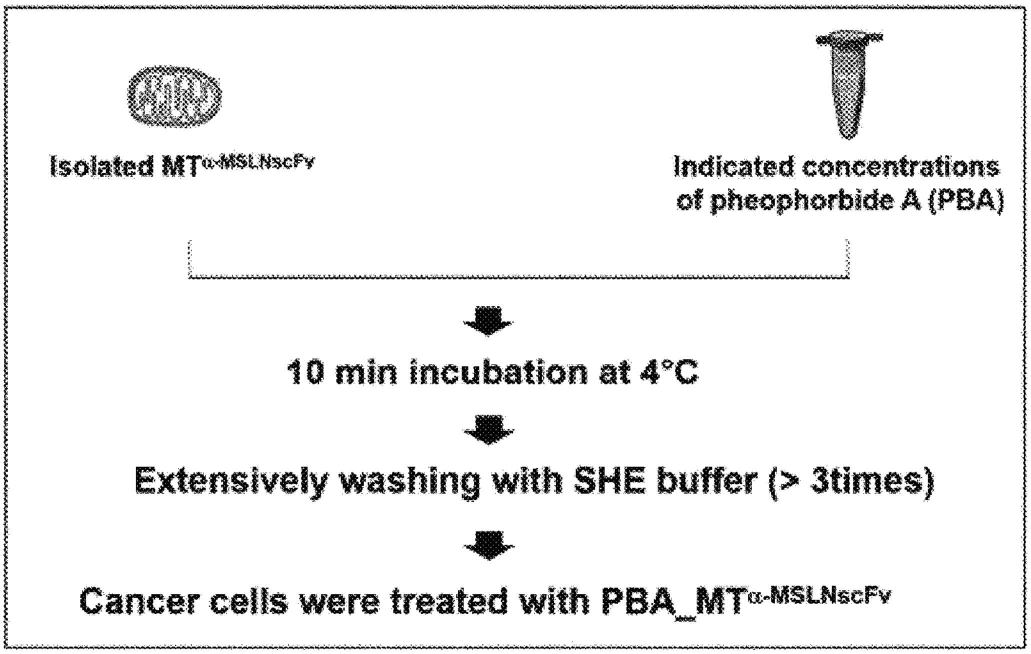
FIG. 54 is a view showing a method for preparing PBA_$MT^{\alpha\text{-}MSLNscFv}$ in which $MT^{\alpha\text{-}MSLNscFv}$ stained with MitoTracker green and pheophorbide A (PBA), a compound payload, are bound.
Figure 55:
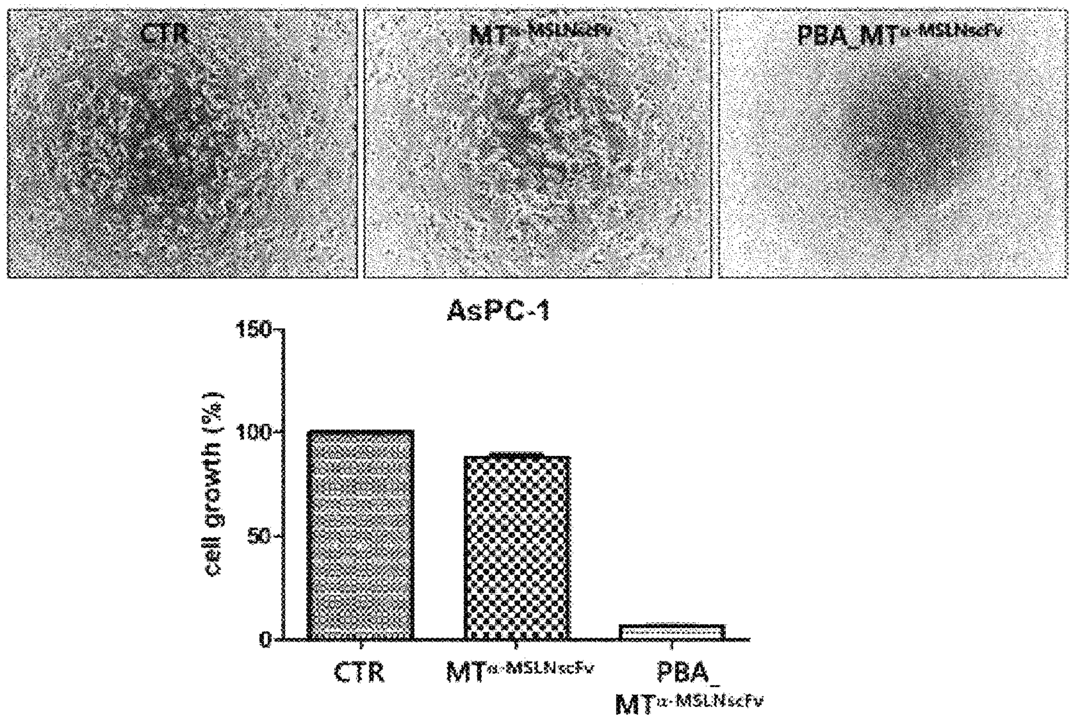
FIG. 55 is a view and graph showing the results of measuring the cytotoxicity by treatment of the human pancreatic cancer cell line (AsPC-1) with $MT^{\alpha\text{-}MSLNscFv}$ or PBA_$MT^{\alpha\text{-}MSLNscFv}$. $MT^{\alpha\text{-}MSLNscFv}$ is the negative control for PBA_$MT^{\alpha\text{-}MSLNscFv}$.
Figure 56:
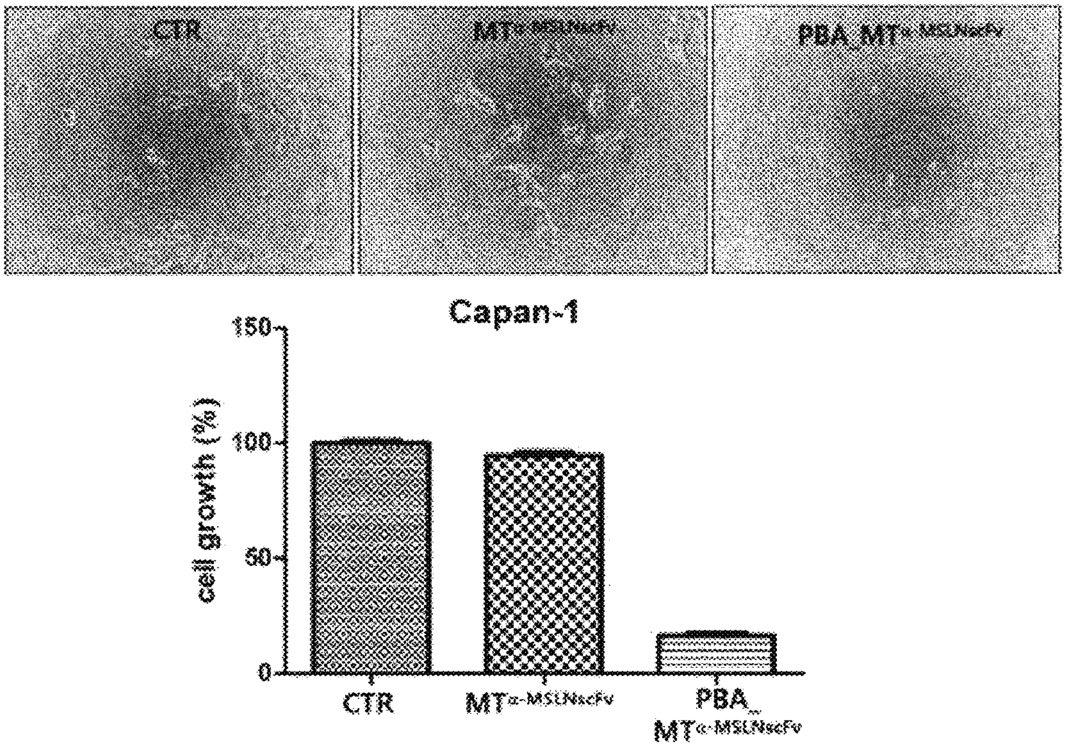
FIG. 56 is a view and graph showing the results of measuring the cytotoxicity by treatment of the human pancreatic cancer cell line (Capan-1) with $MT^{\alpha\text{-}MSLNscFv}$ or PBA_$MT^{\alpha\text{-}MSLNscFv}$. $MT^{\alpha\text{-}MSLNscFv}$ is the negative control for PBA_$MT^{\alpha\text{-}MSLNscFv}$.
Figure 57:
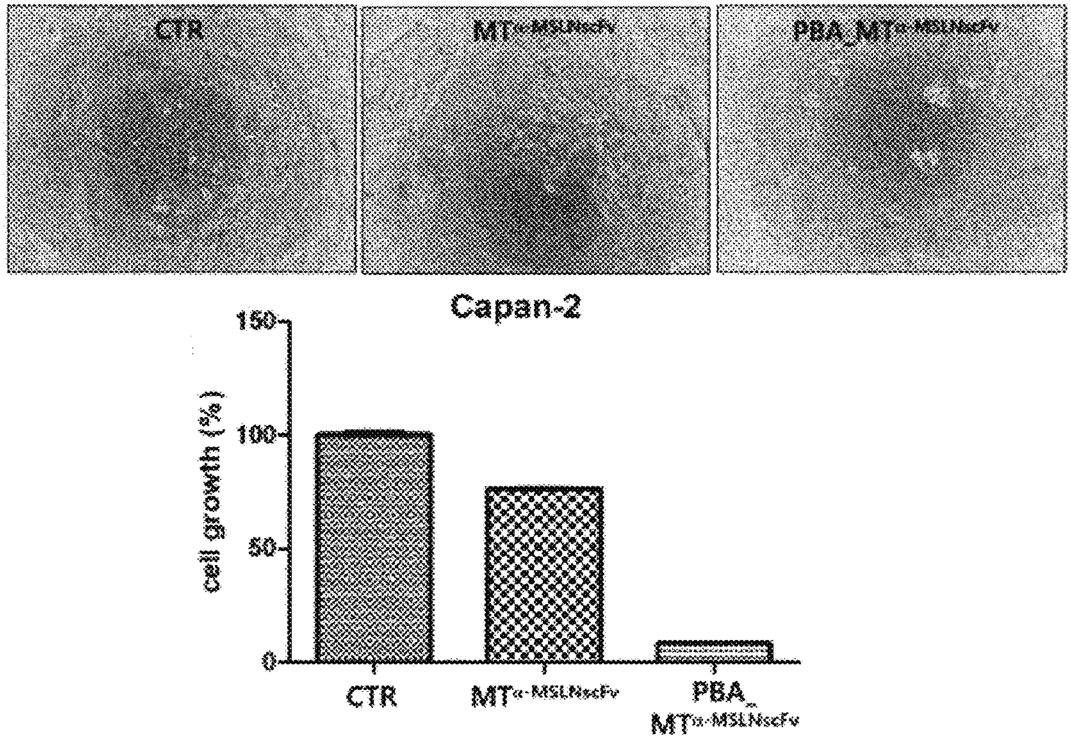
FIG. 57 is a view and graph showing the results of measuring the cytotoxicity by treatment of the human pancreatic cancer cell line (Capan-2) with $MT^{\alpha\text{-}MSLNscFv}$ or PBA_$MT^{\alpha\text{-}MSLNscFv}$. $MT^{\alpha\text{-}MSLNscFv}$ is the negative control for PBA_$MT^{\alpha\text{-}MSLNscFv}$.
Figure 58:
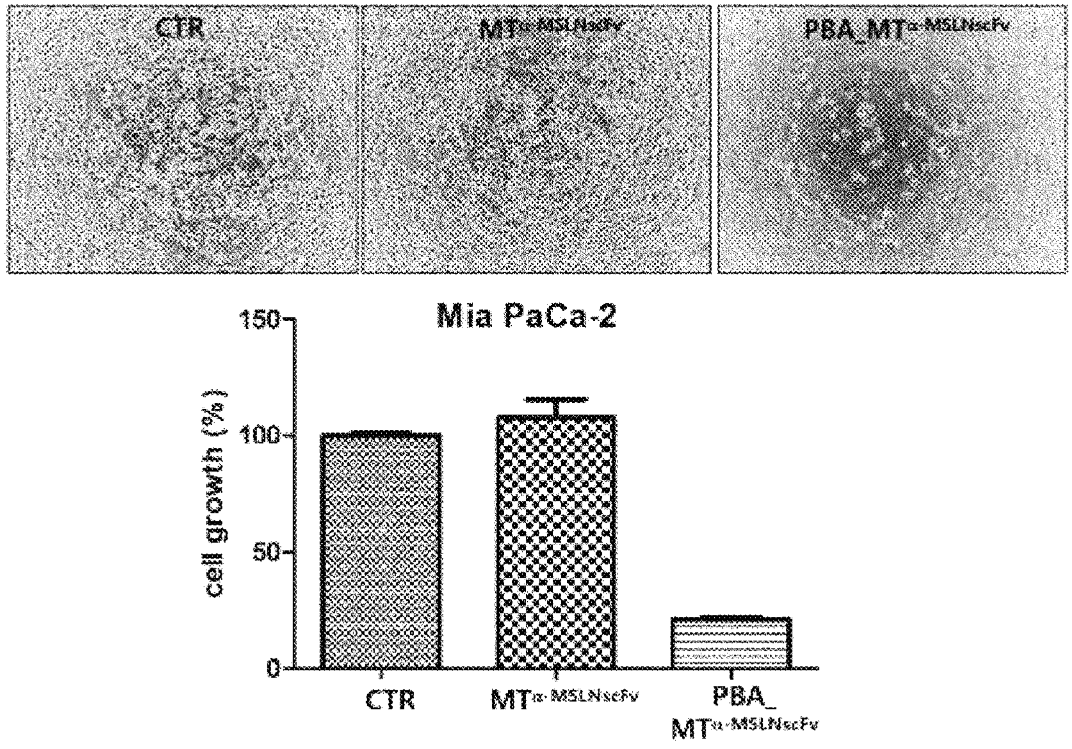
FIG. 58 is a view and graph showing the results of measuring the cytotoxicity by treatment of the human pancreatic cancer cell line (Mia PaCa-2) with $MT^{\alpha\text{-}MSLNscFv}$ or PBA_$MT^{\alpha\text{-}MSLNscFv}$. $MT^{\alpha\text{-}MSLNscFv}$ is the negative control for PBA_$MT^{\alpha\text{-}MSLNscFv}$.

Preparation Example 8. Preparation of Complex of Mitochondria Fused with Anti-MSLNscFv Antibody and Pheophorbide a 100 μg of mitochondria (MT$^{\alpha\text{-}MSLNscFv}$) isolated from the HEK293 cells comprising mitochondria fused with an anti-MSLNscFv antibody were reacted with 100 μM pheophorbide A (PBA) at 4° C. for 10 minutes, and then centrifuged at about 12,000×g for 10 minutes to remove unreacted pheophorbide A. Thereafter, they were washed twice with 500 μL of SHE (250 mM Sucrose, 20 mM HEPES (pH 7.4), 2 mM EGTA) buffer to finally obtain the mitochondria comprising pheophorbide A (PBA_MT$^{\alpha\text{-}MSLNscFv}$) (FIG. 54).

Example 9. Confirmation of Cell Proliferation Inhibitory Ability by Treatment with PBA_MT$^{\alpha\text{-}MSLNscFv}$ In order to confirm the anticancer activity of PBA_MT$^{\alpha\text{-}MSLNscFv}$ obtained in the same manner as in Preparation Example 8 above, after treating the human pancreatic cancer cell line with PBA_MT$^{\alpha\text{-}MSLNscFv}$, the cell proliferation inhibitory effect was evaluated.

Specifically, the human pancreatic cancer cell lines AsPC-1, Capan-1, Capan-2 and Mia PaCa-2 were inoculated into a 96-well plate at $5\times10^3$ cells/well and cultured for 24 hours. Thereafter, the cells were treated with MT$^{\alpha\text{-}MSLNscFv}$ or 1 μg of PBA-MT$^{\alpha\text{-}MSLNscFv}$ and cultured for additional 72 hours, and then cell proliferation was evaluated by WST-1 assay. At this time, the mitochondria-only treated group (MT$^{\alpha\text{-}MSLNscFv}$) was used as a negative control for PBA_MT$^{\alpha\text{-}MSLNscFv}$.

As a result, for the untreated group (CTR), cell proliferation inhibitory effect was not observed in the mitochondria-only treated group (MT$^{\alpha\text{-}MSLNscFv}$). On the other hand, it was confirmed that in PBA_MT$^{\alpha\text{-}MSLNscFv}$ treated group, cell growth was inhibited by about 80% to 95% compared to the untreated group (bottom of FIGS. 55 to 58).

In addition, the morphological change according to treatment with MT$^{\alpha\text{-}MSLNscFv}$ and PBA_MT$^{\alpha\text{-}MSLNscFv}$ in each pancreatic cancer cell line was observed by an inverted microscope. In MT$^{\alpha\text{-}MSLNscFv}$ treated group, almost no morphological change was observed compared to the untreated group, whereas in PBA_MT$^{\alpha\text{-}MSLNscFv}$ treated group, it was confirmed that the cell morphology was altered in all cancer cell lines (top of FIGS. 55 to 58).

Figure 59:
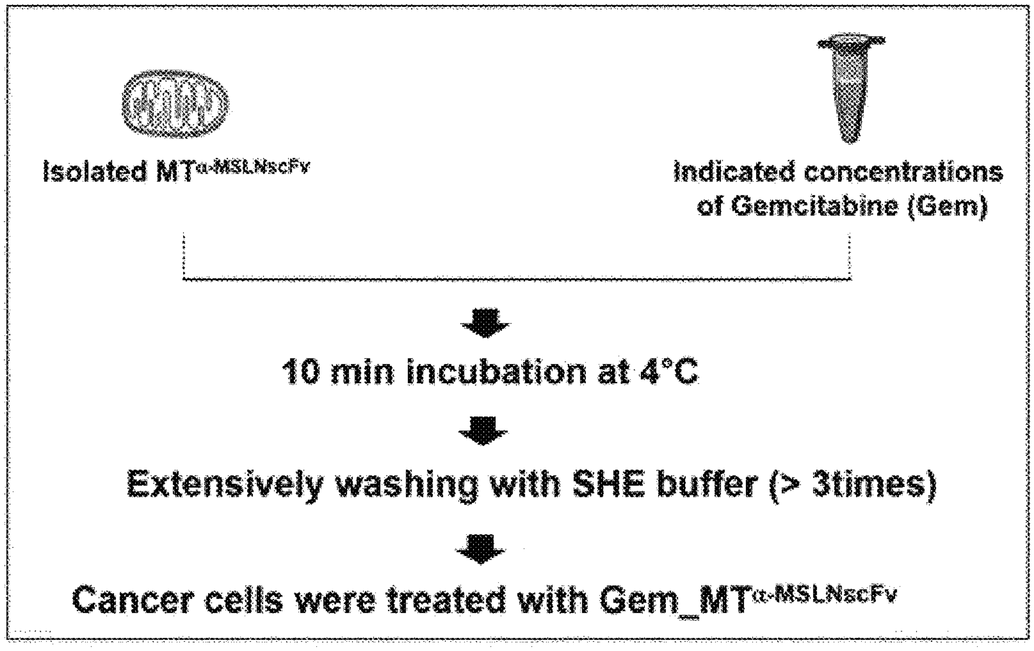
FIG. 59 is a view showing a method for preparing Gem_$MT^{\alpha\text{-}MSLNscFv}$ in which $MT^{\alpha\text{-}MSLNscFv}$ stained with MitoTracker green and gemcitabine, a compound payload, are bound.

Preparation Example 9. Preparation of Complex of Mitochondria Fused with Anti-MSLNscFv Antibody and Gemcitabine 100 μg of mitochondria isolated from the HEK293 cells comprising mitochondria fused with an anti-MSLNscFv antibody were reacted with 100 μM gemcitabine (Gem) at 4° C. for 10 minutes, and then centrifuged at about 12,000×g for 10 minutes to remove unreacted gemcitabine. Thereafter, they were washed twice with 500 μL of SHE (250 mM Sucrose, 20 mM HEPES (pH 7.4), 2 mM EGTA) buffer to finally obtain the mitochondria comprising gemcitabine (Gem_MT$^{\alpha\text{-}MSLNscFv}$) (FIG. 59).

Example 10. Confirmation of Cell Proliferation Inhibitory Ability by Treatment with Gem_MT$^{\alpha\text{-}MSLNscFv}$ In order to confirm the anticancer activity of Gem_MT$^{\alpha\text{-}MSLNscFv}$ obtained in the same manner as in Preparation Example 9 above, after treating the human pancreatic cancer cell line with Gem_MT$^{\alpha\text{-}MSLNscFv}$, the cell proliferation inhibitory effect was evaluated.

Specifically, the human pancreatic cancer cell lines AsPC-1, Capan-1, Capan-2 and Mia PaCa-2 were inoculated into a 96-well plate at about $5\times10^3$ cells/well, respectively, and cultured for 24 hours. After culturing for 24 hours, each cell was treated with MT$^{\alpha\text{-}MSLNscFv}$ or 2 μg of Gem_MT$^{\alpha\text{-}MSLNsCFv}$ and cultured for additional 72 hours, and then cell proliferation was measured by WST-1 assay. At this time, the mitochondria-only treated group (MT$^{\alpha\text{-}MSLNscFv}$) was used as a negative control for Gem_MT$^{\alpha\text{-}MSLNscFv}$.

Figure 60:
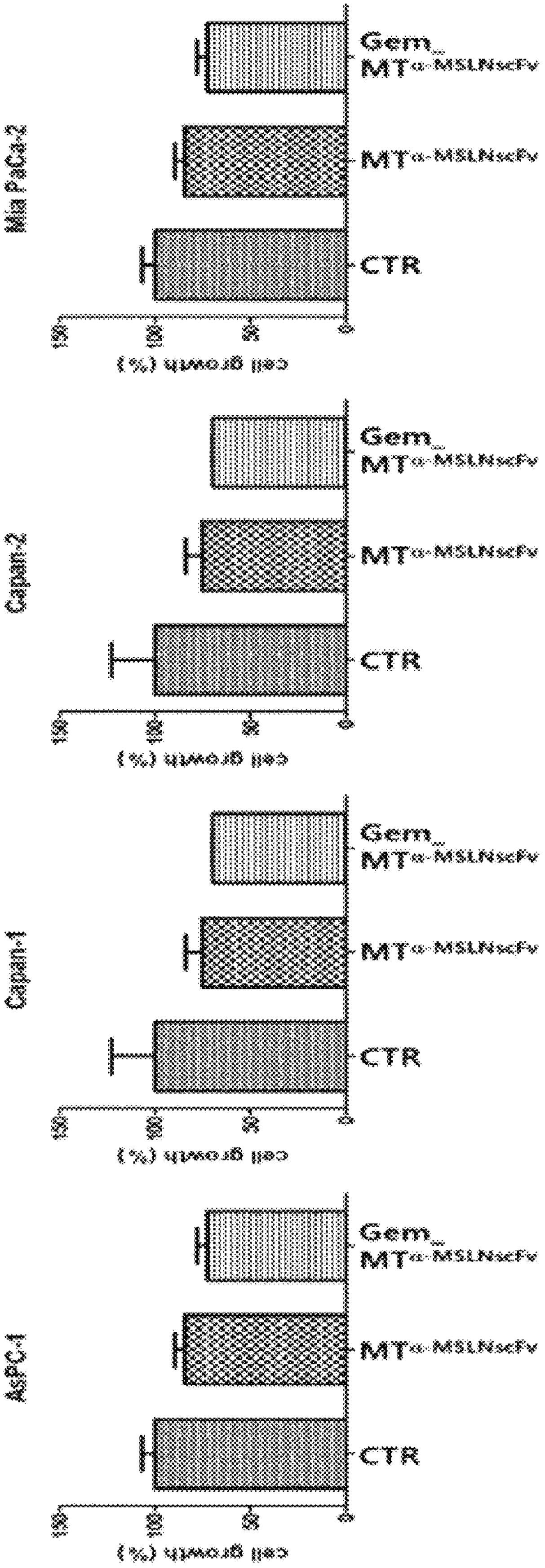
FIG. 60 is a view and graph showing the results of measuring the cytotoxicity by treatment of the human pancreatic cancer cell line (AsPC-1, Capan-1, Capan-2 and Mia PaCa-2) with $MT^{\alpha\text{-}MSLNscFv}$ or Gem_$MT^{\alpha\text{-}MSLNscFv}$. $MT^{\alpha\text{-}MSLNscFv}$ is the negative control for Gem_$MT^{\alpha\text{-}MSLNscFv}$.

As a result, for the untreated group (CTR), cell proliferation inhibitory effect was not observed in the mitochondria-only treated group (MT$^{\alpha\text{-}MSLNscFv}$). On the other hand, it was confirmed that Gem_MT$^{\alpha\text{-}MSLNscFv}$ treated group showed cell growth inhibitory effect by about 20% to 30% compared to the untreated group depending on the cancer cell line (FIG. 60).

Figure 61:
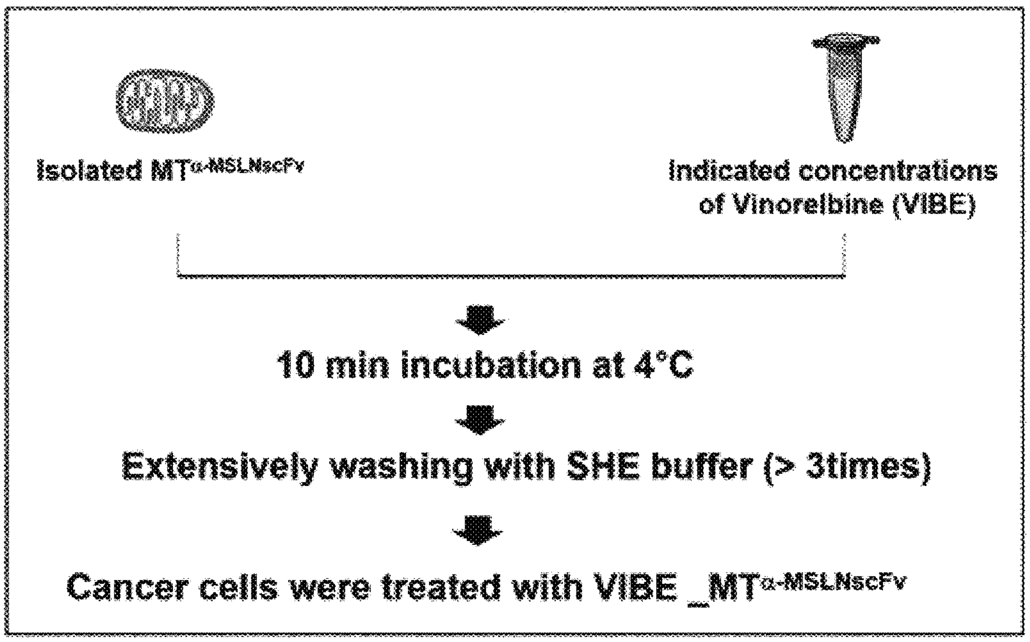
FIG. 61 is a view showing a schematic diagram of a method for preparing VIBE_$MT^{\alpha\text{-}MSLNscFv}$ in which $MT^{\alpha\text{-}MSLNscFv}$ stained with MitoTracker green and vinorelbine, a compound payload, are bound.

Preparation Example 10. Preparation of Complex of Mitochondria Fused with Anti-MSLNscFv Antibody and Vinorelbine 100 μg of mitochondria (MT$^{\alpha\text{-}MSLNscFv}$) isolated from the HEK293 cells comprising mitochondria fused with an anti-MSLNscFv antibody were reacted with 100 μM vinorelbine (VIBE) at 4° C. for 10 minutes, and then centrifuged at about 12,000×g for 10 minutes to remove unreacted vinorelbine. Thereafter, they were washed twice with 500 μL of SHE (250 mM Sucrose, 20 mM HEPES (pH 7.4), 2 mM EGTA) buffer to finally obtain the mitochondria comprising vinorelbine (VIBE_MT$^{\alpha\text{-}MSLNscFv}$) (FIG. 61).

Example 11. Confirmation of Cell Proliferation Inhibitory Ability by Treatment with VIBE_MT$^{\alpha\text{-}MSLNscFv}$ In order to confirm the anticancer activity of VIBE_MT$^{\alpha\text{-}MSLNscFv}$ obtained in the same manner as in Preparation Example 10 above, after treating the human pancreatic cancer cell line with VIBE_MT$^{\alpha\text{-}MSLNscFv}$, the cell proliferation inhibitory effect was evaluated.

Specifically, the human pancreatic cancer cell lines AsPC-1, Capan-1, Capan-2 and MIA PaCa-2 were inoculated into a 96-well plate at about $5\times10^3$ cells/well, respectively, and cultured for 24 hours. After culturing for 24 hours, each cell was treated with MT$^{\alpha\text{-}MSLNscFv}$ or 2 μg of VIBE_MT$^{\alpha\text{-}MSLNscFv}$ and cultured for additional 72 hours, and then cell proliferation was measured by WST-1 assay. At this time, the mitochondria-only treated group (MT$^{\alpha\text{-}MSLNscFv}$) was used as a negative control for VIBE_MT$^{\alpha\text{-}MSLNscFv}$.

Figure 62:
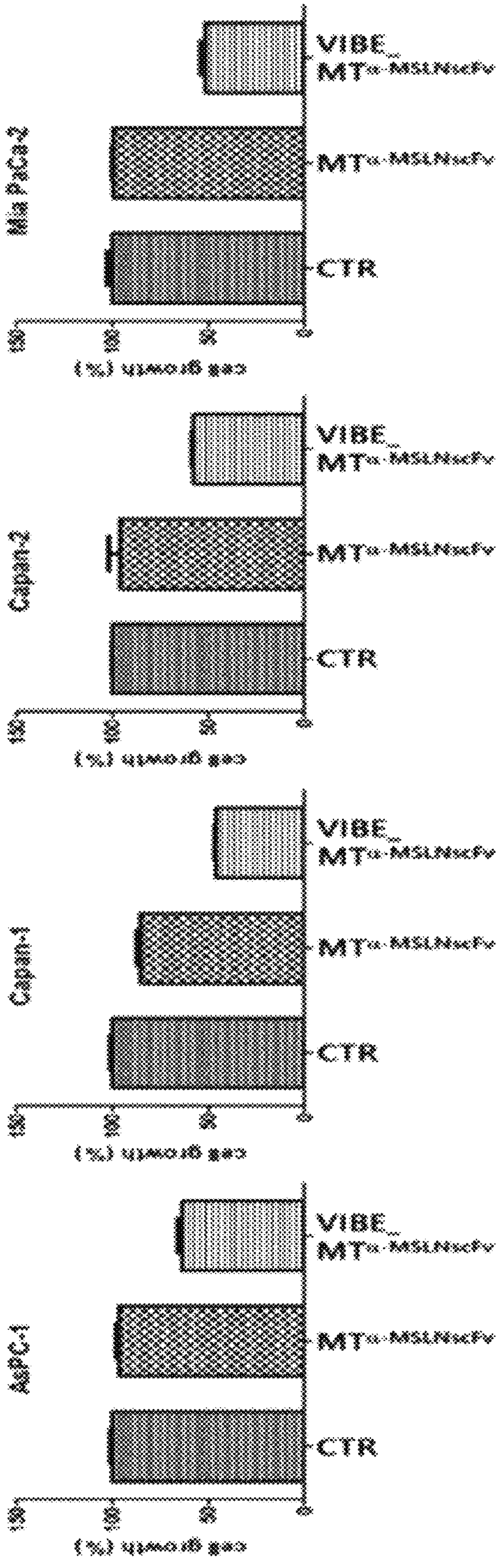
FIG. 62 is a graph showing the results of measuring the cytotoxicity by treatment of the human pancreatic cancer cell line (AsPC-1, Capan-1, Capan-2 and Mia PaCa-2) with $MT^{\alpha\text{-}MSLNscFv}$ or VIBE_$MT^{\alpha\text{-}MSLNscFv}$. $MT^{\alpha\text{-}MSLNscFv}$ is the negative control for VIBE_$MT^{\alpha\text{-}MSLNscFv}$.

As a result, for the untreated group (CTR), cell proliferation inhibitory effect was not observed in the mitochondria-only treated group (MT$^{\alpha\text{-}MSLNscFv}$). On the other hand, it was confirmed that VIBE_MT$^{\alpha\text{-}MSLNscFv}$ treated group showed cell growth inhibitory effect by about 50% compared to the untreated group depending on the cancer cell line (FIG. 62).

Figure 63:
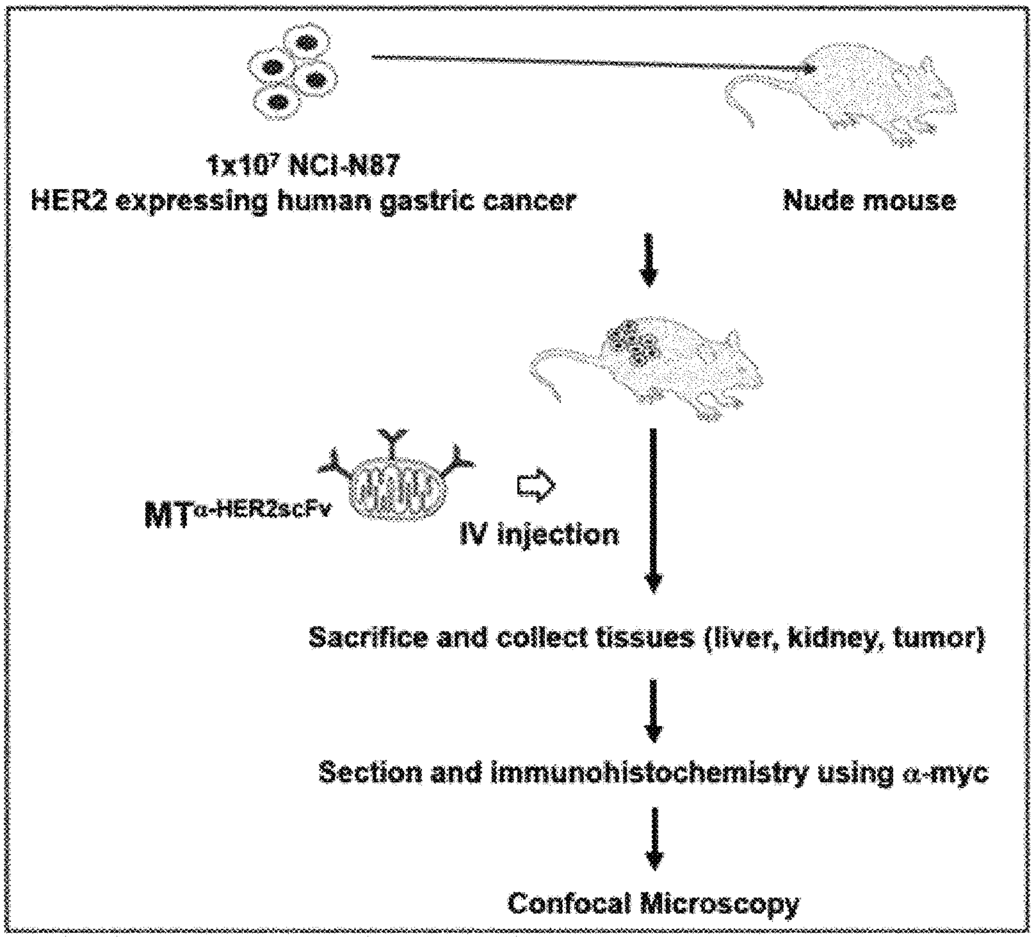
FIG. 63 is a view showing an experimental method for verifying the HER2 targeting ability of $MT^{\alpha\text{-}HER2scFv}$ after administration of $MT^{\alpha\text{-}HER2scFv}$ to a xenograft mouse model formed by transplanting the human gastric cancer cell line NCI-N87 ($HER2^+$).

Example 12. Verification of Tumor Cell Targeting of MT$^{\alpha\text{-}HER2scFv}$ in Xenograft Tumor Mouse Model 5-week-old BALB/c male nude mice (initial body weight of 18~20 g) (Nara Biotech) were acclimatized for 1 week, and then $HER2^+$ human gastric cancer cell line NCI-N87 was subcutaneously transplanted into the lateral abdomen at $1\times10^7$ cells/mouse to construct a xenograft tumor model mouse. When the average volume of the tumor reached 50 $mm^3$ or more, 20 μg of MT$^{\alpha\text{-}HER2scFv}$ was intravenously administered. After 24 hours, the tissues of the mice were extracted. Each extracted tissue was analyzed by immunohistochemistry staining using an anti-myc antibody to confirm the distribution of MT$^{\alpha\text{-}HER2scFv}$ in mouse tissues (FIG. 63).

Example 12.1. Confirmation of Tumor Cell Targeting of MT$^{\alpha\text{-}HER2scFv}$ in Xenograft Tumor Mouse Model Immunohistochemistry staining was performed on the tissues of the mice treated in the same manner as in Example 12 above. An anti-myc antibody (Roche, 11667149001) labeled with mitochondria MT$^{\alpha\text{-}HER2scFv}$ was used as a primary antibody, and an anti-mouse IgG antibody labeled with Alexa Fluor® 488 (Invitrogen, 11001) was used as secondary antibody. At this time, the nuclei of the cells were observed by staining with DAPI.

Figure 64:
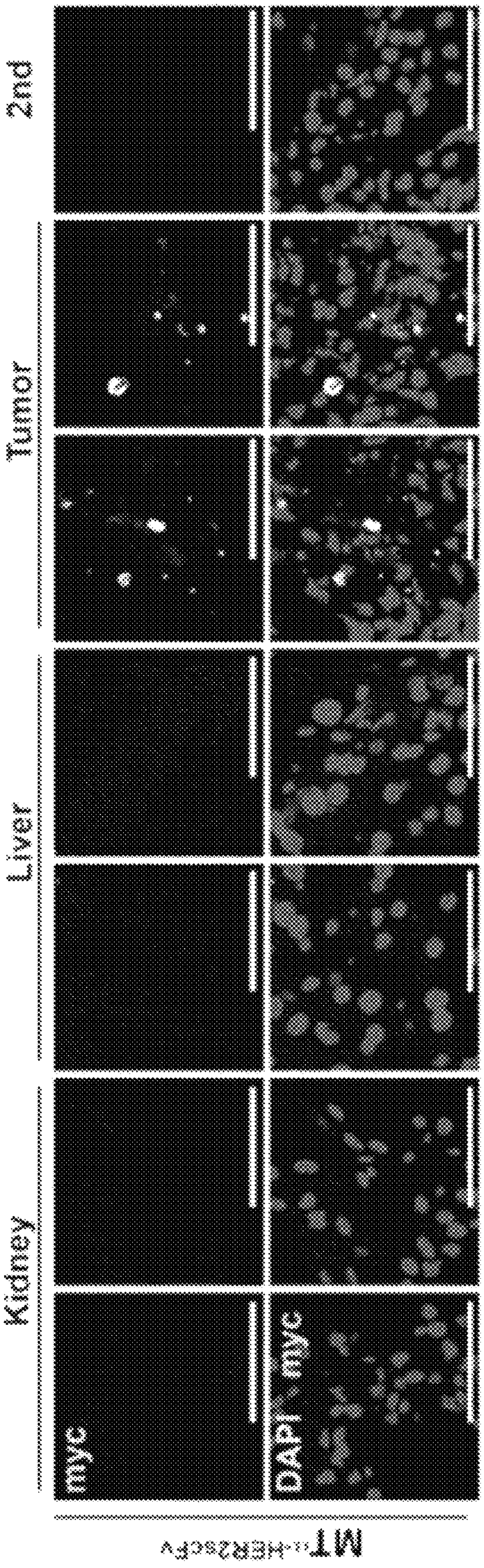
FIG. 64 is a view showing the results of observing that $MT^{\alpha\text{-}HER2scFv}$ is located in the tumor after administration of $MT^{\alpha\text{-}HER2scFv}$ to a xenograft mouse model formed by transplanting the human gastric cancer cell line NCI-N87 ($HER2^+$).

As a result, MT$^{\alpha\text{-}HER2scFv}$ was not observed in kidney and liver tissues, but MT$^{\alpha\text{-}HER2scFv}$ was observed in tumor tissues (FIG. 64). From the above results, it was confirmed that MT$^{\alpha\text{-}HER2scFv}$ injected into the mouse vein specifically targeted NCI-N87 ($HER2^+$) tumor cells subcutaneously transplanted into the lateral abdomen of the mouse.

Figure 65:
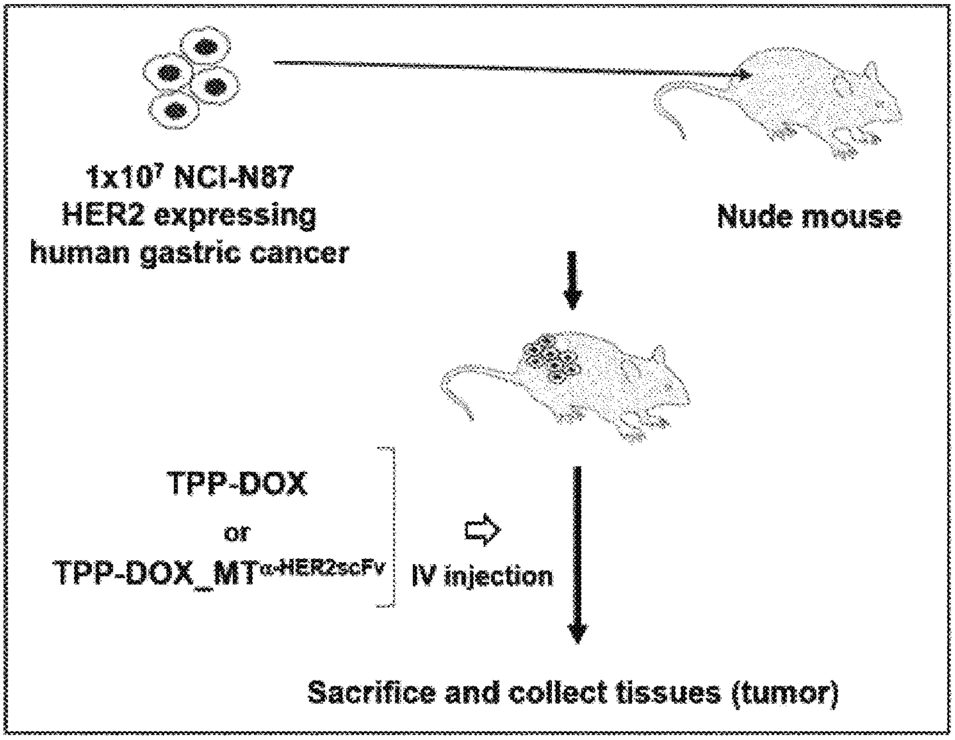
FIG. 65 is a view showing an experimental method for confirming the anticancer efficacy of TPP-DOX or TPP-DOX_$MT^{\alpha\text{-}HER2scFv}$ in a xenograft mouse model formed by transplanting the human gastric cancer cell line NCI-N87 ($HER2^+$).

Example 13. Evaluation of Anticancer Activity of TPP-DOX_MT$^{\alpha\text{-}HER2scFv}$ in Xenograft Tumor Mouse Model 5-week-old BALB/c male nude mice (initial body weight of 18~20 g) (Nara Biotech) were acclimatized for 1 week, and then $HER2^+$ human gastric cancer cell line NCI-N87 was subcutaneously transplanted into the lateral abdomen at $1\times10^7$ cells/mouse to construct a xenograft tumor model mouse. When the average volume of the tumor reached 50~100 $mm^3$, the mice were divided into 3 groups of 7 mice per test group, and 4 μg of TPP-DOX or TPP-DOX_MT$^{\alpha\text{-}HER2scFv}$ was intravenously administered once a week for 4 weeks for a total of 7 times. The tumor size was measured at an interval of 2~4 days, and after 25 days from the start of administration, the tumor tissues were extracted, and the size and weight were measured (FIG. 65).

Figure 66:
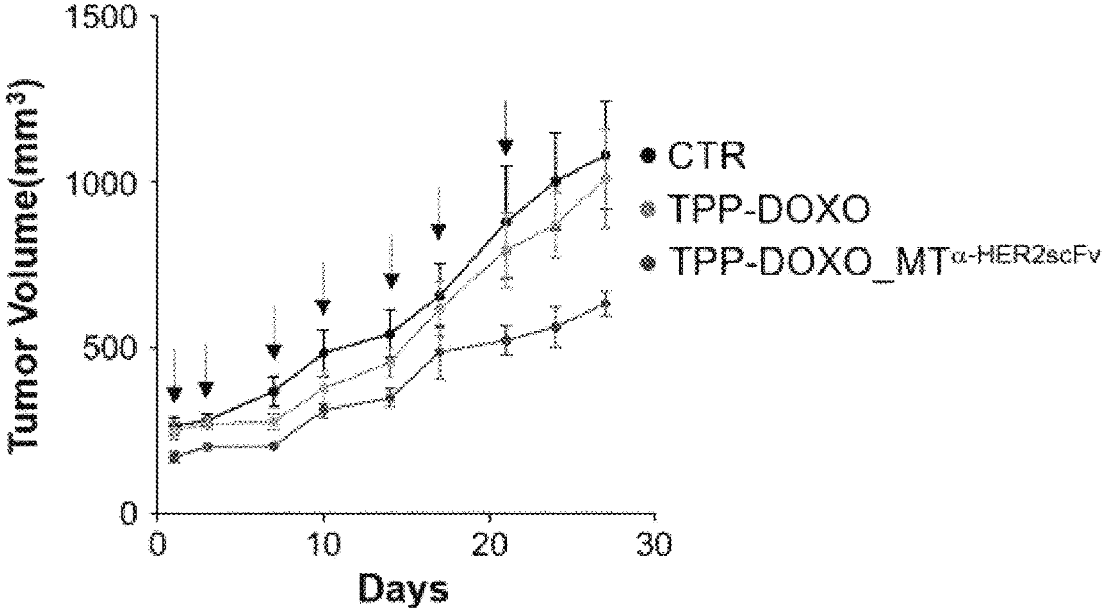
FIG. 66 is a graph showing the results of measuring the tumor size (tumor volume) by date after administration of TPP-DOX or TPP-DOX_$MT^{\alpha\text{-}HER2scFv}$ to a xenograft mouse model formed by transplanting the human gastric cancer cell line NCI-N87 ($HER2^+$).
Figure 67:
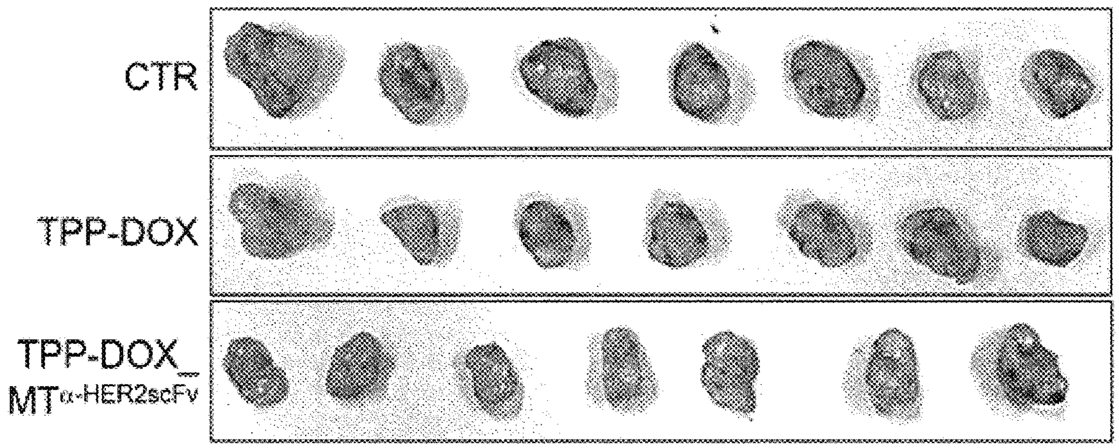
FIG. 67 is a view confirming the size of the tumor extracted after 25 days from the start of administration of TPP-DOX or TPP-DOX_$MT^{\alpha\text{-}HER2scFv}$ in a xenograft mouse model formed by transplanting the human gastric cancer cell line NCI-N87 ($HER2^+$).
Figure 68:
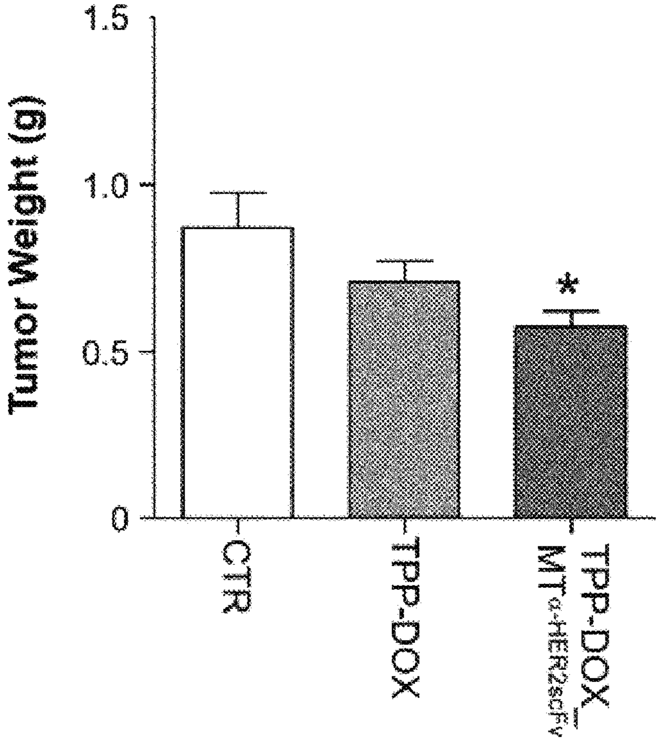
FIG. 68 is a graph showing the results of measuring the weight of the tumor extracted after 25 days from the start of administration of TPP-DOX or TPP-DOX_$MT^{\alpha\text{-}HER2scFv}$ in a xenograft mouse model formed by transplanting the human gastric cancer cell line NCI-N87 ($HER2^+$).

Example 13.1. Confirmation of Tumor Cell Growth Inhibitory Ability of TPP-DOX_MT$^{\alpha\text{-}HER2scFv}$ in Xenograft Tumor Mouse Model As a result of the experiment through the method of Example 13 above, in the case of TPP-DOX administration group, the tumor size was similar until the $30^{th}$ day compared to the control group (CTR). On the other hand, the tumor size in TPP-DOX_MT$^{\alpha\text{-}HER2scFv}$ administration group was significantly reduced compared to the control group (FIG. 66). In addition, the size (FIG. 67) and weight (FIG. 68) of the tumor extracted after the end of the experiment were significantly reduced in TPP-DOX_MT$^{\alpha\text{-}HER2scFv}$ treated group. Statistical processing was performed using Graphpad 5.0 software, and p values were measured with one-way ANOVA (Turkey's) test (*$p<0.05$).

Figure 69:
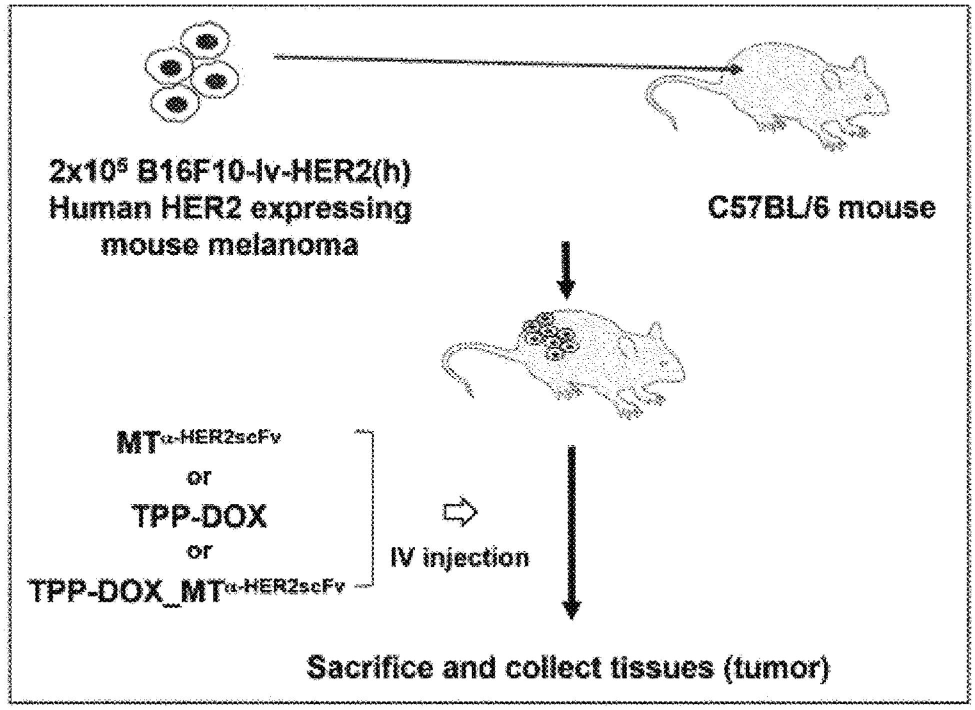
FIG. 69 is a view showing an experimental method for confirming the anticancer efficacy of $MT^{\alpha\text{-}HER2scFv}$, TPP-DOX or TPP-DOX_$MT^{\alpha\text{-}HER2scFv}$ in an allograft mouse model formed by transplanting the mouse melanoma cell line B16F10 that overexpresses human HER2.

Example 14. Evaluation of Anticancer Activity of TPP-DOX_MT$^{\alpha\text{-}HER2scFv}$ in Allograft Tumor Mouse Model 7-week-old C57BL/6 female mice (Samtako Bio Korea) were acclimatized for 1 week, and then the mouse melanoma cell line B16F10 was subcutaneously transplanted into the lateral abdomen of the mice at about $5\times10^5$ cells/mouse to construct an allograft tumor mouse. At this time, B16F10 cells in which the human HER2 gene was overexpressed using lentivirus were used as B16F10 cells. When the average volume of the tumor reached 100~200 $mm^3$, the mice were divided into 4 groups of 3 mice per test group, and $MT^{\alpha\text{-}HER2scFv}$ (20 μg), TPP-DOX (5 μg) or TPP-DOX_$MT^{\alpha\text{-}HER2scFv}$ (TPP-DOX/MT: 5 μg/20 μg) was intravenously administered 3 times a week for 3 weeks. The tumor size was measured 3 times a week, and after the end of the experiment (after 3 weeks from the start of administration), the tumor tissues of the mice were extracted, and the size and weight were measured (FIG. 69).

Figure 70:
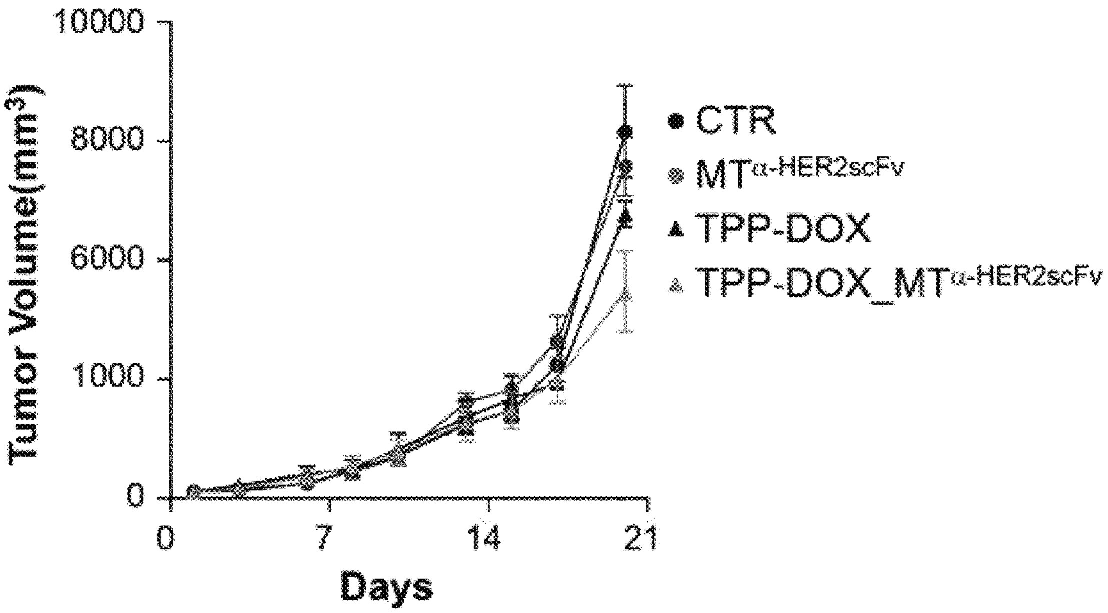
FIG. 70 is a graph showing the results of measuring the tumor size (tumor volume) by date after administration of $MT^{\alpha\text{-}HER2scFv}$, TPP-DOX or TPP-DOX_$MT^{\alpha\text{-}HER2scFv}$ to an allograft mouse model formed by transplanting the mouse melanoma cell line B16F10 that overexpresses human HER2.
Figure 71:
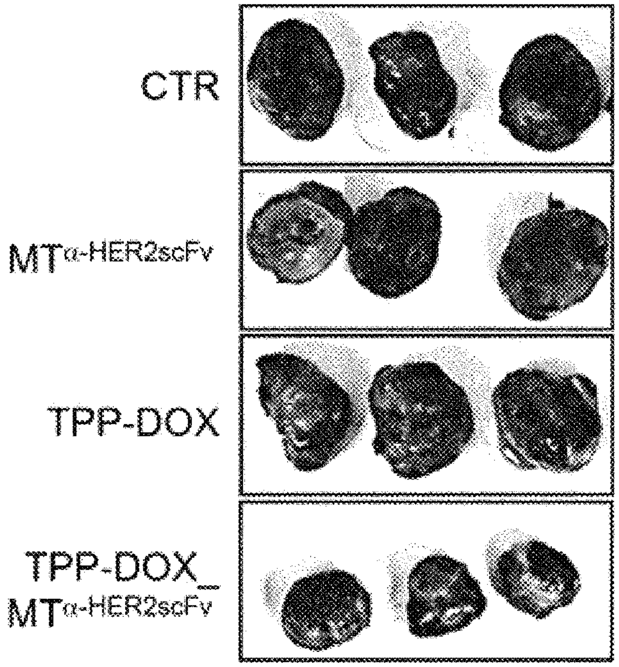
FIG. 71 is a view confirming the size of the tumor extracted after 21 days from the start of administration of $MT^{\alpha\text{-}HER2scFv}$, TPP-DOX or TPP-DOX_$MT^{\alpha\text{-}HER2scFv}$ to an allograft mouse model formed by transplanting the mouse melanoma cell line B16F10 that overexpresses human HER2.
Figure 72:
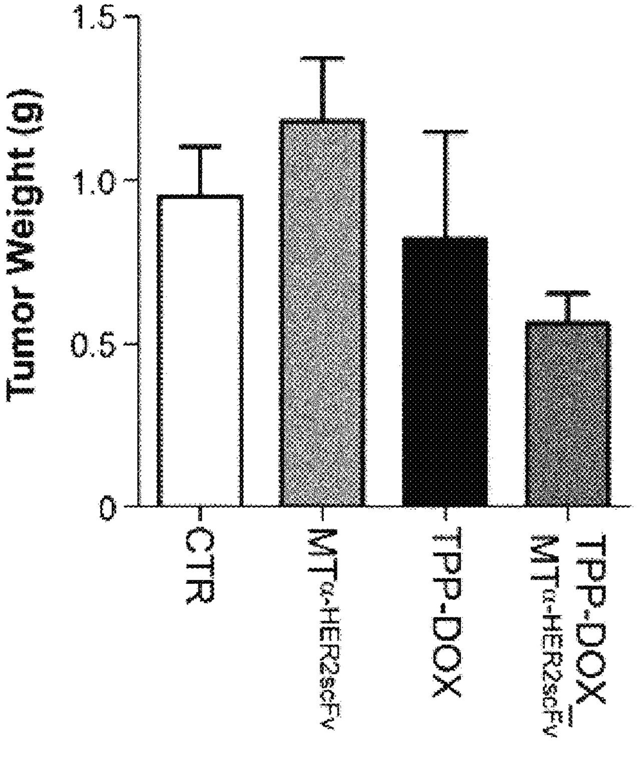
FIG. 72 is a graph showing the results of measuring the weight of the tumor extracted after 21 days from the start of administration of $MT^{\alpha\text{-}HER2scFv}$, TPP-DOX or TPP-DOX_$MT^{\alpha\text{-}HER2scFv}$ to an allograft mouse model formed by transplanting the mouse melanoma cell line B16F10 that overexpresses human HER2.

Example 14.1. Confirmation of Tumor Cell Growth Inhibitory Ability of TPP-DOX_$MT^{\alpha\text{-}HER2scFv}$ in Allogenic Cancer Cell Transplantation Animal Model As a result of the experiment through the method of Example 14 above, in the case of $MT^{\alpha\text{-}HER2scFv}$ and TPP-DOX administration group, the tumor size was similar to that of the control group (CTR). On the other hand, the tumor size in TPP-DOX_$MT^{\alpha\text{-}HER2scFv}$ administration group was significantly reduced compared to the control group (FIG. 70). In addition, the size (FIG. 71) and weight (FIG. 72) of the tumor extracted after the end of the experiment were reduced in TPP-DOX_$MT^{\alpha\text{-}HER2scFv}$ treated group.

Figure 73:
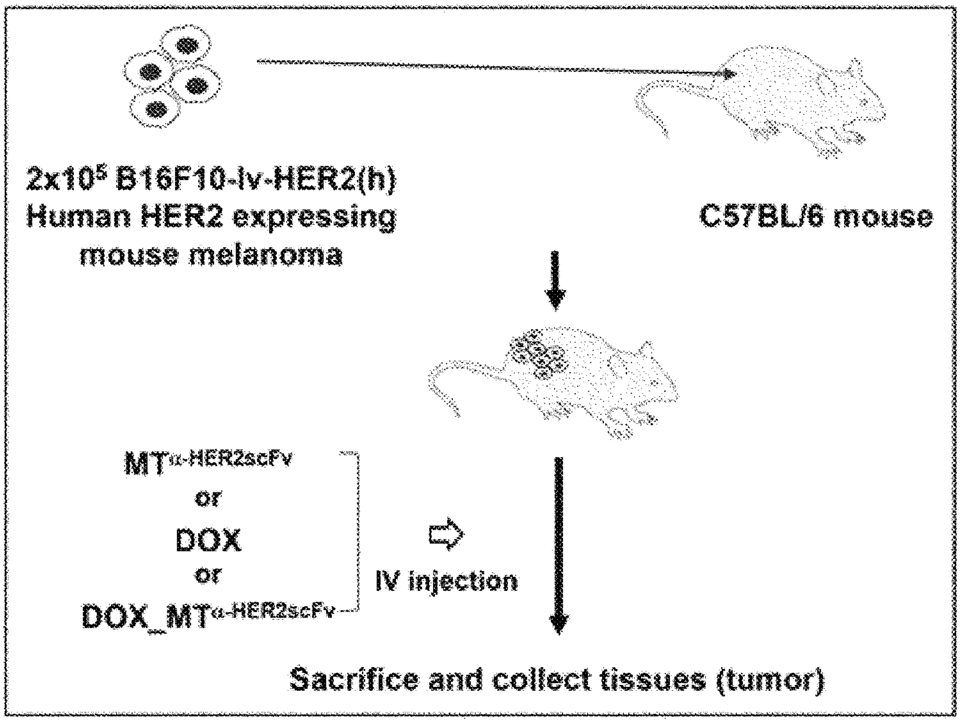
FIG. 73 is a view showing an experimental method for confirming the anticancer efficacy of $MT^{\alpha\text{-}HER2scFv}$, DOX or DOX_$MT^{\alpha\text{-}HER2scFv}$ in an allograft mouse model formed by transplanting the mouse melanoma cell line B16F10 that overexpresses human HER2.

Example 15. Evaluation of Anticancer Activity of DOX_$MT^{\alpha\text{-}HER2scFv}$ in Allograft Tumor Animal Model 7-week-old C57BL/6 female mice (Samtako Bio Korea) were acclimatized for 1 week, and then the mouse melanoma cell line B16F10 was subcutaneously transplanted into the lateral abdomen of the mice at about $5\times10^5$ cells/mouse to construct an allograft tumor mouse. At this time, B16F10 cells in which the human HER2 gene was overexpressed using lentivirus were used as B16F10 cells. When the average volume of the tumor reached 100~200 $mm^3$, the mice were divided into 4 groups of 3 mice per test group, and $MT^{\alpha\text{-}HER2scFv}$ (20 μg), DOX (4 μg) or DOX_$MT^{\alpha\text{-}HER2scFv}$ (TPP-DOX/MT: 4 μg/20 μg) was intravenously administered 3 times a week for 3 weeks. The tumor size was measured 3 times a week, and after the end of the experiment (after 3 weeks from the start of administration), the tumor tissues of the mice were extracted, and the size and weight were measured (FIG. 73).

Example 15.1. Confirmation of Tumor Cell Growth Inhibitory Ability of DOX_$MT^{\alpha\text{-}HER2scFv}$ in Allograft Tumor Animal Model As a result of the experiment through the method of Example 14 above, in the case of $MT^{\alpha\text{-}HER2scFv}$ administration group, the tumor size was similar to that of the control group (CTR).

Figure 74:
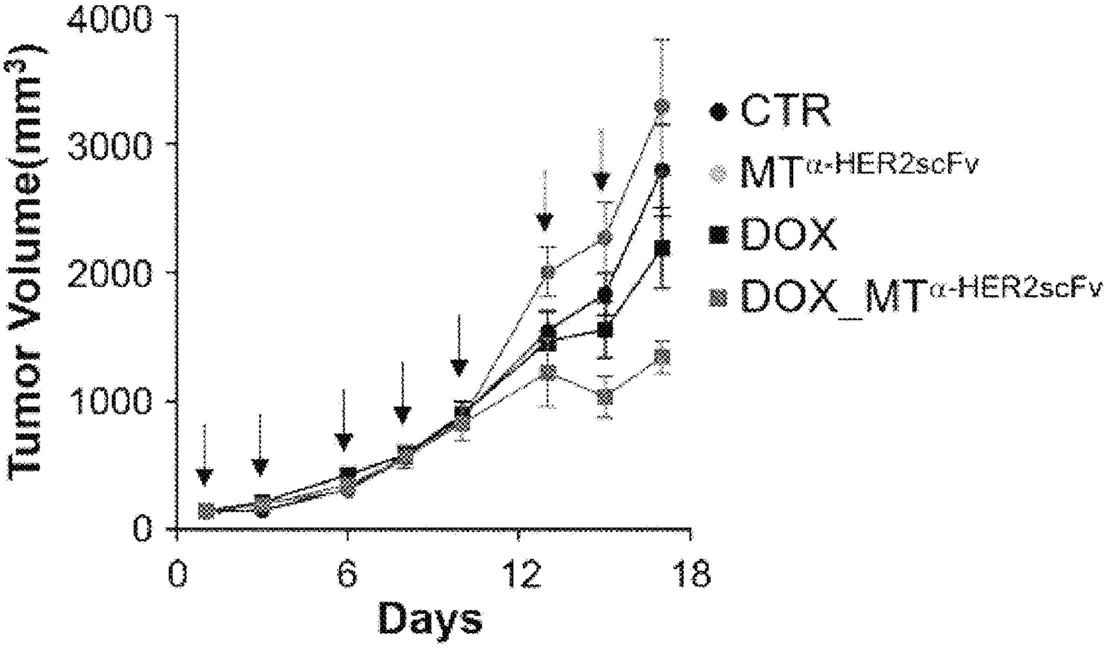
FIG. 74 is a graph showing the results of measuring the tumor size by date after administration of $MT^{\alpha\text{-}HER2scFv}$, DOX or DOX_$MT^{\alpha\text{-}HER2scFv}$ to an allograft mouse model formed by transplanting the mouse melanoma cell line B16F10 that overexpresses human HER2.
Figure 75:
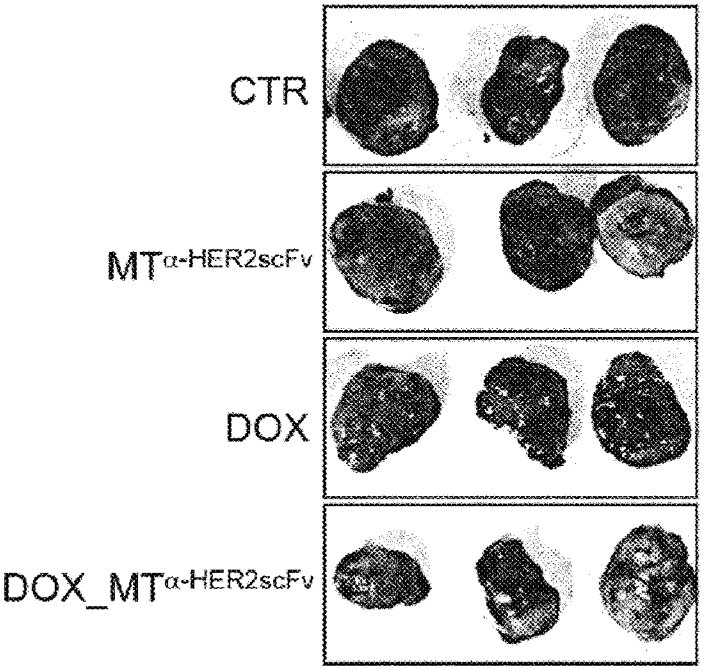
FIG. 75 is a view confirming the size of the tumor extracted after 21 days from the start of administration of $MT^{\alpha\text{-}HER2scFv}$, TPP-DOX or TPP-DOX_$MT^{\alpha\text{-}HER2scFv}$ to an allograft mouse model formed by transplanting the mouse melanoma cell line B16F10 that overexpresses human HER2.
Figure 76:
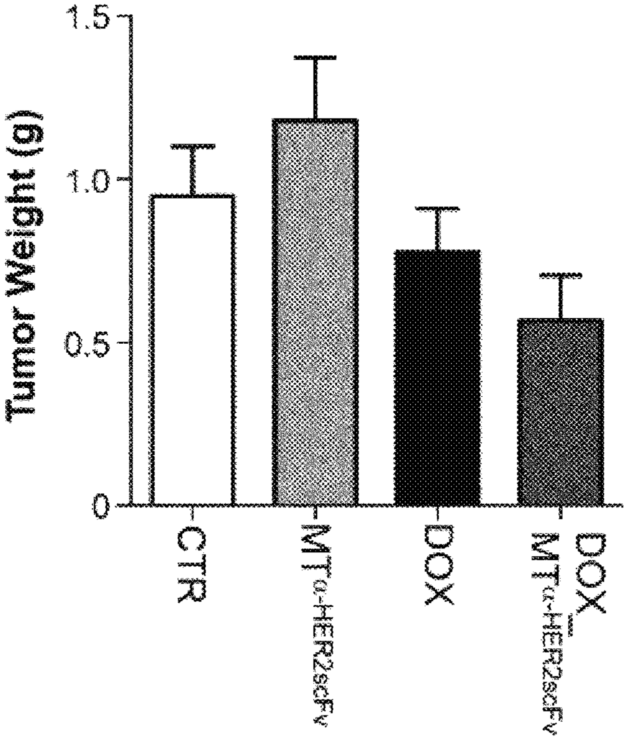
FIG. 76 is a graph showing the results of measuring the weight of the tumor extracted after 21 days from the start of administration of $MT^{\alpha\text{-}HER2scFv}$, DOX or DOX_ $MT^{\alpha\text{-}HER2scFv}$ to an allograft mouse model formed by transplanting the mouse melanoma cell line B16F10 that overexpresses human HER2.

On the other hand, the tumor size in DOX administration group and DOX_$MT^{\alpha\text{-}HER2scFv}$ administration group was significantly reduced compared to the control group. In addition, it was confirmed that the tumor size in DOX_$MT^{\alpha\text{-}HER2scFv}$ administration group was further reduced compared to DOX treated group (FIG. 74). In addition, the size (FIG. 75) and weight (FIG. 76) of the tumor extracted after the end of the experiment was reduced in DOX_$MT^{\alpha\text{-}HER2scFv}$ administration group compared to the control group.

Free Text of Sequence Listing

SEQ ID NO: 1: T2p53 primer
SEQ ID NO: 2: Xp53 primer
SEQ ID NO: 3: nucleotides sequence coding p53
SEQ ID NO: 4: NdeUB primer
SEQ ID NO: 5: T2UB primer
SEQ ID NO: 6: nucleotides sequence coding UB-p53
SEQ ID NO: 7: NdeTOM70 primer
SEQ ID NO: 8: TOM70-AS primer
SEQ ID NO: 9: TOM70UB-S primer
SEQ ID NO: 10: T2UB-AS primer
SEQ ID NO: 11: nucleotides sequence coding TOM70-UB-p53
SEQ ID NO: 12: TOM70 $(G)_3$-AS primer
SEQ ID NO: 13: (G)3UB-S primer
SEQ ID NO: 14: Xp53 (noT) primer
SEQ ID NO: 15: nucleotides sequence coding TOM70-(GGGGS)3-UB-p53
SEQ ID NO: 16: B (G)3p53
SEQ ID NO: 17: nucleotides sequence coding TOM70-(GGGGS)3-p53
SEQ ID NO: 18: Xp53 (noT) primer
SEQ ID NO: 19: XTOM7 primer
SEQ ID NO: 20: LTOM7 primer
SEQ ID NO: 21: nucleotides sequence coding UB-p53-TOM7
SEQ ID NO: 22: Rp53 primer
SEQ ID NO: 23: nucleotides sequence coding p53-myc/His
SEQ ID NO: 24: T2GZMB primer
SEQ ID NO: 25: XGZMB (noT) primer
SEQ ID NO: 26: nucleotides sequence coding GranzymeB
SEQ ID NO: 27: nucleotides sequence coding TOM70-(GGGGS)3-UB-Granzyme B
SEQ ID NO: 28: nucleotides sequence coding UB-Granzyme B-TOM7
SEQ ID NO: 29: T2RKIP primer
SEQ ID NO: 30: XRKIP (noT) primer
SEQ ID NO: 31: nucleotides sequence coding RKIP
SEQ ID NO: 32: nucleotides sequence coding TOM70-(GGGGS)3-UB-RKIP
SEQ ID NO: 33: T2PTEN primer
SEQ ID NO: 34: XPTEN (noT) primer
SEQ ID NO: 35: nucleotides sequence coding PTEN
SEQ ID NO: 36: nucleotides sequence coding TOM70-(GGGGS)3-UB-PTEN
SEQ ID NO: 37: nucleotides sequence coding scFvHER2
SEQ ID NO: 38: nucleotides sequence coding UB-scFvHER2-TOM7
SEQ ID NO: 39: RscFvHER2 primer
SEQ ID NO: 40: XTOM7 (noT) primer
SEQ ID NO: 41: nucleotides sequence coding scFvHER2-TOM7-myc/His
SEQ ID NO: 42: nucleotides sequence coding scFvMEL
SEQ ID NO: 43: nucleotides sequence coding UB-scFvMEL-TOM7
SEQ ID NO: 44: RscFvMEL primer
SEQ ID NO: 45: nucleotides sequence coding scFvMEL-TOM7-myc/His
SEQ ID NO: 46: nucleotides sequence coding scFvPD-L1

SEQ ID NO: 47: nucleotides sequence coding scFvPD-L1-TOM7-myc/His
SEQ ID NO: 48: amino acid sequence of p53
SEQ ID NO: 49: amino acid sequence of UB-p53
SEQ ID NO: 50: amino acid sequence of TOM70-UB-p53
SEQ ID NO: 51: amino acid sequence of TOM70-(GGGGS)3-UB-p53
SEQ ID NO: 52: amino acid sequence of TOM70-(GGGGS)3-p53
SEQ ID NO: 53: amino acid sequence of UB-p53-TOM7
SEQ ID NO: 54: amino acid sequence of p53-myc/His
SEQ ID NO: 55: amino acid sequence of GranzymeB
SEQ ID NO: 56: amino acid sequence of TOM70-(GGGGS)3-UB-Granzyme B
SEQ ID NO: 57: amino acid sequence of UB-Granzyme B-TOM7
SEQ ID NO: 58: amino acid sequence of RKIP
SEQ ID NO: 59: amino acid sequence of TOM70-(GGGGS)3-UB-RKIP
SEQ ID NO: 60: amino acid sequence of PTEN
SEQ ID NO: 61: amino acid sequence of TOM70-(GGGGS)3-UB-PTEN
SEQ ID NO: 62: amino acid sequence of scFvHER2
SEQ ID NO: 63: amino acid sequence of UB-scFvHER2-TOM7
SEQ ID NO: 64: amino acid sequence of scFvHER2-TOM7-myc/His
SEQ ID NO: 65: amino acid sequence of scFvMEL
SEQ ID NO: 66: amino acid sequence of UB-scFvMEL-TOM7
SEQ ID NO: 67: amino acid sequence of scFvMEL-TOM7-myc/His
SEQ ID NO: 68: amino acid sequence of scFvPD-L1
SEQ ID NO: 69: amino acid sequence of scFvPD-L1-TOM7-myc/His
SEQ ID NO: 70: linker
SEQ ID NO: 71: amino acid sequence of ubiquitin
SEQ ID NO: 72: nucleotides sequence coding ubiquitin
SEQ ID NO: 73: amino acid sequence of p53
SEQ ID NO: 74: nucleotides sequence coding p53
SEQ ID NO: 75: TOM70 of *S. cerevisiae*
SEQ ID NO: 76: TOM70 of *Homo sapiens*
SEQ ID NO: 77: TOM20 of *S. cerevisiae*
SEQ ID NO: 78: TOM20 of *Homo sapiens*
SEQ ID NO: 79: OM45 of *S. cerevisiae*
SEQ ID NO: 80: TOM5 of *S. cerevisiae*
SEQ ID NO: 81: TOM5 of *Homo sapiens*
SEQ ID NO: 82: TOM7 of *S. cerevisiae*
SEQ ID NO: 83: TOM7 of *Homo sapiens*
SEQ ID NO: 84: TOM22 of *S. cerevisiae*
SEQ ID NO: 85: TOM22 of *Homo sapiens*
SEQ ID NO: 86: Fis1 of *S. cerevisiae*
SEQ ID NO: 87: Fis1 of *Homo sapiens*
SEQ ID NO: 88: Bcl-2 alpha of *Homo sapiens*
SEQ ID NO: 89: VAMP1 of *S. cerevisiae*
SEQ ID NO: 90: VAMP1 of *Homo sapiens*
SEQ ID NO: 91: P53-promoter-S
SEQ ID NO: 92: P53-promoter-AS
SEQ ID NO: 93: nucleotides sequence coding scFvPDL1-myc-TOM7
SEQ ID NO: 94: amino acid sequence of scFvPDL1-myc-TOM7
SEQ ID NO: 95: nucleotides sequence coding scFvHER2
SEQ ID NO: 96: amino acid sequence of scFvHER2
SEQ ID NO: 97: nucleotides sequence coding scFvHER2-myc-TOM7
SEQ ID NO: 98: amino acid sequence of scFvHER2-myc-TOM7
SEQ ID NO: 99: nucleotides sequence coding scFvMSLN
SEQ ID NO: 100: amino acid sequence of scFvMSLN
SEQ ID NO: 101: nucleotides sequence coding scFvMSLN-myc-TOM7
SEQ ID NO: 102: amino acid sequence of scFvMSLN-myc-TOM7

The invention claimed is:

1. A modified anticancer agent in which TPP or a derivative thereof is bound to an anticancer agent, wherein the anticancer agent is contained in a modified mitochondrion, wherein the modified mitochondrion is a mitochondrion in which an scFv specifically binding to a tumor-associated antigen is bound to the surface of the mitochondrion.

2. A modified mitochondrion comprising an anticancer agent, wherein the anticancer agent is one to which triphenylphosphonium (TPP) or a derivative thereof is bound, wherein the mitochondrion is a modified mitochondrion in which a single chain variable region fragment (scFv) specifically binding to a tumor-associated antigen is bound to the surface of the mitochondrion.

3. The modified mitochondrion according to claim 2, wherein the anticancer agent is selected from the group consisting of a chemical anticancer agent, a target anticancer agent and an anthelmintic agent.

4. The modified mitochondrion according to claim 3, wherein the chemical anticancer agent is a topoisomerase inhibitor.

5. The modified mitochondrion according to claim 3, wherein the target anticancer agent is any one selected from the group consisting of compounds targeting BTK, Bcr-abl, EGFR, PDGFR/VEGFR/FGFR family, MEK/RAF, HER2/Neu, CDK, ubiquitin, JAK, MAP2K, ALK, PARP, TGFβRI, Proteasome, Bcl-2 Braf, C-Met, VR1, VR2, VR3, c-kit, AXL and RET.

6. The modified mitochondrion according to claim 3, wherein the anthelmintic agent is any one selected from the group consisting of an OXPHOS (oxidative phosphorylation) inhibitor, a glycolysis inhibitor, a glycolysis related indirect inhibitor, a PPP (pentose phosphate pathway) inhibitor and an autophagy inhibitor.

7. The modified mitochondrion according to claim 2, wherein the tumor-associated antigen is any one selected from the group consisting of CD19, CD20, melanoma antigen E (MAGE), NY-ESO-1, carcinoembryonic antigen (CEA), mucin 1 cell surface associated (MUC-1), prostatic acid phosphatase (PAP), prostate specific antigen (PSA), survivin, tyrosine related protein 1 (tyrp1), tyrosine related protein 2 (tyrp2), Brachyury, Mesothelin, Epidermal growth factor receptor (EGFR), human epidermal growth factor receptor 2 (HER-2), ERBB2, Wilms tumor protein (WT1), FAP, EpCAM, PD-L1, ACPP, CPTIA, IFNG, CD274, FOLR1, EPCAM, ICAM2, NCAM1, LRRC4, UNC5H2 LILRB2, CEACAM, Nectin-3 and a combination thereof.

8. The modified mitochondrion according to claim 2, wherein the cancer is any one selected from the group consisting of breast cancer, lung cancer, pancreatic cancer, glioblastoma, gastric cancer, liver cancer, colorectal cancer, prostate cancer, ovarian cancer, cervical cancer, thyroid cancer, laryngeal cancer, acute myeloid leukemia, brain tumor, neuroblastoma, retinoblastoma, head and neck cancer, salivary gland cancer and lymphoma.

9. A pharmaceutical composition for the prevention or treatment of cancer, comprising the modified mitochondrion according to claim 1 as an active ingredient.

10. A method for treating cancer, comprising administering the modified mitochondrion according to claim 1 to a subject.

11. A method for preparing mitochondrion comprising an anticancer agent, comprising:

mixing the anticancer agent and an isolated mitochondrion, wherein the anticancer agent is one to which triphenylphosphonium (TPP) or a derivative thereof is bound, wherein the mitochondrion is a modified mitochondrion in which an scFv specifically binding to a tumor-associated antigen is bound to the surface of the mitochondrion.

* * * * *